(12) United States Patent
Kehler et al.

(10) Patent No.: US 10,011,606 B2
(45) Date of Patent: Jul. 3, 2018

(54) IMIDAZOPYRAZINONES AS PDE1 INHIBITORS

(71) Applicant: H. Lundbeck A/S, Valby (DK)

(72) Inventors: Jan Kehler, Lyngby (DK); Lars Kyhn Rasmussen, Vanløse (DK); Morten Langgård, Glostrup (DK); Mikkel Jessing, Frederiksberg (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 15/615,380

(22) Filed: Jun. 6, 2017

(65) Prior Publication Data

US 2017/0291903 A1    Oct. 12, 2017

Related U.S. Application Data

(63) Continuation of application No. 15/142,116, filed on Apr. 29, 2016.

(30) Foreign Application Priority Data

| Apr. 30, 2015 | (DK) | 201500261 |
| Oct. 29, 2015 | (DK) | 201500666 |
| Apr. 4, 2016  | (DK) | 201600202 |

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................. C07D 487/04; C07D 519/00
See application file for complete search history.

(56) References Cited

U.S. PATENT DOCUMENTS

| 2006/0135767 A1 | 6/2006  | Feng et al.    |
| 2008/0194592 A1 | 8/2008  | Mates et al.   |
| 2010/0190771 A1 | 7/2010  | Claffey et al. |
| 2011/0281832 A1 | 11/2011 | Li et al.      |
| 2016/0083391 A1 | 3/2016  | Burdi et al.   |
| 2016/0083400 A1 | 3/2016  | Burdi et al.   |
| 2016/0311831 A1 | 10/2016 | Kehler et al.  |
| 2016/0318939 A1 | 11/2016 | Kehler et al.  |
| 2017/0291901 A1 | 10/2017 | Juhl et al.    |
| 2017/0298072 A1 | 10/2017 | Kehler et al.  |

FOREIGN PATENT DOCUMENTS

| EP | 2305262       | 4/2011  |
| GB | 973361        | 10/1964 |
| JP | 2015-052588   | 2/2016  |
| JP | 2016-011511   | 2/2016  |
| WO | WO 2004/018474 | 3/2004 |
| WO | WO 2004/026876 | 4/2004 |
| WO | WO 2004/099211 | 11/2004 |
| WO | WO 2008/070095 | 6/2008  |
| WO | WO 2008/139293 | 11/2008 |
| WO | WO 2009/121919 A1 | 10/2009 |
| WO | WO 2010/026214 A1 | 3/2010 |
| WO | WO 2010/065152 | 6/2010  |
| WO | WO 2010/084438 | 7/2010  |
| WO | WO 2011/153136 | 12/2011 |
| WO | WO 2012/040048 | 3/2012  |
| WO | WO 2012/040230 | 3/2012  |
| WO | WO 2012/171016 | 12/2012 |
| WO | WO 2013/053690 | 4/2013  |
| WO | WO 2013/110768 | 8/2013  |
| WO | WO 2013/192225 | 12/2013 |
| WO | WO 2013/192229 | 12/2013 |
| WO | WO 2014/151409 | 9/2014  |
| WO | WO 2016/042775 | 3/2016  |
| WO | WO 2016/055618 | 4/2016  |
| WO | WO 2016/147659 | 9/2016  |
| WO | WO 2016/170064 A1 | 10/2016 |
| WO | WO 2016/174188 | 11/2016 |
| WO | WO 2017/139186 | 8/2017  |

OTHER PUBLICATIONS

Document from Chemical Library, May 18, 2011, Supplier: ChemDiv., Inc. (Year: 2011).*
Berge, S.M., et al. (1977) "Pharmaceutical Salts," J. Pharma. Sci. 66:1-16.
Bernard, A., et al. (2012) "Transcriptional Architecture of the Primate Neocortex," Neuron 73:1083-1099.
Blokland, A., et al. (2012) "PDE Inhibition and Cognition Enhancement," Expert Opin. Thera. Patients 22(4):349-354.
CAS Registry No. 1296334-75-2 (May 18, 2011).
Chan, S., et al. (2011) "PDE1 Isozymes, Key Regulators of Pathological Vascular Remodeling," Current Opin. Pharmacol. 11:720-724.
Finlander, P., et al. (1983) "Phosphorus Pentoxide in Organic Synthesis V. Phosphorus Pentoxide and Amine Hydrochlorides as Reagents in the Synthesis of 1,5-dihydro-1-methyl-4H-pyrazolo[3,4-d]pyrimidin-4-ones," Chemica Scripta 22(4):171-176 (Chemical Abstracts Only).
Francis, S.H., et al. (2011) "Mammalian Cyclic Nucleotide Phosphodiesterases: Molecular Mechanisms and Physiological Functions," Physiol. Rev. 91:651-690.
International Search Report PCT/EP2015/073417 (WO 2016/055618) (dated 2015) (5 pages).
International Search Report PCT/EP2016/058910 (WO 2016/170064) (dated 2016) (5 pages).
International Search Report PCT/EP2016/059583 (WO 2016/174188) (dated 2016) (4 pages).
International Search Report PCT/EP2017/058332 (dated 2017) (6 pages).
Medina, A.E. (2011) "Therapeutic Utility of Phosphodiesterase Type I Inhibitors in Neurological Conditions," Frontiers Neurosci. 5: Article 21.

(Continued)

*Primary Examiner* — Sudhakar Katakam
(74) *Attorney, Agent, or Firm* — Wolf, Greenfield & Sacks, P.C.

(57) ABSTRACT

The present invention provides imidazopyrazinones as PDE1 inhibitors and their use as a medicament, in particular for the treatment of neurodegenerative disorders and psychiatric disorders.

24 Claims, No Drawings

(56) References Cited

OTHER PUBLICATIONS

Written Opinion of the International Searching Authority PCT/EP2015/073417 (WO 2016/055618) (dated 2015) (6 pages).
Written Opinion of the International Searching Authority PCT/EP2016/058910 (WO 2016/170064) (dated 2016) (5 pages).
Written Opinion of the International Searching Authority PCT/EP2016/059583 (WO 2016/174188) (dated 2016) (6 pages).
Written Opinion of the International Searching Authority PCT/EP2017/058332 (dated 2017) (10 pages).
Anonymous (2003) "FDA Mulls Drug to Slow Late-Stage Alzheimer's," CNN Health (2 pages).
Damasio, A.R. (1996) "Alzheimer's Disease and Related Dementias," Cecil Textbook of Medicine, $20^{th}$ edition 2:1992-1996.

* cited by examiner

IMIDAZOPYRAZINONES AS PDE1 INHIBITORS

CROSS-REFERENCE TO RELATED APPLICATIONS

This application is a continuation of U.S. patent application Ser. No. 15/142,116 (filed on Apr. 29, 2016; pending), which application claims priority to Danish Patent Applications No.: PA 2015 00261 (filed on Apr. 30, 2015), PA 2015 00666 (filed on Oct. 29, 2015 and PA 2016 00202 (filed on Apr. 4, 2016), each of which applications is herein incorporated by reference in its entirety.

FIELD OF THE INVENTION

The present invention provides compounds that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

Throughout this application, various publications are referenced in full. The disclosures of these publications are hereby incorporated by reference into this application to describe more fully the state of the art to which this invention pertains.

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriads of signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain that contains two $Ca^{2+}$/CaM binding domains and two phosphorylation sites differentiate their corresponding proteins and modulate their biochemical functions. PDE1 is a dual substrate PDE and the PDE1C-subtype has equal activity towards cAMP and cGMP (Km≈1-3 µM), whereas the subtypes PDE1A and PDE1B have a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signaling pathways, preferably in the nervous system and PDE1 inhibitors can enhance the levels of the second messengers cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 (February), 21) has suggested the potential for the therapeutic use of PDE1 inhibitors in neurological disorders, like e.g. Alzheimer's, Parkinson's and Huntington's Diseases and in psychiatric disorders like e.g. Attention Deficit Hyperactivity Disorder (ADHD), restless leg syndrome, depression, anxiety, narcolepsy, cognitive impairment and cognitive impairment associated with schizophrenia (CIAS). There have also been patent applications claiming that PDE1 inhibitors are useful in diseases that may be alleviated by the enhancement of progesterone-signaling such as female sexual dysfunction (e.g. WO 2008/070095).

WO 2013/053690 A1 discloses imidazopyrazinones that are inhibitors of the PDE9 enzyme.

The compounds of the invention may offer alternatives to current marketed treatments for neurodegenerative and/or psychiatric disorders, treatments which are not efficacious in all patients. Hence, there remains a need for alternative methods of treatment of such diseases.

SUMMARY OF THE INVENTION

PDE1 enzymes are expressed in the Central Nervous System (CNS), making this gene family an attractive source of new targets for the treatment of psychiatric and neurodegenerative disorders.

The objective of the present invention is to provide compounds that are PDE1 inhibitors, and as such are useful to treat neurodegenerative disorders and psychiatric disorders. Preferably, said compounds are at least a ten-fold stronger as PDE1 inhibitors than as PDE9 inhibitors in order to prevent potentially unwanted effects associated with PDE9 inhibition.

Accordingly, the present invention relates to compounds of formula (I)

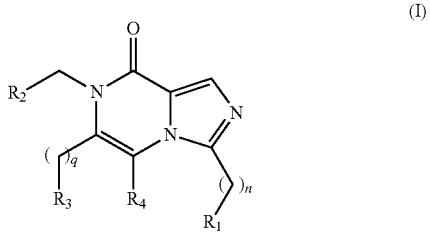

wherein:
- n is 0 or 1;
- q is 0 or 1;
- R1 is selected from the group consisting of benzyl, indanyl, indoline and 5-membered heteroaryls; all of which can be substituted with a substituent selected from the group consisting of halogen and $C_1$-$C_3$ alkyl; or
- R1 is selected from the group consisting of saturated monocyclic rings containing 4-6 carbon atoms and 1-2 nitrogen atoms; all of which can be substituted one or more times with one or more substituents selected from the group consisting of methyl, fluorine and sulfonamide; or
- R1 is selected from the group consisting of lactams containing 4-6 carbon atoms; all of which can be substituted one or more times with one or more substituents selected from the group consisting of methyl and fluorine; or
- R1 is selected from the group consisting of bicyclic ethers such as, 7-oxabicyclo[2.2.1]heptane; all of which can be substituted one or more times with one or more substituents selected from the group consisting of methyl and fluorine; or
- R1 is selected from the group consisting of linear or branched $C_1$-$C_8$ alkyl, saturated monocyclic $C_3$-$C_8$ cycloalkyl, oxetanyl, tetrahydrofuranyl and tetrahydropyranyl; all of which can be substituted one or more times with one or more substituents selected from the group consisting of methyl, fluorine, hydroxy, cyano or methoxy; or
- R1 is a linear or branched $C_1$-$C_3$ alkyl, which is substituted with a substituent selected from phenyl and 5-membered heteroaryl, wherein said 5-membered heteroaryl can be substituted with one or more $C_1$-$C_3$ alkyls; or
- R1 is selected from the group consisting of morpholine, tetrahydrofuran-3-amine, hexahydro-2H-furo[3,2-b]pyrrole and homomorpholine; all of which can be subsituted with one or more substituents selected from the group consisting of $C_1$-$C_3$ alkyl;
- R2 is selected from the group consisting of hydrogen, linear or branched $C_1$-$C_8$ alkyl, phenyl, saturated monocyclic $C_3$-$C_8$ cycloalkyl, oxetanyl, benzo[d][1,3]dioxolyl, tetrahydrofuranyl and tetrahydropyranyl; or
- R2 is phenyl or pyridyl substituted with one or more substituents selected from the group consisting of hydroxyl, amino, cyano, halogen, $C_1$-$C_3$ alkyl, $C_1$-$C_3$ alkoxy, $C_3$-$C_5$ cycloalkoxy, $C_3$-$C_5$ cycloalkyl-methoxy, $C_1$-$C_3$ fluoroalkoxy, and —NC(O)CH$_3$; or
- R2 is a 5-membered heteroaryl which can be substituted one or more times with $C_1$-$C_3$ alkyl;
- R3 is selected from the group consisting of hydrogen, halogen, $C_1$-$C_5$ alkyl, $C_3$-$C_5$ cycloalkyl and phenyl; or
- R3 is selected from the group consisting of phenyl substituted one or more times with $C_1$-$C_3$ alkyl; methyl substituted one, two or three times with fluorine; ethyl substituted one, two or three times with fluorine;
- R4 is hydrogen;

and tautomers and pharmaceutically acceptable addition salts thereof;
with the proviso that R2 and R3 cannot be hydrogen at the same time;
with the proviso, that the compound of formula (I) is not one of the three following compounds:
3-methyl-7-(4-(trifluoromethoxy)benzyl)imidazo[1,5-a]pyrazin-8(7H)-one;
7-butyl-3-methylimidazo[1,5-a]pyrazin-8(7H)-one; and
7-(4-methoxybenzyl)-3-methylimidazo[1,5-a]pyrazin-8(7H)-one.

Reference to Compound I includes the free base of Compound I, pharmaceutically acceptable salts of Compound I, such as acid addition salts of Compound I, racemic mixtures of Compound I, or the corresponding enantiomer and/or optical isomer of Compound I, and polymorphic and amorphic forms of Compound I as well as tautomeric forms of Compound I. Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

In one embodiment, the invention relates to a compound according to formula (I) for use in therapy.

In one embodiment, the invention relates to a compound according to formula (I), for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a pharmaceutical composition comprising a compound according formula (I), and one or more pharmaceutically acceptable carrier or excipient.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) to a patient in need thereof.

DETAILED DESCRIPTION OF THE INVENTION

Embodiments of the Invention

The following notation is applied: an embodiment of the invention is identified as Ei, where i is an integer indicating the number of the embodiment. An embodiment Ei' specifying a specific embodiment a previously listed embodiment Ei is identified as Ei'(Ei), e.g. E2 (E1) means "in an embodiment E2 of embodiment E1".

Where an embodiment is a combination of two embodiments the notation is similarly Ei"(Ei and Ei'), e.g. E3 (E2 and E1) means "in an embodiment E3 of any of embodiments E2 and E1"

Where an embodiment is a combination of more than two embodiments the notation is similarly Ei'"(Ei, Ei' and Ei"), e.g. E4 (E1, E2 and E3) means "in an embodiment E4 of any of embodiments E1, E2 and E3"

In a first embodiment E1, the present invention relates to compounds of formula (I)

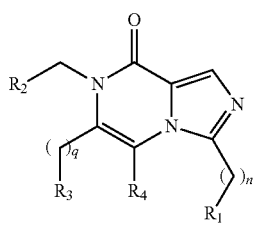

(I)

wherein
n is 0 or 1;
q is 0 or 1;
R1 is selected from the group consisting of benzyl, indanyl, indoline and 5-membered heteroaryls; all of which can be substituted with a substituent selected from the group consisting of halogen and $C_1$-$C_3$ alkyl; or
R1 is selected from the group consisting of saturated monocyclic rings containing 4-6 carbon atoms and 1-2 nitrogen atoms; all of which can be substituted one or more times with one or more substituents selected from the group consisting of methyl, fluorine and sulfonamide; or
R1 is selected from the group consisting of lactams containing 4-6 carbon atoms; all of which can be substituted one or more times with one or more substituents selected from the group consisting of methyl and fluorine; or
R1 is selected from the group consisting of bicyclic ethers such as, 7-oxabicyclo[2.2.1]heptane; all of which can be substituted one or more times with one or more substituents selected from the group consisting of methyl and fluorine; or
R1 is selected from the group consisting of linear or branched $C_1$-$C_8$ alkyl, saturated monocyclic $C_3$-$C_8$ cycloalkyl, oxetanyl, tetrahydrofuranyl and tetrahydropyranyl; all of which can be substituted one or more times with one or more substituents selected from the group consisting of methyl, fluorine, hydroxy, cyano or methoxy; or
R1 is a linear or branched $C_1$-$C_3$ alkyl, which is substituted with a substituent selected from phenyl and 5-membered heteroaryl, wherein said 5-membered heteroaryl can be substituted with one or more $C_1$-$C_3$ alkyls; or
R1 is selected from the group consisting of morpholine, tetrahydrofuran-3-amine, hexahydro-2H-furo[3,2-b]pyrrole and homomorpholine; all of which can be subsituted with one or more substituents selected from the group consisting of $C_1$-$C_3$ alkyl;
R2 is selected from the group consisting of hydrogen, linear or branched $C_1$-$C_8$ alkyl, phenyl, saturated monocyclic $C_3$-$C_8$ cycloalkyl, oxetanyl, benzo[d][1,3]dioxolyl, tetrahydrofuranyl and tetrahydropyranyl; or
R2 is phenyl or pyridyl substituted with one or more substituents selected from the group consisting of hydroxyl, amino, cyano, halogen, $C_1$-$C_3$ alkyl, $C_1$-$C_3$ alkoxy, $C_3$-$C_5$ cycloalkoxy, $C_3$-$C_5$ cycloalkyl-methoxy, $C_1$-$C_3$ fluoroalkoxy, and —NC(O)CH$_3$; or
R2 is a 5-membered heteroaryl which can be substituted with one or more $C_1$-$C_3$ alkyl;
R3 is selected from the group consisting of hydrogen, halogen, $C_1$-$C_5$ alkyl, $C_3$-$C_5$ cycloalkyl and phenyl; or
R3 is selected from the group consisting of phenyl substituted one or more times with $C_1$-$C_3$ alkyl; methyl substituted one, two or three times with fluorine; ethyl substituted one, two or three times with fluorine;
R4 is hydrogen;
and tautomers and pharmaceutically acceptable addition salts thereof;
with the proviso that R2 and R3 cannot be hydrogen at the same time;
with the proviso, that the compound of formula (I) is not one of the three following compounds:
3-methyl-7-(4-(trifluoromethoxy)benzyl)imidazo[1,5-a]pyrazin-8(7H)-one;
7-butyl-3-methylimidazo[1,5-a]pyrazin-8(7H)-one; and
7-(4-methoxybenzyl)-3-methylimidazo[1,5-a]pyrazin-8(7H)-one.

Additional embodiments include:
E2 (E1) n is 0 or 1;
q is 0 or 1;
R1 is selected from the group consisting of linear or branched $C_1$-$C_8$ alkyl, saturated monocyclic $C_3$-$C_8$ cycloalkyl, oxetanyl, tetrahydrofuranyl, and tetrahydropyranyl;
R2 is selected from the group consisting of, linear or branched $C_1$-$C_8$ alkyl, phenyl, and saturated monocyclic $C_3$-$C_8$ cycloalkyl; or
R2 is selected from the group consisting of phenyl substituted with one or more times with one or more substituents selected from the group consisting of halogen, $C_1$-$C_3$ alkyl and methoxy;
R$_3$ is selected from the group consisting of hydrogen, $C_1$-$C_3$ alkyl, halogen and benzyl;
R$_4$ is hydrogen.
E3 (E1 or E2) R1 is tetrahydropyranyl.
E4 (E1 or E2) R1 is $C_1$-$C_3$ alkyl or $C_3$-$C_5$ cycloalkyl.
E5 (E4) R1 is propyl or cyclopropyl
E6 (E1 to E5) R2 is phenyl.
E7 (E1 to E5) R2 is substituted phenyl, wherein the one or more substituents are selected from the group consisting of fluorine, chlorine, methyl and methoxy.
E8 (E1 to E5) R2 is saturated monocyclic $C_3$-$C_8$ cycloalkyl.
E9 (E1 and E8) R2 is saturated monocyclic $C_5$-$C_7$ cycloalkyl.
E10 (E1 to E5) R2 is $C_1$-$C_3$ alkyl.
E11 (E1 and E10) R2 is methyl, ethyl or isopropyl
E12 (E1 to E11) R3 is bromine E13 (E1 to E11) R3 is methyl
E14 (E1 to E11) R3 is selected from hydrogen and methyl; and
  R2 is selected from the group consisting of linear or branched $C_1$-$C_8$ alkyl, phenyl, saturated monocyclic $C_3$-$C_8$ cycloalkyl, oxetanyl, tetrahydrofuranyl and tetrahydropyranyl; or
  R2 is phenyl or pyridyl substituted with one or more substituents selected from the group consisting of hydroxyl, amino, cyano, halogen, $C_1$-$C_3$ alkyl, $C_1$-$C_3$ alkoxy, $C_1$-$C_3$ fluoroalkoxy, and —NC(O)CH$_3$; or
  R2 is a 5-membered heteroaryl which can be substituted with $C_1$-$C_3$ alkyl.
E15 (E1 to E14) n is 0.
E16 (E1 to E14) n is 1.
E17 (E1 to E15) q is 0.
E18 (E1 to E15) q is 1.
E19 (E1), the compound of formula (I) is selected among the compounds listed in Table 1, in the form of the free base, one or more tautomers thereof or a pharmaceutically acceptable salt thereof.
E20 (E1 to E19) the compound has a PDE1A, PDE1B or PDE1C IC$_{50}$ value, determined as described in the section "PDE1 inhibition assay", of 10 micro molar or less, such as 5 micro molar or less, such as 4 micro molar or less, such as 3 micro molar or less, such as 2 micro molar or less, such as 1 micro molar or less, such as 500 nM or less, such as 400 nM or less, such as 300 nM or less, such as 200 nM or less, such as 100 nM or less.
E21 (E1) the compound is selected from the compounds listed in Table 1 and pharmaceutically acceptable salts thereof.
E22 (E1 to E21) the compound is at least 10 times stronger PDE1 inhibitors than PDE9 inhibitors, such as at least 50 times stronger PDE1 inhibitors than PDE9 inhibitors or even at least 100 times stronger PDE1 inhibitors than PDE9 inhibitors.
E23 (E1 to E22) the compound is for use as a medicament.
E24 (E1 to E22) the compound is for use in the treatment of AttentionDeficit Hyperactivity Disorder (ADHD).
E25 (E1 to E22) a pharmaceutical composition comprising a therapeutically effective amount of a compound of any of embodiments (E1) to (E22), and one or more pharmaceutically acceptable carriers, diluents and excipients.
E26 (E25) the pharmaceutical composition is for the treatment of neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS) or another brain disease like restless leg syndrome.
E27 (E1 to E22) a compound of any of embodiments (E1) to (E22) for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS) or another brain disease like restless leg syndrome.
E28 (E1 to E22) a method of treating a subject suffering from neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS) or another brain disease like restless leg syndrome, which method comprises administering to said subject an amount of a compound of formula I effective in inhibiting PDE1.
E29 (E1 to E22) Use of a compound of any of embodiments (E1) to (E21) in the manufacture of a medicament for use in the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS) or another brain disease like restless leg syndrome.

Definitions

Pde1 Enzymes

The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.

Substituents

As used in the context of the present invention, the terms "halo" and "halogen" are used interchangeably and refer to fluorine, chlorine, bromine or iodine.

A given range may interchangeably be indicated with "-" (dash) or "to", e.g. the term "$C_1$-$C_3$ alkyl" is equivalent to "$C_1$ to $C_3$ alkyl".

The terms "$C_1$-$C_3$ alkyl", "$C_1$-$C_4$ alkyl", "$C_1$-$C_5$ alkyl", "$C_1$-$C_6$ alkyl", "$C_1$-$C_7$ alkyl" and "$C_1$-$C_8$ alkyl" refer to a linear (i.e. unbranched) or branched saturated hydrocarbon having from one up to eight carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl, n-hexyl, n-heptyl and n-octyl.

The term saturated monocyclic $C_3$-$C_8$ cycloalkyl refers to cyclopropyl, cyclobutyl, cyclopentyl, cyclohexyl, cycloheptyl and cyclooctyl. The term $C_3$-$C_5$ cycloalkyl refers to cyclopropyl, cyclobutyl and cyclopentyl.

The term "$C_1$-$C_3$ alkoxy" refers to a moiety of the formula —OR', wherein R' indicates $C_1$-$C_3$ alkyl as defined above. The term "$C_3$-$C_5$ cycloalkoxy" refers to a moiety of the formula —OR', wherein R' indicates $C_3$-$C_5$ cycloalkyl as defined above. The term "$C_3$-$C_5$ cycloalkyl-methoxy" refers to a moiety of the formula —OCH$_2$R', wherein R' indicates $C_3$-$C_5$ cycloalkyl as defined above. $C_1$-$C_3$ fluoroalkoxy refers to a $C_1$-$C_3$ alkoxy substituted with one or more fluorine.

5-membered heteroaryls are defined as 5 membered aromatic rings containing at least one atom selected frin nitrogen, sulfur and oxygen. Examples include, but are not limited to thiazole, thiophene and isoxazole.

The term "lactams containing 4-6 carbon atoms" refers to pyrrolidin-2-one, piperidin-2-one or azepan-2-one.

Isomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

The above also applies where compounds of the invention contain more than two chiral centers.

PDE1 Inhibitors and PDE9 Inhibitors

In the context of the present invention a compound is considered to be a PDE1 inhibitor if the amount required to reach the $IC_{50}$ level of one or more of the three PDE1 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less. In preferred embodiments the required amount of PDE1 inhibitor required to reach the $IC_{50}$ level of PDE1B is 400 nM or less, such as 300 nM or less, 200 nM or less, 100 nM or less, or even 80 nM or less, such as 50 nM or less, for example 25 nM or less.

In a preferred embodiment the compounds of the present invention are at least a ten-fold stronger as PDE1 inhibitors as PDE9 inhibitors, i.e. the amount of the compound required to reach the $IC_{50}$ level of one or more of the three PDE1 isoforms is at least a ten-fold less than the amount of the same compound required to reach the $IC_{50}$ level of the PDE9 enzyme.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Therapeutically Effective Amount

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

Pharmaceutical Compositions

The present invention further provides a pharmaceutical composition comprising a therapeutically effective amount of a compound of formula (I) and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21$^{st}$ Edition, Gennaro, Ed., Mack Publishing Co., Easton, Pa., 2005.

The pharmaceutical compositions may be specifically formulated for administration by any suitable route such as oral, rectal, nasal, pulmonary, topical (including buccal and sublingual), transdermal and parenteral (including subcutaneous, intramuscular and intravenous) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day.

Typical oral dosages further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

The present invention also provides a process for making a pharmaceutical composition comprising mixing a therapeutically effective amount of a compound of formula (I) and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. One example is an acid addition salt of a compound which has the same utility as of a free base. When a compound of formula (I) contains a free base such salts are prepared in a conventional manner by treating a solution or suspension of a free base of formula (I) with a pharmaceutically acceptable acid. Representative examples of suitable organic and inorganic acids are described above.

For parenteral administration, solutions of the compounds of formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of formula (I) may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of formula (I) and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tableting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compounds of formula (I) are PDE1 enzyme inhibitors and as such are useful to treat associated neurological and psychiatric disorders.

The invention thus provides a compound of formula (I) or a pharmaceutically acceptable acid addition salt thereof, as well as a pharmaceutical composition containing such a compound, for use in the treatment of another brain disease which could be a neurodegenerative disorder or a psychiatric disorder. In a preferred embodiment the neurodegenerative disorder is selected from the group consisting of Alzheimer's Disease, Parkinson's Disease and Huntington's Disease. In another preferred embodiment the psychiatric disorder is selected from the group consisting of Attention Deficit Hyperactivity Disorder (ADHD), depression, anxiety, narcolepsy, cognitive impairment and cognitive impairment associated with schizophrenia (CIAS). Other brain diseases could be e.g. restless leg syndrome.

The present invention provides a method of treating a mammal, including a human, suffering from a neurodegenerative disorder selected from the group consisting of Alzheimer's Disease, Parkinson's Disease and Huntington's Disease, which method comprises administering to the subject a therapeutically effective amount of a compound of formula (I).

This invention further provides a method of treating a neurodegenerative disorder in a mammal, including a human, which method comprises administering to said mammal an amount of a compound of formula (I) effective in inhibiting PDE1.

This invention also provides a method of treating a subject suffering from a psychiatric disorder, which method comprises administering to the subject a therapeutically effective amount of a compound of formula (I). Examples of psychiatric disorders that can be treated according to the present invention include Attention Deficit Hyperactivity Disorder (ADHD), depression, anxiety, narcolepsy, cognitive impairment and cognitive impairment associated with schizophrenia (CIAS).

This invention also provides a method of treating a subject suffering from another brain disorder such as restless leg syndrome.

Further, the invention is directed to the use of a compound of formula (I) in the manufacture of a medicament for the treatment of a neurodegenerative disorder, such as Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS).

Further, the invention is directed to the use of a compound of formula (I) in the manufacture of a medicament for the treatment of another brain disease, such as restless leg syndrome The invention is also directed to a compound of formula (I) for use as a medicine. In a specific embodiment the compound of formula (I) for use in the treatment of a neurodegenerative disorder, such as Alzheimer's Disease, Parkinson's Disease and Huntington's Disease or for the treatment of a psychiatric disorder such as Attention Deficit Hyperactivity Disorder (ADHD), depression, anxiety, narcolepsy cognitive impairment and cognitive impairment associated with schizophrenia (CIAS) or for the treatment of another brain disease like restless leg syndrome.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

Compounds of the invention

| Example | Name | PDE1A, $IC_{50}$ (nM) | PDE1B, $IC_{50}$ (nM) | PDE1C, $IC_{50}$ (nM) | % inhibition of PDE9 at 10 microM |
|---|---|---|---|---|---|
| 1 | 7-(3-Fluorobenzyl)-3-propylimidazo[1,5-a]pyrazin-8(7H)-one | 801 | 790 | 300 | −12 |
| 2 | 6-Benzyl-7-(3-fluorobenzyl)-3-(tetrahydro-2H-pyran-4-yl)imidazo[1,5-a]pyrazin-8(7H)-one | 51 | 14 | 11 | −14 |
| 3 | 6-Benzyl-7-(cyclohexylmethyl)-3-(tetrahydro-2H-pyran-4-yl)imidazo[1,5-a]pyrazin-8(7H)-one | 8 | 12 | 6 | −6 |
| 4 | 7-(Cyclohexylmethyl)-6-methyl-3-(tetrahydro-2H-pyran-4-yl)imidazo[1,5-a]pyrazin-8(7H)-one | 11 | 25 | 7 | −5 |
| 5 | 7-(3-Fluorobenzyl)-6-methyl-3-(tetrahydro-2H-pyran-4-yl)imidazo[1,5-a]pyrazin-8(7H)-one | 108 | 120 | 14 | 18 |
| 6 | 3-Cyclopropyl-7-(3-fluorobenzyl)imidazo[1,5-a]pyrazin-8(7H)-one | 68% (at 2 μM) | 81% (at 2 μM) | 290 | 25 |
| 7 | 7-(Cyclopentylmethyl)-3-cyclopropylimidazo[1,5-a]pyrazin-8(7H)-one | 60% (at 2 μM) | 85% (at 2 μM) | 230 | 1 |
| 8 | 7-(Cyclohexylmethyl)-3-cyclopropylimidazo[1,5-a]pyrazin-8(7H)-one | 252 | 67 | 100 | 9 |
| 9 | 7-(3-Fluorobenzyl)-3-(tetrahydro-2H-pyran-4-yl)imidazo[1,5-a]pyrazin-8(7H)-one | 68% (at 2 μM) | 90% (at 2 μM) | 170 | 2 |
| 10 | 7-(Cyclopentylmethyl)-3-(tetrahydro-2H-pyran-4-yl)imidazo[1,5-a]pyrazin-8(7H)-one | 73% (at 2 μM) | 88% (at 2 μM) | 79 | 8 |
| 11 | 7-(Cyclohexylmethyl)-3-(tetrahydro-2H-pyran-4-yl)imidazo[1,5-a]pyrazin-8(7H)-one | 113 | 72 | 43 | 18 |
| 12 | 7-(Cycloheptylmethyl)-3-(tetrahydro-2H-pyran-4-yl)imidazo[1,5-a]pyrazin-8(7H)-one | 30 | 21 | 16 | 12 |
| 13 | 7-(Cycloheptylmethyl)-3-cyclopropylimidazo[1,5-a]pyrazin-8(7H)-one | 87 | 50 | 62 | 7 |

TABLE 1-continued

Compounds of the invention

| Example | Name | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 14 | 7-(4-Chlorobenzyl)-6-methyl-3-(tetrahydro-2H-pyran-4-yl)imidazo[1,5-a]pyrazin-8(7H)-one | 18 | 15 | 51 | 22 |
| 15 | 6-Bromo-7-(3-fluorobenzyl)-3-(tetrahydro-2H-pyran-4-yl)imidazo[1,5-a]pyrazin-8(7H)-one | 58 | 115 | 15 | 15 |
| 16 | 7-Benzyl-6-methyl-3-(tetrahydro-2H-pyran-4-yl)imidazo[1,5-a]pyrazin-8(7H)-one | 85 | 57 | 12 | 19 |
| 17 | 7-(2-Fluorobenzyl)-6-methyl-3-(tetrahydro-2H-pyran-4-yl)imidazo[1,5-a]pyrazin-8(7H)-one | 42 | 36 | 9 | 7 |
| 18 | 7-(3-Chlorobenzyl)-6-methyl-3-(tetrahydro-2H-pyran-4-yl)imidazo[1,5-a]pyrazin-8(7H)-one | 57 | 49 | 8 | 31 |
| 19 | 7-(2-Chlorobenzyl)-6-methyl-3-(tetrahydro-2H-pyran-4-yl)imidazo[1,5-a]pyrazin-8(7H)-one | 46 | 68 | 10 | 18 |
| 20 | 7-(3-Methoxybenzyl)-6-methyl-3-(tetrahydro-2H-pyran-4-yl)imidazo[1,5-a]pyrazin-8(7H)-one | 416 | 175 | 62 | −38 |
| 21 | 6-Methyl-7-(2-methylbenzyl)-3-(tetrahydro-2H-pyran-4-yl)imidazo[1,5-a]pyrazin-8(7H)-one | 242 | 195 | 30 | −14 |
| 22 | 6-Methyl-7-(4-methylbenzyl)-3-(tetrahydro-2H-pyran-4-yl)imidazo[1,5-a]pyrazin-8(7H)-one | 75 | 28 | 67 | 50 |
| 23 | 7-(4-Methoxybenzyl)-6-methyl-3-(tetrahydro-2H-pyran-4-yl)imidazo[1,5-a]pyrazin-8(7H)-one | 14 | 12 | 19 | 16 |
| 24 | 7-(4-Fluorobenzyl)-6-methyl-3-(tetrahydro-2H-pyran-4-yl)imidazo[1,5-a]pyrazin-8(7H)-one | 38 | 43 | 17 | −1 |
| 25 | 6-Methyl-7-(3-methylbenzyl)-3-(tetrahydro-2H-pyran-4-yl)imidazo[1,5-a]pyrazin-8(7H)-one | 63 | 57 | 9 | −42 |
| 26 | 7-(3-fluorobenzyl)-6-methyl-3-(4-methyltetrahydro-2H-pyran-4-yl)imidazo[1,5-a]pyrazin-8(7H)-one | 234 | 218 | 47 | −2 |
| 27 | 4-(7-(3-fluorobenzyl)-6-methyl-8-oxo-7,8-dihydroimidazo[1,5-a]pyrazin-3-yl)tetrahydro-2H-pyran-4-carbonitrile | 603 | 699 | 103 | 5 |
| 28 | 7-(3-fluorobenzyl)-3-(4-methoxytetrahydro-2H-pyran-4-yl)-6-methylimidazo[1,5-a]pyrazin-8(7H)-one | 663 | 737 | 72 | 13 |
| 29 | 7-(3-fluorobenzyl)-3-(4-fluorotetrahydro-2H-pyran-4-yl)-6-methylimidazo[1,5-a]pyrazin-8(7H)-one | 493 | 249 | 50 | 16 |
| 30, isomer 1 | 7-(3-fluorobenzyl)-6-methyl-3-(tetrahydro-2H-pyran-2-yl)imidazo[1,5-a]pyrazin-8(7H)-one, stereoisomer 1 | 20% (at 1 μM) | 615 | 225 | −11 |
| 30, isomer 2 | 7-(3-fluorobenzyl)-6-methyl-3-(tetrahydro-2H-pyran-2-yl)imidazo[1,5-a]pyrazin-8(7H)-one, stereoisomer 2 | 27% (at 1 μM) | 40% (at 1 μM) | 215 | 28 |

TABLE 1-continued

Compounds of the invention

| Example | Name | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 31, isomer 1 | 7-(3-fluorobenzyl)-6-methyl-3-(tetrahydrofuran-3-yl)imidazo[1,5-a]pyrazin-8(7H)-one, stereoisomer 1 | 337 | 106 | 27 | −1 |
| 31, isomer 2 | 7-(3-fluorobenzyl)-6-methyl-3-(tetrahydrofuran-3-yl)imidazo[1,5-a]pyrazin-8(7H)-one, stereoisomer 2 | 347 | 138 | 31 | 5 |
| 32, isomer 1 | 7-(3-fluorobenzyl)-6-methyl-3-(3-methyltetrahydrofuran-3-yl)imidazo[1,5-a]pyrazin-8(7H)-one, stereoisomer 1 | 257 | 122 | 22 | −1 |
| 32, isomer 2 | 7-(3-fluorobenzyl)-6-methyl-3-(3-methyltetrahydrofuran-3-yl)imidazo[1,5-a]pyrazin-8(7H)-one, stereoisomer 2 | 401 | 170 | 40 | 16 |
| 33 | 7-(3-fluorobenzyl)-6-methyl-3-(1-methylcyclopropyl)imidazo[1,5-a]pyrazin-8(7H)-one | 94 | 52 | 7 | −2 |
| 34 | 3-(2,2-difluorocyclopropyl)-7-(3-fluorobenzyl)-6-methylimidazo[1,5-a]pyrazin-8(7H)-one | 331 | 359 | 93 | 0 |
| 35, isomer 1 | 7-(3-fluorobenzyl)-6-methyl-3-(2-methylcyclopropyl)imidazo[1,5-a]pyrazin-8(7H)-one, stereoisomer 1 | 193 | 75 | 19 | −11 |
| 35, isomer 2 | 7-(3-fluorobenzyl)-6-methyl-3-(2-methylcyclopropyl)imidazo[1,5-a]pyrazin-8(7H)-one, stereoisomer 2 | 364 | 166 | 41 | 15 |
| 35, isomer 3 | 7-(3-fluorobenzyl)-6-methyl-3-(2-methylcyclopropyl)imidazo[1,5-a]pyrazin-8(7H)-one, stereoisomer 3 | 82 | 18 | 8 | 0 |
| 35, isomer 4 | 7-(3-fluorobenzyl)-6-methyl-3-(2-methylcyclopropyl)imidazo[1,5-a]pyrazin-8(7H)-one, stereoisomer 4 | 43% (at 1 μM) | 360 | 85 | 5 |
| 36, isomer 1 | 7-(3-fluorobenzyl)-6-methyl-3-(2-methyltetrahydrofuran-3-yl)imidazo[1,5-a]pyrazin-8(7H)-one, stereoisomer 1 | 152 | 59 | 15 | 3 |
| 36, isomer 2 | 7-(3-fluorobenzyl)-6-methyl-3-(2-methyltetrahydrofuran-3-yl)imidazo[1,5-a]pyrazin-8(7H)-one, stereoisomer 2 | 282 | 107 | 38 | 11 |
| 36, isomer 3 | 7-(3-fluorobenzyl)-6-methyl-3-(2-methyltetrahydrofuran-3-yl)imidazo[1,5-a]pyrazin-8(7H)-one, stereoisomer 3 | 77 | 21 | 7 | −10 |
| 36, isomer 4 | 7-(3-fluorobenzyl)-6-methyl-3-(2-methyltetrahydrofuran-3-yl)imidazo[1,5-a]pyrazin-8(7H)-one, stereoisomer 4 | 51 | 520 | 40% (at 1 μM) | 11 |
| 37, isomer 1 | 7-(3-fluorobenzyl)-3-(cis-2-fluorocyclopropyl)-6-methylimidazo[1,5-a]pyrazin-8(7H)-one, stereoisomer 1 | 1140 | 1180 | 345 | −2 |
| 37, isomer 2 | 7-(3-fluorobenzyl)-3-(cis-2-fluorocyclopropyl)-6-methylimidazo[1,5-a]pyrazin-8(7H)-one, stereoisomer 2 | 149 | 164 | 55 | 13 |
| 38, isomer 1 | 7-(3-fluorobenzyl)-3-(trans-2-fluorocyclopropyl)-6-methylimidazo[1,5-a]pyrazin-8(7H)-one, stereoisomer 1 | 582 | 601 | 118 | −1 |
| 38, isomer 2 | 7-(3-fluorobenzyl)-3-(trans-2-fluorocyclopropyl)-6-methylimidazo[1,5-a]pyrazin-8(7H)-one, stereoisomer 2 | 667 | 667 | 153 | 2 |

TABLE 1-continued

Compounds of the invention

| Example | Name | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 39 | 7-(4-cyclopropoxybenzyl)-6-methyl-3-(tetrahydro-2H-pyran-4-yl)imidazo[1,5-a]pyrazin-8(7H)-one | 413 | 118 | 364 | 23 |
| 40 | 7-(4-(difluoromethoxy)benzyl)-6-methyl-3-(tetrahydro-2H-pyran-4-yl)imidazo[1,5-a]pyrazin-8(7H)-one | 73 | 27 | 52 | −25 |
| 41 | 6-methyl-3-(tetrahydro-2H-pyran-4-yl)-7-(4-(trifluoromethoxy)benzyl)imidazo[1,5-a]pyrazin-8(7H)-one | 27 | 18 | 52 | −22 |
| 42 | 7-(4-(cyclopropylmethoxy)benzyl)-6-methyl-3-(tetrahydro-2H-pyran-4-yl)imidazo[1,5-a]pyrazin-8(7H)-one | 50% (at 1 μM) | 155 | 55% (at 1 μM) | 15 |
| 43 | 7-benzyl-6-ethyl-3-(tetrahydro-2H-pyran-4-yl)imidazo[1,5-a]pyrazin-8(7H)-one | 105 | 32 | 9 | 6 |
| 44 | 6-ethyl-7-(4-methoxybenzyl)-3-(tetrahydro-2H-pyran-4-yl)imidazo[1,5-a]pyrazin-8(7H)-one | 40 | 5 | 16 | 18 |
| 45 | 3-((6-methyl-8-oxo-3-(tetrahydro-2H-pyran-4-yl)imidazo[1,5-a]pyrazin-7(8H)-yl)methyl)benzonitrile | 64 (at 2 μM) | 54% (at 1 μM) | 149 | 6 |
| 46 | 4-((6-methyl-8-oxo-3-(tetrahydro-2H-pyran-4-yl)imidazo[1,5-a]pyrazin-7(8H)-yl)methyl)benzonitrile | 809 | 58% (at 1 μM) | 9% (at 1 μM) | 14 |
| 47 | N-(4-((6-methyl-8-oxo-3-(tetrahydro-2H-pyran-4-yl)imidazo[1,5-a]pyrazin-7(8H)-yl)methyl)phenyl)acetamide | 0% (at 1 μM) | 388 | 10% (at 1 μM) | 10 |
| 48 | 7-(4-chloro-3-methoxybenzyl)-6-methyl-3-(tetrahydro-2H-pyran-4-yl)imidazo[1,5-a]pyrazin-8(7H)-one | — | 54% (at 1 μM) | 34% (at 1 μM) | 10 |
| 49 | 7-(2-ethylbenzyl)-6-methyl-3-(tetrahydro-2H-pyran-4-yl)imidazo[1,5-a]pyrazin-8(7H)-one | 44 (at 2 μM) | 60% (at 1 μM) | 173 | 1 |
| 50 | 7-(benzo[d][1,3]dioxol-5-ylmethyl)-6-methyl-3-(tetrahydro-2H-pyran-4-yl)imidazo[1,5-a]pyrazin-8(7H)-one | 50 | 16 | 38 | 12 |
| 51 | 7-(3-chloro-4-methoxybenzyl)-6-methyl-3-(tetrahydro-2H-pyran-4-yl)imidazo[1,5-a]pyrazin-8(7H)-one | 199 | 36 | 46 | 1 |
| 52 | 7-(4-aminobenzyl)-6-methyl-3-(tetrahydro-2H-pyran-4-yl)imidazo[1,5-a]pyrazin-8(7H)-one | 0% (at 1 μM) | 388 | 10% (at 1 μM) | −3 |
| 53 | 7-(4-hydroxybenzyl)-6-methyl-3-(tetrahydro-2H-pyran-4-yl)imidazo[1,5-a]pyrazin-8(7H)-one | 401 | 35 | 84 | −41 |
| 54 | 6-ethyl-7-(3-fluorobenzyl)-3-(tetrahydro-2H-pyran-4-yl)imidazo[1,5-a]pyrazin-8(7H)-one | 62 | 53 | 12 | 23 |
| 55, isomer 1 | 7-(4-methoxybenzyl)-6-methyl-3-(2-methyltetrahydrofuran-3-yl)imidazo[1,5-a]pyrazin-8(7H)-one, stereoisomer 1 | 20 | 10 | 17 | 18 |
| 55, isomer 2 | 7-(4-methoxybenzyl)-6-methyl-3-(2-methyltetrahydrofuran-3-yl)imidazo[1,5-a]pyrazin-8(7H)-one, stereoisomer 2 | 86 | 64 | 51 | −13 |

TABLE 1-continued

Compounds of the invention

| Example | Name | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 55, isomer 3 | 7-(4-methoxybenzyl)-6-methyl-3-(2-methyltetrahydrofuran-3-yl)imidazo[1,5-a]pyrazin-8(7H)-one, stereoisomer 3 | 13 | 3 | 8 | 27 |
| 55, isomer 4 | 7-(4-methoxybenzyl)-6-methyl-3-(2-methyltetrahydrofuran-3-yl)imidazo[1,5-a]pyrazin-8(7H)-one, stereoisomer 4 | 137 | 208 | 131 | 1 |
| 56 | 7-(4-methoxybenzyl)-6-methyl-3-propylimidazo[1,5-a]pyrazin-8(7H)-one | 65 | 21 | 43 | 7 |
| 57 | 7-((6-methoxypyridin-3-yl)methyl)-6-methyl-3-(tetrahydro-2H-pyran-4-yl)imidazo[1,5-a]pyrazin-8(7H)-one | 45 | 26 | 84 | −5 |
| 58 | 6,7-dimethyl-3-(tetrahydro-2H-pyran-4-yl)imidazo[1,5-a]pyrazin-8(7H)-one | 58% (at 10 μM) | 1767 | 44% (at 10 μM) | 36 |
| 59 | 7-ethyl-6-methyl-3-(tetrahydro-2H-pyran-4-yl)imidazo[1,5-a]pyrazin-8(7H)-one | 2333 | 496 | 1737 | −13 |
| 60 | 6-methyl-7-propyl-3-(tetrahydro-2H-pyran-4-yl)imidazo[1,5-a]pyrazin-8(7H)-one | 810 | 221 | 423 | −13 |
| 61 | 7-isopropyl-6-methyl-3-(tetrahydro-2H-pyran-4-yl)imidazo[1,5-a]pyrazin-8(7H)-one | 4% (at 10 μM) | 50% (at 10 μM) | 47% (at 10 μM) | 4 |
| 62 | 7-isopentyl-6-methyl-3-(tetrahydro-2H-pyran-4-yl)imidazo[1,5-a]pyrazin-8(7H)-one | 1078 | 558 | 93 | 7 |
| 63 | 7-(cyclopentylmethyl)-6-methyl-3-(tetrahydro-2H-pyran-4-yl)imidazo[1,5-a]pyrazin-8(7H)-one | 183 | 82 | 17 | −3 |
| 64 | 2-((6-methyl-8-oxo-3-(tetrahydro-2H-pyran-4-yl)imidazo[1,5-a]pyrazin-7(8H)-yl)methyl)benzonitrile | 624 | 528 | 103 | 11 |
| 65 | 7-(cycloheptylmethyl)-6-methyl-3-(tetrahydro-2H-pyran-4-yl)imidazo[1,5-a]pyrazin-8(7H)-one | 10 | 6 | 5 | 11 |
| 66, trans | 6-methyl-7-(((trans)-4-methylcyclohexyl)methyl)-3-(tetrahydro-2H-pyran-4-yl)imidazo[1,5-a]pyrazin-8(7H)-one | 35 | 11 | 46 | −2 |
| 66, cis | 6-methyl-7-(((cis)-4-methylcyclohexyl)methyl)-3-(tetrahydro-2H-pyran-4-yl)imidazo[1,5-a]pyrazin-8(7H)-one | 7 | 6 | 4 | −3 |
| 67 | 7-(((cis)-4-methoxycyclohexyl)methyl)-6-methyl-3-(tetrahydro-2H-pyran-4-yl)imidazo[1,5-a]pyrazin-8(7H)-one | 234 | 87 | 307 | 10 |
| 68 | 7-(((trans)-4-methoxycyclohexyl)methyl)-6-methyl-3-(tetrahydro-2H-pyran-4-yl)imidazo[1,5-a]pyrazin-8(7H)-one | 323 | 127 | 1859 | 5 |
| 69 | 7-(4-methoxybenzyl)-6-methyl-3-(3-methyltetrahydro-2H-pyran-4-yl)imidazo[1,5-a]pyrazin-8(7H)-one | 13 | 8 | 24 | 2 |
| 70 | 7-(4-methoxybenzyl)-6-methyl-3-((1R,2R,4S)-2-methyl-7-oxabicyclo[2.2.1]heptan-2-yl)imidazo[1,5-a]pyrazin-8(7H)-one | 29 | 17 | 28 | −11 |

TABLE 1-continued

Compounds of the invention

| Example | Name | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 71 | (S)-7-(4-methoxybenzyl)-6-methyl-3-(1-phenylethyl)imidazo[1,5-a]pyrazin-8(7H)-one | 211 | 238 | 538 | 13 |
| 72 | (R)-7-(4-methoxybenzyl)-6-methyl-3-(1-phenylethyl)imidazo[1,5-a]pyrazin-8(7H)-one | 90 | 12 | 43 | 9 |
| 73 | 3-(1,4-dimethylpiperidin-4-yl)-7-(4-methoxybenzyl)-6-methylimidazo[1,5-a]pyrazin-8(7H)-one | 1923 | 1446 | 2450 | nd |
| 74 | 3-(6-chloro-2,3-dihydro-1H-inden-1-yl)-7-(4-methoxybenzyl)-6-methylimidazo[1,5-a]pyrazin-8(7H)-one | 5 | 2 | 3 | −19 |
| 75 | 7-(4-methoxybenzyl)-6-methyl-3-(3-methyl-5-oxopyrrolidin-3-yl)imidazo[1,5-a]pyrazin-8(7H)-one | 236 | 297 | 360 | 8 |
| 76 | 3-(1-methoxy-2-methylpropan-2-yl)-7-(4-methoxybenzyl)-6-methylimidazo[1,5-a]pyrazin-8(7H)-one | 122 | 44 | 126 | −14 |
| 77 | 3-isopropyl-7-(4-methoxybenzyl)-6-methylimidazo[1,5-a]pyrazin-8(7H)-one | 13 | 7 | 20 | nd |
| 78 | 6-methyl-7-((2-methylthiazol-4-yl)methyl)-3-(tetrahydro-2H-pyran-4-yl)imidazo[1,5-a]pyrazin-8(7H)-one | 1691 | 641 | 251 | 6 |
| 79 | 6-methyl-3-(tetrahydro-2H-pyran-4-yl)-7-(thiophen-3-ylmethyl)imidazo[1,5-a]pyrazin-8(7H)-one | 228 | 112 | 15 | 14 |
| 80 | 6-methyl-3-(tetrahydro-2H-pyran-4-yl)-7-(thiazol-4-ylmethyl)imidazo[1,5-a]pyrazin-8(7H)-one | 72% (at 10 μM) | 1310 | 496 | 18 |
| 81 | 7-((3,5-dimethylisoxazol-4-yl)methyl)-6-methyl-3-(tetrahydro-2H-pyran-4-yl)imidazo[1,5-a]pyrazin-8(7H)-one | 27% (at 10 μM) | 36% (at 10 μM) | 2305 | 36 |
| 82 | 6-methyl-7-((5-methylisoxazol-3-yl)methyl)-3-(tetrahydro-2H-pyran-4-yl)imidazo[1,5-a]pyrazin-8(7H)-one | 67% (at 10 μM) | 1498 | 1034 | 7 |
| 83 | 6-methyl-7-((3-methylisoxazol-5-yl)methyl)-3-(tetrahydro-2H-pyran-4-yl)imidazo[1,5-a]pyrazin-8(7H)-one | 4444 | 2289 | 1606 | −4 |
| 84 | 3-(2,6-dimethyltetrahydro-2H-pyran-4-yl)-7-(4-methoxybenzyl)-6-methylimidazo[1,5-a]pyrazin-8(7H)-one | 627 | 103 | 337 | −5 |
| 85 | 7-(cyclohexylmethyl)-6-methyl-3-propylimidazo[1,5-a]pyrazin-8(7H)-one | 120 | 32 | 32 | 7 |
| 86 | 3-(2-hydroxypropan-2-yl)-7-(4-methoxybenzyl)-6-methylimidazo[1,5-a]pyrazin-8(7H)-one | 193 | 118 | 214 | −11 |
| 87 | 3-(2-fluoropropan-2-yl)-7-(4-methoxybenzyl)-6-methylimidazo[1,5-a]pyrazin-8(7H)-one | 108 | 124 | 276 | 10 |
| 88 | 7-(4-methoxybenzyl)-6-methyl-3-(7-oxoazepan-4-yl)imidazo[1,5-a]pyrazin-8(7H)-one | 484 | 308 | 548 | −32 |
| 89 | 7-(4-methoxybenzyl)-6-methyl-3-(5-methyltetrahydrofuran-3-yl)imidazo[1,5-a]pyrazin-8(7H)-one | 65% (at 10 μM) | 128 | 303 | 1 |

TABLE 1-continued

Compounds of the invention

| Example | Name | PDE1A, IC$_{50}$ (nM) | PDE1B, IC$_{50}$ (nM) | PDE1C, IC$_{50}$ (nM) | % inhibition of PDE9 at 10 microM |
|---|---|---|---|---|---|
| 90 | 7-(4-methoxybenzyl)-6-methyl-3-(1-(4-methylthiazol-2-yl)ethyl)imidazo[1,5-a]pyrazin-8(7H)-one | 34 | 15 | 23 | 10 |
| 91 | 3-(7-(4-methoxybenzyl)-6-methyl-8-oxo-7,8-dihydroimidazo[1,5-a]pyrazin-3-yl)-3-methylpyrrolidine-1-sulfonamide | 181 | 185 | 417 | 20 |
| 92 | 6-(cyclopentylmethyl)-7-(4-methoxybenzyl)-3-(tetrahydro-2H-pyran-4-yl)imidazo[1,5-a]pyrazin-8(7H)-one | 71 | 11 | 79 | 57 |
| 93 | 3-(morpholino)-7-(4-methoxybenzyl)-6-methylimidazo[1,5-a]pyrazin-8(7H)-one | 96 | 52 | 99 | 23 |
| 94 | 7-(4-methoxybenzyl)-6-methyl-3-((tetrahydrofuran-3-yl)amino)imidazo[1,5-a]pyrazin-8(7H)-one | 2516 | 465 | 1231 | −5 |
| 95 | (R)-7-(4-methoxybenzyl)-6-methyl-3-(3-methylmorpholino)imidazo[1,5-a]pyrazin-8(7H)-one | 258 | 162 | 218 | 9 |
| 96 | (S)-7-(4-methoxybenzyl)-6-methyl-3-(3-methylmorpholino)imidazo[1,5-a]pyrazin-8(7H)-one | 48 | 38 | 51 | nd |
| 97 | 7-(4-methoxybenzyl)-6-methyl-3-(1,4-oxazepan-4-yl)imidazo[1,5-a]pyrazin-8(7H)-one | 202 | 82 | 128 | −8 |
| 98 | 3-(2,2-dimethylmorpholino)-7-(4-methoxybenzyl)-6-methylimidazo[1,5-a]pyrazin-8(7H)-one | 287 | 102 | 135 | 4 |
| 99, isomer 1 | 7-(3-fluorobenzyl)-3-(hexahydro-4H-furo[3,2-b]pyrrol-4-yl)-6-methylimidazo[1,5-a]pyrazin-8(7H)-one, isomer 1 | 241 | 134 | 27 | 9 |
| 99, isomer 2 | 7-(3-fluorobenzyl)-3-(hexahydro-4H-furo[3,2-b]pyrrol-4-yl)-6-methylimidazo[1,5-a]pyrazin-8(7H)-one, isomer 2 | 47% (at 10 μM) | 760 | 119 | 6 |
| 100, isomer 1 | 7-(3-fluorobenzyl)-6-methyl-3-(tetrahydro-2H-pyran-3-yl)imidazo[1,5-a]pyrazin-8(7H)-one, stereoisomer 1 | 306 | 223 | 43 | 11 |
| 100, isomer 2 | 7-(3-fluorobenzyl)-6-methyl-3-(tetrahydro-2H-pyran-3-yl)imidazo[1,5-a]pyrazin-8(7H)-one, stereoisomer 2 | 333 | 93 | 33 | −21 | nd means "not determined"

Table 1 lists the $IC_{50}$ value for inhibition of PDE1 by the compounds of the invention. The $IC_{50}$ value refers to the concentration (nM) of the compound required to reach 50% inhibition of the PDE1 enzyme at the specified substrate concentration.

For certain compounds, the inhibition of PDE is listed as % inhibition at a certain concentration.

For comparative purpose, the table also lists % inhibition of PDE9 at 10 μM.

PDE1 and PDE9 assays are described in the Experimental Section.

Experimental Section

Preparation of the Compounds of the Invention

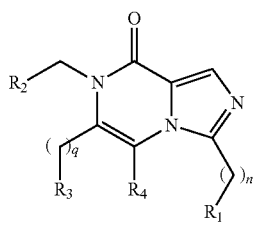

(I)

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XII" (published with Wiley-Interscience, ISSN: 1934-4783). Preferred methods include, but are not limited to, those described below.

The schemes are representative of methods useful in synthesizing the compounds of the present invention. They are not to constrain the scope of the invention in any way. Unless otherwise indicated, in the reaction schemes and discussion that follow, $R_1$-$R_4$ are as defined in claim 1.

General Methods:

Method 1:

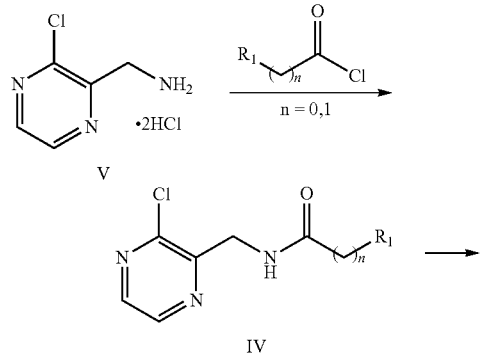

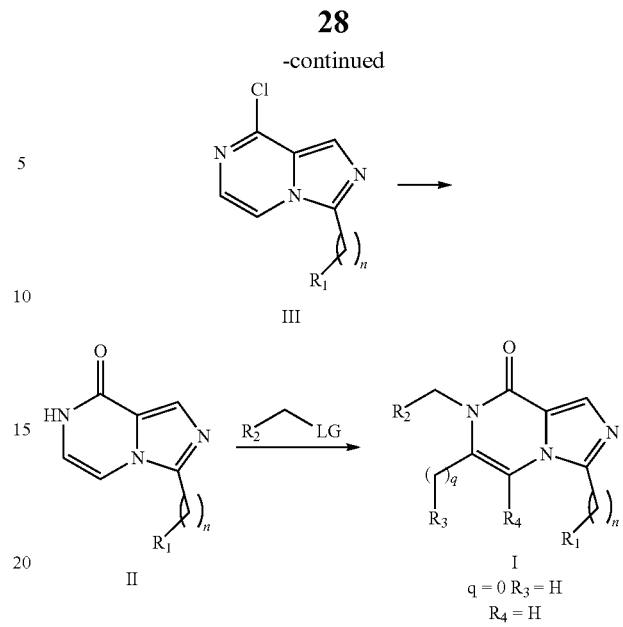

In brief, compounds of the invention can be prepared from the commercial available (3-chloropyrazin-2-yl)methanamine dihydrochloride V (CAS: 867165-53-5). Reacting (3-chloropyrazin-2-yl)methanamine dihydrochloride V with an acid derivative exemplified by but not limited to an acid chloride under conditions appropriate for amide formation, using a base exemplified by but not limited to triethylamine and a solvent/solvent mixture such as dimethylformamide and dichloromethane yields amide IV. Intermediate III can be prepared from IV by treatment with phosphoryl chloride in a solvent such as dioxane. The 8-chloroimidazo[1,5-a]pyrazine III is converted to imidazo[1,5-a]pyrazin-8(7H)-one II under standard hydrolysis conditions exemplified by but not limited to hydrochloric acid in a solvent mixture such as water and 1,4-dioxane. Compound I is formed from imidazo[1,5-a]pyrazin-8(7H)-one II by treatment with an alkylating reagent exemplified by but not limited to an alkyl bromide using a base exemplified but not limited to potassium carbonate in a solvent such as dimethylformamide.

Method 2:

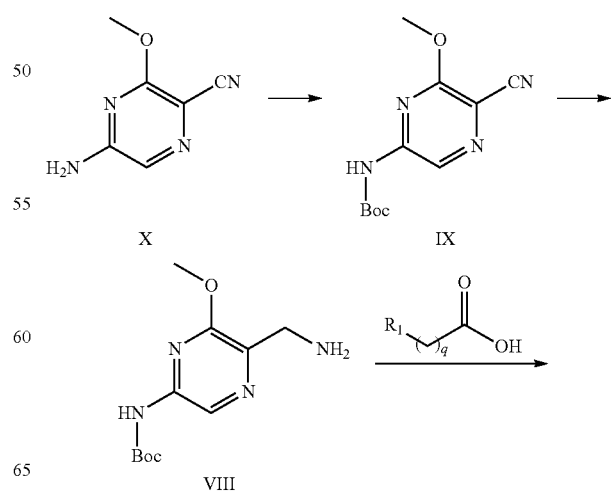

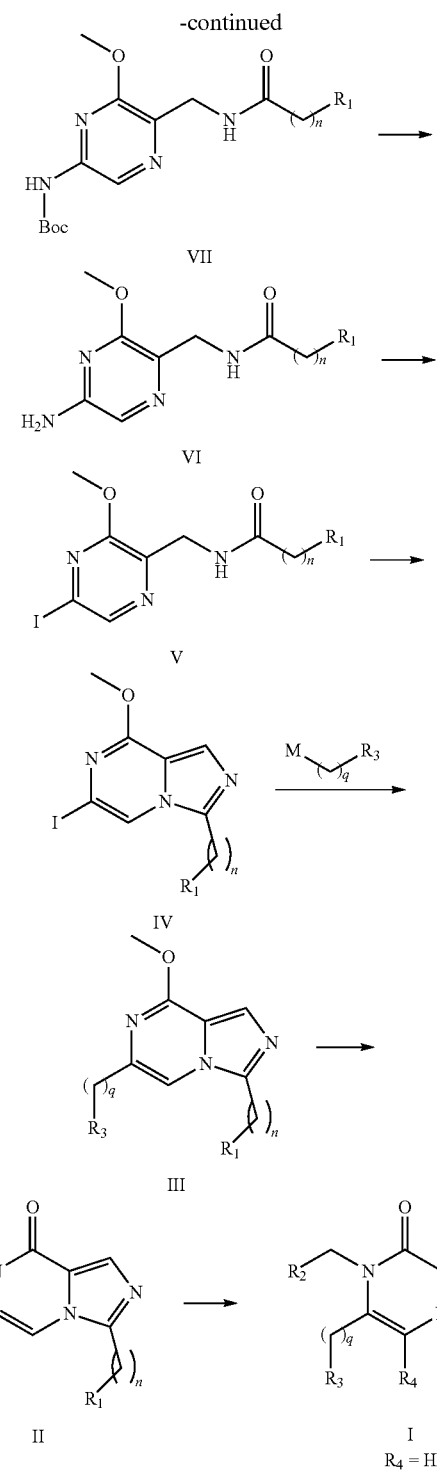

prepared by employing compounds of formula VIII and a carboxylic acid using standard amide bond forming conditions exemplified but not limited to HATU (1-[Bis(dimethylamino)methylene]-1H-1,2,3-triazolo[4,5-b]pyridinium 3-oxid hexafluorophosphate), a base, exemplified but not limited to triethylamine in a solvent such as dichloromethane. Boc protected compounds of formula VII can be deprotected to compounds of formula VI using standard de-protection conditions exemplified by but not limited to trifluoroacetic acid in a solvent such as dichloromethane. Treating compounds of formula VI with isoamyl nitrite, copper iodide and diiodomethane in a solvent such as tetrahydrofuran yields compounds of formula V. Compounds of formula V can be converted to imidazopyrazines of formula IV by treatment with phosphoryl chloride in a solvent such as 1,4-dioxane. Imidazopyrazines of formula III are prepared from IV using standard cross coupling reaction conditions exemplified by but not limited to a Suzuki-Miyaura cross-coupling reaction. Such conditions for the cross coupling reaction are exemplified by but not limited to using; a boronic acid ester, potassium carbonate as the base, a mixture of 1,4-dioxane and water as the solvent and [1,1'-bis(diphenylphosphino) ferrocene]dichloropalladium(II) (Pd(dppf)Cl$_2$) as the catalyst. Imidazo[1,5-a]pyrazin-8(7H)-ones of formula II are prepared by treating compounds of formula III with an acid exemplified but not limited to hydrochloric acid in a mixture of solvents such as water and methanol. Imidazo[1,5-a]pyrazin-8(7H)-ones of formula I are prepared by alkylation of II with an alkylating reagent exemplified but not limited to alkylbromide using a base exemplified but not limited to potassium carbonate in a solvent such as dimethylformamide.

Method 3:

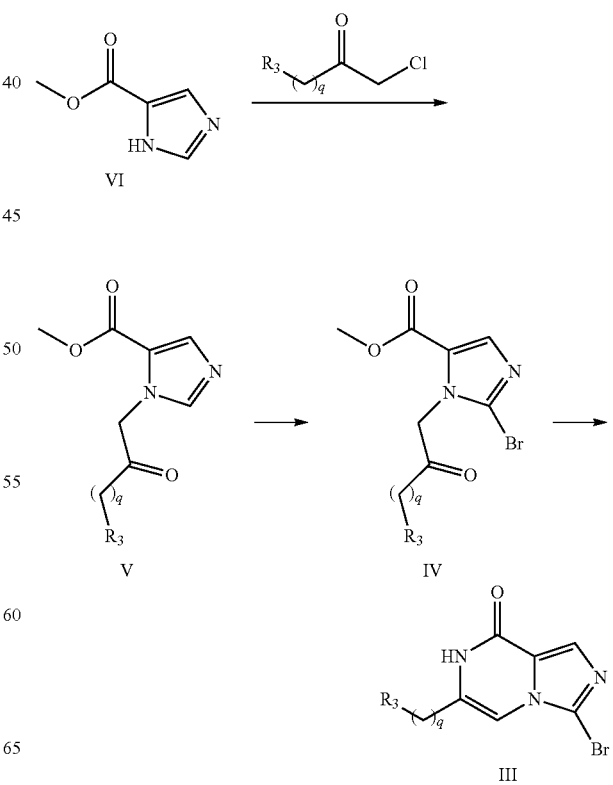

In brief, compounds of the invention can be prepared from the commercial available 5-amino-3-methoxypyrazine-2-carbonitrile X (CAS: 1137478-55-7). Reaction of 5-amino-3-methoxypyrazine-2-carbonitrile X with di-tert-butyl dicarbonate and a catalyst exemplified by but not limited to N,N-dimethylpyridin-4-amine in a solvent such as dichloromethane gives pyrazine IX. Hydrogenation of IX with a catalyst exemplified but not limited to Raney Nickel under an atmosphere of hydrogen in a solvent such as methanol yields amine VIII. Compounds of formula VII can be

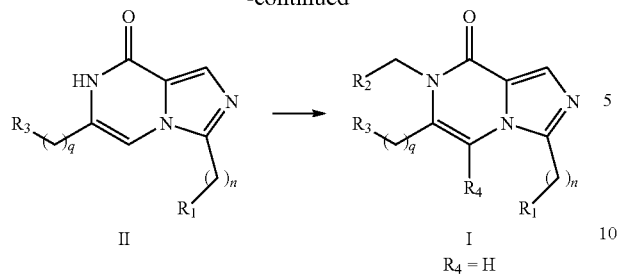

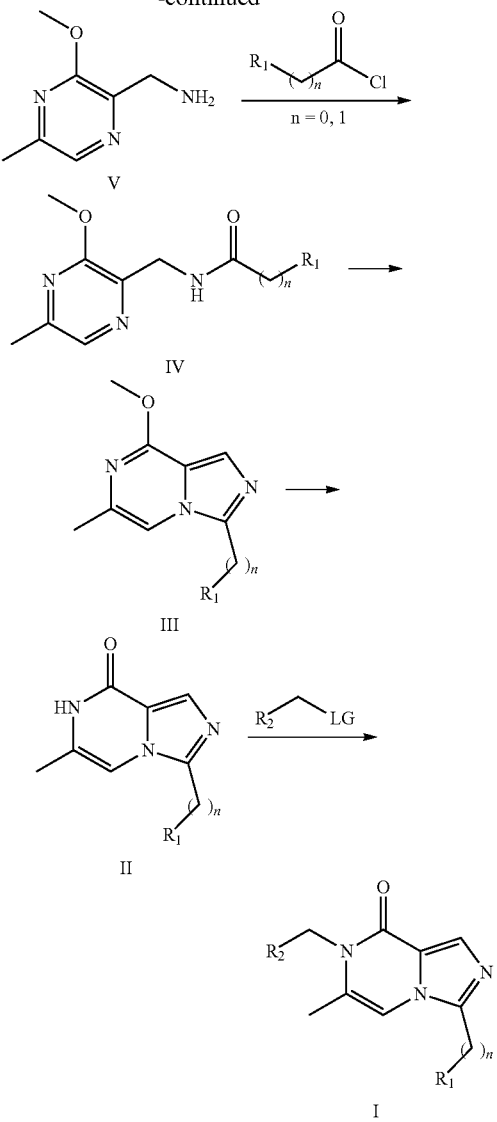

In brief, compounds of the invention can be prepared from the commercial available methyl 1H-imidazole-5-carboxylate VI (CAS: 17325-26-7). Reaction of methyl 1H-imidazole-5-carboxylate VI with an α-halogenated ketone exemplified but not limited to an α-chloroketone, under the influence of a base exemplified but not limited to potassium carbonate in a solvent such as acetone yields the imidazole V. Treating imidazole V with a brominating reagent exemplified but not limited to N-bromosuccinimide (NBS) in the presence of a radical initiator exemplified by but not limited to azobisisobutyronitrile (AIBN) gives imidazole IV. Compounds of the formula III are formed by treatment imidazole IV with ammonium acetate in a solvent such as 1,4-dioxane. Compounds of the formula II can be prepared from intermediate III using standard cross-coupling reaction conditions exemplified by but not limited to a Suzuki-Miyaura cross-coupling reaction. Such conditions for the cross-coupling reaction are exemplified by but not limited to using; a boronic acid ester, potassium carbonate as the base, a mixture of 1,4-dioxane and water as the solvent and Pd(dppf)Cl$_2$ as the catalyst. In some examples R$_1$ contains an unsaturated carbon-carbon bond which can be reduced by hydrogenation under conditions known to the person skilled in the art. Imidazo[1,5-a]pyrazin-8(7H)-ones of formula I are prepared by alkylation of II with an alkylating reagent exemplified by but not limited to alkylbromide using a base exemplified by but not limited to potassium carbonate in a solvent such as dimethylformamide.

Method 4:

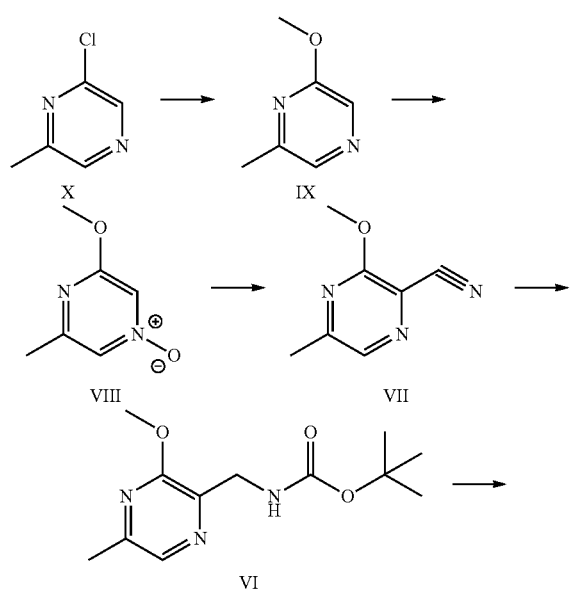

In brief, compounds of the invention can be prepared from the commercial available 2-chloro-6-methylpyrazine X (CAS: 38557-71-0). Reacting 2-chloro-6-methylpyrazine X with Sodium methoxide in methanol yields pyrazine IX. N-oxide VIII can be prepared from IX, by treatment with an oxidant, not limited to sodium metaborate and hydrogen peroxide, in a solvent such as acetic acid. Reacting VIII with a cyanide source, such as trimethylsilyl cyanide and zinc (II)bromide, using a base exemplified by but not limited to triethylamine and a solvent/solvent mixture such as acetonitrile yields cyanide VII. Reduction of VII, not limited to Raney nickel and hydrogen, in the presence of Boc-anhydride, produces carbamate VI. Amine V can be liberated by use of trifluoro acetic acid, but not limited to, from VI. Reacting amine V with an acid derivative exemplified by but not limited to an acid chloride under conditions appropriate for amide formation, using a base exemplified by but not limited to triethylamine and a solvent/solvent mixture such as dimethylformamide and dichloromethane yields amide IV. Intermediate III can be prepared from IV by treatment with phosphoryl chloride in a solvent such as dioxane. The 8-chloroimidazo[1,5-a]pyrazine III is converted to imidazo

[1,5-a]pyrazin-8(7H)-one II under standard hydrolysis conditions exemplified by but not limited to hydrochloric acid in a solvent mixture such as water and 1,4-dioxane. Compound I is formed from imidazo[1,5-a]pyrazin-8(7H)-one II by treatment with an alkylating reagent exemplified by but not limited to an alkyl bromide using a base exemplified but not limited to potassium carbonate in a solvent such as dimethylformamide.

Analytical Methods

Analytical LC-MS data were obtained using the methods identified below.

Method 1:

An Agilent 1200 LCMS system with ELS detector was used. Column: XBridge ShieldRP18, 5 μm, 50×2.1 mm; Column temperature: 40° C.; Solvent system: A=water/NH$_3$*H$_2$O (99.95:0.05) and B=acetonitrile; Method: Linear gradient elution with A:B=99:1 to 0:100 in 3.4 minutes and with a flow rate of 0.8 mL/min.

Method 2:

A Shimadzu 20 MS instrument equipped with atmospheric pressure photo ionisation ion source and a Shimadzu LC-20AB system was used. Column: MERCK, RP-18e 25-2 mm; Column temperature: 50° C.; Solvent system: A=water/trifluoroacetic acid (99.9625.0375) and B=acetonitrile/trifluoroacetic acid (99.981:0.019); Method: A linear gradient elution A:B=95:5 to A:B=5:95 in 0.7 minutes, then A:B=5:95 for 0.4 minutes, then with a linear gradient elution to A:B 95:5 for 0.4 minutes with a constant flow rate of 1.5 mL/min.

Method 3:

An Agilent 1200 LCMS system with ELS detector was used. Column: Agilent TC-C18 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method 4:

An Agilent 1200 LCMS system with ELS detector was used. Column: Agilent TC-C18 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method 5:

A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/minute.

Method 6:

A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/minute.

Method 7:

A Waters Acquity UPLC-MS was used. Column: Acquity UPLC HSS T3 C18 1.8 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=98:02 to 0:100 in 1.0 minutes and with a flow rate of 1.2 mL/min.

Method 8:

An Agilent 1200 LCMS system with ELS detector was used. Phenomenex Luna-C18, μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method 9:

An Agilent 1200 LCMS system with ELS detector was used. Column: Xtimate C18 2.1*30 mm, 3 um; 2.0×50 mm; Column temperature: 50° C.; Solvent system: A=water/trifluoroacetic acid (99.9996:0.0004) and B=acetonitrile/trifluoroacetic acid (99.9998:0.0002); Method: Linear gradient elution with A:B=100:0 to 70:30 in 3.0 minutes and with a flow rate of 0.8 mL/min.

Method 10:

An Agilent 1200 LCMS system with ELS detector was used. Column: Xtimate C18 2.1*30 mm, 3 um; 2.0×50 mm; Column temperature: 50° C.; Solvent system: A=water/trifluoroacetic acid (99.9996:0.0004) and B=acetonitrile/trifluoroacetic acid (99.9998:0.0002); Method: Linear gradient elution with A:B=100:0 to 40:60 in 1.5 minutes and with a flow rate of 1.2 mL/min.

Method 11:

An Agilent 1200 LCMS system with ELS detector was used. Column: Waters XBridge ShieldRP18, 2.1*50 mm, 5 μm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method 12:

An Agilent 1100 LCMS system with ELS detector was used. Column: YMC ODS-AQ 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 5:95 in 3.5 minutes and with a flow rate of 0.8 mL/min.

Method 13:

An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method 14:

An Agilent 1200 LCMS system with ELS detector was used. Column: Xtimate C18 2.1*30 mm, 3 um; 2.0×50 mm; Column temperature: 50° C.; Solvent system: A=water/trifluoroacetic acid (99.9996:0.0004) and B=acetonitrile/trifluoroacetic acid (99.9998:0.0002); Method: Linear gradient elution with A:B=100:0 to 40:60 in 6.0 minutes and with a flow rate of 0.8 mL/min.

Method 15:

An Agilent 1200 LCMS system with ELS detector was used. Column: MERCK, RP-18e 25-2 mm; Column temperature: 50° C.; Solvent system: A=water/trifluoroacetic acid (99.9996:0.0004) and B=acetonitrile/trifluoroacetic acid (99.9998:0.0002); Method: Linear gradient elution with A:B=95:5 to 5:95 in 0.7 minutes and with a flow rate of 1.5 mL/min.

Method 16:

An Agilent 1200 LCMS system with ELS detector was used. Column: Xtimate C18 2.1*30 mm, 3 um; 2.0×50 mm; Column temperature: 50° C.; Solvent system: A=water/ trifluoroacetic acid (99.9996:0.0004) and B=acetonitrile/trifluoroacetic acid (99.9998:0.0002); Method: Linear gradient elution with A:B=100:0 to 40:60 in 0.9 minutes and with a flow rate of 1.2 mL/min.

Method 17:

An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method 18:

An Agilent 1200 LCMS system with ELS detector was used. Column: Waters XBridge ShieldRP18, 2.1*50 mm, 5 μm; Column temperature: 40° C.; Solvent system: A=water/ammonia (99.95:0.05) and B=acetonitrile; Method: Linear gradient elution with A:B=85:15 to 0:100 in 3.4 minutes and with a flow rate of 0.8 mL/min.

Method 19:

A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=98:2 to 0.1:99.9 in 1.0 minutes and with a flow rate of 1.2 mL/minute.

Preparative LC-MS-purification was performed on a PE Sciex API 150EX instrument with atmospheric pressure chemical ionization. Column: 50×20 mm YMC ODS-A with 5 μm particle size; Solvent system: A=water/trifluoroacetic acid (99.965:0.035) and B=acetonitrile/water/trifluoroacetic acid (94.965:5:0.035); Method: Linear gradient elution with A:B=80:20 to 0:100 in 7 minutes and with a flow rate of 22.7 mL/minute. Fraction collection was performed by split-flow MS detection.

Preparative SFC was performed on a Thar 80 instrument. Exemplified conditions can be, but not limited to: Column AD 250×30 mm with 20 μm particle size; Column temperature: 38° C., Mobile phase: Supercritical CO$_2$/EtOH (0.2% NH$_3$H$_2$O)=45/55.

Intermediates

N-((3-chloropyrazin-2-yl)methyl)butyramide

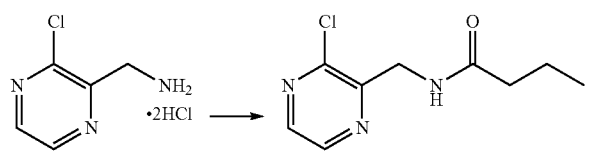

To an ice-cold solution of (3-chloropyrazin-2-yl)methanamine (2.0 g, 14 mmol) in dichloromethane (50 mL) and dimethylformamide (10 mL) was added triethylamine (4.5 g, 45 mmol), followed by butyryl chloride (2.0 g, 14 mmol). The reaction was allowed to warm to room temperature and stirred for 1 hour. The reaction mixture was quenched with water and extracted with dichloromethane (2×250 mL). The combined organic phases were washed with brine, dried over Na$_2$SO$_4$ and concentrated in vacuo to afford N-((3-chloropyrazin-2-yl)methyl)butyramide 2.4 g (81%).

8-Chloro-3-propylimidazo[1,5-a]pyrazine

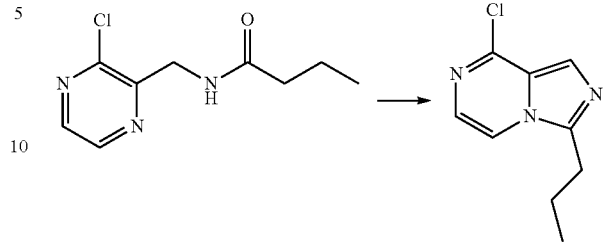

To a solution of N-((3-chloropyrazin-2-yl)methyl)butyramide (2.4 g, 11 mmol) in 1,4-dioxane (20 mL) was added POCl$_3$ (3.44 g, 22.5 mmol). The mixture was stirred at 100° C. for 2 hrs and then cooled on an ice-bath. Saturated. aq. NaHCO$_3$ was added carefully and the mixture was extracted with dichloromethane (2×50 mL). The combined organic phases were washed with brine, dried over Na$_2$SO$_4$ and concentrated in vacuo to give 8-chloro-3-propylimidazo[1,5-a]pyrazine 2 g (63%).

3-Propylimidazo[1,5-a]pyrazin-8(7H)-one

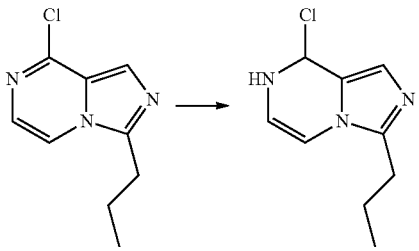

A solution of 3-propylimidazo[1,5-a]pyrazin-8(7H)-one (100 mg, 0.51 mmol) in a mixture of 1,4-dioxane (10 mL) and H$_2$O (4 mL) was stirred at 100° C. for 2 hours. The reaction mixture was concentrated in vacuo and the residue was diluted with dichloromethane (50 mL), washed with NaHCO$_3$(aq), then brine, dried over Na$_2$SO$_4$ and concentrated in vacuo to give 3-propylimidazo[1,5-a]pyrazin-8(7H)-one 50 mg (55%).

Methyl 1-(2-oxopropyl)-1H-imidazole-5-carboxylate

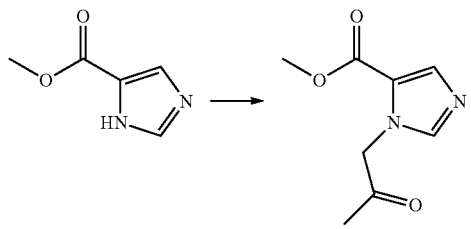

A mixture of methyl 1H-imidazole-5-carboxylate (20 g, 0.16 mol), 1-chloropropan-2-one (22 g, 0.24 mol), and potassium carbonate (44 g, 0.32 mol) in acetone (400 mL) was stirred at 30° C. for 12 hours. The reaction mixture was concentrated in vacuo, the residue was diluted with ethyl acetate (200 mL) and washed with H₂O (3×50 mL). The organic layer was dried over Na₂SO₄ and concentrated in vacuo. The residue was purified by flash chromatography using a gradient of petroleum ether and ethyl acetate to give methyl 1-(2-oxopropyl)-1H-imidazole-5-carboxylate 10 g (35%).

Methyl
2-bromo-1-(2-oxopropyl)-1H-imidazole-5-carboxylate

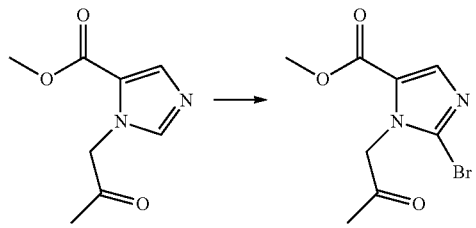

A mixture of methyl 1-(2-oxopropyl)-1H-imidazole-5-carboxylate (10 g, 55 mmol), N-bromosuccinimide (12.7 g, 71.4 mmol) and azobisisobutyronitrile (1.8 g, 11 mmol) in chloroform (100 mL) was stirred at 50° C. for 12 hours. The mixture was concentrated in vacuo. The residue was purified by flash chromatography using a gradient of petroleum ether and ethyl acetate to give methyl 2-bromo-1-(2-oxopropyl)-1H-imidazole-5-carboxylate 13 g (91%).

3-Bromo-6-methylimidazo[1,5-a]pyrazin-8(7H)-one

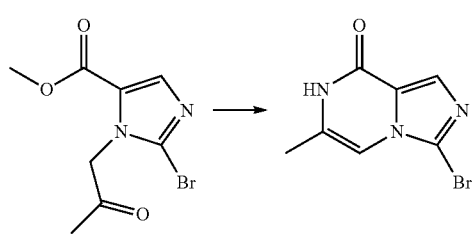

A mixture of methyl 2-bromo-1-(2-oxopropyl)-1H-imidazole-5-carboxylate (14 g, 50 mmol) and ammonium acetate (16.5 g, 215 mmol) in 1,4-dioxane (150 mL) was stirred at 60° C. for 12 hours. The mixture was then stirred at 90° C. for another 24 hours. The reaction mixture was concentrated in vacuo and the residue was diluted with ethyl acetate (600 mL) and washed with water (3×100 mL). The combined organic phases were dried with anhydrous Na₂SO₄ and concentrated in vacuo. The residue was purified by flash chromatography using a gradient of petroleum ether and ethyl acetate to give 3-bromo-6-methylimidazo[1,5-a]pyrazin-8(7H)-one 4.8 g (39%).

3-(3,6-Dihydro-2H-pyran-4-yl)-6-methylimidazo[1,5-a]pyrazin-8(7H)-one

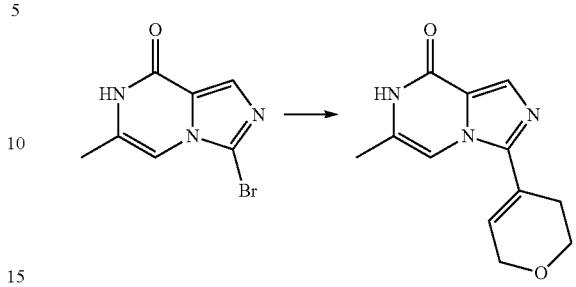

A mixture of 3-bromo-6-methylimidazo[1,5-a]pyrazin-8(7H)-one (4.5 g, 20 mmol), 2-(3,6-dihydro-2H-pyran-4-yl)-4,4,5,5-tetramethyl-1,3,2-dioxaborolane (4.97 g, 23.7 mmol), Pd(dppf)Cl₂ (2.9 g, 3.95 mmol), potassium carbonate (5.5 g, 39 mmol) and H₂O (10 mL) in 1,4-dioxane (40 mL) was stirred at 100° C. for 12 hours. The mixture was filtered and the filtrate was concentrated in vacuo. The residue was purified by flash chromatography using a gradient of dichloromethane and methanol to give 3-(3,6-dihydro-2H-pyran-4-yl)-6-methylimidazo[1,5-a]pyrazin-8(7H)-one 4.0 g (88%).

6-Methyl-3-(tetrahydro-2H-pyran-4-yl)imidazo[1,5-a]pyrazin-8(7H)-one

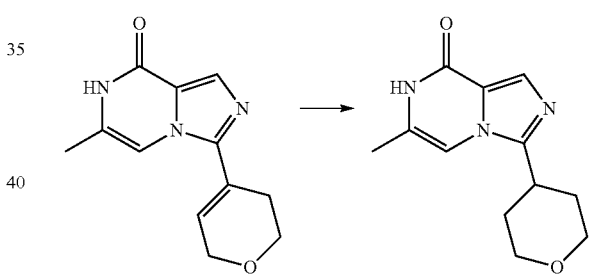

A mixture of 3-(3,6-dihydro-2H-pyran-4-yl)-6-methylimidazo[1,5-a]pyrazin-8(7H)-one (4.0 g, 17 mmol) and 10% Pd/C (300 mg) in tetrahydrofuran (15 mL) was stirred at 15° C. for 7 hrs under an atmosphere of hydrogen. The reaction mixture was filtered and the filtrate was concentrated in vacuo to afford 6-methyl-3-(tetrahydro-2H-pyran-4-yl)imidazo[1,5-a]pyrazin-8(7H)-one 3.5 g (87%).

Tert-butyl
(5-cyano-6-methoxypyrazin-2-yl)carbamate

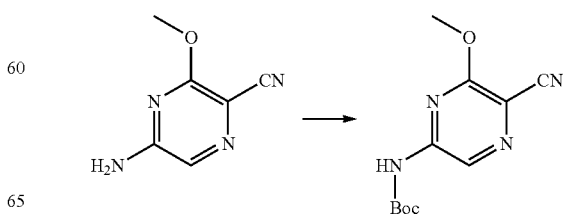

A solution of 5-amino-3-methoxypyrazine-2-carbonitrile (4.70 g, 31.3 mmol), di-tert-butyl dicarbonate (8.9 g, 41 mmol), N,N-dimethylpyridin-4-amine (38 mg, 0.31 mmol) in dichloromethane (150 mL) was stirred at 30° C. for 12 hours. The reaction mixture was concentrated in vacuo. The residue was purified by flash chromatography using a gradient of petroleum ether and ethyl acetat to afford tert-butyl (5-cyano-6-methoxypyrazin-2-yl)carbamate 9.0 g (80%).

Tert-butyl (5-(aminomethyl)-6-methoxypyrazin-2-yl)carbamate

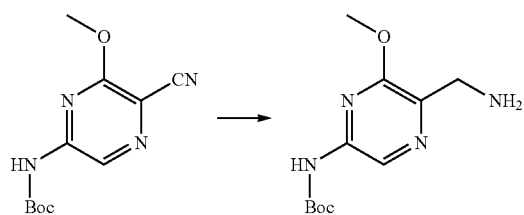 [SMILES: COc1nc(NC(=O)OC(C)(C)C)cnc1C#N ; COc1nc(NC(=O)OC(C)(C)C)cnc1CN]

A mixture of tert-butyl (5-cyano-6-methoxypyrazin-2-yl)carbamate (9.0 g, 36 mmol), Raney Ni 40-60 mesh (5 g) and sat. $NH_3$ in methanol (2 mL) in methanol (100 mL) was stirred at 30° C. for 12 hrs under $H_2$ (45 psi). The reaction was filtered and concentrated in vacuo to afford tert-butyl (5-(aminomethyl)-6-methoxypyrazin-2-yl)carbamate 10 g, sufficiently pure for the next step.

Tert-butyl (6-methoxy-5-((tetrahydro-2H-pyran-4-carboxamido)methyl)pyrazin-2-yl)carbamate

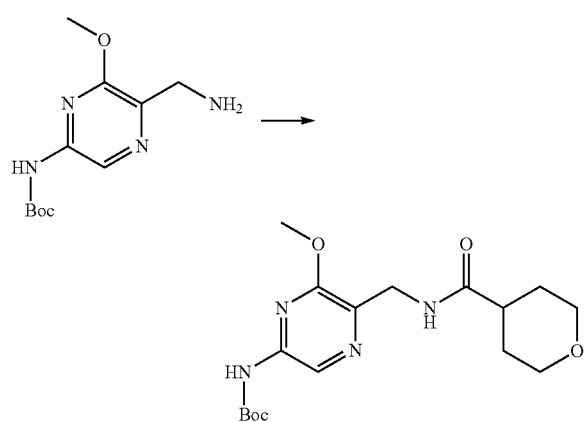

A solution of tert-butyl (5-(aminomethyl)-6-methoxypyrazin-2-yl)carbamate (10.0 g, 31.5 mmol), tetrahydro-2H-pyran-4-carboxylic acid (4.50 g, 34.6 mmol), triethylamine (6.37 g, 62.9 mmol) and 1-[bis(dimethylamino)methylene]-1H-1,2,3-triazolo[4,5-b]pyridinium 3-oxide hexafluoro phosphate (13.2 g, 34.6 mmol) in dichloromethane (120 mL) was stirred at 30° C. for 12 hours. The reaction mixture was concentrated in vacuo and the residue was purified by flash chromatography using a gradient of petroleum ether and ethyl acetate to afford tert-butyl (6-methoxy-5-((tetrahydro-2H-pyran-4-carboxamido)methyl)pyrazin-2-yl)carbamate 8 g (69.4%).

N-((5-Amino-3-methoxypyrazin-2-yl)methyl)tetrahydro-2H-pyran-4-carboxamide

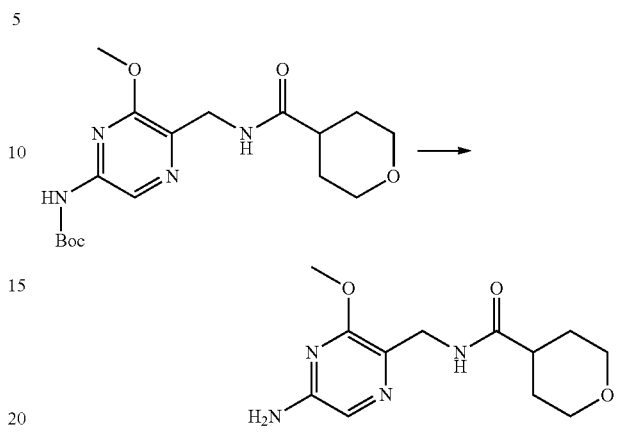

A solution of tert-butyl (6-methoxy-5-((tetrahydro-2H-pyran-4-carboxamido)methyl)pyrazin-2-yl)carbamate (8 g, 21.8 mmol) and trifluoroacetic acid (40 mL) in dichloromethane (40 mL) was stirred at 30° C. for 12 hours. The reaction mixture was concentrated in vacuo. The residue was diluted with dichloromethane (100 mL), and washed with $NaHCO_3$ until pH=8. The organic layer was washed with water (3×20 mL), dried and concentrated in vacuo. The residue was purified by flash chromatography using a gradient of petroleum ether and ethyl acetate to yield N-((5-amino-3-methoxypyrazin-2-yl)methyl)tetrahydro-2H-pyran-4-carboxamide 4 g (65.4%).

N-((5-Iodo-3-methoxypyrazin-2-yl)methyl)tetrahydro-2H-pyran-4-carboxamide

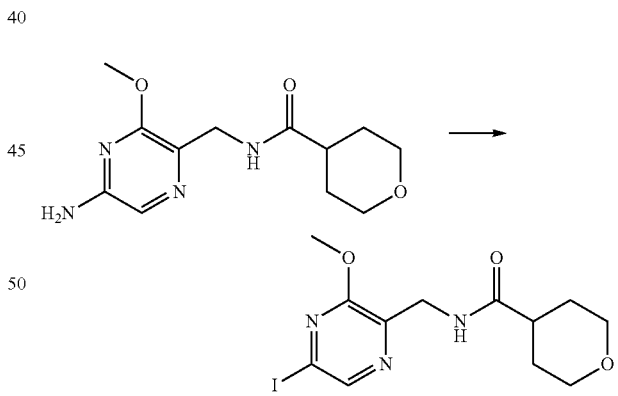

A solution of N-((5-amino-3-methoxypyrazin-2-yl)methyl)tetrahydro-2H-pyran-4-carboxamide (2.40 g, 9.01 mmol), copper(I)iodide (1.72 g, 9.01 mmol), isoamyl nitrite (1.58 g, 13.5 mmol) and diiodomethane (2.41 g, 9.01 mmol) in tetrahydrofuran (50 mL) was stirred at 75° C. for 6 hours. The mixture was filtered and concentrated in vacuo. The residue was purified by flash chromatography using a gradient of petroleum ether and ethyl acetate to afford N-((5-iodo-3-methoxypyrazin-2-yl)methyl)tetrahydro-2H-pyran-4-carboxamide 2.20 g (64.7%).

6-Iodo-8-methoxy-3-(tetrahydro-2H-pyran-4-yl) imidazo[1,5-a]pyrazine

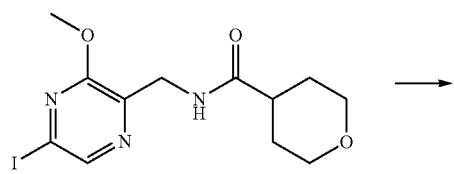

To a solution of N-((5-iodo-3-methoxypyrazin-2-yl)methyl)tetrahydro-2H-pyran-4-carboxamide (2 g, 5.30 mmol) in 1,4-dioxane (60 mL) was added phosphoryl chloride (8.13 g, 53.0 mmol) at 0° C. The reaction was stirred at 85° C. for 12 hours. The mixture was concentrated in vacuo. The residue was diluted with dichloromethane (100 mL) and ice-water (60 mL), followed by saturated aqueous NaHCO₃ (30 mL). The organic phase was separated and the water phase was extracted with dichloromethane (3×20 mL). The combined organic phases were combined, dried and concentrated in vacuo. The residue was purified by flash chromatography using a gradient of petroleum ether and ethyl acetate to yield 6-iodo-8-methoxy-3-(tetrahydro-2H-pyran-4-yl)imidazo[1,5-a]pyrazine 500 mg (23.6%).

6-Benzyl-8-methoxy-3-(tetrahydro-2H-pyran-4-yl) imidazo[1,5-a]pyrazine

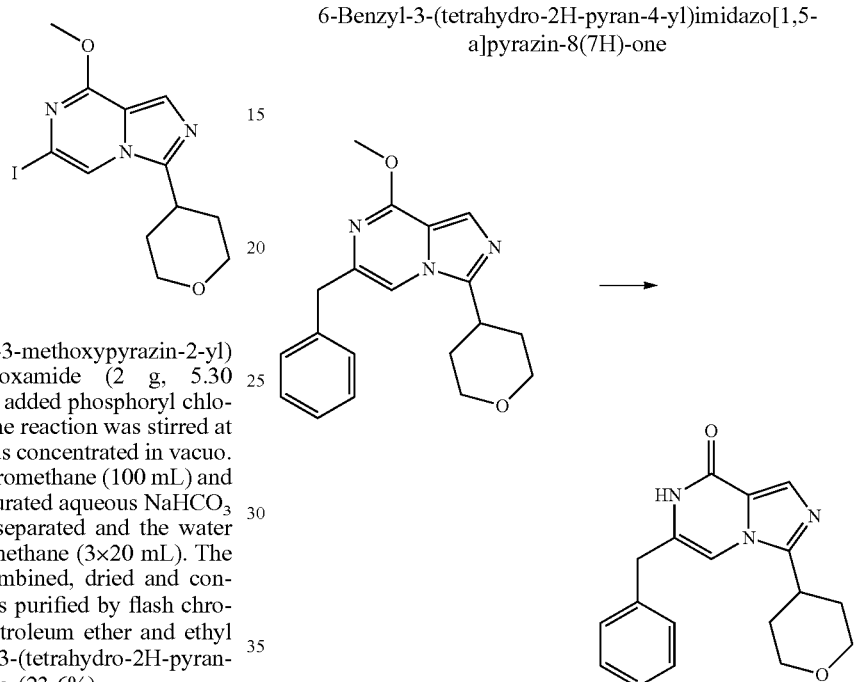

A mixture of 6-iodo-8-methoxy-3-(tetrahydro-2H-pyran-4-yl)imidazo[1,5-a]pyrazine (500 mg, 1.39 mmol), 2-benzyl-4,4,5,5-tetramethyl-1,3,2-dioxaborolane (911 mg, 4.18 mmol), Pd(dppf)Cl₂ (51 mg, 0.07 mmol), K₂CO₃ (577 mg, 4.18 mmol) and H₂O (3 mL) in 1,4-dioxane (15 mL) was stirred at 80° C. for 12 hrs under an atmosphere of N₂. It was then filtered and the filtrate was concentrated in vacuo. The residue was purified by flash chromatography using a gradient of petroleum ether and ethyl acetate to yield 6-benzyl-8-methoxy-3-(tetrahydro-2H-pyran-4-yl)imidazo[1,5-a]pyrazine 260 mg (52%).

6-Benzyl-3-(tetrahydro-2H-pyran-4-yl)imidazo[1,5-a]pyrazin-8(7H)-one

A solution of 6-benzyl-8-methoxy-3-(tetrahydro-2H-pyran-4-yl)imidazo[1,5-a]pyrazine (320 mg, 0.990 mmol) and 2 M aq. HCl (8 mL) in methanol (20 mL) was stirred at 60° C. for 12 hours. The solution was concentrated in vacuo. The residue was purified by flash chromatography using a gradient of petroleum ether and ethyl acetate to yield 6-benzyl-3-(tetrahydro-2H-pyran-4-yl)imidazo[1,5-a]pyrazin-8(7H)-one 230 mg (68%).

N-((3-chloropyrazin-2-yl)methyl)tetrahydro-2H-pyran-4-carboxamide

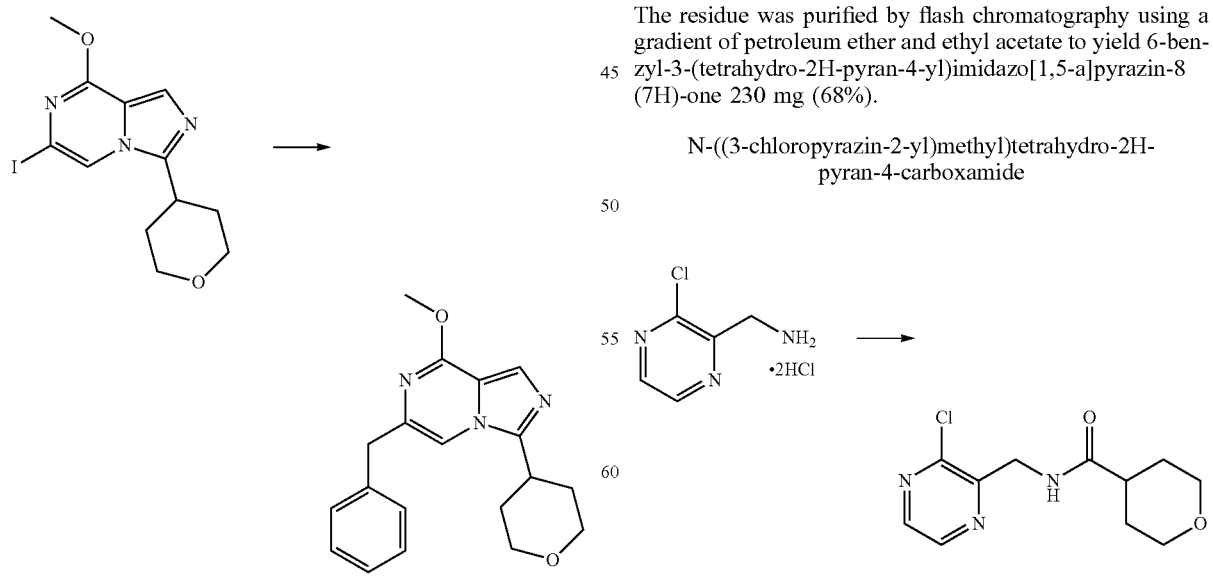

To a solution of (3-chloropyrazin-2-yl)methanamine dihydrochloride (3.8 g, 18 mmol) in anhydrous DMF (20 mL) was added triethylamine (5.7 g, 56 mmol). The mixture was cooled to 0° C., tetrahydro-2H-pyran-4-carbonyl chloride (2.9 g, 19 mmol) was added dropwise. The mixture was stirred at 0° C. for 0.5 hours. The reaction mixture was diluted with water (50 mL) and extracted with ethyl acetate (3×80 mL). The combined organic phases were washed with brine (50 mL), dried over $Na_2SO_4$ and concentrated in vacuo. The residue was purified by flash chromatography eluting with ethyl acetate to afford N-((3-chloropyrazin-2-yl)methyl)tetrahydro-2H-pyran-4-carboxamide 2.4 g (54%).

8-Chloro-3-(tetrahydro-2H-pyran-4-yl)imidazo[1,5-a]pyrazine

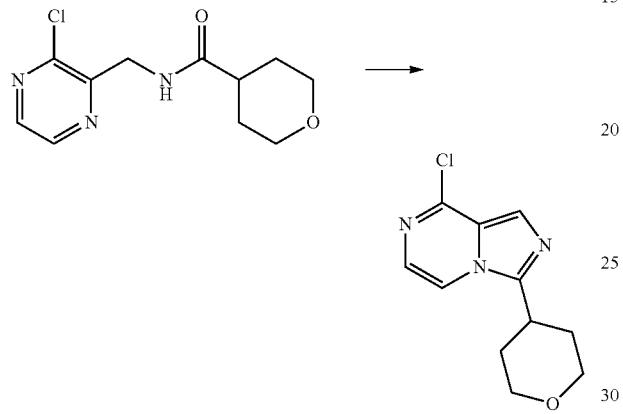

To a solution of N-((3-chloropyrazin-2-yl)methyl)tetrahydro-2H-pyran-4-carboxamide (2.5 g, 9.8 mmol) in anhydrous 1,4-dioxane (20 mL) was added phosphoryl chloride (3.4 g, 22 mmol). The reaction was stirred at 80° C. for 2 hours. Then the solution was cooled and poured into water (100 mL), pH was adjusted to 8-9 by the addition of saturated aqueous $K_2CO_3$. The crude mixture was extracted with ethyl acetate (2×100 mL). The combined organic phases were washed with brine (50 mL), dried over $Na_2SO_4$ and concentrated in vacuo. The residue was purified by flash chromatography using a gradient of petroleum ether and ethyl acetate to yield 8-chloro-3-(tetrahydro-2H-pyran-4-yl)imidazo[1,5-a]pyrazine 2.1 g (90%).

3-(Tetrahydro-2H-pyran-4-yl)imidazo[1,5-a]pyrazin-8(7H)-one

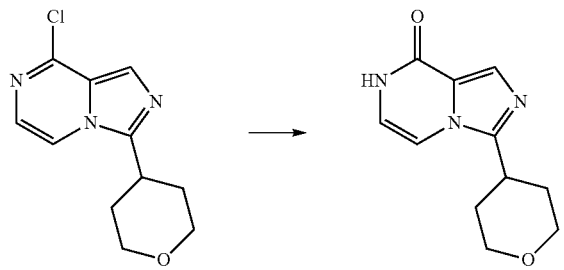 [SMILES: Clc1nccn2c(C3CCOCC3)ncc12 ; O=c1[nH]ccn2c(C3CCOCC3)ncc12]

To a solution of 8-chloro-3-(tetrahydro-2H-pyran-4-yl)imidazo[1,5-a]pyrazine (2.1 g, 8.8 mmol) in 1,4-dioxane (20 mL) was added 2 M aq. HCl (10 mL). The solution was stirred at 80° C. for 2 hours. The mixture was cooled and pH was adjusted to 8-9 by addition of saturated aqueous $K_2CO_3$. The crude mixture was concentrated in vacuo and the residue was dissolved in methanol (150 mL) and filtered. The filtrate was concentrated in vacuo and the residue was purified by flash chromatography using a mixture of dichloromethane and methanol (10:1) to give 3-(tetrahydro-2H-pyran-4-yl)imidazo[1,5-a]pyrazin-8(7H)-one 1.6 g (81%).

$^1$H NMR (DMSO-$d_6$, 400 MHz): δ 10.55 (s, 1H), 7.63 (s, 1H), 7.39 (d, J=6.0 Hz, 1H), 6.60 (s, 1H), 3.91-3.88 (m, 2H), 3.49-3.42 (m, 2H), 3.34-3.29 (m, 1H), 1.82-1.72 (m, 4H).

LC-MS: (m/z) 220.1 (MH$^+$) $t_R$ (minutes, method 3)=1.37 minutes

N-((3-Chloropyrazin-2-yl)methyl)cyclopropanecarboxamide

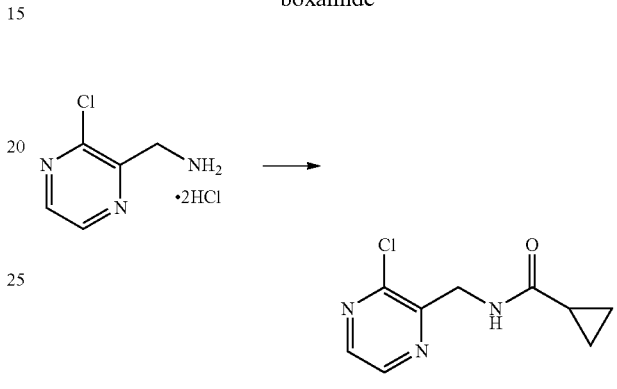

To a solution of (3-chloropyrazin-2-yl)methanamine dihydrochloride (4.0 g, 19 mmol) in anhydrous DMF (20 mL) was added $Et_3N$ (1.9 g, 18.5 mmol). The mixture was cooled to 0° C. and cyclopropanecarbonyl chloride (2.3 g, 22 mmol) was added dropwise. The reaction was stirred at 0° C. for 0.5 hours. The reaction mixture was diluted with water (50 mL), extracted with ethyl acetate (2×100 mL). The combined organic phases were washed with brine (40 mL), dried over $Na_2SO_4$ and concentrated in vacuo. The residue was purified by flash chromatography eluting with petroleum ether/ethyl acetate 2/1 to yield N-((3-chloropyrazin-2-yl)methyl)cyclopropanecarboxamide 3.3 g (85%).

8-Chloro-3-cyclopropylimidazo[1,5-a]pyrazine

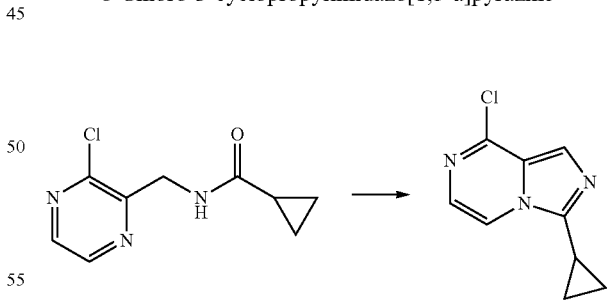

To a solution of N-((3-chloropyrazin-2-yl)methyl)cyclopropanecarboxamide (3.3 g, 15.6 mmol) in anhydrous 1,4-dioxane (30 mL) was added phosphoryl chloride (5.3 g, 35 mmol). The reaction was stirred at 80° C. for 2 hours. Then the solution was cooled on an ice-bath and poured into water (50 mL). The pH was adjusted to 8-9 by addition of saturated aqueous $K_2CO_3$. The mixture was extracted with ethyl acetate (2×50 mL). The combined organic phases were washed with brine (50 mL), dried over $Na_2SO_4$ and concentrated in vacuo. The residue was purified by flash chromatography using petroleum ether/ethyl acetate 3:1 to yield 8-chloro-3-cyclopropylimidazo[1,5-a]pyrazine 2.4 g (80%).

3-Cyclopropylimidazo[1,5-a]pyrazin-8(7H)-one

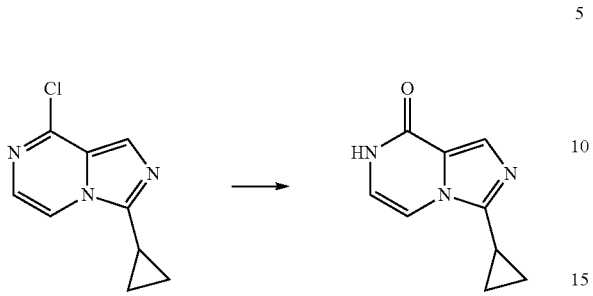

To a solution of 8-chloro-3-cyclopropylimidazo[1,5-a]pyrazine (2.5 g, 13 mmol) in 1,4-dioxane (20 mL) was added 2 M aq. HCl (10 mL). The solution was stirred at 80° C. for 2 hrs. The mixture was cooled on an ice-bath and pH adjusted to 8-9 by addition of saturated aqueous $K_2CO_3$. The mixture was concentrated in vacuo and the residue was dissolved in methanol (150 mL) and filtered. The filtrate was concentrated in vacuo and the residue was purified by flash chromatography using dichloromethane/methanol 10/1 to afford 3-cyclopropylimidazo[1,5-a]pyrazin-8(7H)-one 1.9 g (83%).

$^1$H NMR (DMSO-$d_6$, 400 MHz): δ 10.49 (s, 1H), 7.54 (s, 1H), 7.41 (d, J=5.6 Hz, 1H), 6.61 (d, J=5.6 Hz, 1H), 2.29-2.24 (m, 1H), 0.99-0.89 (m, 4H).

LC-MS: (m/z) 176.1 (MH$^+$) $t_R$ (minutes, method 1)=1.04 minutes

N-((5-Bromo-3-methoxypyrazin-2-yl)methyl)tetrahydro-2H-pyran-4-carboxamide

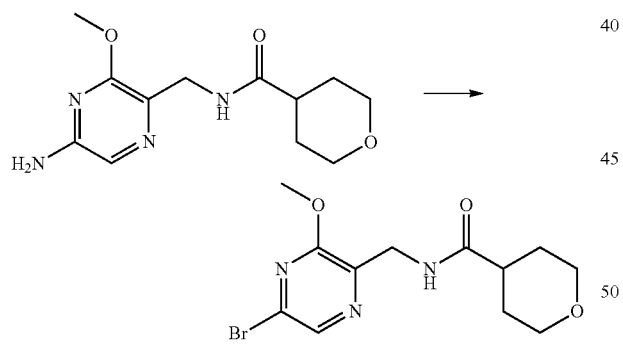

A solution of $NaNO_2$ (972 mg, 14.09 mmol) in $H_2O$ (100 mL) was added to a stirred solution of N-((5-amino-3-methoxypyrazin-2-yl)methyl)tetrahydro-2H-pyran-4-carboxamide (2.5 g, 9.4 mmol) in 40% aq. HBr (33 mL) at 0° C. After stirring for 1.5 hrs, CuBr (2.02 g, 14.1 mmol) was added and the mixture was stirred at 70° C. for 1 hour. The pH value was adjusted to pH 8 by addition of saturated aqueous $NaHCO_3$. The mixture was filtered and the filtrate was concentrated in vacuo. The residue was purified by flash chromatography using a gradient of petroleum ether and ethyl acetate to yield N-((5-bromo-3-methoxypyrazin-2-yl)methyl)tetrahydro-2H-pyran-4-carboxamide 800 mg (25%).

LC-MS: (m/z) 331.8 (MH$^+$) $t_R$ (minutes, method 2)=0.723 minutes

6-Bromo-8-methoxy-3-(tetrahydro-2H-pyran-4-yl)imidazo[1,5-a]pyrazine

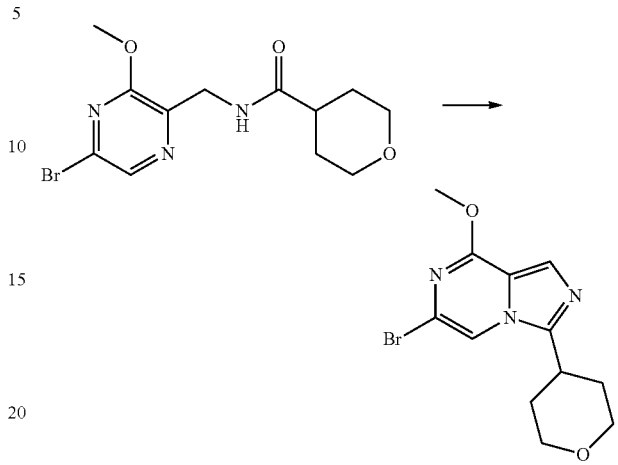

To a solution of N-((5-bromo-3-methoxypyrazin-2-yl)methyl)tetrahydro-2H-pyran-4-carboxamide (800 mg, 2.42 mmol) in 1,4-dioxane (30 mL) was added phosphoryl chloride (3.8 g, 25 mmol) at 0° C. The mixture was heated to 70° C. and stirred for 1 hour. The mixture was concentrated in vacuo and the residue was diluted with dichloromethane (100 mL) and ice-water (60 mL). The pH value was adjusted to pH 8 by addition of saturated aqueous $NaHCO_3$. The organic phase was separated and aqueous phase was extracted with dichloromethane (3×30 mL). The combined organic phases were dried and concentrated in vacuo. The residue was purified by flash chromatography using a gradient of dichloromethane and methanol to yield 6-bromo-8-methoxy-3-(tetrahydro-2H-pyran-4-yl)imidazo[1,5-a]pyrazine 500 mg (66%).

LC-MS: (m/z) 313.7 (MH$^+$) $t_R$ (minutes, method 2)=0.740 minutes

6-Bromo-3-(tetrahydro-2H-pyran-4-yl)imidazo[1,5-a]pyrazin-8(7H)-one

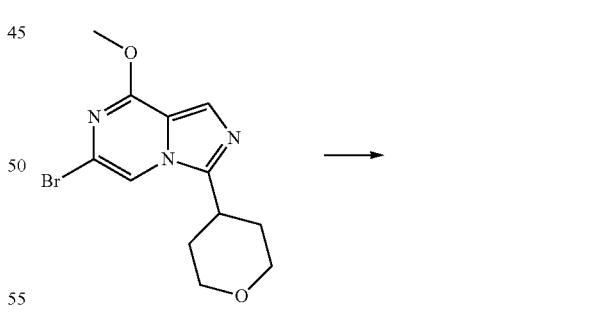

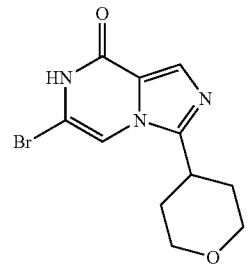

To a solution of 6-bromo-8-methoxy-3-(tetrahydro-2H-pyran-4-yl)imidazo[1,5-a]pyrazine (200 mg, 0.641 mmol) in dichloromethane (30 mL) was added boron tribromide (1.61 g, 6.41 mmol) at 0° C. The reaction was warmed to 20° C. and stirred for 3 hours. The solution was quenched with water (2 mL) at 0° C. The reaction was concentrated in vacuo and the residue was purified by flash chromatography using a gradient of dichloromethane and methanol to yield 6-bromo-3-(tetrahydro-2H-pyran-4-yl)imidazo[1,5-a]pyrazin-8(7H)-one 130 mg (68%).

LC-MS: (m/z) 299.7 (MH$^+$) $t_R$ (minutes, method 2)=0.730 minutes 2-methoxy-6-methylpyrazine

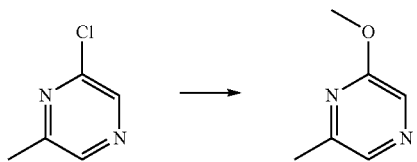

To a suspension of 2-chloro-6-methylpyrazine (24 g, 186.7 mmol) in anhydrous MeOH (240 mL) was added NaOMe (12.1 g, 224 mmol). The mixture was stirred at 60-70° C. for 16 hours. The mixture was cooled and filtered. The filtrate was concentrated in vacuo to give 2-methoxy-6-methylpyrazine (22 g, 95% yield). $^1$H NMR (CDCl$_3$ 400 MHz): δ 7.98 (s, 1H), 7.94 (s, 1H), 3.91 (s, 3H), 3.40 (s, 3H). LC-MS: $t_R$=1.47 min (method 14), m/z=124.8 [M+H]$^+$.

3-methoxy-5-methylpyrazine 1-oxide

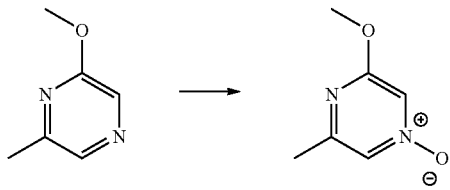

To a solution of 2-methoxy-6-methylpyrazine (21.3 g, 171.6 mmol) in AcOH (150 mL) was added NaBO$_2$·H$_2$O$_2$·3H$_2$O (31.7 g, 205.9 mmol). The mixture was stirred at 80° C. for 16 hours. The mixture was concentrated in vacuo and diluted with 2 M aq. NaOH (300 mL). The mixture was extracted with EtOAc (200 mL×4). The organic layer was washed with brine (100 mL), dried over Na$_2$SO$_4$ and concentrated in vacuo to give 3-methoxy-5-methylpyrazine 1-oxide (14.4 g, 60% yield).

3-methoxy-5-methylpyrazine-2-carbonitrile

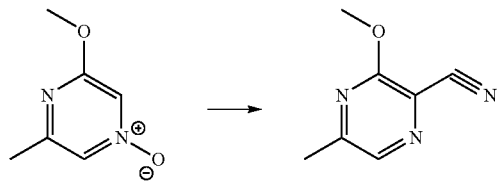

To a mixture of 3-methoxy-5-methylpyrazine 1-oxide (10 g, 71.4 mmol) in MeCN (200 mL) was added TMSCN (24.8 g, 249.8 mmol) and triethylamine (36.1 g, 356.8 mmol), ZnBr$_2$ (32.1 g, 142.7 mmol). The mixture was stirred at 85-90° C. for 16 hours. The mixture was concentrated in vacuo. The residue was diluted with DCM (500 mL) and filtered. The filtrate was washed with water (300 mL) and brine (200 mL). The organic layer was dried over Na$_2$SO$_4$ and concentrated in vacuo. The residue was purified by silica gel chromatography (petroleum ether:ethyl acetate=5:1) to give 3-methoxy-5-methyl pyrazine-2-carbonitrile (4.1 g, 38% yield).

tert-butyl ((3-methoxy-5-methylpyrazin-2-yl)methyl)carbamate

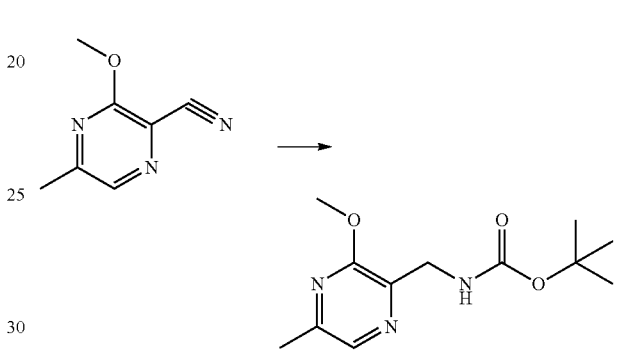

To a solution of 3-methoxy-5-methylpyrazine-2-carbonitrile (6.22 g, 41.7 mmol) in MeOH (100 mL) was added (Boc)$_2$O (13.65 g, 62.6 mmol) and Raney Ni (2.0 g). The mixture was stirred at 20-25° C. under H$_2$ (45 psi) for 16 hours. The mixture was filtered and the filtrate was concentrated in vacuo. The residue was purified by silica gel chromatography (petroleum ether:ethyl acetate=5:1) to give tert-butyl ((3-methoxy-5-methyl pyrazin-2-yl)methyl)carbamate (7.7 g, 72% yield).

LC-MS: $t_R$=0.70 min (method 15), m/z=254.0 [M+H]$^+$.

(3-methoxy-5-methylpyrazin-2-yl)methanamine

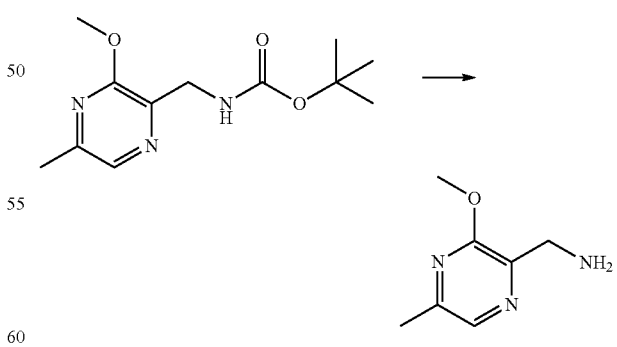

To a solution of tert-butyl ((3-methoxy-5-methylpyrazin-2-yl)methyl)carbamate (7.7 g, 30.3 mmol) in THF (50 mL) was added TFA (20 mL). The mixture was stirred at 80° C. for 2 hours. The mixture was concentrated in vacuo. The residue was diluted with 2 M aq. NaOH (200 mL), extracted with DCM (100 mL×2). The organic layer was washed with brine (50 mL), dried over Na$_2$SO$_4$ and concentrated in vacuo to give (3-methoxy-5-methylpyrazin-2-yl)methanamine (2.5 g, 54% yield).

$^1$H NMR (CDCl$_3$ 400 MHz): δ 7.90 (s, 1H), 3.96 (s, 3H), 3.93 (s, 2H), 2.42 (s, 3H), 1.69 (s, 2H).

LC-MS: t$_R$=0.73 min(method 16), m/z=154.2 [M+H]$^+$.

Compounds of the Invention

Example 1

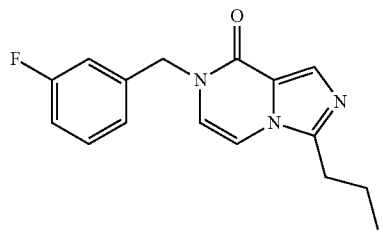 [SMILES: CCCc1ncc2c(=O)n(Cc3cccc(F)c3)ccn12]

7-(3-Fluorobenzyl)-3-propylimidazo[1,5-a]pyrazin-8(7H)-one

To a solution of 3-propylimidazo[1,5-a]pyrazin-8(7H)-one (1.2 g, 6.8 mmol) in DMF (10 mL) was added potassium carbonate (1.4 g, 10 mmol) and 1-(bromomethyl)-3-fluorobenzene (1.54 g, 8.13 mmol). The mixture was stirred at 60-70° C. for 2 hrs and then cooled to room temperature. To the reaction was added water (75 mL) and it was extracted with ethyl acetate (2×50 mL). The combined organic phases were washed with brine, dried and concentrated in vacuo. The residue purified by flash chromatography to yield 1.5 g (78%) of 7-(3-fluorobenzyl)-3-propylimidazo[1,5-a]pyrazin-8(7H)-one.

$^1$H NMR (DMSO-d$_6$, 400 MHz): δ 7.70 (s, 1H), 7.46-7.37 (m, 2H), 7.17-7.09 (m, 3H), 7.00 (d, J=6.0 Hz, 1H), 5.02 (s, 2H), 2.83 (t, 2H), 1.75-1.66 (m, 2H), 0.91 (t, 3H).

LC-MS: (m/z) 286.1 (MH$^+$) t$_R$ (minutes, method 3)=2.19 minutes

Example 2

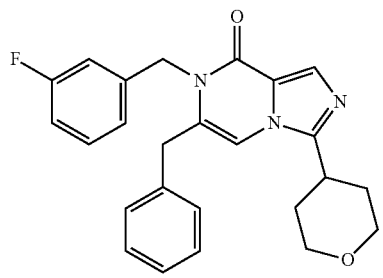 [SMILES: O=c1c2cnc(C3CCOCC3)n2cc(Cc2ccccc2)n1Cc1cccc(F)c1]

6-Benzyl-7-(3-fluorobenzyl)-3-(tetrahydro-2H-pyran-4-yl)imidazo[1,5-a]pyrazin-8(7H)-one A mixture of 6-benzyl-3-(tetrahydro-2H-pyran-4-yl)imidazo[1,5-a]pyrazin-8(7H)-one (200 mg, 0.647 mmol), 1-(bromomethyl)-3-fluorobenzene (159 mg, 840 μmol) and potassium carbonate (179 mg, 1.29 mmol) in DMF (6 mL) was stirred at 60° C. for 12 hours. The reaction mixture was concentrated in vacuo and the residue was diluted with dichloromethane (20 mL) and washed with water (3×5 mL). The combined organic phases were dried, filtered and concentrated in vacuo. The residue was purified by preparative TLC, eluting with petroleum ether and ethyl acetate 1:2, to yield 6-benzyl-7-(3-fluorobenzyl)-3-(tetrahydro-2H-pyran-4-yl)imidazo[1,5-a]pyrazin-8(7H)-one 80 mg (28%).

$^1$H NMR (CDCl$_3$, 400 MHz): δ 7.97 (s, 1H), 7.39-7.30 (m, 4H), 7.17 (d, J=7.53 Hz, 2H), 6.94-6.92 (m, 2H), 6.83 (d, J=9.54 Hz, 1H), 6.74 (s, 1H), 5.06 (s., 2H), 4.12 (d, J=12.05 Hz, 2H), 3.74 (s, 2H), 3.58-3.52 (m, 2H), 3.03-3.09 (m, 1H), 2.19-2.09 (m, 2H), 1.89 (d, J=13.55 Hz, 2H).

LC-MS: (m/z) 418.2 (MH$^+$) t$_R$ (minutes, method 3)=2.69 minutes

Example 3

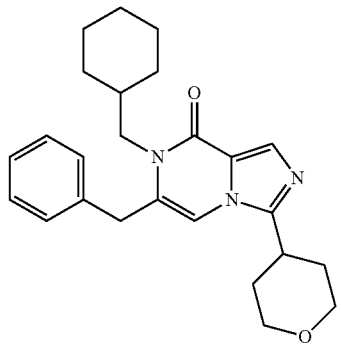 [SMILES: O=c1c2cnc(C3CCOCC3)n2cc(Cc2ccccc2)n1CC1CCCCC1]

6-Benzyl-7-(cyclohexylmethyl)-3-(tetrahydro-2H-pyran-4-yl)imidazo[1,5-a]pyrazin-8(7H)-one A mixture of 6-benzyl-3-(tetrahydro-2H-pyran-4-yl)imidazo[1,5-a]pyrazin-8(7H)-one (60 mg, 0.19 mmol), (bromomethyl)cyclohexane (52 mg, 0.29 mmol) and potassium carbonate (54 mg, 0.39 mmol) in DMF (10 mL) was stirred at 75° C. for 12 hours. The reaction mixture was concentrated in vauo. The residue was diluted with dichloromethane (20 mL) and washed with water (3×5 mL). The combined organic phases were dried, filtered and concentrated in vacuo. The residue was purified by preparative TLC, eluting with petroleum ether and ethyl acetate 1:2, to yield 6-benzyl-7-(cyclohexylmethyl)-3-(tetrahydro-2H-pyran-4-yl)imidazo[1,5-a]pyrazin-8(7H)-one 15 mg (8.1%).

$^1$H NMR (CDCl$_3$, 400 MHz): δ 7.87 (s, 1H), 7.42-7.30 (m, 3H), 7.19 (d, J=7.34 Hz, 2H), 6.65 (s, 1H), 4.11 (d, J=11.25 Hz, 2H), 3.90 (s, 2H), 3.66 (d, J=6.36 Hz, 2H), 3.54 (t, J=10.76 Hz, 2H), 3.05-2.99 (m, 1H), 2.18-2.04 (m, 2H), 1.86 (d, J=13.94 Hz, 2H), 1.63-1.77 (m, 7H), 1.18-1.15 (m, 2H), 1.04-1.01 (m, 2H).

LC-MS: (m/z) 406.2 (MH$^+$) t$_R$ (minutes, method 4)=2.38 minutes

Example 4

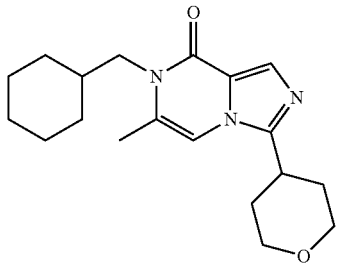 [SMILES: Cc1cn2c(C3CCOCC3)ncc2c(=O)n1CC1CCCCC1]

7-(Cyclohexylmethyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (50 mg, 0.21 mmol), (bromomethyl)cyclohexane (57 mg, 0.32 mmol) and potassium carbonate (59 mg, 0.43 mmol) in DMF (2 mL) was stirred at 60° C. for 12 hours. The reaction mixture was concentrated in vacuo. The residue was diluted with dichloromethane (20 mL) and washed with water (3×5 mL). The combined organic phases were dried, filtered and concentrated in vacuo. The residue was purified by preparative LC-MS to yield 7-(cyclohexylmethyl)-6-methyl-3-(tetrahydro-2H-pyran-4-yl)imidazo[1,5-a]pyrazin-8(7H)-one 20 mg (28%).

$^1$H NMR (CDCl$_3$, 400 MHz): δ 7.85 (s, 1H), 6.71 (s, 1H), 4.13 (d, J=11.04 Hz, 2H), 3.78 (d, J=7.03 Hz, 2H), 3.66-3.53 (m, 2H), 3.11-3.05 (m, 1H), 2.27 (s, 3H), 2.20-2.05 (m, 2H), 1.88 (d, J=12.05 Hz, 2H), 1.80-1.64 (m, 6H), 1.25-1.13 (m, 3H), 1.12-0.99 (m, 2H).

LC-MS: (m/z) 330.2 (MH$^+$) $t_R$ (minutes, method 3)=2.49 minutes

Example 5

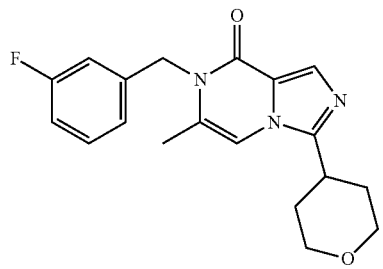 [SMILES: Cc1cn2c(C3CCOCC3)ncc2c(=O)n1Cc1cccc(F)c1]

7-(3-Fluorobenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (50 mg, 0.21 mmol), 1-(bromomethyl)-3-fluorobenzene (60 mg, 0.32 mmol) and K$_2$CO$_3$ (59 mg, 0.43 mmol) in DMF (2 mL) was stirred at 60° C. for 12 hours. The reaction mixture was concentrated in vacuo. The residue was diluted with dichloromethane (20 mL) and washed with water (3×5 mL). The organic layer was dried and concentrated in vacuo. The residue was purified by preparative LC-MS to give 7-(3-fluorobenzyl)-6-methyl-3-(tetrahydro-2H-pyran-4-yl)imidazo[1,5-a]pyrazin-8(7H)-one 20 mg (27%).

$^1$H NMR (CDCl$_3$, 400 MHz): δ 7.94 (s, 1H), 7.34-7.29 (m, 1H), 7.03-6.94 (m, 2H), 6.90 (d, J=9.70 Hz, 1H), 6.77 (s, 1H), 5.23 (s, 2H), 4.14 (d, J=10.14 Hz, 2H), 3.59 (td, J=11.69, 1.76 Hz, 2H), 3.15-3.05 (m, 1H), 2.18 (s, 3H), 2.17-2.08 (m, 2H), 1.90 (d, J=13.45 Hz, 2H).

LC-MS: (m/z) 342.2 (MH$^+$) $t_R$ (minutes, method 3)=2.34 minutes

Example 6

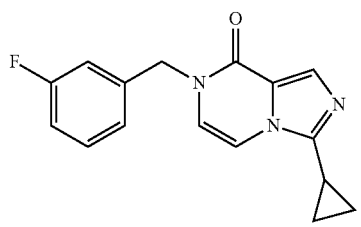 [SMILES: O=c1c2cnc(C3CC3)n2ccn1Cc1cccc(F)c1]

3-Cyclopropyl-7-(3-fluorobenzyl)imidazo[1,5-a]pyrazin-8(7H)-one

To a solution of 3-cyclopropylimidazo[1,5-a]pyrazin-8(7H)-one (300 mg, 1.71 mmol) in anhydrous DMF (5 mL) was added K$_2$CO$_3$ (355 mg, 2.57 mmol) and 1-(bromomethyl)-3-fluorobenzene (388 mg, 2.05 mmol). The mixture was stirred at 65° C. for 16 hours. The mixture was filtered and the filtrate was purified by preparative-HPLC to yield 3-cyclopropyl-7-(3-fluorobenzyl)imidazo[1,5-a]pyrazin-8(7H)-one 280 mg (58%).

$^1$H NMR (DMSO-d$_6$ 400 MHz): δ 7.59-7.56 (m, 2H), 7.36-7.33 (m, 1H), 7.13-7.09 (m, 3H), 6.98 (d, J=6.0 Hz, 1H), 4.98 (s, 2H), 2.29-2.24 (m, 1H), 1.00-0.90 (m, 4H).

LC-MS: (m/z) 284.1 (MH$^+$) $t_R$ (minutes, method 3)=2.23 minutes

Example 7

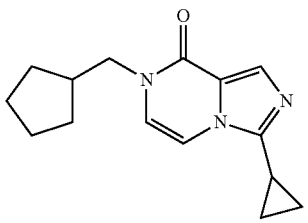 [SMILES: O=c1c2cnc(C3CC3)n2ccn1CC1CCCC1]

7-(Cyclopentylmethyl)-3-cyclopropylimidazo[1,5-a]pyrazin-8(7H)-one

To a solution of 3-cyclopropylimidazo[1,5-a]pyrazin-8(7H)-one (300 mg, 1.71 mmol) in anhydrous DMF (5 mL) was added K$_2$CO$_3$ (355 mg, 2.57 mmol) and (bromomethyl)cyclopentane (335 mg, 2.05 mmol). The reaction was stirred at 65° C. for 16 hours. The mixture was filtered and the filtrate was purified by preparative LC-MS to yield 7-(cyclopentylmethyl)-3-cyclopropylimidazo[1,5-a]pyrazin-8(7H)-one 210 mg (47%).

¹H NMR (DMSO-d₆, 400 MHz): δ 7.53 (s, 1H), 7.51 (d, J=6.0 Hz, 1H), 6.90 (d, J=6.0 Hz, 1H), 3.69 (d, J=7.6 Hz, 2H), 2.29-2.24 (m, 2H), 1.58-1.45 (m, 6H), 1.22-1.19 (m, 2H), 1.00-0.89 (m, 4H).

LC-MS: (m/z) 258.2 (MH⁺) t$_R$ (minutes, method 3)=2.24 minutes

Example 8

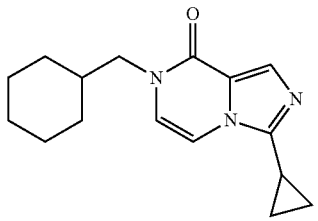 [SMILES: O=c1c2cnc(C3CC3)n2ccn1CC1CCCCC1]

7-(Cyclohexylmethyl)-3-cyclopropylimidazo[1,5-a]pyrazin-8(7H)-one

To a solution of 3-cyclopropylimidazo[1,5-a]pyrazin-8(7H)-one (300 mg, 1.71 mmol) in anhydrous DMF (5 mL) was added K₂CO₃ (355 mg, 2.57 mmol) and (bromomethyl)cyclohexane (363 mg, 2.05 mmol). The reaction was stirred at 65° C. for 16 hours. The reaction mixture was filtered and the filtrate was purified by preparative LC-MS to yield 7-(cyclohexylmethyl)-3-cyclopropylimidazo[1,5-a]pyrazin-8(7H)-one 195 mg (42%).

¹H NMR (DMSO-d₆, 400 MHz): δ 7.53-7.49 (m, 2H), 6.84 (d, J=6.0 Hz, 1H), 3.59 (d, J=7.6 Hz, 2H), 2.27-2.25 (m, 1H), 1.68-1.55 (m, 6H), 1.10-0.89 (m, 9H).

LC-MS: (m/z) 272.2 (MH⁺) t$_R$ (minutes, method 3)=2.40 minutes

Example 9

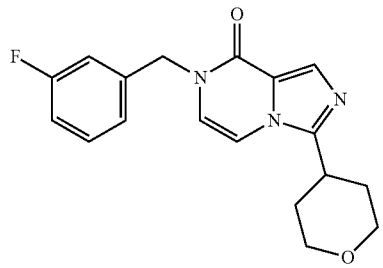 [SMILES: O=c1c2cnc(C3CCOCC3)n2ccn1Cc1cccc(F)c1]

7-(3-Fluorobenzyl)-3-(tetrahydro-2H-pyran-4-yl)imidazo[1,5-a]pyrazin-8(7H)-one

To a solution of 3-(tetrahydro-2H-pyran-4-yl)imidazo[1,5-a]pyrazin-8(7H)-one (200 mg, 0.91 mmol) in anhydrous DMF (5 mL) was added K₂CO₃ (189 mg, 1.37 mmol) and 1-(bromomethyl)-3-fluorobenzene (207 mg, 1.10 mmol). The reaction mixture was stirred at 60° C. for 16 hours. The mixture was filtered and the filtrate was purified by preparative LC-MS to afford 7-(3-fluorobenzyl)-3-(tetrahydro-2H-pyran-4-yl)imidazo[1,5-a]pyrazin-8(7H)-one 190 mg (64%).

¹H NMR (DMSO-d₆, 400 Mhz): δ 7.68 (s, 1H), 7.54 (d, J=6.0 Hz, 1H), 7.36-7.33 (m, 1H), 7.14-7.09 (m, 3H), 6.99 (d, J=6.0 Hz, 1H), 4.99 (s, 2H), 3.91-3.88 (m, 2H), 3.48-3.42 (m, 2H), 3.30-3.29 (m, 1H), 1.81-1.73 (m, 4H).

LC-MS: (m/z) 328.1 (MH⁺) t$_R$ (minutes, method 1)=1.92 minutes

Example 10

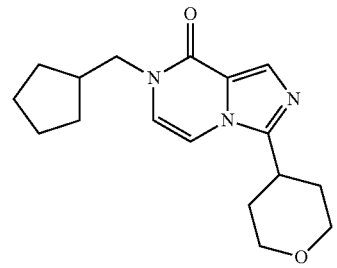 [SMILES: O=c1c2cnc(C3CCOCC3)n2ccn1CC1CCCC1]

7-(Cyclopentylmethyl)-3-(tetrahydro-2H-pyran-4-yl)imidazo[1,5-a]pyrazin-8(7H)-one To a solution of 3-(tetrahydro-2H-pyran-4-yl)imidazo[1,5-a]pyrazin-8(7H)-one (400 mg, 1.82 mmol) in anhydrous DMF (5 mL) was added K₂CO₃ (503 mg, 3.64 mmol) and (bromomethyl)cyclopentane (445 mg, 2.73 mmol). The reaction mixture was stirred at 60° C. for 16 hours. The mixture was filtered and the filtrate was purified by preparative LC-MS to afford 7-(cyclopentylmethyl)-3-(tetrahydro-2H-pyran-4-yl)imidazo[1,5-a]pyrazin-8(7H)-one 290 mg (53%).

¹H NMR (DMSO-d₆, 400 Mhz): δ 7.62 (s, 1H), 7.49 (d, J=6.0 Hz, 1H), 6.90 (d, J=6.0 Hz, 1H), 3.91-3.88 (m, 2H), 3.69 (d, J=7.6 Hz, 2H), 3.48-3.43 (m, 2H), 3.42-3.31 (m, 1H), 2.27-2.24 (m, 1H), 1.78-1.73 (m, 4H), 1.58-1.44 (m, 6H), 1.21-1.20 (m, 2H).

LC-MS: (m/z) 302.2 (MH⁺) t$_R$ (minutes, method 3)=2.29 minutes

Example 11

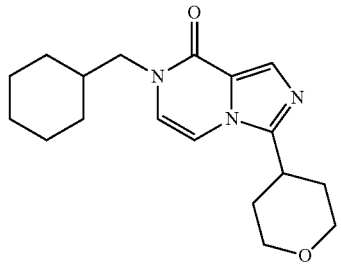 [SMILES: O=c1c2cnc(C3CCOCC3)n2ccn1CC1CCCCC1]

7-(Cyclohexylmethyl)-3-(tetrahydro-2H-pyran-4-yl)imidazo[1,5-a]pyrazin-8(7H)-one To a solution of 3-(tetrahydro-2H-pyran-4-yl)imidazo[1,5-a]pyrazin-8(7H)-one (300 mg, 1.37 mmol) in anhydrous DMF (5 mL) was added K₂CO₃ (379 mg, 2.74 mmol) and (bromomethyl)cyclohexane (364 mg, 2.06 mmol). The reaction mixture was stirred at 60° C. for 16 hours. The mixture was filtered and the filtrate was purified by preparative LC-MS to yield 7-(cyclohexylmethyl)-3-(tetrahydro-2H-pyran-4-yl)imidazo[1,5-a]pyrazin-8(7H)-one 240 mg (55%).

$^1$H NMR (DMSO-$d_6$, 400 Mhz): δ 7.62 (s, 1H), 7.47 (d, J=6.0 Hz, 1H), 6.84 (d, J=6.2 Hz, 1H), 3.91-3.88 (m, 2H), 3.60 (d, J=7.2 Hz, 2H), 3.48-3.42 (m, 2H), 3.30-3.29 (m, 1H), 1.78-1.52 (m, 10H), 1.10-1.06 (m, 3H), 0.93-0.91 (m, 2H). LC-MS: (m/z) 316.2 (MH$^+$) $t_R$ (minutes, method 3)=2.44 minutes.

Example 12

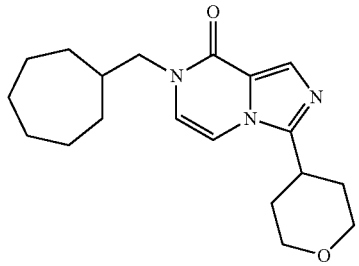 [SMILES: O=c1c2cnc(C3CCOCC3)n2ccn1CC1CCCCCC1]

7-(Cycloheptylmethyl)-3-(tetrahydro-2H-pyran-4-yl)imidazo[1,5-a]pyrazin-8(7H)-one To a solution of 3-(tetrahydro-2H-pyran-4-yl)imidazo[1,5-a]pyrazin-8(7H)-one (300 mg, 1.37 mmol) in anhydrous DMF (4 mL) was added K$_2$CO$_3$ (568 mg, 4.11 mmol) and cycloheptylmethyl methanesulfonate (565 mg, 2.74 mmol). The reaction mixture was stirred at 95° C. for 16 hours. The mixture was filtered and the filtrate was purified by preparative LC-MS to afford 7-(cycloheptylmethyl)-3-(tetrahydro-2H-pyran-4-yl)imidazo[1,5-a]pyrazin-8(7H)-one 140 mg (30%).

$^1$H NMR (DMSO-$d_6$, 400 MHz): δ 7.62 (s, 1H), 6.48 (d, J=5.6 Hz, 1H), 6.87 (d, J=6.0 Hz, 1H), 3.91-3.88 (m, 2H), 3.59 (d, J=7.6 Hz, 2H), 3.48-3.42 (m, 2H), 3.31-3.26 (m, 1H), 1.90-1.73 (m, 5H), 1.57-1.43 (m, 10H), 1.13-1.11 (m, 2H).

LC-MS: (m/z) 330.2 (MH$^+$) $t_R$ (minutes, method 3)=2.58 minutes

Example 13

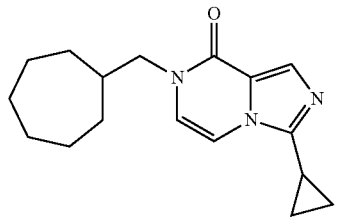 [SMILES: O=c1c2cnc(C3CC3)n2ccn1CC1CCCCCC1]

7-(Cycloheptylmethyl)-3-cyclopropylimidazo[1,5-a]pyrazin-8(7H)-one

To a solution of 3-cyclopropylimidazo[1,5-a]pyrazin-8(7H)-one (300 mg, 1.71 mmol) in anhydrous DMF (4 mL) was added K$_2$CO$_3$ (709 mg, 5.1 mmol) and cycloheptylmethyl methanesulfonate (706 mg, 3.42 mmol). The reaction mixture was stirred at 95° C. for 16 hours. The mixture was filtered and the filtrate was purified by preparative LC-MS to afford 7-(cycloheptylmethyl)-3-cyclopropylimidazo[1,5-a]pyrazin-8(7H)-one 115 mg (24%).

$^1$H NMR (DMSO-$d_6$, 400 MHz): δ 7.55-7.52 (m, 2H), 6.89 (d, J=6.0 Hz, 1H), 3.61 (d, J=7.6 Hz, 2H), 2.32-2.27 (m, 1H), 1.91 (brs, 1H), 1.91-1.02 (m, 12H), 1.01-0.91 (m, 4H).

LC-MS: (m/z) 286.2 (MH$^+$) $t_R$ (minutes, method 3)=2.54 minutes.

Example 14

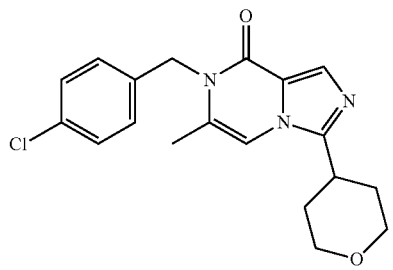 [SMILES: Cc1cn2c(C3CCOCC3)ncc2c(=O)n1Cc1ccc(Cl)cc1]

7-(4-Chlorobenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-4-chlorobenzene (132 mg, 0.643 mmol) and Cs$_2$CO$_3$ (280 mg, 0.857 mmol) in DMF (2.0 mL) was stirred at 70° C. for 12 hours. The reaction mixture was filtered and the filtrate was concentrated in vacuo. The residue was purified by preparative LC-MS to afford 7-(4-chlorobenzyl)-6-methyl-3-(tetrahydro-2H-pyran-4-yl)imidazo[1,5-a]pyrazin-8(7H)-one 53 mg (34%).

$^1$H NMR (CDCl$_3$, 400 MHz): δ 7.93 (s, 1H), 7.30 (d, J=8.4 Hz, 2H), 7.16 (d, J=8.4 Hz, 2H), 6.76 (s, 1H), 5.20 (s, 2H), 4.13 (d, J=10.8 Hz, 2H), 3.62-3.56 (m, 2H), 3.12-3.05 (m, 1H), 2.18 (s, 3H), 2.16-2.09 (m, 2H), 1.89 (d, J=13.2 Hz, 2H).

LC-MS: (m/z) 358.1 (MH$^+$) $t_R$ (minutes, method 3)=2.46 minutes

Example 15

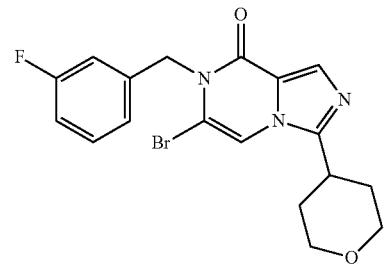 [SMILES: O=c1c2cnc(C3CCOCC3)n2cc(Br)n1Cc1cccc(F)c1]

6-Bromo-7-(3-fluorobenzyl)-3-(tetrahydro-2H-pyran-4-yl)imidazo[1,5-a]pyrazin-8(7H)-one A mixture of 6-bromo-3-(tetrahydro-2H-pyran-4-yl)imidazo[1,5-a]pyrazin-8(7H)-one (100 mg, 0.335 mmol), 1-(bromomethyl)-3-fluorobenzene (95 mg, 0.50 mmol) and $K_2CO_3$ (93 mg, 0.67 mmol) in DMF (2.0 mL) was stirred at 60° C. for 12 hours. The reaction mixture was concentrated in vacuo. The residue was purified by preparative LC-MS to give 6-bromo-7-(3-fluorobenzyl)-3-(tetrahydro-2H-pyran-4-yl)imidazo[1,5-a]pyrazin-8(7H)-one 30 mg (22%).

$^1$H NMR (CDCl$_3$, 400 MHz): δ 7.95 (s, 1H), 7.34-7.27 (m, 1H), 7.18 (s, 1H), 7.11 (d, J=7.6 Hz, 1H), 7.03-6.99 (m, 2H), 5.39 (s, 2H), 4.13 (d, J=12.0 Hz, 2H), 3.62-3.56 (m, 2H), 3.11-3.05 (m, 1H), 2.18-2.08 (m, 2H), 1.88 (d, J=14.0 Hz, 2H).

LC-MS: (m/z) 408.0 (MH$^+$) t$_R$ (minutes, method 3)=2.65 minutes

Example 16

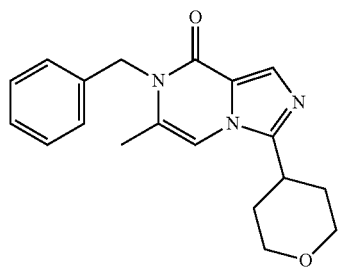 [SMILES: Cc1cn2c(C3CCOCC3)ncc2c(=O)n1Cc1ccccc1]

7-Benzyl-6-methyl-3-(tetrahydro-2H-pyran-4-yl)imidazo[1,5-a]pyrazin-8(7H)-one

A mixture of 6-methyl-3-(tetrahydro-2H-pyran-4-yl)imidazo[1,5-a]pyrazin-8(7H)-one (100 mg, 0.429 mmol), (bromomethyl)benzene (110 mg, 0.643 mmol) and $K_2CO_3$ (119 mg, 0.857 mmol) in DMF (1.0 mL) was stirred at 60° C. for 3 hours. The mixture was filtered and the filtrate was concentrated in vacuo. The residue was purified by preparative LC-MS to yield 7-benzyl-6-methyl-3-(tetrahydro-2H-pyran-4-yl)imidazo[1,5-a]pyrazin-8(7H)-one 39 mg (28%).

$^1$H NMR (CDCl$_3$, 400 MHz): δ 7.93 (s, 1H), 7.35-7.29 (m, 3H), 7.21 (d, J=7.6 Hz, 2H), 6.75 (s, 1H), 5.25 (s, 2H), 4.13 (d, J=11.6 Hz, 2H), 3.61-3.56 (m, 2H), 3.13-3.06 (m, 1H), 2.19 (s, 3H), 2.15-2.08 (m, 2H), 1.89 (d, J=13.2 Hz, 2H).

LC-MS: (m/z) 324.2 (MH$^+$) t$_R$ (minutes, method 3)=2.25 minutes

Example 17

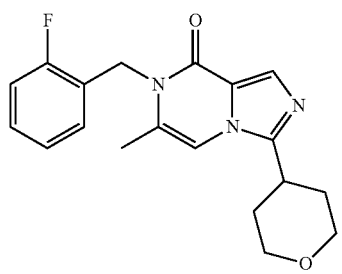 [SMILES: Cc1cn2c(C3CCOCC3)ncc2c(=O)n1Cc1ccccc1F]

7-(2-Fluorobenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-2-fluorobenzene (122 mg, 0.643 mmol) and Cs2CO3 (279 mg, 0.857 mmol) in DMF (2.0 mL) was stirred at 70° C. for 1 hour. The mixture was filtered and the filtrate was concentrated in vacuo. The residue was purified by preparative LC-MS to afford 7-(2-fluorobenzyl)-6-methyl-3-(tetrahydro-2H-pyran-4-yl)imidazo[1,5-a]pyrazin-8(7H)-one 49 mg (33%).

1H NMR (CDCl$_3$, 400 MHz): δ 7.93 (s, 1H), 7.27-7.23 (m, 1H), 7.11-7.06 (m, 3H), 6.77 (s, 1H), 5.28 (s, 2H), 4.13 (d, J=10.4 Hz, 2H), 3.62-3.56 (m, 2H), 3.12-3.07 (m, 1H), 2.19 (s, 3H), 2.16-2.10 (m, 2H), 1.89 (d, J=12.0 Hz, 2H).

LC-MS: (m/z) 342.1 (MH$^+$) t$_R$ (minutes, method 3)=2.30 minutes

Example 18

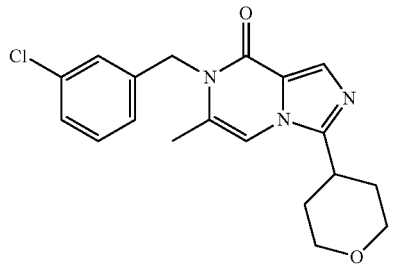 [SMILES: Cc1cn2c(C3CCOCC3)ncc2c(=O)n1Cc1cccc(Cl)c1]

7-(3-Chlorobenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-3-chlorobenzene (132 mg, 0.643 mmol) and $K_2CO_3$ (119 mg, 0.857 mmol) in DMF (1.0 mL) was stirred at 65° C. for 12 hours. To the mixture was added Cs$_2$CO$_3$ (280 mg, 0.857 mmol) and the reaction was stirred at 80° C. for another 1 hour. The reaction mixture was filtered and the filtrate was concentrated in vacuo. The residue was purified by preparative LC-MS to afford 7-(3-chlorobenzyl)-6-methyl-3-(tetrahydro-2H-pyran-4-yl)imidazo[1,5-a]pyrazin-8(7H)-one 49 mg (32%).

$^1$H NMR (CDCl$_3$, 400 MHz): δ 7.92 (s, 1H), 7.25-7.24 (m, 2H), 7.16 (s, 1H), 7.10-7.07 (m, 1H), 6.75 (s, 1H), 5.19 (s, 2H), 4.11 (d, J=10.4 Hz, 2H), 3.60-3.54 (m, 2H), 3.12-3.05 (m, 1H), 2.16 (s, 3H), 2.14-2.07 (m, 2H), 1.87 (d, J=12.0 Hz, 2H).

LC-MS: (m/z) 358.1 (MH$^+$) t$_R$ (minutes, method 3)=2.44 minutes

Example 19

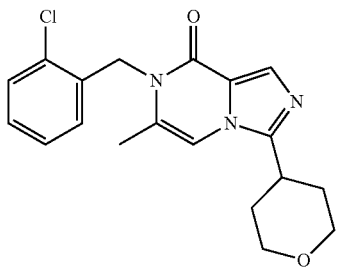

7-(2-Chlorobenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-2-chlorobenzene (132 mg, 0.643 mmol) and $Cs_2CO_3$ (279 mg, 0.857 mmol) in DMF (2.0 mL) was stirred at 80° C. for 12 hours. The mixture was filtered and the filtrate was concentrated in vacuo. The residue was purified by preparative LC-MS to yield 7-(2-chlorobenzyl)-6-methyl-3-(tetrahydro-2H-pyran-4-yl)imidazo[1,5-a]pyrazin-8(7H)-one 55 mg (36%).

$^1$H NMR (CDCl$_3$, 400 MHz): δ 7.95 (s, 1H), 7.42-7.40 (m, 1H), 7.25-7.20 (m, 2H), 6.93 (d, J=7.2 Hz, 1H), 6.80 (s, 1H), 5.32 (s, 2H), 4.14 (d, J=10.8 Hz, 2H), 3.63-3.57 (m, 2H), 3.14-3.07 (m, 1H), 2.20-2.10 (m, 2H), 2.13 (s, 3H), 1.91 (d, J=13.2 Hz, 2H).

LC-MS: (m/z) 358.1 (MH$^+$) $t_R$ (minutes, method 3)=2.46 minutes

Example 20

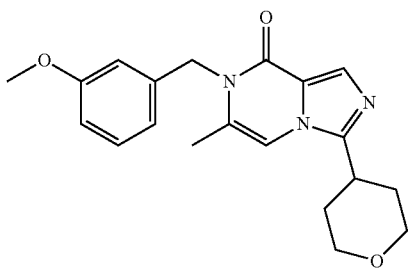 [SMILES: COc1cccc(Cn2c(C)cn3c(C4CCOCC4)ncc3c2=O)c1]

7-(3-Methoxybenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-3-methoxybenzene (129 mg, 0.643 mmol) and $Cs_2CO_3$ (280 mg, 0.857 mmol) in DMF (1.0 mL) was stirred at 80° C. for 12 hours. The reaction mixture was filtered and the filtrate was concentrated in vacuo. The residue was purified by preparative LC-MS to yield 7-(3-methoxybenzyl)-6-methyl-3-(tetrahydro-2H-pyran-4-yl)imidazo[1,5-a]pyrazin-8(7H)-one 68 mg (45%).

$^1$H NMR (CDCl$_3$, 400 MHz): δ 7.92 (s, 1H), 7.27-7.23 (m, 1H), 6.82-6.77 (m, 2H), 6.74 (s, 2H), 5.21 (s, 2H), 4.13 (d, J=10.8 Hz, 2H), 3.78 (s, 3H), 3.62-3.56 (m, 2H), 3.12-3.08 (m, 1H), 2.19 (s, 3H), 2.19-2.10 (m, 2H), 1.89 (d, J=13.2 Hz, 2H).

LC-MS: (m/z) 354.2 (MH$^+$) $t_R$ (minutes, method 3)=2.28 minutes

Example 21

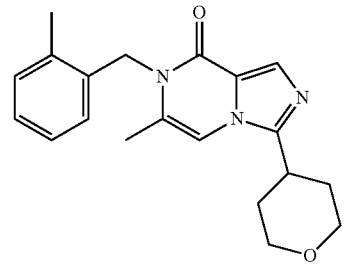 [SMILES: Cc1ccccc1Cn1c(C)cn2c(C3CCOCC3)ncc2c1=O]

6-Methyl-7-(2-methylbenzyl)-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-2-methylbenzene (119 mg, 0.643 mmol) and $K_2CO_3$ (119 mg, 0.857 mmol) in DMF (2.0 mL) was stirred at 60° C. for 12 hours. To the mixture was added additionally $Cs_2CO_3$ (280 mg, 0.86 mmol) and the reaction stirred at 70° C. for another 13 hours. The reaction mixture was filtered and the filtrate was concentrated in vacuo. The residue was purified by preparative LC-MS to afford 6-methyl-7-(2-methylbenzyl)-3-(tetrahydro-2H-pyran-4-yl)imidazo[1,5-a]pyrazin-8(7H)-one 23 mg (16%).

$^1$H NMR (CDCl$_3$, 400 MHz): δ 7.93 (s, 1H), 7.21-7.12 (m, 3H), 6.80 (s, 1H), 6.78 (d, J=7.6 Hz, 1H), 5.18 (s, 2H), 4.15 (d, J=10.8 Hz, 2H), 3.63-3.57 (m, 2H), 3.15-3.09 (m, 1H), 2.40 (s, 3H), 2.20-2.13 (m, 2H), 2.11 (s, 3H), 1.92 (d, J=13.2 Hz, 2H).

LC-MS: (m/z) 338.2 (MH$^+$) $t_R$ (minutes, method 3)=2.37 minutes

Example 22

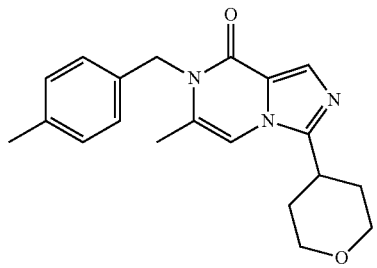 [SMILES: Cc1ccc(Cn2c(C)cn3c(C4CCOCC4)ncc3c2=O)cc1]

6-Methyl-7-(4-methylbenzyl)-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-4-methylbenzene (119 mg, 0.643 mmol)

and Cs₂CO₃ (280 mg, 0.857 mmol) in DMF (2.0 mL) was stirred at 70° C. for 12 hours. The mixture was filtered and the filtrate was concentrated in vacuo. The residue was purified by preparative LC-MS to afford 6-methyl-7-(4-methylbenzyl)-3-(tetrahydro-2H-pyran-4-yl)imidazo[1,5-a]pyrazin-8(7H)-one 68 mg (47%).

¹H NMR (CDCl₃, 400 MHz): δ 7.92 (s, 1H), 7.14-7.09 (m, 4H), 6.74 (s, 1H), 5.20 (s, 2H), 4.13 (d, J=10.4 Hz, 2H), 3.62-3.56 (m, 2H), 3.11-3.06 (m, 1H), 2.32 (s, 3H), 2.19 (s, 3H), 2.19-2.08 (m, 2H), 1.88 (d, J=13.2 Hz, 2H).

LC-MS: (m/z) 338.2 (MH+) tR (minutes, method 3)=2.41 minutes.

Example 23

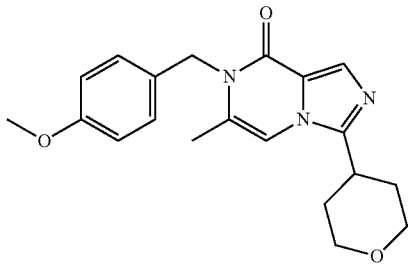 [SMILES: COc1ccc(Cn2c(C)cn3c(C4CCOCC4)ncc3c2=O)cc1]

7-(4-Methoxybenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.43 mmol), 1-(bromomethyl)-4-methoxybenzene (129 mg, 0.643 mmol) and Cs2CO3 (280 mg, 0.857 mmol) in DMF (2.0 mL) was stirred at 70° C. for 12 hours. The mixture was filtered and the filtrate was concentrated in vacuo. The residue was purified by preparative LC-MS to afford 7-(4-methoxybenzyl)-6-methyl-3-(tetrahydro-2H-pyran-4-yl)imidazo[1,5-a]pyrazin-8(7H)-one 60 mg (39%).

¹H NMR (CDCl₃, 400 MHz): δ 7.93 (s, 1H), 7.17 (d, J=8.4 Hz, 2H), 6.86 (d, J=8.4 Hz, 2H), 6.73 (s, 1H), 5.17 (s, 2H), 4.13 (d, J=10.0 Hz, 2H), 3.79 (s, 3H), 3.58 (t, J=12.0 Hz, 2H), 3.11-3.05 (m, 1H), 2.21 (s, 3H), 2.18-2.08 (m, 2H), 1.88 (d, J=13.6 Hz, 2H).

LC-MS: (m/z) 354.2 (MH⁺) t_R (minutes, method 3)=2.26 minutes.

Example 24

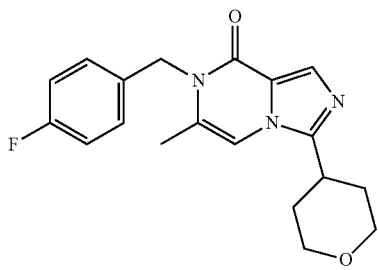 [SMILES: Cc1cn2c(C3CCOCC3)ncc2c(=O)n1Cc1ccc(F)cc1]

7-(4-Fluorobenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-4-fluorobenzene (122 mg, 0.643 mmol) and Cs₂CO₃ (279 mg, 0.857 mmol) in DMF (2.0 mL) was stirred at 70° C. for 12 hours. The mixture was filtered and the filtrate was concentrated in vacuo. The residue was purified by preparative LC-MS to yield 7-(4-fluorobenzyl)-6-methyl-3-(tetrahydro-2H-pyran-4-yl)imidazo[1,5-a]pyrazin-8(7H)-one 30 mg (21%).

¹H NMR (CDCl₃, 400 MHz): δ 7.93 (s, 1H), 7.22-7.19 (m, 2H), 7.04-7.00 (m, 2H), 6.75 (s, 1H), 5.20 (s, 2H), 4.13 (d, J=11.2 Hz, 2H), 3.62-3.60 (m, 2H), 3.17-3.06 (m, 1H), 2.19 (s, 3H), 2.14-2.08 (m, 2H), 1.88 (d, J=13.6 Hz, 2H).

LC-MS: (m/z) 342.1 (MH⁺) t_R (minutes, method 3)=2.30 minutes

Example 25

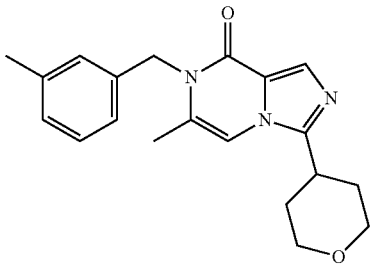 [SMILES: Cc1cccc(Cn2c(C)cn3c(C4CCOCC4)ncc3c2=O)c1]

6-Methyl-7-(3-methylbenzyl)-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 0.429 mmol), 1-(bromomethyl)-3-methylbenzene (119 mg, 0.643 mmol) and Cs₂CO₃ (280 mg, 0.857 mmol) in DMF (1 mL) was stirred at 80° C. for 12 hours. The mixture was filtered and the filtrate was concentrated in vacuo. The residue was purified by preparative LC-MS to afford 6-methyl-7-(3-methylbenzyl)-3-(tetrahydro-2H-pyran-4-yl)imidazo[1,5-a]pyrazin-8(7H)-one 62 mg (43%).

¹H NMR (CDCl₃, 400 MHz): δ 7.93 (s, 1H), 7.21 (t, J=7.2 Hz, 1H), 7.08 (d, J=7.6 Hz, 1H), 7.02-6.98 (m, 2H), 6.74 (s, 1H), 5.21 (s, 2H), 4.13 (d, J=10.8 Hz, 2H), 3.62-3.56 (m, 2H), 3.12-3.07 (m, 1H), 2.33 (s, 3H), 2.19 (s, 3H), 2.19-2.09 (m, 2H), 1.89 (d, J=13.2 Hz, 2H).

LC-MS: (m/z) 338.1 (MH⁺) t_R (minutes, method 3)=2.40 minutes.

Example 26

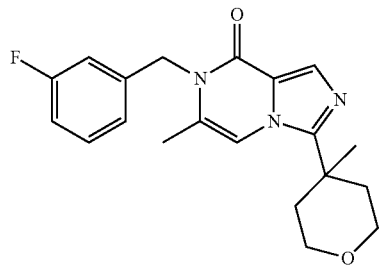 [SMILES: Cc1cn2c(C3(C)CCOCC3)ncc2c(=O)n1Cc1cccc(F)c1]

7-(3-fluorobenzyl)-6-methyl-3-(4-methyltetrahydro-2H-pyran-4-yl)imidazo[1,5-a]pyrazin-8(7H)-one Step 1: To a solution of (3-methoxy-5-methylpyrazin-2-yl)methanamine (150 mg, 0.98 mmol) and 4-methyltetrahydro-2H-pyran-4-carboxylic acid (212 mg, 1.5 mmol) in DCM (6 mL) was added HATU (670 mg, 1.8 mmol) and Et₃N (198 mg, 1.96 mmol). The mixture was stirred at 20-25° C. for 1 hour. The mixture was diluted with DCM (50 mL), washed with water (30 mL) and brine (30 mL). The organic layer was dried over Na₂SO₄ and concentrated in vacuo. The residue was purified by silica gel chromatography (petroleum ether:ethyl acetate=3:1) to give N-((3-methoxy-5-methylpyrazin-2-yl)methyl)-4-methyltetrahydro-2H-pyran-4-carboxamide (250 mg, 91% yield).

Step 2: To a solution of N-((3-methoxy-5-methylpyrazin-2-yl)methyl)-4-methyltetrahydro-2H-pyran-4-carboxamide (300 mg, 1.07 mmol) in dioxane (5 mL) was added POCl₃ (660 mg, 4.3 mmol). The solution was stirred at 80-90° C. for 3 hours. The mixture was concentrated in vacuo, diluted with DCM (50 mL) and slowly added into water (30 mL). The organic layer was washed with brine (20 mL) and dried over Na₂SO₄, concentrated in vacuo to give 8-methoxy-6-methyl-3-(4-methyltetrahydro-2H-pyran-4-yl)imidazo[1,5-a]pyrazine (250 mg, 89% yield).

Step 3: To a solution of 8-methoxy-6-methyl-3-(4-methyltetrahydro-2H-pyran-4-yl)imidazo[1,5-a]pyrazine (200 mg, 0.77 mmol) in dioxane (10 mL) was added 2M HCl(aq) (10 mL). The solution was stirred at 80-90° C. for 1 hour. The mixture was cooled and added saturated aqueous NaHCO₃ (100 mL), extracted with DCM (100 mL×2). The organic layer was washed with brine (50 mL), dried over Na₂SO₄ and concentrated in vacuo to give 6-methyl-3-(4-methyltetrahydro-2H-pyran-4-yl)imidazo[1,5-a]pyrazin-8(7H)-one (160 mg, 68% yield).

LC-MS: $t_R$=0.89 min (method 10), m/z=248.3 [M+H]⁺.

Step 4: To a solution of 6-methyl-3-(4-methyltetrahydro-2H-pyran-4-yl)imidazo[1,5-a]pyrazin-8(7H)-one (200 mg, 0.81 mmol) and 1-(bromomethyl)-3-fluorobenzene (183 mg, 0.97 mmol) in anhydrous DMF (5 mL) was added K₂CO₃ (168 mg, 1.21 mmol). The mixture was stirred at 60-70° C. for 16 h. The mixture was cooled and diluted with water (20 mL), extracted with EtOAc (30 mL×2). The organic layer was washed with brine (20 mL), dried over Na₂SO₄ and concentrated in vacuo. The residue was purified by silica gel chromatography (petroleum ether:ethyl acetate=1:2) to give 7-(3-fluorobenzyl)-6-methyl-3-(4-methyltetrahydro-2H-pyran-4-yl)imidazo[1,5-a]pyrazin-8(7H)-one (90 mg, 31% yield) as a off-white solid.

¹H NMR (CDCl₃ 400 MHz): δ 7.94 (s, 1H), 7.33-7.28 (m, 1H), 7.02-6.91 (m, 4H), 5.22 (s, 2H), 3.85-3.80 (m, 2H), 3.73-3.67 (m, 2H), 2.45-2.41 (m, 2H), 2.17 (s, 3H), 1.86-1.79 (m, 2H), 1.49 (s, 3H).

LC-MS: $t_R$=2.46 min (method 3), m/z=356.2 [M+H]⁺.

Example 27

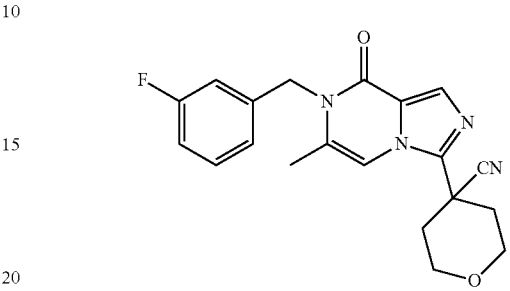

4-(7-(3-fluorobenzyl)-6-methyl-8-oxo-7,8-dihydroimidazo[1,5-a]pyrazin-3-yl)tetrahydro-2H-pyran-4-carbonitrile Step 1: To a solution of (3-methoxy-5-methylpyrazin-2-yl)methanamine (100 mg, 0.65 mmol) and 4-cyanotetrahydro-2H-pyran-4-carboxylic acid (152 mg, 0.98 mmol) in DCM (6 mL) was added HATU (447 mg, 1.18 mmol) and Et₃N (132 mg, 1.31 mmol). The mixture was stirred at 20-25° C. for 1 hour. The mixture was diluted with DCM (30 ml), washed with water (20 mL) and brine (20 mL). The organic layer was dried over Na₂SO₄ and concentrated in vacuo. The residue was purified by silica gel chromatography (petroleum ether:ethyl acetate=1:1) to give 4-cyano-N-((3-methoxy-5-methylpyrazin-2-yl)methyl)tetrahydro-2H-pyran-4-carboxamide (100 mg, 53% yield).

LC-MS: $t_R$=0.61 min (method 2), m/z=290.9 [M+H]⁺.

Step 2: To a solution of 4-cyano-N-((3-methoxy-5-methylpyrazin-2-yl)methyl)tetrahydro-2H-pyran-4-carboxamide (100 mg, 0.34 mmol) in dioxane (5 mL) was added POCl₃ (330 mg, 2.15 mmol). The solution was stirred at 80-90° C. for 2 h. The mixture was cooled and slowly added into water (50 mL), extracted with EtOAc (30 mL×2). The organic layer was washed with brine (20 mL), dried over Na₂SO₄ and concentrated in vacuo to give 4-(8-methoxy-6-methylimidazo[1,5-a]pyrazin-3-yl)tetrahydro-2H-pyran-4-carbonitrile (80 mg, 85% yield).

Step 3: To a solution of 4-(8-methoxy-6-methylimidazo[1,5-a]pyrazin-3-yl)tetrahydro-2H-pyran-4-carbonitrile (80 mg, 0.29 mmol) in dioxane (4 mL) was added 2M HCl(aq) (2 mL). The solution was stirred at 80-90° C. for 2 h. The mixture was concentrated in vacuo and added saturated aqueous NaHCO₃ (50 mL). The mixture was extracted with DCM (50 mL×2). The organic layer was washed with brine (20 mL) and concentrated in vacuo to give 4-(6-methyl-8-oxo-7,8-dihydroimidazo[1,5-a]pyrazin-3-yl)tetrahydro-2H-pyran-4-carbonitrile (70 mg, 92% yield) as a off-white solid.

LC-MS: $t_R$=0.98 min (method 10), m/z=259.2 [M+H]⁺.

Step 4: To a solution of 4-(6-methyl-8-oxo-7,8-dihydroimidazo[1,5-a]pyrazin-3-yl)tetrahydro-2H-pyran-4-carbonitrile (70 mg, 0.27 mmol) in anhydrous DMF (5 mL) was added 1-(bromomethyl)-3-fluoro-benzene (77 mg, 0.41 mmol) and K₂CO₃ (75 mg, 0.54 mmol). The mixture was stirred at 70-80° C. for 2 h. The mixture was cooled and filtered. The filtrate was purified by preparative LC-MS to give 4-(7-(3-fluorobenzyl)-6-methyl-8-oxo-7,8-dihydroimidazo[1,5-a]pyrazin-3-yl)tetrahydro-2H-pyran-4-carbonitrile (65 mg, 65% yield).

¹H NMR (CDCl₃ 400 MHz): δ 7.97 (s, 1H), 7.34-7.31 (m, 1H), 7.16 (s, 1H), 7.02-6.92 (m, 3H), 5.26 (s, 2H), 4.13-4.10 (m, 2H), 3.97-3.91 (m, 2H), 2.50-2.43 (m, 2H), 2.35-2.32 (m, 2H), 2.24 (s, 3H).

LC-MS: $t_R$=2.69 min (method 3), m/z=367.1 [M+H]⁺.

Example 28

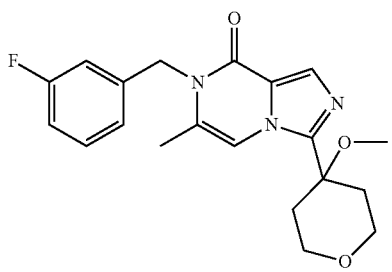 [SMILES: COC1(c2ncc3c(=O)n(Cc4cccc(F)c4)c(C)cn23)CCOCC1]

7-(3-fluorobenzyl)-3-(4-methoxytetrahydro-2H-pyran-4-yl)-6-methylimidazo[1,5-a]pyrazin-8(7H)-one Step 1: To a solution of 3-bromo-6-methylimidazo[1,5-a]pyrazin-8(7H)-one (500 mg, 2.2 mmol) and 1-(bromomethyl)-3-fluorobenzene (497 mg, 2.6 mmol) in DMF (5 mL) was added K₂CO₃ (605 mg, 4.4 mmol). The mixture was stirred at 60° C. for 12 hours. The mixture was diluted with water (20 mL) and extracted with EtOAc (10 mL×3). The combine organic layer was washed with water (10 mL×2); dried over Na2SO4 and evaporated under vacuum to give 3-bromo-7-(3-fluorobenzyl)-6-methylimidazo[1,5-a]pyrazin-8(7H)-one (420 mg, 57% yield).

Step 2: To a solution of 3-bromo-7-(3-fluorobenzyl)-6-methylimidazo[1,5-a]pyrazin-8(7H)-one (200 mg, 0.6 mmol) in THF (10 mL) was added n-BuLi (0.31 mL, 0.77 mmol) at −78° C. The mixture was stirred at −78° C. for 30 minutes. tetrahydro-4H-pyran-4-one (77 mg, 0.77 mmol) was added at −78° C. The mixture was stirred at −78° C. for 1 hour. The mixture was quenched with saturated aqueous NH₄Cl (0.5 mL) and evaporated under vacuum. The residue was dissolved in DCM (20 mL) and washed with water (10 mL). The organic layer was dried over Na₂SO₄ and evaporated. The residue was washed with EtOAc (3 mL) and filtered. The filter cake was dried under vacuum to give 7-(3-fluorobenzyl)-3-(4-hydroxytetrahydro-2H-pyran-4-yl)-6-methylimidazo[1,5-a]pyrazin-8(7H)-one (100 mg, 47% yield).

Step 3: To a solution of 7-(3-fluorobenzyl)-3-(4-hydroxytetrahydro-2H-pyran-4-yl)-6-methylimidazo[1,5-a]pyrazin-8(7H)-one (80 mg, 0.22 mmol) in THF (5 mL) was added NaH (60% in mineral oil, 13.4 mg, 0.36 mmol) at 0° C. The mixture was stirred at 20° C. for 30 minutes. MeI (64 mg, 0.45 mmol) was added at 0° C. The mixture was stirred at 20° C. for 11.5 hours. The mixture was quenched with saturated aqueous NH₄Cl (0.5 mL) and evaporated under vacuum. The residue was dissolved in DCM (10 mL) and washed with water (4 mL). The organic layer was dried over Na₂SO₄ and evaporated. The residue was purified by preparative TLC (EtOAc) to give 7-(3-fluorobenzyl)-3-(4-methoxytetrahydro-2H-pyran-4-yl)-6-methylimidazo[1,5-a]pyrazin-8(7H)-one (25 mg, 30% yield).

¹H NMR (CDCl₃, 400 MHz): δ 7.93 (s, 1H), 7.36 (s, 1H), 7.31 (dd, J=8.0 Hz, J=14.0 Hz, 1H), 7.03-6.92 (m, 3H), 5.23 (s, 2H), 3.91-3.80 (m, 4H), 3.07 (s, 3H), 2.38-2.31 (m, 2H), 2.17 (s, 3H), 2.14-2.10 (m, 2H).

LC-MS: $t_R$=2.73 min (method 3), m/z=372.1 [M+H]⁺.

Example 29

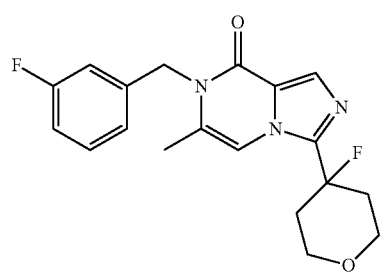

7-(3-fluorobenzyl)-3-(4-fluorotetrahydro-2H-pyran-4-yl)-6-methylimidazo[1,5-a]pyrazin-8(7H)-one Step 1: To a solution of 3-bromo-7-(3-fluorobenzyl)-6-methylimidazo[1,5-a]pyrazin-8(7H)-one (100 mg, 0.3 mmol) in dry THF (5 mL) was added n-BuLi (2.5 M, 0.15 mpL) (2.5 M in n-hexane) dropwise. The mixture was stirred at −78° C. for 0.5 hours. Then tetrahydro-4H-pyran-4-one (45 mg, 0.45 mmol) was added to the mixture. The mixture was stirred at −78° C. for 2 hours. The mixture was quenched with saturated aqueous NH₄Cl (2 mL). The mixture was extracted with DCM (20 mL×2). The combined organic layer was washed with H₂O (10 mL), brine (10 mL), dried over Na₂SO₄, filtered and concentrated to give the crude product. The crude product was purified by flash chromatography on silica gel (1%~10% MeOH in DCM) to give 7-(3-fluorobenzyl)-3-(4-hydroxytetrahydro-2H-pyran-4-yl)-6-methylimidazo[1,5-a]pyrazin-8(7H)-one (40 mg, 38% yield).

LC-MS: $t_R$=0.671 min (method 2), m/z=358.1 [M+H]⁺.

Step 2: To a solution of 7-(3-fluorobenzyl)-3-(4-fluorotetrahydro-2H-pyran-4-yl)-6-methylimidazo[1,5-a]pyrazin-8(7H)-one (40 mg, 111.9 μmol) in dry DCM (4 mL) was added DAST (diethylaminosulfur trifluoride) (28 mg, 170 μmol) at 0° C. The mixture was stirred at 0° C. for 2 hours. Water (10 mL) was added to the mixture. The mixture was extracted with DCM (20 mL×2). The combined organic layer was washed with H₂O (20 mL), dried over Na₂SO₄, filtered and concentrated to give the crude product. The crude product was purified by preparative TLC (DCM/MeOH=10/1) to give 7-(3-fluorobenzyl)-3-(4-fluorotetrahydro-2H-pyran-4-yl)-6-methylimidazo[1,5-a]pyrazin-8(7H)-one (12.83 mg, 32% yield).

¹H NMR (CDCl₃ 400 MHz): δ 7.93 (s, 1H), 7.34-7.28 (m, 1H), 7.21 (s, 1H), 7.01-6.98 (m, 2H), 6.92 (d, J=9.6 Hz, 1H), 5.24 (s, 2H), 4.00-3.89 (m, 4H), 2.57-2.42 (m, 2H), 2.23-2.18 (m, 5H).

LC-MS: $t_R$=2.753 min (method 3), m/z=360.1 [M+H]⁺.

Example 30

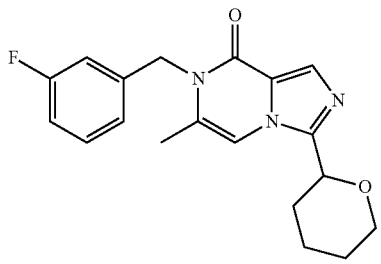 [SMILES: Cc1cn2c(C3CCCCO3)ncc2c(=O)n1Cc1cccc(F)c1]

7-(3-fluorobenzyl)-6-methyl-3-(tetrahydro-2H-pyran-2-yl)imidazo[1,5-a]pyrazin-8(7H)-one, stereoisomer 1 and 2

Step 1: To a solution of (3-methoxy-5-methylpyrazin-2-yl)methanamine (200 mg, 1.31 mmol) in DCM (8 mL) was added tetrahydro-2H-pyran-2-carboxylic acid (255 mg, 1.96 mmol) and HATU (894 mg, 2.35 mmol), Et$_3$N (264 mg, 2.61 mmol). The solution was stirred at 20-25° C. for 1 hour. The mixture was diluted with water (30 mL), extracted with DCM (40 mL×2). The organic layer was washed with brine (20 mL), dried over Na$_2$SO$_4$ and concentrated in vacuo. The residue was purified by silica gel chromatography (petroleum ether:ethyl acetate=1:1) to give N-((3-methoxy-5-methylpyrazin-2-yl)methyl)tetrahydro-2H-pyran-2-carboxamide (250 mg, 72% yield). LC-MS: $t_R$=0.70 min (method 2), m/z=266.2 [M+H]$^+$.

Step 2: To a solution of N-((3-methoxy-5-methylpyrazin-2-yl)methyl)tetrahydro-2H-pyran-2-carboxamide (250 mg, 0.94 mmol) in dioxane (8 mL) was added POCl$_3$ (480 mg, 3.13 mmol). The solution was stirred at 90° C. for 2 h. The mixture was cooled and concentrated in vacuo. The residue was diluted with DCM (50 mL), washed with saturated aqueous NaHCO$_3$ (aq) (50 mL) and brine (50 mL). The organic layer was dried over Na$_2$SO$_4$ and concentrated in vacuo to give 8-methoxy-6-methyl-3-(tetrahydro-2H-pyran-2-yl)imidazo[1,5-a]pyrazine (200 mg, 86% yield).

Step 3: To a solution of 8-methoxy-6-methyl-3-(tetrahydro-2H-pyran-2-yl)imidazo[1,5-a]pyrazine (270 mg, 1.09 mmol) in dioxane (8 mL) was added 2M HCl(aq) (4 mL). The solution was stirred at 90° C. for 1 hour. The mixture was concentrated in vacuo and added saturated aqueous NaHCO$_3$ (50 mL). The mixture was extracted with DCM (50 mL×2). The organic layer was washed with brine (50 mL) and concentrated in vacuo to give 6-methyl-3-(tetrahydro-2H-pyran-2-yl)imidazo[1,5-a]pyrazin-8(7H)-one (200 mg, 79% yield).

Step 4: To a solution of 6-methyl-3-(tetrahydro-2H-pyran-2-yl)imidazo[1,5-a]pyrazin-8(7H)-one (200 mg, 0.86 mmol) in anhydrous DMF (10 mL) was added K$_2$CO$_3$ (237 mg, 1.71 mmol) and 1-(bromomethyl)-3-fluorobenzene (243 mg, 1.29 mmol). The mixture was stirred at 80° C. for 24 h. The mixture was cooled and diluted with water (100 mL), extracted with EtOAc (50 mL×3). The organic layer was washed with brine (50 mL), dried over Na$_2$SO$_4$ and concentrated in vacuo to give 7-(3-fluorobenzyl)-6-methyl-3-(tetrahydro-2H-pyran-2-yl)imidazo[1,5-a]pyrazin-8(7H)-one (130 mg, 44% yield).

Step 5: 7-(3-fluorobenzyl)-6-methyl-3-(tetrahydro-2H-pyran-2-yl)imidazo[1,5-a]pyrazin-8(7H)-one (130 mg, 380.8 μmol) was purified by SFC.

7-(3-fluorobenzyl)-6-methyl-3-(tetrahydro-2H-pyran-2-yl)imidazo[1,5-a]pyrazin-8(7H)-one, stereoisomer 1 (35 mg, 27% yield) was obtained.

$^1$H NMR (CDCl$_3$ 400 MHz): δ 7.91 (s, 1H), 7.32-7.28 (m, 1H), 7.19 (s, 1H), 6.98-6.94 (m, 2H), 6.89 (d, J=9.6 Hz, 1H), 5.23 (s, 2H), 4.76 (t, J=6.4 Hz, 1H), 4.06 (d, J=10.8 Hz, 1H), 3.67 (t, J=10.8 Hz, 1H), 2.23 (s, 3H), 2.17-2.05 (m, 3H), 1.74-1.68 (m, 3H).

LC-MS: $t_R$=2.33 min (method 3), m/z=342.1 [M+H]$^+$. SFC: $t_R$=5.478 min, ee %=99.90%. $[\alpha]_D^{20}$ +16.00 (c=0.10, CHCl$_3$).

7-(3-fluorobenzyl)-6-methyl-3-(tetrahydro-2H-pyran-2-yl)imidazo[1,5-a]pyrazin-8(7H)-one, stereoisomer 2 (33 mg, yield: 35%) was obtained.

$^1$H NMR (CDCl$_3$ 400 MHz): δ 7.92 (s, 1H), 7.32-7.28 (m, 1H), 7.19 (s, 1H), 6.98-6.94 (m, 2H), 6.89 (d, J=9.2 Hz, 1H), 5.23 (s, 2H), 4.77 (t, J=6.8 Hz, 1H), 4.06 (d, J=10.8 Hz, 1H), 3.67 (t, J=10.8 Hz, 1H), 2.17 (s, 3H), 2.12-2.02 (m, 3H), 1.74-1.68 (m, 3H).

LC-MS: $t_R$=2.33 min (method 3), m/z=342.1 [M+H]$^+$. SFC: $t_R$=5.789 min, ee %=98.92%. $[\alpha]_D^{20}$ −23.33 (c=0.10, CHCl$_3$).

Example 31

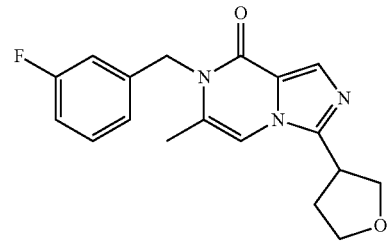 [SMILES: Cc1cn2c(C3CCOC3)ncc2c(=O)n1Cc1cccc(F)c1]

7-(3-fluorobenzyl)-6-methyl-3-(tetrahydrofuran-3-yl)imidazo[1,5-a]pyrazin-8(7H)-one, stereoisomer 1 and 2

Step 1: To a solution of (3-methoxy-5-methylpyrazin-2-yl)methanamine (200 mg, 1.3 mmol) in dry DCM (10 mL) was added tetrahydrofuran-3-carboxylic acid (228 mg, 2.0 mmol), Et$_3$N (265 mg, 2.6 mmol) and HATU (747 mg, 2.0 mmol). The mixture was stirred at 15° C. for 16 hours. Water (10 mL) was added to the mixture. The organic layer was washed with brine (10 mL), dried over Na$_2$SO$_4$, filtered and concentrated to give the crude product. The crude product was purified by flash chromatography on silica gel (10%~100% ethyl acetate in petroleum ether) to give N-((3-methoxy-5-methylpyrazin-2-yl)methyl)tetrahydrofuran-3-carboxamide (200 mg, 61% yield).

Step 2: To a solution of N-((3-methoxy-5-methylpyrazin-2-yl)methyl)tetrahydrofuran-3-carboxamide (300 mg, 1.19 mmol) in dioxane (5 mL) was added POCl$_3$ (366 mg, 2.39 mmol). The mixture was heated at 90° C. for 2 hours. The mixture was cooled to 15° C. and adjusted to pH=8 by saturated aqueous NaHCO$_3$. The aqueous layer was extracted with DCM (20 mL×2). The combined organic layer was washed with H$_2$O (20 ml), brine (20 mL), dried over Na₂SO₄, filtered and concentrated to give 8-methoxy-6-methyl-3-(tetrahydrofuran-3-yl)imidazo[1,5-a]pyrazine (300 mg).

Step 3: To a solution of 8-methoxy-6-methyl-3-(tetrahydrofuran-3-yl)imidazo[1,5-a]pyrazine (300 mg, 1.29 mmol) in dioxane (5 mL) was added 2 N HCl (2 mL). The mixture was heated at 90° C. for 1 hour. The mixture was cooled to 15° C. and extracted with DCM (20 mL×2). The combined organic layer was washed with H₂O (20 mL), brine (20 mL), dried over Na₂SO₄, filtered and concentrated to give 6-methyl-3-(tetrahydrofuran-3-yl)imidazo[1,5-a]pyrazin-8(7H)-one (210 mg, 74% yield).

Step 4: To a solution of 6-methyl-3-(tetrahydrofuran-3-yl)imidazo[1,5-a]pyrazin-8(7H)-one (200 mg, 912.24 μmol) in dry DMF (5 mL) was added 1-(bromomethyl)-3-fluorobenzene (259 mg, 1.37 mmol) and K₂CO₃ (252 mg, 1.82 mmol). The mixture was stirred at 60° C. for 16 hours. The mixture was concentrated and the residue was dissolved in DCM (20 mL) and H₂O (10 mL). The aqueous layer was extracted with DCM (20 mL×2). The combined organic layer was washed with H₂O (20 mL), brine (20 mL), dried over Na₂SO₄, filtered and concentrated to give the crude product. The crude product was purified by flash chromatography on silica gel (10%~100% ethyl acetate in petroleum ether) to give 7-(3-fluorobenzyl)-6-methyl-3-(tetrahydrofuran-3-yl)imidazo[1,5-a]pyrazin-8(7H)-one (40 mg, 13% yield).

Step 5: 7-(3-fluorobenzyl)-6-methyl-3-(tetrahydrofuran-3-yl)imidazo[1,5-a]pyrazin-8(7H)-one (40 mg, 122.2 μmol) was purified by SFC to give 7-(3-fluorobenzyl)-6-methyl-3-(tetrahydrofuran-3-yl)imidazo[1,5-a]pyrazin-8(7H)-one, stereoisomer 1 (16.43 mg, 41% yield).

¹H NMR (CDCl₃ 400 MHz): δ 7.90 (s, 1H), 7.31-7.28 (m, 1H), 6.98-6.93 (m, 2H), 6.89 (d, J=9.2 Hz, 1H), 6.79 (s, 1H), 5.21 (s, 2H), 4.19-4.17 (m, 1H), 4.12-4.09 (m, 1H), 4.05-3.95 (m, 2H), 3.66-3.62 (m, 1H), 2.40 (q, J=7.2 Hz, 2H), 2.16 (s, 3H).

LC-MS: $t_R$=1.964 min (method 3), m/z=328.0 [M+H]⁺. SFC: $t_R$=4.503 min, ee %=99.8%; $[\alpha]_D^{20}$ +14.7 (c=0.10, DCM).

7-(3-fluorobenzyl)-6-methyl-3-(tetrahydrofuran-3-yl)imidazo[1,5-a]pyrazin-8(7H)-one, stereoisomer 2 (15.58 mg, 38% yield).

¹H NMR (CDCl₃ 400 MHz): δ 7.90 (s, 1H), 7.29-7.27 (m, 1H), 6.98-6.92 (m, 2H), 6.89 (d, J=9.6 Hz, 1H), 6.79 (s, 1H), 5.21 (s, 2H), 4.19 (t, J=8.4 Hz, 1H), 4.11-4.09 (m, 1H), 4.05-4.03 (m, 1H), 3.97-3.95 (m, 1H), 3.66-3.62 (m, 1H), 2.38 (q, J=7.6 Hz, 2H), 2.16 (s, 3H).

LC-MS: $t_R$=1.957 min (method 3), m/z=328.0 [M+H]⁺. SFC: $t_R$=4.779 min, ee %=96%; $[\alpha]_D^{20}$ −14.0 (c=0.10, DCM).

Example 32

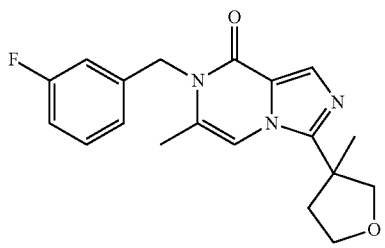 [SMILES: Cc1cn2c(C3(C)CCOC3)ncc2c(=O)n1Cc1cccc(F)c1]

7-(3-fluorobenzyl)-6-methyl-3-(3-methyltetrahydrofuran-3-yl)imidazo[1,5-a]pyrazin-8(7H)-one, stereoisomer 1 and 2

Step 1: To a solution of (3-methoxy-5-methylpyrazin-2-yl)methanamine (200 mg, 1.3 mmol) in DCM (6 mL) was added 3-methyltetrahydrofuran-3-carboxylic acid (255 mg, 1.9 mmol) and HATU (894 mg, 2.4 mmol), Et₃N (264 mg, 2.6 mmol). The solution was stirred at 20-25° C. for 1 hour. Water (40 ml) was added, the mixture was extracted with DCM (40 mL×2). The organic layer was washed with brine (30 mL), dried over Na₂SO₄ and concentrated in vacuo. The residue was purified by silica gel chromatography(petroleum ether:ethyl acetate=1:1) to give N-((3-methoxy-5-methylpyrazin-2-yl)methyl)-3-methyltetrahydrofuran-3-carboxamide (300 mg, 67% yield, 78% purity).

Step 2: To a solution of N-((3-methoxy-5-methylpyrazin-2-yl)methyl)-3-methyltetrahydrofuran-3-carboxamide (400 mg, 1.5 mmol) in dioxane (6 mL) was added POCl₃ (880 mg, 5.7 mmol). The solution was stirred at 80-90° C. for 2 h. The mixture was cooled and concentrated in vacuo. The residue was diluted with DCM (50 mL), washed with saturated aqueous NaHCO₃ (50 mL) and brine (50 mL). The organic layer was dried over Na₂SO₄ and concentrated in vacuo to give 8-methoxy-6-methyl-3-(3-methyltetrahydrofuran-3-yl)imidazo[1,5-a]pyrazine (350 mg, 94% yield).

Step 3: To a solution of 8-methoxy-6-methyl-3-(3-methyltetrahydrofuran-3-yl)imidazo[1,5-a]pyrazine (300 mg, 1.2 mmol) in dioxane (8 mL) was added 2M HCl(aq) (4 mL). The solution was stirred at 80-90° C. for 1 hour. The mixture was concentrated in vacuo and added saturated aqueous NaHCO₃ (50 mL). The mixture was extracted with DCM (50 mL×2). The organic layer was washed with brine (20 mL) and concentrated in vacuo to give 6-methyl-3-(3-methyltetrahydrofuran-3-yl)imidazo[1,5-a]pyrazin-8(7H)-one (260 mg, 92% yield).

Step 4: To a solution of 6-methyl-3-(3-methyltetrahydrofuran-3-yl)imidazo[1,5-a]pyrazin-8(7H)-one (260 mg, 1.1 mmol) in anhydrous DMF (10 mL) was added K₂CO₃ (308 mg, 2.2 mmol) and 1-(bromomethyl)-3-fluorobenzene (316 mg, 1.7 mmol). The mixture was stirred at 70-80° C. for 2 h. The mixture was cooled and diluted with water (50 mL), extracted with EtOAc (50 mL×2). The organic layer was washed with brine (20 mL), dried over Na₂SO₄ and concentrated in vacuo to give 7-(3-fluorobenzyl)-6-methyl-3-(3-methyltetrahydrofuran-3-yl)imidazo[1,5-a]pyrazin-8(7H)-one (160 mg, 42% yield).

Step 5: 7-(3-fluorobenzyl)-6-methyl-3-(3-methyltetrahydrofuran-3-yl)imidazo[1,5-a]pyrazin-8(7H)-one (160 mg, 0.47 mmol) was separated by SFC to give 7-(3-fluorobenzyl)-6-methyl-3-(3-methyltetrahydrofuran-3-yl)imidazo[1,5-a]pyrazin-8(7H)-one, stereoisomer 1 (37 mg, 23% yield) as a off-white solid. ¹H NMR (CDCl₃ 400 MHz): δ 7.88 (s, 1H), 7.32-7.26 (m, 1H), 6.94-6.82 (m, 4H), 5.21 (s, 2H), 4.33 (d, J=8.8 Hz, 1H), 4.07-4.04 (m, 1H), 4.00-3.98 (m, 1H), 3.87 (d, J=8.8 Hz, 1H), 2.62-2.57 (m, 1H), 2.16 (s, 3H), 2.14-2.09 (m, 1H), 1.60 (s, 3H), LC-MS: $t_R$=2.47 min (method 3), m/z=342.1 [M+H]⁺. SFC: $t_R$=4.91 min, ee %>99%. $[\alpha]_D^{20}$ =+5.0 (c=0.10, MeOH).

7-(3-fluorobenzyl)-6-methyl-3-(3-methyltetrahydrofuran-3-yl)imidazo[1,5-a]pyrazin-8(7H)-one, stereoisomer 2 (44 mg, 27% yield) as a off-white solid.

¹H NMR (CDCl₃ 400 MHz): δ 7.82 (s, 1H), 7.24-7.20 (m, 1H), 6.94-6.82 (m, 4H), 5.15 (s, 2H), 4.27 (d, J=8.8 Hz, 1H), 4.01-3.99 (m, 1H), 3.96-3.92 (m, 1H), 3.81 (d, J=8.8 Hz,

1H), 2.57-2.51 (m, 1H), 2.10 (s, 3H), 2.09-2.04 (m, 1H), 1.54 (s, 3H).

LC-MS: $t_R$=2.47 min (method 3), m/z=342.1 [M+H]$^+$.

SFC: $t_R$=5.33 min, ee %>99%. $[\alpha]_D^{20}$ =–3.0 (c=0.10, MeOH).

Example 33

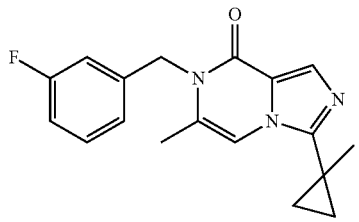 [SMILES: Cc1cn2c(C3(C)CC3)ncc2c(=O)n1Cc1cccc(F)c1]

7-(3-fluorobenzyl)-6-methyl-3-(1-methylcyclopropyl)imidazo[1,5-a]pyrazin-8(7H)-one Step 1: To a solution of 1-methylcyclopropane-1-carboxylic acid (500 mg, 4.99 mmol) in DCM (2 mL) was added (COCl)$_2$ (3.17 g, 24.95 mmol). The solution was stirred at 40° C. for 2 h. The reaction mixture was concentrated in vacuo to give 1-methylcyclopropane-1-carbonyl chloride (500 mg, 85% yield).

Step 2: A solution of (3-methoxy-5-methylpyrazin-2-yl)methanamine (100 mg, 0.65 mmol) in anhydrous DCM (3 mL) was cooled to 0° C. Then a solution of 1-methylcyclopropane-1-carbonyl chloride (100 mg, 0.85 mmol) in anhydous DCM (2 mL) was added dropwise and stirred at 0° C. for 15 min. The mixture was diluted with DCM (20 mL), washed with saturated aqueous NaHCO$_3$ (20 mL), brine (20 mL) and dried over Na$_2$SO$_4$. The organic layer was concentrated in vacuo to give N-((3-methoxy-5-methylpyrazin-2-yl)methyl)-1-methylcyclopropane-1-carboxamide (120 mg, 78% yield).

LC-MS: $t_R$=0.66 min (method 2), m/z=236.1 [M+H]$^+$.

Step 3: To a solution of N-((3-methoxy-5-methylpyrazin-2-yl)methyl)-1-methylcyclopropane-1-carboxamide (120 mg, 0.51 mmol) in dioxane (5 mL) was added POCl$_3$ (590 mg, 3.85 mmol). The solution was stirred at 80-90° C. for 2 h. The mixture was cooled and slowly added into water (50 mL), extracted with EtOAc (30 mL×2). The organic layer was washed with brine (20 mL), dried over Na$_2$SO$_4$ and concentrated in vacuo to give 8-methoxy-6-methyl-3-(1-methylcyclopropyl)imidazo[1,5-a]pyrazine (80 mg, 72% yield).

Step 4: To a solution of 8-methoxy-6-methyl-3-(1-methylcyclopropyl)imidazo[1,5-a]pyrazine (80 mg, 0.37 mmol) in dioxane (5 mL) was added 2M HCl (aq) (2 mL). The solution was stirred at 80-90° C. for 1 hour. The mixture was concentrated in vacuo and added saturated aqueous NaHCO$_3$ (50 mL). The mixture was extracted with DCM (50 mL×2). The organic layer was washed with brine (20 mL) and concentrated in vacuo to give 6-methyl-3-(1-methylcyclopropyl)imidazo[1,5-a]pyrazin-8(7H)-one (70 mg, 94% yield).

Step 5: To a solution of 6-methyl-3-(1-methylcyclopropyl)imidazo[1,5-a]pyrazin-8(7H)-one (70 mg, 0.34 mmol) in anhydrous DMF (4 mL) was added 1-(bromomethyl)-3-fluoro-benzene (98 mg, 0.52 mmol) and K$_2$CO$_3$ (95 mg, 0.69 mmol). The mixture was stirred at 70-80° C. for 1 hour. The mixture was cooled and filtered. The filtrate was purified by preparative LC-MS to give 7-(3-fluorobenzyl)-6-methyl-3-(1-methylcyclopropyl)imidazo[1,5-a]pyrazin-8(7H)-one (35 mg, 32% yield).

$^1$H NMR (CDCl$_3$ 400 MHz): δ 7.84 (s, 1H), 7.33-7.39 (m, 1H), 7.01-6.89 (m, 4H), 5.23 (s, 2H), 2.20 (s, 3H), 1.60 (s, 3H), 1.11-1.09 (m, 2H), 0.88-0.85 (m, 2H).

LC-MS: $t_R$=2.34 min (method 3), m/z=312.1 [M+H]$^+$.

Example 34

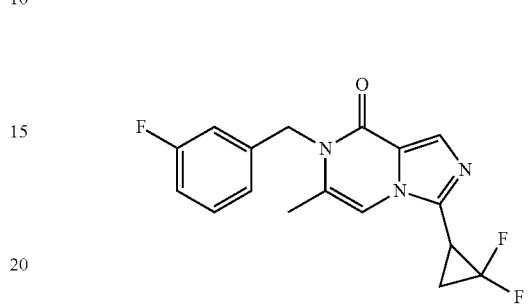

3-(2,2-difluorocyclopropyl)-7-(3-fluorobenzyl)-6-methylimidazo[1,5-a]pyrazin-8(7H)-one Step 1: To a solution of (3-methoxy-5-methylpyrazin-2-yl)methanamine (100 mg, 0.65 mmol) in DCM (5 mL) was added 2,2-difluorocyclopropane-1-carboxylic acid (120 mg, 0.98 mmol) and HATU (447 mg, 1.18 mmol), Et$_3$N (132 mg, 1.31 mmol). The solution was stirred at 20-25° C. for 1 hour. The mixture was diluted with water (20 mL), extracted with DCM (30 mL×2). The organic layer was washed with brine (20 mL), dried over Na$_2$SO$_4$ and concentrated in vacuo. The residue was purified by silica gel chromatography(petroleum ether:ethyl acetate=1:1) to give 2,2-difluoro-N-((3-methoxy-5-methylpyrazin-2-yl)methyl)cyclopropane-1-carboxamide (200 mg, 89% yield, 75% purity).

Step 2. To a solution of 2,2-difluoro-N-((3-methoxy-5-methylpyrazin-2-yl)methyl)cyclopropane-1-carboxamide (200 mg, 0.58 mmol, 75% purity) in dioxane (5 mL) was added POCl$_3$ (1.12 g, 7.3 mmol). The solution was stirred at 90° C. for 2 h. The mixture was cooled and concentrated in vacuo. The residue was diluted with DCM (50 mL), washed with saturated aqueous NaHCO$_3$(aq) (50 mL) and brine (50 mL). The organic layer was dried over Na$_2$SO$_4$ and concentrated in vacuo to give 3-(2,2-difluorocyclopropyl)-8-methoxy-6-methylimidazo[1,5-a]pyrazine (120 mg, 86% yield).

Step 3: To a solution of 3-(2,2-difluorocyclopropyl)-8-methoxy-6-methylimidazo[1,5-a]pyrazine (120 mg, 0.50 mmol) in dioxane (5 mL) was added 2M HCl(aq) (3 mL). The solution was stirred at 80° C. for 1 hour. The mixture was concentrated in vacuo and added saturated aqueous NaHCO$_3$ (50 mL). The mixture was extracted with DCM (50 mL×2). The organic layer was washed with brine (20 mL) and concentrated in vacuo to give 3-(2,2-difluorocyclopropyl)-6-methylimidazo[1,5-a]pyrazin-8(7H)-one (100 mg, 89% yield).

LC-MS: $t_R$=0.94 min (method 10), m/z=226.2 [M+H]$^+$.

Step 4: To a solution of 3-(2,2-difluorocyclopropyl)-6-methylimidazo[1,5-a]pyrazin-8(7H)-one (100 mg, 0.44 mmol) in anhydrous DMF (5 mL) was added K$_2$CO$_3$ (123 mg, 0.89 mmol) and 1-(bromomethyl)-3-fluorobenzene (126 mg, 0.67 mmol). The mixture was stirred at 80° C. for 1 hour. The mixture was cooled and filtered. The filtrate was purified by preparative LC-MS to give 3-(2,2-difluorocyclopropyl)-7-(3-fluorobenzyl)-6-methylimidazo[1,5-a]pyrazin-8(7H)-one (40 mg, 27% yield) as a white solid.

$^1$H NMR (CDCl$_3$ 400 MHz): δ 7.90 (s, 1H), 7.30-7.28 (m, 1H), 6.98-6.84 (m, 4H), 5.28-5.16 (m, 2H), 2.80-2.73 (m, 1H), 2.38-2.37 (m, 1H), 2.19 (s, 3H), 2.05-2.04 (m, 1H).

LC-MS: $t_R$=2.67 min (method 3), m/z=334.1 [M+H]$^+$.

Example 35

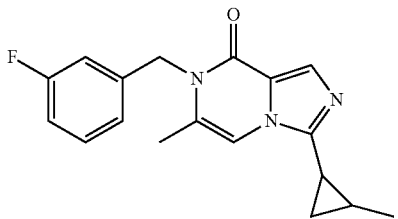 [SMILES: Cc1cn2c(C3CC3C)ncc2c(=O)n1Cc1cccc(F)c1]

7-(3-fluorobenzyl)-6-methyl-3-(2-methylcyclopropyl)imidazo[1,5-a]pyrazin-8(7H)-one, stereoisomer 1, 2, 3 and 4

Step 1: To a solution of (3-methoxy-5-methylpyrazin-2-yl)methanamine (100 mg, 652.8 μmol) and 2-methylcyclopropane-1-carboxylic acid (98 mg, 979.2 μmol) in DCM (5 mL) was added HATU (446.8 mg, 1.2 mmol) and triethylamine (132.1 mg, 1.3 mmol). The mixture was stirred at 24° C. for 16 h. The mixture was diluted with DCM (20 mL) and washed with water (15 mL). The aqueous layer was extracted with DCM (2*30 mL). The combined organic layer was washed with brine (20 mL), dried over Na$_2$SO$_4$, filtered and concentrated. The residue was purified by preparative TLC (ethyl acetate) to give N-((3-methoxy-5-methylpyrazin-2-yl)methyl)-2-methylcyclopropane-1-carboxamide (150 mg, 95% yield).

Step 2: To a solution of N-((3-methoxy-5-methylpyrazin-2-yl)methyl)-2-methylcyclopropane-1-carboxamide (150 mg, 636 μmol) in dioxane (5 mL) was added POCl$_3$ (400 mg, 2.6 mmol). The mixture was stirred at 90° C. for 2 h. The mixture was cooled down to 25° C., neutralized with saturated aqueous NaHCO$_3$ and extracted with ethyl acetate (3×30 mL). The combined organic layer was washed with brine (30 mL), dried over Na$_2$SO$_4$, filtered and concentrated to give the crude 8-methoxy-6-methyl-3-(2-methylcyclopropyl)imidazo[1,5-a]pyrazine (130 mg, 94% yield). This crude product was used directly for the next step.

Step 3: A solution of 8-methoxy-6-methyl-3-(2-methylcyclopropyl)imidazo[1,5-a]pyrazine (120 mg, 552.3 μmol) in dioxane (5 mL) and HCl (2 M, 2 mL) was stirred at 80° C. for 1 hour. The mixture was cooled to 25° C., neutralized with saturated aqueous NaHCO$_3$ and extracted with ethyl acetate (3×20 mL). The combined organic layer was washed with brine (20 mL), dried over Na$_2$SO$_4$, filtered and concentrated to give the crude 6-methyl-3-(2-methylcyclopropyl)imidazo[1,5-a]pyrazin-8(7H)-one (100 mg, 89% yield). This crude product was used directly for the next step.

Step 4: To a solution of 6-methyl-3-(2-methylcyclopropyl)imidazo[1,5-a]pyrazin-8(7H)-one (100 mg, 492.0 μmol) and 1-(bromomethyl)-3-fluorobenzene (139.5 mg, 738.0 μmol) in DMF (5 mL) was added K$_2$CO$_3$ (136 mg, 984 μmol). The mixture was stirred at 60-70° C. for 16 h. The mixture was cooled to 25° C., diluted with water (15 mL), extracted with ethyl acetate (3×30 mL). The combined organic layer was washed with brine (30 mL), dried over Na$_2$SO$_4$, filtered and concentrated. The residue was purified by column chromatography on silica gel (eluent of 0%~50% ethyl acetate in petroleum ether) to give 7-(3-fluorobenzyl)-6-methyl-3-(2-methylcyclopropyl)imidazo[1,5-a]pyrazin-8(7H)-one (80 mg, 52% yield).

Step 5: 7-(3-fluorobenzyl)-6-methyl-3-(2-methylcyclopropyl)imidazo[1,5-a]pyrazin-8(7H)-one (100 mg, 321.2 μmol) was purified by SFC.

7-(3-fluorobenzyl)-6-methyl-3-(2-methylcyclopropyl)imidazo[1,5-a]pyrazin-8(7H)-one, stereoisomer 1 (35 mg, 27% yield) was obtained.

$^1$H NMR (CDCl$_3$ 400 MHz): δ 7.83 (s, 1H), 7.33-7.29 (m, 1H), 7.00-6.94 (m, 2H), 6.91-6.89 (m, 2H), 5.23 (s, 2H), 2.19 (s, 3H), 1.59-1.55 (m, 1H), 1.54-1.50 (m, 1H), 1.35-1.30 (m, 1H), 1.27 (d, J=6.0 Hz, 3H), 0.89-0.88 (m, 1H).

LC-MS: $t_R$=2.03 min (method 3), m/z=312.1 [M+H]$^+$. SFC: $t_R$=4.466 min, ee %>99%. [α]$_D^{20}$ +29.3 (c=0.10, CHCl$_3$).

7-(3-fluorobenzyl)-6-methyl-3-(2-methylcyclopropyl)imidazo[1,5-a]pyrazin-8(7H)-one, stereoisomer 2 (26 mg, 26% yield) was obtained.

$^1$H NMR (CDCl$_3$ 400 MHz): δ 7.84 (s, 1H), 7.32-7.29 (m, 1H), 7.00-6.96 (m, 2H), 6.90-6.89 (m, 2H), 5.23 (s, 2H), 2.19 (s, 3H), 1.62-1.60 (m, 1H), 1.55-1.53 (m, 1H), 1.36-1.34 (m, 1H), 1.27 (d, J=5.6 Hz, 3H), 0.91-0.89 (m, 1H).

LC-MS: $t_R$=2.02 min (method 3), m/z=312.1 [M+H]$^+$. SFC: $t_R$=5.227 min, ee %>99%. [α]$_D^{20}$ −15.0 (C=0.10, CHCl$_3$).

7-(3-fluorobenzyl)-6-methyl-3-(2-methylcyclopropyl)imidazo[1,5-a]pyrazin-8(7H)-one, stereoisomer 3 (8.0 mg, 8% yield) was obtained.

$^1$H NMR (CDCl$_3$ 400 MHz): δ 7.89 (s, 1H), 7.33-7.30 (m, 1H), 7.01-6.91 (m, 4H), 5.29 (d, J=16.0 Hz, 1H), 5.17 (d, J=16.0 Hz, 1H), 2.19 (s, 3H), 2.01-1.97 (m, 1H), 1.39-1.27 (m, 1H), 1.23-1.20 (m, 2H), 0.91 (d, J=6.0 Hz, 3H).

LC-MS: $t_R$=1.98 min (method 3), m/z=312.1 [M+H]$^+$. SFC: $t_R$=6.995 min, ee %>99%. [α]$_D^{20}$ +37.0 (c=0.10, CHCl$_3$).

7-(3-fluorobenzyl)-6-methyl-3-(2-methylcyclopropyl)imidazo[1,5-a]pyrazin-8(7H)-one, stereoisomer 4 (9.0 mg, 9% yield) was obtained.

$^1$H NMR (CDCl$_3$ 400 MHz): δ 7.86 (s, 1H), 7.29-7.26 (m, 1H), 6.99-6.88 (m, 4H), 5.27 (d, J=16.0 Hz, 1H), 5.15 (d, J=16.0 Hz, 1H), 2.17 (s, 3H), 1.97-1.95 (m, 1H), 1.58-1.53 (m, 1H), 1.23-1.20 (m, 2H), 0.91 (d, J=6.0 Hz, 3H).

LC-MS: $t_R$=1.98 min (method 3), m/z=312.1 [M+H]$^+$. SFC: $t_R$=8.704 min, ee %>99%. [α]$_D^{20}$ −66.7 (c=0.10, CHCl$_3$).

Example 36

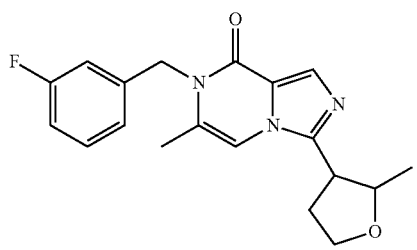 [SMILES: Cc1cn2c(C3CCOC3C)ncc2c(=O)n1Cc1cccc(F)c1]

7-(3-fluorobenzyl)-6-methyl-3-(2-methyltetrahydrofuran-3-yl)imidazo[1,5-a]pyrazin-8(7H)-one, stereoisomer 1, 2, 3 and 4

Step 1: To a solution of (3-methoxy-5-methylpyrazin-2-yl)methanamine (300 mg, 2.0 mmol), 2-methyltetrahydrofuran-3-carboxylic acid (382 mg, 2.9 mmol) in DCM (10 mL) was added HATU (1.3 g, 3.5 mmol) and triethylamine (396 mg, 3.9 mmol). The mixture was stirred at 24° C. for 16 h. The mixture was diluted with DCM (30 mL) and washed with water (20 mL). The aqueous layer was extracted with DCM (2×30 mL). The combined organic layer was washed with brine (30 mL), dried over Na$_2$SO$_4$, filtered and concentrated. The residue was purified by column chromatography on silica gel (0%~70% ethyl acetate in petroleum ether) to give N-((3-methoxy-5-methylpyrazin-2-yl)methyl)-2-methyltetrahydrofuran-3-carboxamide (350 mg, 62% yield).

Step 2: To a solution of N-((3-methoxy-5-methylpyrazin-2-yl)methyl)-2-methyltetrahydrofuran-3-carboxamide (350 mg, 1.3 mmol) in dioxane (5 mL) was added POCl$_3$ (720 mg, 4.7 mmol). The mixture was stirred at 90° C. for 2 h. The mixture was cooled to 25° C., neutralized with saturated aq.NaHCO$_3$ and extracted with ethyl acetate (2×30 mL). The combined organic layer was washed with brine (20 mL), dried over Na$_2$SO$_4$, filtered and concentrated to give crude 8-methoxy-6-methyl-3-(2-methyltetrahydrofuran-3-yl)imidazo[1,5-a]pyrazine (320 mg). The crude was used directly for the next step.

Step 3: A solution of 8-methoxy-6-methyl-3-(2-methyltetrahydrofuran-3-yl)imidazo[1,5-a]pyrazine (320 mg, 1.3 mmol) in dioxane (5 mL) and HCl (2 M, 2 mL) was stirred at 80° C.-90° C. for 21.5 hours. The mixture was cooled down to 25° C., neutralized with saturated aq.NaHCO$_3$, extracted with DCM (3×30 mL). The combined organic layer was washed with brine (30 mL), dried over Na$_2$SO$_4$, filtered and concentrated to give crude 6-methyl-3-(2-methyltetrahydrofuran-3-yl)imidazo[1,5-a]pyrazin-8(7H)-one (300 mg). The crude product was used directly for the next step.

Step 4: To a solution of 6-methyl-3-(2-methyltetrahydrofuran-3-yl)imidazo[1,5-a]pyrazin-8(7H)-one (250 mg, 1.1 mmol) in DMF (8 mL) was added 1-(bromomethyl)-3-fluorobenzene (304 mg, 1.6 mmol) and K$_2$CO$_3$ (296 mg, 2.1 mmol). The mixture was stirred at 60-70° C. for 16 h. The mixture was cooled down to 25° C. and diluted with water (15 mL), extracted with ethyl acetate (3×30 mL). The combined organic layer was washed with brine (30 mL), dried over Na$_2$SO$_4$, filtered and concentrated. The residue was purified by column chromatography on silica gel (eluent of 0%~30% ethyl acetate in petroleum ether) to give 7-(3-fluorobenzyl)-6-methyl-3-(2-methyltetrahydrofuran-3-yl)imidazo[1,5-a]pyrazin-8(7H)-one (170 mg, 47% yield).

Step 5: 7-(3-fluorobenzyl)-6-methyl-3-(2-methyltetrahydrofuran-3-yl)imidazo[1,5-a]pyrazin-8(7H)-one (220 mg, 644 μmol) was purified by SFC.

7-(3-fluorobenzyl)-6-methyl-3-(2-methyltetrahydrofuran-3-yl)imidazo[1,5-a]pyrazin-8(7H)-one, stereoisomer 1 (20 mg, 9% yield).

$^1$H NMR (CDCl$_3$ 400 MHz 400 MHz): δ 7.95 (s, 1H), 7.34-7.28 (m, 1H), 7.01-6.89 (m, 3H), 6.79 (s, 1H), 5.23 (s, 2H), 4.35-4.30 (m, 1H), 4.13-4.07 (m, 2H), 3.12-3.06 (m, 1H), 2.50-2.37 (m, 2H), 2.19 (s, 3H), 1.35 (d, J=6.0 Hz, 3H).

LC-MS: t$_R$=2.12 min (method 3), m/z=342.1 [M+H]$^+$.

SFC: t$_R$=4.812 min, ee %>99%. [α]$_D^{20}$ −24.3 (c=0.10, CHCl$_3$).

7-(3-fluorobenzyl)-6-methyl-3-(2-methyltetrahydrofuran-3-yl)imidazo[1,5-a]pyrazin-8(7H)-one, stereoisomer 2 (10 mg, 5% yield).

$^1$H NMR (CDCl$_3$ 400 MHz): δ 7.93 (s, 1H), 7.31-7.26 (m, 1H), 6.99-6.87 (m, 3H), 6.76 (s, 1H), 5.21 (s, 2H), 4.32-4.27 (m, 1H), 4.10-4.04 (m, 2H), 3.10-3.03 (m, 1H), 2.48-2.35 (m, 2H), 2.17 (s, 3H), 1.33 (d, J=6.4 Hz, 3H).

LC-MS: t$_R$=2.07 min (method 3), m/z=342.1 [M+H]$^+$.

SFC: t$_R$=5.088 min, ee %=97.9%. [α]$_D^{20}$ +10.3 (c=0.10, CHCl$_3$).

7-(3-fluorobenzyl)-6-methyl-3-(2-methyltetrahydrofuran-3-yl)imidazo[1,5-a]pyrazin-8(7H)-one, stereoisomer 3 (38.0 mg, 17% yield).

$^1$H NMR (CDCl$_3$ 400 MHz): δ 7.95 (s, 1H), 7.31-7.29 (m, 1H), 7.01-6.89 (m, 3H), 6.83 (s, 1H), 5.29 (d, J=16.4 Hz, 1H), 5.17 (d, J=16.4 Hz, 1H), 4.35-4.28 (m, 2H), 3.91-3.87 (m, 1H), 3.71-3.67 (m, 1H), 2.72-2.67 (m, 1H), 2.44-2.40 (m, 1H), 2.18 (s, 3H), 0.90 (d, J=6.4 Hz, 3H).

LC-MS: t$_R$=2.02 min (method 3), m/z=342.1 [M+H]$^+$.
SFC: t$_R$=5.516 min, ee %>99%. [α]$_D^{20}$ +46.3 (c=0.10, CHCl$_3$).

7-(3-fluorobenzyl)-6-methyl-3-(2-methyltetrahydrofuran-3-yl)imidazo[1,5-a]pyrazin-8(7H)-one, stereoisomer 4 (30.0 mg, 14% yield). $^1$H NMR (CDCl$_3$ 400 MHz): δ 7.95 (s, 1H), 7.33-7.30 (m, 1H), 7.01-6.90 (m, 3H), 6.83 (s, 1H), 5.29 (d, J=16.4 Hz, 1H), 5.17 (d, J=16.4 Hz, 1H), 4.37-4.28 (m, 2H), 3.91-3.87 (m, 1H), 3.71-3.69 (m, 1H), 2.72-2.68 (m, 1H), 2.45-2.40 (m, 1H), 2.18 (s, 3H), 0.90 (d, J=6.8 Hz, 3H).

LC-MS: t$_R$=1.98 min (method 3), m/z=342.1 [M+H]$^+$.
SFC: t$_R$=6.304 min, ee %>99%. [α]$_D^{20}$ −47.0 (c=0.10, CHCl$_3$).

Example 37

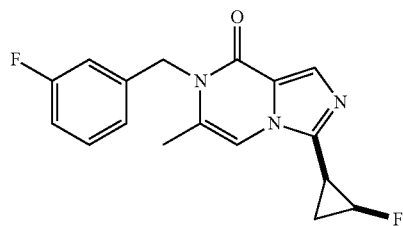

7-(3-fluorobenzyl)-3-(cis-2-fluorocyclopropyl)-6-methylimidazo[1,5-a]pyrazin-8(7H)-one, stereoisomer 1 and 2

Step 1: A solution of (3-methoxy-5-methylpyrazin-2-yl)methanamine hydrochloride (400 mg, 2.1 mmol) and triethylamine (662 mg, 6.5 mmol) in DCM (8 mL) was cooled to 0° C., 2-fluorocyclopropane-1-carbonyl chloride (251 mg, 2.1 mmol) was added dropwise and the mixture was stirred at 0° C. for 0.5 h. The mixture was diluted with water (10 mL), extracted with DCM (20 mL×2). The organic layer was washed with brine (20 mL), dried over Na$_2$SO$_4$ and concentrated in vauco. The residue was purified by preparative TLC (petroleum ether:ethyl acetate=1:1) to give cis-2-fluoro-N-((3-methoxy-5-methylpyrazin-2-yl)methyl)cyclopropane-1-carboxamide (200 mg, 40% yield) and (1 S, 2R)-2-fluoro-N-((3-methoxy-5-methylpyrazin-2-yl)methyl)cyclopropane-1-carboxamide (200 mg, 40% yield) all.

Step 2: To a solution of cis-2-fluoro-N-((3-methoxy-5-methylpyrazin-2-yl)methyl)cyclopropane-1-carboxamide (260 mg, 1.1 mmol) in dioxane (10 mL) was added POCl$_3$ (500 mg, 3.3 mmol). The solution was stirred at 80-90° C. for 2 h. The mixture was concentrated in vacuo and diluted with NaHCO$_3$ (30 mL), extracted with DCM (50 mL×2). The organic layer was washed with brine (30 mL), dried over Na$_2$SO$_4$ and concentrated in vacuo to give 3-(cis-2-fluorocyclopropyl)-8-methoxy-6-methylimidazo[1,5-a]pyrazine (220 mg, 91% yield).

Step 3: A solution of 3-(cis-2-fluorocyclopropyl)-8-methoxy-6-methylimidazo[1,5-a]pyrazine (220 mg, 994 μmol) in 2N HCl (aq) (5 mL) and dioxane (10 mL) was stirred at 80-90° C. for 1 hour. The mixture was concentrated in vacuo. The residue was diluted with NaHCO$_3$(aq) (30 mL), extracted with DCM (30 mL×3). The organic layer was washed with brine (30 mL), dried over Na$_2$SO$_4$ and concentrated in vacuo to give 3-(cis-2-fluorocyclopropyl)-6-methylimidazo[1,5-a]pyrazin-8(7H)-one (200 mg, 97% yield).

Step 4: To a solution of 3-(cis-2-fluorocyclopropyl)-6-methyl imidazo[1,5-a]pyrazin-8(7H)-one (200 mg, 965 μmol) in anhydrous DMF (10 mL) was added K$_2$CO$_3$ (133 mg, 965 μmol) and 1-(bromomethyl)-3-fluorobenzene (274 mg, 1.5 mmol). The mixture was stirred at 60-70° C. for 16 h and 80° C. for 21 h. The mixture was cooled and filtered and he filtrate was purified by preparative LC-MS to give 7-(3-fluorobenzyl)-3-(cis-2-fluorocyclopropyl)-6-methyl-imidazo[1,5-a]pyrazin-8(7H)-one (80 mg, 26% yield).

Step 5: 7-(3-fluorobenzyl)-3-(cis-2-fluorocyclopropyl)-6-methylimidazo[1,5-a]pyrazin-8(7H)-one (80 mg, 253 μmol) was separated by SFC.

7-(3-fluorobenzyl)-3-(cis-2-fluorocyclopropyl)-6-methylimidazo[1,5-a]pyrazin-8(7H)-one, stereoisomer 1 (25 mg, 30% yield).

$^1$H NMR (CDCl$_3$ Varian_H_400 MHz): δ 7.92 (s, 1H), 7.32-7.26 (m, 1H), 7.00-6.88 (m, 4H), 5.29-5.15 (m, 2H), 5.02-4.84 (m, 1H), 2.18 (s, 3H), 2.12-1.99 (m, 2H), 1.44-1.25 (m, 1H).

LC-MS: $t_R$=2.00 min (method 8), m/z=316.1 [M+H]$^+$. SFC: $t_R$=6.53 min, ee %>99%. $[\alpha]_D^{20}$ −84.00 (c=0.10, MeOH).

7-(3-fluorobenzyl)-3-(cis-2-fluorocyclopropyl)-6-methylimidazo[1,5-a]pyrazin-8(7H)-one, stereoisomer 2 (15 mg, 18% yield). $^1$H NMR (CDCl$_3$ Varian_H_400 MHz): δ 7.93 (s, 1H), 7.33-7.30 (m, 1H), 7.00-6.90 (m, 4H), 5.31-5.17 (m, 2H), 5.04-4.86 (m, 1H), 2.20 (s, 3H), 2.12-2.00 (m, 2H), 1.46-1.42 (m, 1H).

LC-MS: $t_R$=1.99 min (method 8), m/z=316.1 [M+H]$^+$. SFC: $t_R$=5.06 min, ee %>99%. $[\alpha]_D^{20}$ +75.00 (c=0.10, MeOH).

Example 38

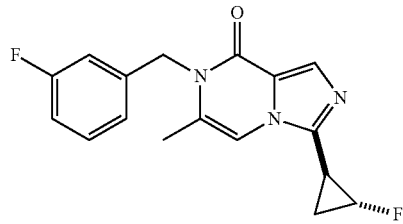

7-(3-fluorobenzyl)-3-(trans-2-fluorocyclopropyl)-6-methylimidazo[1,5-a]pyrazin-8(7H)-one, stereoisomer 1 and 2

Step 1: To a solution of trans-2-fluoro-N-((3-methoxy-5-methylpyrazin-2-yl)methyl)cyclopropane-1-carboxamide (280 mg, 1.1 mmol) in dioxane (10 mL) was added POCl$_3$ (540 mg, 3.5 mmol). The solution was stirred at 80-90° C. for 2 h. The mixture was concentrated in vacuo and diluted with NaHCO$_3$ (30 mL), extracted with DCM (50 mL×2). The organic layer was washed with brine (30 mL), dried over Na$_2$SO$_4$ and concentrated in vacuo to give 3-(trans-2-fluorocyclopropyl)-8-methoxy-6-methylimidazo[1,5-a]pyrazine (240 mg, 93% yield).

Step 2: A solution of 3-(trans-2-fluorocyclopropyl)-8-methoxy-6-methylimidazo[1,5-a]pyrazine (240 mg, 1.1 mmol) in 2N HCl (aq) (5 mL) and dioxane (10 mL) was stirred at 80-90° C. for 1 hour. The mixture was concentrated in vacuo. The residue was diluted with NaHCO$_3$(aq) (30 mL), extracted with DCM (30 mL×3). The organic layer was washed with brine (30 mL), dried over Na$_2$SO$_4$ and concentrated in vacuo to give 3-(trans-2-fluorocyclopropyl)-6-methylimidazo[1,5-a]pyrazin-8(7H)-one (220 mg, 98% yield).

Step 3: To a solution of 3-(trans-2-fluorocyclopropyl)-6-methylimidazo[1,5-a]pyrazin-8(7H)-one (220 mg, 1.1 mmol) in anhydrous DMF (10 mL) was added K$_2$CO$_3$ (293 mg, 2.1 mmol) and 1-(bromomethyl)-3-fluorobenzene (300 mg, 1.6 mmol). The mixture was stirred at 60-70° C. for 16 h and 80° C. for 21 h. The mixture was cooled and filtered and the filtrate was purified by preparative LC-MS to give 7-(3-fluorobenzyl)-3-(trans-2-fluorocyclopropyl)-6-methylimidazo[1,5-a]pyrazin-8(7H)-one (250 mg, 77% yield).

Step 4: 7-(3-fluorobenzyl)-3-(trans-2-fluorocyclopropyl)-6-methylimidazo[1,5-a]pyrazin-8(7H)-one (250 mg, 793 μmol) was separated by SFC.

7-(3-fluorobenzyl)-3-(trans-2-fluorocyclopropyl)-6-methylimidazo[1,5-a]pyrazin-8(7H)-one, stereoisomer 1 (15 mg, 17% yield).

$^1$H NMR (CDCl$_3$ 400 MHz): δ 7.81 (s, 1H), 7.31-7.27 (m, 1H), 6.98-6.86 (m, 4H), 5.22 (s, 2H), 5.01-4.84 (m, 1H), 2.43-2.38 (m, 1H), 2.19 (s, 3H), 1.72-1.65 (m, 1H), 1.58-1.55 (m, 1H).

LC-MS: $t_R$=2.24 min (method 8), m/z=316.1 [M+H]$^+$. SFC: $t_R$=2.83 min, ee %>99%. $[\alpha]_D^{20}$ +29.00 (c=0.10, MeOH).

7-(3-fluorobenzyl)-3-(trans-2-fluorocyclopropyl)-6-methylimidazo[1,5-a]pyrazin-8(7H)-one, stereoisomer 2 (45 mg, 17% yield).

$^1$H NMR (CDCl$_3$ 400 MHz): δ 7.81 (s, 1H), 7.29-7.28 (m, 1H), 6.98-6.86 (m, 4H), 5.22 (s, 2H), 5.01-4.84 (m, 1H), 2.45-2.38 (m, 1H), 2.19 (s, 3H), 1.71-1.64 (m, 1H), 1.59-1.54 (m, 1H).
LC-MS: $t_R$=2.23 min (method 8), m/z=316.1 [M+H]⁺. SFC: $t_R$=3.69 min, ee %>99%. $[\alpha]_D^{20}$ −31 (c=0.10, MeOH).

Example 39

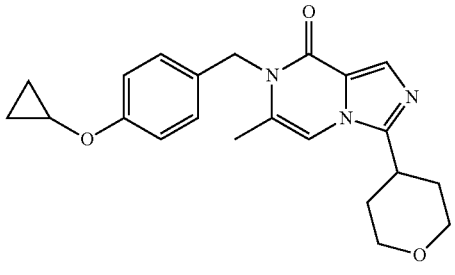 [SMILES: Cc1cn2c(C3CCOCC3)ncc2c(=O)n1Cc1ccc(OC2CC2)cc1]

7-(4-cyclopropoxybenzyl)-6-methyl-3-(tetrahydro-2H-pyran-4-yl)imidazo[1,5-a]pyrazin-8(7H)-one Step 1: A solution of 1-bromo-4-cyclopropoxybenzene (900 mg, 4.22 mmol) in THF (20 mL, anhydrous) was added n-BuLi (2.5 M, 2.6 mL) at −78° C. and stirred at −78° C. for 2 hours under N₂. Then, thereto was added dropwise DMF (926 mg, 12.66 mmol, anhydrous) at −78° C. and it was stirred for 2 hours. The solution was quenched with NH₄Cl (aq. 1 mL) at −78° C. and stirred at 0° C. for 0.5 hour. The mixture was diluted with ethyl acetate (10 mL). The mixture was filtered and the filtrate was concentrated under vacuum. The residue was diluted with ethyl acetate (30 mL), washed with brine (3×15 mL). The organic layer was dried with anhydrous Na2SO4, filtered and concentrated in vacuum to give 4-cyclopropoxybenzaldehyde (700 mg). LC-MS: $t_R$=0.800 min (method 2), m/z=162.8 [M+H]⁺.

Step 2: A solution of 4-cyclopropoxybenzaldehyde (700 mg) in MeOH (15 mL, anhydrous) was added NaBH₄ (319 mg, 8.44 mmol) at 0° C. and stirred at 0° C. for 1 hour. The solution was quenched with saturated aqueous NH₄Cl (aq. 0.5 mL). The mixture was concentrated under vacuum. The residue was purified by silica gel chromatography petroleum ether/ethyl acetate=10/1, 1/1) to give (4-cyclopropoxyphenyl)methanol (540 mg, 78% yield).

Step 3: A solution of (4-cyclopropoxyphenyl)methanol (500 mg, 3.1 mmol) and Et₃N (617 mg, 6.1 mmol) in anhydrous DCM (10 mL) was cooled to 0° C., then MsCl (1.41 g, 12.3 mmol) was added dropwise. The solution was stirred at 0° C. for 0.5 h. The mixture was diluted with water (50 mL), extracted with DCM (50 mL×2). The organic layer was washed with brine (30 mL), dried over Na₂SO₄ and concentrated in vacuo to afford 4-cyclopropoxybenzyl methanesulfonate (600 mg, 81% yield).

Step 4: A mixture of 6-methyl-3-(tetrahydro-2H-pyran-4-yl)imidazo[1,5-a]pyrazin-8(7H)-one (250 mg, 1.07 mmol), 4-cyclopropoxybenzyl methanesulfonate (311 mg, 1.28 mmol) and Cs₂CO₃ (698 mg, 2.14 mmol) in DMF (6.0 mL, anhydrous) was stirred at 60° C. for 12 hours. The mixture was filtered and the filtrate was concentrated under vacuum. The residue was purified by silica gel chromatography (petroleum ether/ethyl acetate=10/1, 0/1) to give 7-(4-cyclopropoxybenzyl)-6-methyl-3-(tetrahydro-2H-pyran-4-yl)imidazo[1,5-a]pyrazin-8(7H)-one (320 mg, 77% yield).

¹H NMR (CDCl₃, 400 MHz): δ 7.92 (s, 1H), 7.15 (d, J=8.8 Hz, 2H), 6.99 (d, J=8.8 Hz, 2H), 6.73 (s, 1H), 5.17 (s, 2H), 4.12 (d, J=10.4 Hz, 2H), 3.71-3.69 (m, 1H), 3.67-3.55 (m, 2H), 3.09-3.07 (m, 1H), 2.21 (s, 3H), 2.18-2.03 (m, 2H), 1.88 (d, J=13.2 Hz, 2H), 0.79-0.71 (m, 4H).
LC-MS: $t_R$=2.154 min (method 3), m/z=380.1 [M+H]⁺.

Example 40

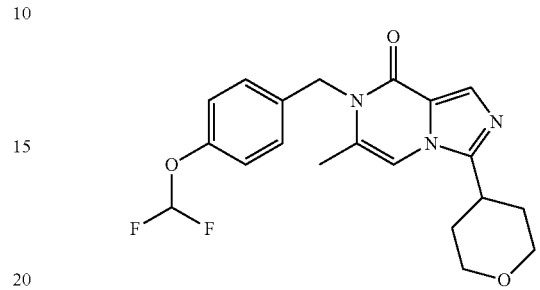

7-(4-(difluoromethoxy)benzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (400 mg, 1.7 mmol), 1-(bromomethyl)-4-(difluoromethoxy)benzene (608 mg, 2.6 mmol), Cs₂CO₃ (1.11 g, 3.4 mmol) in DMF (50 mL) was stirred at 60° C. for 12 hours. The reaction mixture was concentrated. The residue was purified by silica gel chromatography (petroleum ether:ethyl acetate=5:1-0:1) to give 7-(4-(difluoromethoxy)benzyl)-6-methyl-3-(tetrahydro-2H-pyran-4-yl)imidazo[1,5-a]pyrazin-8(7H)-one (360 mg, yield: 52%).

¹H NMR (CDCl₃, 400 MHz): δ 7.91 (s, 1H), 7.20 (d, J=9.2 Hz, 2H), 7.07 (d, J=8.0 Hz, 2H), 6.73 (s, 1H), 6.46 (t, J=73.6 Hz, 1H), 5.19 (s, 2H), 4.11 (d, J=10.8 Hz, 2H), 3.56 (td, J=12.0, 2.0 Hz, 2H), 3.10-3.04 (m, 1H), 2.17-2.06 (m, 5H), 1.86 (d, J=13.2 Hz, 2H).
LC-MS: $t_R$=1.85 min (method 3), m/z=390.1 [M+H]⁺.

Example 41

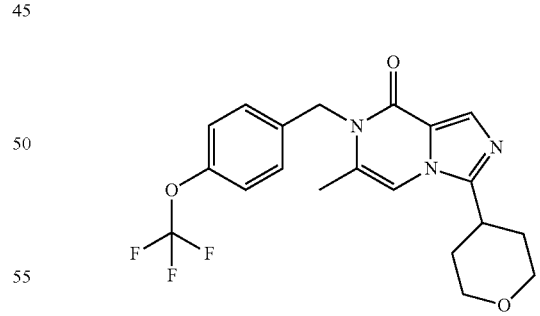

6-methyl-3-(tetrahydro-2H-pyran-4-yl)-7-(4-(trifluoromethoxy)benzyl)imidazo[1,5-a]pyrazin-8(7H)-one A mixture of 6-methyl-3-(tetrahydro-2H-pyran-4-yl)imidazo[1,5-a]pyrazin-8(7H)-one (400 mg, 1.7 mmol), 1-(bromomethyl)-4-(trifluoromethoxy)benzene (654 mg, 2.6 mmol) and Cs₂CO₃ (1.11 g, 3.4 mmol) in DMF (50 mL) was stirred at 60° C. for 12 h. The reaction mixture was concentrated. The residue was purified by silica gel chromatography (petroleum ether:ethyl acetate=5:1~0:1) to give 6-methyl-3-(tetrahydro-2H-pyran-4-yl)-7-(4-(trifluoromethoxy)benzyl)imidazo[1,5-a]pyrazin-8(7H)-one (300 mg, yield: 41%).

$^1$H NMR (CDCl$_3$, 400 MHz): δ 7.91 (s, 1H), 7.25-7.22 (m, 2H), 7.17-7.15 (m, 2H), 6.74 (s, 1H), 5.21 (s, 2H), 4.11 (d, J=10.4 Hz, 2H), 3.56 (td, J=11.2, 2.0 Hz, 2H), 3.10-3.04 (m, 1H), 2.17-2.06 (m, 5H), 1.86 (d, J=13.6 Hz, 2H).

LC-MS: $t_R$=2.05 min (method 3), m/z=408.1 [M+H]$^+$.

Example 42

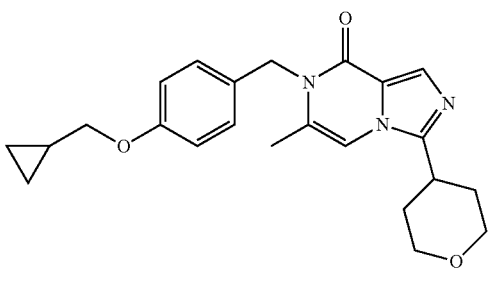 [SMILES: Cc1cn2c(C3CCOCC3)ncc2c(=O)n1Cc1ccc(OCC2CC2)cc1]

7-(4-(cyclopropylmethoxy)benzyl)-6-methyl-3-(tetrahydro-2H-pyran-4-yl)imidazo[1,5-a]pyrazin-8(7H)-one Step 1: A mixture of 4-hydroxybenzaldehyde (1.0 g, 8.19 mmol), (bromomethyl)cyclopropane (1.33 g, 9.83 mmol) and K$_2$CO$_3$ (2.26 g, 16.38 mmol) in DMF (10.0 mL, anhydrous) was stirred at 20° C. for 12 hours. The solution was diluted with water (20 mL). The aqueous phase was extracted with ethyl acetate (60 mL×3). The combined organic phase was washed with brine (20 mL×1), dried over anhydrous Na$_2$SO$_4$, filtered and concentrated in vacuum. The residue was purified by silica gel chromatography (petroleum ether/ethyl acetate=10/1, 1/1) to give 4-(cyclopropylmethoxy)benzaldehyde (1.3 g, 87% yield).

Step 2: A solution of 4-(cyclopropylmethoxy)benzaldehyde (1.3 g, 7.4 mmol) in MeOH (30 mL) was cooled to 0° C., then NaBH$_4$ (558 mg, 14.8 mmol) was added and the mixture was stirred at 0° C. for 1 hour. The mixture was quenched with sat. brine (aq) (50 mL), extracted with EtOAc (50 mL×2). The organic layer was washed with brine, dried over Na$_2$SO$_4$ and concentrated in vacuo to afford (4-(cyclopropylmethoxy)phenyl)methanol (1.21 g, 92% yield).

Step 3. A solution of (4-(cyclopropylmethoxy)phenyl)methanol (800 mg, 4.5 mmol) and Et$_3$N (907 mg, 9.0 mmol) in DCM (10 mL) was cooled to 0° C., then MsCl (617 mg, 5.4 mmol) was added dropwise. The solution was stirred at 0° C. for 0.5 h. The mixture was diluted with water (50 mL), extracted with DCM (50 mL×2). The organic layer was washed with brine (30 mL), dried over Na$_2$SO$_4$ and concentrated in vacuo to afford 4-(cyclopropylmethoxy)benzyl methanesulfonate (760 mg, 66% yield).

Step 4: A mixture of 6-methyl-3-(tetrahydro-2H-pyran-4-yl)imidazo[1,5-a]pyrazin-8(7H)-one (300 mg, 1.29 mmol), 4-(cyclopropylmethoxy)benzyl methanesulfonate (429 mg, 1.68 mmol) and Cs$_2$CO$_3$ (841 mg, 2.58 mmol) in DMF (6 mL, anhydrous) was stirred at 60° C. for 12 hours. The mixture was filtered and the filtrate was concentrated under vacuum. The residue was purified by silica gel chromatography (column height: 250 mm, diameter: 100 mm, 100-200 mesh silica gel, Petroleum ether/Ethyl acetate=10/1, 0/1) to give 7-(4-(cyclopropylmethoxy)benzyl)-6-methyl-3-(tetrahydro-2H-pyran-4-yl)imidazo[1,5-a]pyrazin-8(7H)-one (360 mg, 68% yield).

$^1$H NMR (CDCl$_3$, 400 MHz): δ 7.92 (s, 1H), 7.14 (d, J=8.8 Hz, 2H), 6.85 (d, J=9.2 Hz, 2H), 6.73 (s, 1H), 5.16 (s, 2H), 4.12 (d, J=10.8 Hz, 2H), 3.77 (d, J=6.8 Hz, 2H), 3.61-3.55 (m, 2H), 3.10-3.04 (m, 1H), 2.20-2.09 (m, 5H), 1.88 (d, J=13.2 Hz, 2H), 1.27-1.24 (m, 1H), 0.66-0.61 (m, 2H), 0.35-0.33 (m, 2H).

LC-MS: $t_R$=2.238 min (method 3), m/z=394.1 [M+H]$^+$.

Example 43

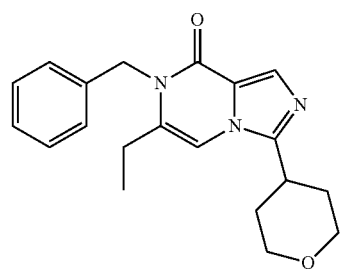 [SMILES: CCc1cn2c(C3CCOCC3)ncc2c(=O)n1Cc1ccccc1]

7-benzyl-6-ethyl-3-(tetrahydro-2H-pyran-4-yl)imidazo[1,5-a]pyrazin-8(7H)-one

A mixture of 6-ethyl-3-(tetrahydro-2H-pyran-4-yl)imidazo[1,5-a]pyrazin-8(7H)-one (100 mg, 404 μmol), bromomethylbenzene (83 mg, 485.26 μmol) and Cs$_2$CO$_3$ (264 mg, 809 μmol) in DMF (3.0 mL) was stirred at 60° C. for 16 hours. The reaction mixture was filtered and the filtrate was concentrated. The residue was purified by HPLC to give 7-benzyl-6-ethyl-3-(tetrahydro-2H-pyran-4-yl)imidazo[1,5-a]pyrazin-8(7H)-one (56.0 mg, 41.0% yield).

$^1$H NMR (CDCl$_3$ 400 MHz): δ 7.91 (s, 1H), 7.32-7.26 (m, 3H), 7.22-7.15 (m, 2H), 6.69 (s, 1H), 5.25 (s, 2H), 4.12 (d, J=10.8 Hz, 2H), 3.62-3.56 (m, 2H), 3.14-3.07 (m, 1H), 2.53-2.48 (m, 2H), 2.17-2.09 (m, 2H), 1.89 (d, J=13.2 Hz, 2H), 1.22 (t, J=7.2 Hz, 3H).

LC-MS: $t_R$=2.042 min (method 3), m/z=338.2 [M+H]$^+$.

Example 44

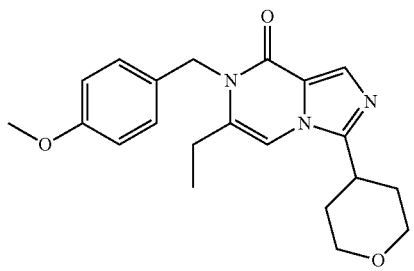 [SMILES: CCc1cn2c(C3CCOCC3)ncc2c(=O)n1Cc1ccc(OC)cc1]

6-ethyl-7-(4-methoxybenzyl)-3-(tetrahydro-2H-pyran-4-yl)imidazo[1,5-a]pyrazin-8(7H)-one A mixture of 6-ethyl-3-(tetrahydro-2H-pyran-4-yl)imidazo[1,5-a]pyrazin-8(7H)-one (100 mg, 404 μmol), 1-(bromomethyl)-4-methoxy-benzene (98 mg, 485 µmol) and Cs₂CO₃ (264 mg, 809 µmol) in DMF (5.0 mL) was stirred at 60° C. for 16 hours. The reaction mixture was filtered and the filtrate was concentrated. The residue was purified by HPLC to give 6-ethyl-7-(4-methoxybenzyl)-3-(tetrahydro-2H-pyran-4-yl)imidazo[1,5-a]pyrazin-8(7H)-one (65 mg, 42.3% yield).

¹H NMR (CDCl₃ 400 MHz): δ 7.91 (s, 1H), 7.12 (d, J=8.0 Hz, 2H), 6.83 (d, J=7.6 Hz, 2H), 6.68 (s, 1H), 5.18 (s, 2H), 4.12 (d, J=11.6 Hz, 2H), 3.77 (s, 3H), 3.61-3.55 (m, 2H), 3.12-3.07 (m, 1H), 2.56-2.51 (m, 2H), 2.16-2.08 (m, 2H), 1.88 (d, J=13.2 Hz, 2H), 1.22 (t, J=7.2 Hz, 3H).

LC-MS: $t_R$=2.050 min (method 3), m/z=368.2 [M+H]⁺.

Example 45

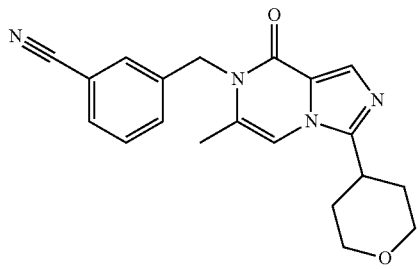 [SMILES: Cc1cn2c(C3CCOCC3)ncc2c(=O)n1Cc1cccc(C#N)c1]

3-((6-methyl-8-oxo-3-(tetrahydro-2H-pyran-4-yl)imidazo[1,5-a]pyrazin-7(8H)-yl)methyl)benzonitrile A mixture of 6-methyl-3-(tetrahydro-2H-pyran-4-yl)imidazo[1,5-a]pyrazin-8(7H)-one (100 mg, 428.69 µmol), 3-(bromomethyl)benzonitrile (126 mg, 643.03 µmol) and Cs₂CO₃ (279 mg, 858 µmol) in DMF (3 mL) was stirred at 70° C. for 6 hours. The mixture was filtered and the filtrate was concentrated under vacuum. The residue was purified by preparative LC-MS to afford 3-((6-methyl-8-oxo-3-(tetrahydro-2H-pyran-4-yl)imidazo[1,5-a]pyrazin-7(8H)-yl)methyl)benzonitrile (35 mg, 23% yield).

¹H NMR (CDCl₃ 400 MHz): δ 7.95 (s, 1H), 7.59 (d, J=6.8 Hz, 1H), 7.51-7.45 (m, 3H), 6.80 (s, 1H), 5.25 (s, 2H), 4.14 (d, J=10.8 Hz, 2H), 3.63-3.57 (m, 2H), 3.14-3.08 (m, 1H), 2.19-2.10 (m, 5H), 1.91 (d, J=13.2 Hz, 2H).

LC-MS: $t_R$=2.164 min (method 3), m/z=349.1 [M+H]⁺.

Example 46

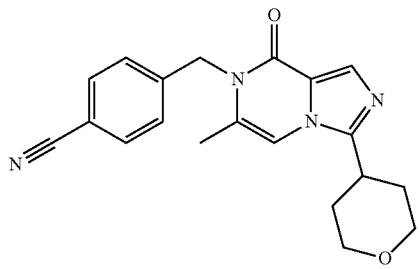 [SMILES: Cc1cn2c(C3CCOCC3)ncc2c(=O)n1Cc1ccc(C#N)cc1]

4-((6-methyl-8-oxo-3-(tetrahydro-2H-pyran-4-yl)imidazo[1,5-a]pyrazin-7(8H)-yl)methyl)benzonitrile A mixture of 6-methyl-3-(tetrahydro-2H-pyran-4-yl)imidazo[1,5-a]pyrazin-8(7H)-one (100 mg, 428.69 µmol), 4-(bromomethyl)benzonitrile (126 mg, 643.04 µmol) and Cs2CO₃ (279 mg, 858 µmol) in DMF (3 mL) was stirred at 60° C. for 2 hours. The mixture was filtered and the filtrate was concentrated under vacuum. The residue was purified by silica gel chromatography (petroleum ether/ethyl acetate=10/1, 1/5) to afford 4-((6-methyl-8-oxo-3-(tetrahydro-2H-pyran-4-yl)imidazo[1,5-a]pyrazin-7(8H)-yl)methyl)benzonitrile (65 mg, 43% yield).

¹H NMR (CDCl₃ 400 MHz): δ 7.94 (s, 1H), 7.64 (d, J=8.0 Hz, 2H), 7.32 (d, J=8.4 Hz, 2H), 6.79 (s, 1H), 5.28 (s, 2H), 4.14 (d, J=11.2 Hz, 2H), 3.62-3.56 (m, 2H), 3.13-3.07 (m, 1H), 2.19-2.09 (m, 5H), 1.89 (d, J=13.2 Hz, 2H).

LC-MS: $t_R$=2.160 min (method 3), m/z=349.2 [M+H]⁺.

Example 47

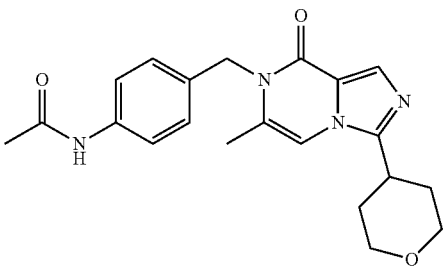 [SMILES: CC(=O)Nc1ccc(Cn2c(C)cn3c(C4CCOCC4)ncc3c2=O)cc1]

N-(4-((6-methyl-8-oxo-3-(tetrahydro-2H-pyran-4-yl)imidazo[1,5-a]pyrazin-7(8H)-yl)methyl)phenyl)acetamide Step 1: A mixture of 6-methyl-3-(tetrahydro-2H-pyran-4-yl)imidazo[1,5-a]pyrazin-8(7H)-one (200 mg, 858 µmol), 1-(bromomethyl)-4-nitrobenzene (278 mg, 1.29 mmol) and Cs₂CO₃ (559 mg, 1.71 mmol) in DMF (4 mL) was stirred at 60° C. for 2 hours. The mixture was filtered and the filtrate was concentrated under vacuum. The residue was purified by silica gel chromatography (petroleum ether/ethyl acetate=10/1, 1/5) to afford 6-methyl-7-(4-nitrobenzyl)-3-(tetrahydro-2H-pyran-4-yl)imidazo[1,5-a]pyrazin-8(7H)-one (270 mg, 85% yield). LC-MS: $t_R$=0.612 min (method 2), m/z=368.8 [M+H]⁺.

Step 2: A mixture of 6-methyl-7-(4-nitrobenzyl)-3-(tetrahydro-2H-pyran-4-yl)imidazo[1,5-a]pyrazin-8(7H)-one (200 mg, 542.90 µmol), Fe (152 mg, 2.71 mmol), NH₄Cl (88 mg, 1.63 mmol) and MeOH (10 mL) in H₂O (10 mL) was stirred at 70° C. for 4 hours. The mixture was filtered and the filtrate was concentrated under vacuum. The residue was purified by silica gel chromatography (dichloromethane/methanol=1/0, 15/1) to afford 7-(4-aminobenzyl)-6-methyl-3-(tetrahydro-2H-pyran-4-yl)imidazo[1,5-a]pyrazin-8(7H)-one (170 mg, 93% yield). LC-MS: $t_R$=0.287 min (method 2), m/z=338.9 [M+H]⁺.

Step 3: A mixture of 7-(4-aminobenzyl)-6-methyl-3-(tetrahydro-2H-pyran-4-yl)imidazo[1,5-a]pyrazin-8(7H)-one (120 mg, 354.61 µmol), acetyl acetate (60 mg, 588.65 µmol) and triethylamine (144 mg, 1.42 mmol) in dioxane (10 mL) was stirred at 90° C. for 6 hours. The solution was quenched with water (2 mL) and stirred at 60° C. for 2 hours. Then it was concentrated under vacuum. The residue was purified by silica gel chromatography (dichloromethane/methanol=1/0, 15/1) to afford N-(4-((6-methyl-8-oxo-3-(tetrahydro-2H-pyran-4-yl)imidazo[1,5-a]pyrazin-7(8H)-yl)methyl)phenyl)acetamide (120 mg, 86.52% yield).

$^1$H NMR (CDCl$_3$ 400 MHz): δ 7.92 (s, 1H), 7.44 (d, J=8.4 Hz, 2H), 7.17 (d, J=8.4 Hz, 2H), 6.74 (s, 1H), 5.19 (s, 2H), 4.13 (d, J=10.4 Hz, 2H), 3.59 (t, J=10.0 Hz, 2H), 3.12-3.06 (m, 1H), 2.19-2.09 (m, 8H), 1.88 (d, J=13.2 Hz, 2H).

LC-MS: $t_R$=1.593 min (method 3), m/z=381.1 [M+H]$^+$.

Example 48

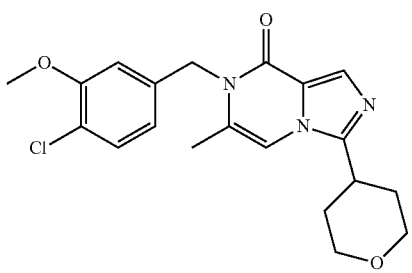 [SMILES: COc1cc(Cn2c(C)cn3c(C4CCOCC4)ncc3c2=O)ccc1Cl]

7-(4-chloro-3-methoxybenzyl)-6-methyl-3-(tetrahydro-2H-pyran-4-yl)imidazo[1,5-a]pyrazin-8(7H)-one To a suspension of 6-methyl-3-(tetrahydro-2H-pyran-4-yl)imidazo[1,5-a]pyrazin-8(7H)-one (100 mg, 429 μmol) in dry DMF (2 mL) was added Cs$_2$CO$_3$ (279 mg, 858 μmol) and 4-(bromomethyl)-1-chloro-2-methoxybenzene (151 mg, 643 μmol). The mixture was purged with N$_2$ for 2 min and heated at 60° C. for 16 hours. The mixture was concentrated. DCM (30 ml) was added to the residue. It was filtered and the filter cake was washed with DCM (20 mL). The filtrate was concentrated and purified by flash chromatography on silica gel (10%~100% ethyl acetate in petroleum ether) to give 7-(4-chloro-3-methoxybenzyl)-6-methyl-3-(tetrahydro-2H-pyran-4-yl)imidazo[1,5-a]pyrazin-8(7H)-one (99.01 mg, 60% yield).

$^1$H NMR (CDCl$_3$ 400 MHz): δ 7.93 (s, 1H), 7.30 (d, J=8.4 Hz, 1H), 6.85 (d, J=1.6 Hz, 1H), 6.75 (s, 1H), 6.72-6.69 (m, 1H), 5.17 (s, 2H), 4.14-4.11 (m, 2H), 3.86 (s, 3H), 3.61-3.55 (m, 2H), 3.10-3.06 (m, 1H), 2.20 (s, 3H), 2.18-2.11 (m, 2H), 1.89-1.86 (m, 2H).

LC-MS: $t_R$=2.466 min (method 3), m/z=388.1 [M+H]$^+$.

Example 49

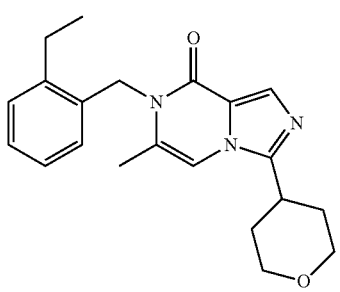 [SMILES: CCc1ccccc1Cn1c(C)cn2c(C3CCOCC3)ncc2c1=O]

7-(2-ethylbenzyl)-6-methyl-3-(tetrahydro-2H-pyran-4-yl)imidazo[1,5-a]pyrazin-8(7H)-one Step 1: A solution of (2-ethylphenyl)methanol (500 mg, 3.67 mmol) and triethylamine (742 mg, 7.34 mmol) in DCM (5 mL) was added MsCl (1.0 g, 8.73 mmol) at 0° C. and stirred at 0° C. for 0.5 hour. Then it was stirred at 20° C. for 1 hour. The mixture was quenched with water (0.5 mL), and diluted with DCM (10 mL). The mixture was added NaHCO$_3$ (aq.) until pH=8. The organic layer was washed with water (3×5 mL), dried with anhydrous Na$_2$SO$_4$, filtered and concentrated under vacuum to give 2-ethylbenzyl methanesulfonate (600 mg), which was used into the next step without further purification.

Step 2: A mixture of 6-methyl-3-(tetrahydro-2H-pyran-4-yl)imidazo[1,5-a]pyrazin-8(7H)-one (150 mg, 643 μmol), 2-ethylbenzyl methanesulfonate (276 mg) and Cs$_2$CO$_3$ (419 mg, 1.29 mmol) in DMF (5 mL) was stirred at 60° C. for 12 hours. The mixture was filtered and the filtrate was concentrated under vacuum. The residue was purified by preparative LC-MS to afford 7-(2-ethylbenzyl)-6-methyl-3-(tetrahydro-2H-pyran-4-yl)imidazo[1,5-a]pyrazin-8(7H)-one (90 mg, 40% yield).

$^1$H NMR (CDCl$_3$ 400 MHz): δ 7.93 (s, 1H), 7.25-7.21 (m, 2H), 7.14-7.10 (m, 1H), 6.81-6.77 (m, 2H), 5.25 (s, 2H), 4.14 (d, J=11.2 Hz, 2H), 3.60 (t, J=12.0 Hz, 2H), 3.15-3.09 (m, 1H), 2.78-2.72 (m, 2H), 2.21-2.13 (m, 5H), 1.91 (d, J=13.6 Hz, 2H), 1.31 (t, J=7.6 Hz, 3H).

LC-MS: $t_R$=2.533 min (method 3), m/z=352.2 [M+H]$^+$.

Example 50

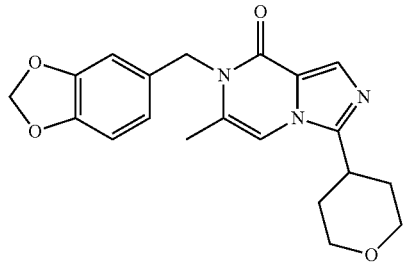 [SMILES: Cc1cn2c(C3CCOCC3)ncc2c(=O)n1Cc1ccc2c(c1)OCO2]

7-(benzo[d][1,3]dioxol-5-ylmethyl)-6-methyl-3-(tetrahydro-2H-pyran-4-yl)imidazo[1,5-a]pyrazin-8(7H)-one To a suspension of 6-methyl-3-(tetrahydro-2H-pyran-4-yl)imidazo[1,5-a]pyrazin-8(7H)-one (100 mg, 429 μmol) in dry DMF (2 mL) was added Cs$_2$CO$_3$ (279 mg, 858 μmol) and 5-(bromomethyl)benzo[d][1,3]dioxole (138 mg, 643 μmol). The mixture was bubbled with N$_2$ for 2 min and heated at 60° C. for 16 hours. The mixture was concentrated. DCM (30 mL) was added to the residue. It was filtered and the filter cake was washed with DCM (20 mL). The filtrate was concentrated and purified by flash chromatography on silica gel (10%~100% ethyl acetate in petroleum ether) to give 7-(benzo[d][1,3]dioxol-5-ylmethyl)-6-methyl-3-(tetrahydro-2H-pyran-4-yl)imidazo[1,5-a]pyrazin-8(7H)-one (81.74 mg, 52% yield).

$^1$H NMR (CDCl$_3$ 400 MHz): δ 7.92 (s, 1H), 6.76-6.69 (m, 4H), 5.95-5.93 (m, 2H), 5.13 (s, 2H), 4.14-4.11 (m, 2H), 3.61-3.55 (m, 2H), 3.10-3.05 (m, 1H), 2.21 (s, 3H), 2.20-2.10 (m, 2H), 1.90-1.86 (m, 2H).

LC-MS: $t_R$=2.245 min (method 3), m/z=368.2 [M+H]$^+$.

Example 51

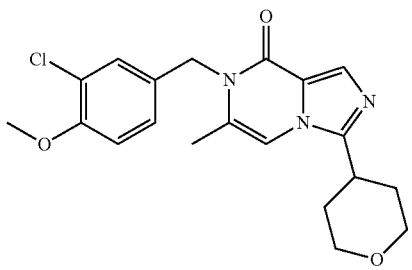 [SMILES: COc1ccc(Cn2c(C)cn3c(C4CCOCC4)ncc3c2=O)cc1Cl]

7-(3-chloro-4-methoxybenzyl)-6-methyl-3-(tetrahydro-2H-pyran-4-yl)imidazo[1,5-a]pyrazin-8(7H)-one A mixture of 6-methyl-3-(tetrahydro-2H-pyran-4-yl)imidazo[1,5-a]pyrazin-8(7H)-one (100 mg, 427 μmol), 4-(bromomethyl)-2-chloro-1-methoxybenzene (151 mg, 643 μmol) and Cs$_2$CO$_3$ (279 mg, 858 μmol) in DMF (3 mL) was stirred at 60° C. for 2 hours. The mixture was filtered and the filtrate was concentrated under vacuum. The residue was purified by silica gel chromatography (detroleum ether/ethyl acetate=10/1, 0/1) to afford 7-(3-chloro-4-methoxybenzyl)-6-methyl-3-(tetrahydro-2H-pyran-4-yl)imidazo[1,5-a]pyrazin-8(7H)-one (110 mg, 65% yield).

$^1$H NMR (CDCl$_3$ 400 MHz): δ 7.93 (s, 1H), 7.24 (d, J=0.8 Hz, 1H), 7.12-7.10 (m, 1H), 6.88 (d, J=8.4 Hz, 1H), 6.75 (s, 1H), 5.15 (s, 2H), 4.13 (d, J=10.4 Hz, 2H), 3.88 (s, 3H), 3.62-3.56 (m, 2H), 3.12-3.06 (m, 1H), 2.20-2.09 (m, 5H), 1.89 (d, J=13.2 Hz, 2H).

LC-MS: $t_R$=2.414 min (method 3), m/z=388.1 [M+H]$^+$.

Example 52

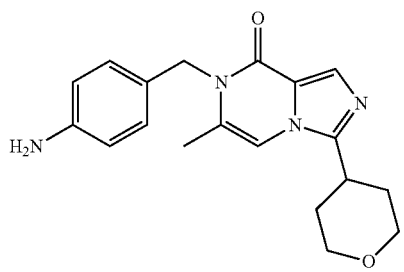 [SMILES: Cc1cn2c(C3CCOCC3)ncc2c(=O)n1Cc1ccc(N)cc1]

7-(4-aminobenzyl)-6-methyl-3-(tetrahydro-2H-pyran-4-yl)imidazo[1,5-a]pyrazin-8(7H)-one A solution of N-(4-((6-methyl-8-oxo-3-(tetrahydro-2H-pyran-4-yl)imidazo[1,5-a]pyrazin-7(8H)-yl)methyl)phenyl)acetamide (100 mg, 263 μmol), NaOH (63 mg, 1.58 mmol) and MeOH (1 mL) in H$_2$O (1 mL) was stirred at 90° C. for 12 hours. The solution was added KHSO$_4$ (aq.) until pH=7 and concentrated under vacuum. The residue was purified by preparative TLC (DCM: MeOH=10:1). to afford 7-(4-aminobenzyl)-6-methyl-3-(tetrahydro-2H-pyran-4-yl)imidazo[1,5-a]pyrazin-8(7H)-one (50 mg, 56% yield).

$^1$H NMR (CDCl$_3$ 400 MHz): δ 7.91 (s, 1H), 7.04 (d, J=8.4 Hz, 2H), 6.71 (s, 1H), 6.63 (d, J=8.4 Hz, 2H), 5.12 (s, 2H), 4.13 (d, J=12.0 Hz, 2H), 3.67 (brs, 2H), 3.61-3.55 (m, 4H), 3.10-3.05 (m, 1H), 2.21 (s, 3H), 2.17-2.08 (m, 2H), 1.88 (d, J=13.2 Hz, 2H).

LC-MS: $t_R$=1.273 min (method 3), m/z=339.1 [M+H]$^+$.

Example 53

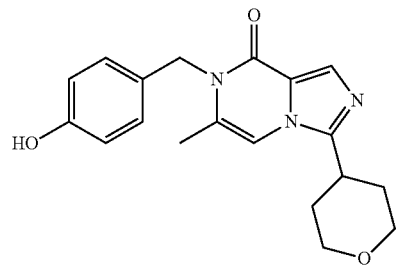 [SMILES: Cc1cn2c(C3CCOCC3)ncc2c(=O)n1Cc1ccc(O)cc1]

7-(4-hydroxybenzyl)-6-methyl-3-(tetrahydro-2H-pyran-4-yl)imidazo[1,5-a]pyrazin-8(7H)-one A solution of 7-(4-methoxybenzyl)-6-methyl-3-(tetrahydro-2H-pyran-4-yl)imidazo[1,5-a]pyrazin-8(7H)-one (2.0 g, 5.66 mmol) in DCM (32 mL) was added BBr$_3$ (4.3 g, 16.98 mmol) at 0° C. and stirred at 20° C. for 3 hours. The solution was quenched with H$_2$O (5 mL) at 0° C. The mixture was stirred at 0° C. for 1 hour and then to it was added NaHCO$_3$ (saturated aqueous) until pH=6. The mixture was concentrated under vacuum. The residue was diluted with DCM (20 mL) and MeOH (2 mL). Then it was filtered and the filtrate was concentrated under vacuum. The residue was added into KOH (60 mL, 2 M, aq.) at 20° C. and stirred at 50° C. for 1 hour. The solution was added KHSO$_4$ (saturated aqueous) until pH=6, the mixture was concentrated under vacuum. The residue was purified by silica gel chromatography (dichloromethane/methanol=1/0, 15/1) to afford 7-(4-hydroxybenzyl)-6-methyl-3-(tetrahydro-2H-pyran-4-yl)imidazo[1,5-a]pyrazin-8(7H)-one (460 mg, 24% yield).

$^1$H NMR (DMSO Varian_H_400 MHz): δ 9.39 (s, 1H), 7.70 (s, 1H), 7.46 (s, 1H), 6.99 (d, J=8.4 Hz, 2H), 6.70 (d, J=8.4 Hz, 2H), 5.06 (s, 2H), 3.96-3.93 (m, 2H), 3.52-3.45 (m, 2H), 3.29-3.16 (m, 1H), 2.15 (s, 3H), 1.83-1.77 (m, 4H).

LC-MS: $t_R$=1.62 min (method 8), m/z=340.1 [M+H]$^+$.

Example 54

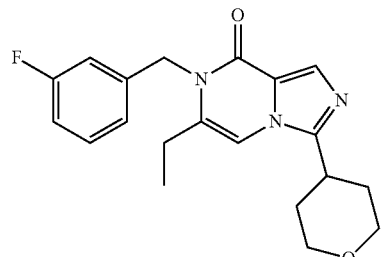

6-ethyl-7-(3-fluorobenzyl)-3-(tetrahydro-2H-pyran-4-yl)imidazo[1,5-a]pyrazin-8(7H)-one Step 1: A mixture of methyl 1H-imidazole-5-carboxylate (1.6 g, 13 mmol), 1-bromobutan-2-one (2.0 g, 13 mmol) and K$_2$CO$_3$ (3.5 g, 25 mmol) in acetone (20 mL) was stirred at 40° C. for 12 hours. The mixture was concentrated under vacuum. The residue was purified by silica gel chromatography (petroleum ether/ethyl acetate=10/1, 0/1) to give methyl 1-(2-oxobutyl)-1H-imidazole-5-carboxylate (750 mg, 30% yield).

Step 2: A mixture of methyl 1-(2-oxobutyl)-1H-imidazole-5-carboxylate (700 mg, 3.59 mmol), NBS (831 mg, 4.67 mmol), and AIBN (118 mg, 718 µmol) in CHCl$_3$ (20 mL) was stirred at 50° C. for 12 hours. The mixture was concentrated under vacuum. The residue was purified by silica gel chromatography (petroleum ether/ethyl acetate=10/1, 1/2) to give methyl 2-bromo-1-(2-oxobutyl)-1H-imidazole-5-carboxylate (650 mg, 66% yield). LC-MS: $t_R$=0.585 min (method 2), m/z=274.7 [M+H]$^+$ Step 3: A mixture of methyl 2-bromo-1-(2-oxobutyl)-1H-imidazole-5-carboxylate (650 mg, 2.36 mmol) and NH$_4$OAc (727.64 mg, 9.44 mmol) in 1,4-dioxane (15 mL) was stirred at 90° C. for 3 days. The mixture was concentrated under vacuum. The residue was purified by silica gel chromatography (petroleum ether/ethyl acetate=10/1, 1/1) to give 3-bromo-6-ethylimidazo[1,5-a]pyrazin-8(7H)-one (500 mg, 88% yield). LC-MS: $t_R$=0.542 min (method 2), m/z=241.8 [M+H]$^+$ Step 4: A mixture of 3-bromo-6-ethylimidazo[1,5-a]pyrazin-8(7H)-one (500 mg, 2.07 mmol), 2-(3,6-dihydro-2H-pyran-4-yl)-4,4,5,5-tetramethyl-1,3,2-dioxaborolane (522 mg, 2.48 mmol), K$_2$CO$_3$ (572 mg, 4.14 mmol), Pd(dppf)Cl$_2$ (303 mg, 414 µmol) and H$_2$O (5 mL) in 1,4-dioxane (20 mL) was stirred at 100° C. for 12 hours. The mixture was filtered and the filtrate was concentrated under vacuum. The residue was purified by silica gel chromatography (Dichloromethane/Methanol=1/0, 15/1) to give 3-(3,6-dihydro-2H-pyran-4-yl)-6-ethylimidazo[1,5-a]pyrazin-8(7H)-one (400 mg, 78.78% yield). LC-MS: $t_R$=0.430 min (method 2), m/z=245.8 [M+H]$^+$ Step 5: A mixture of 3-(3,6-dihydro-2H-pyran-4-yl)-6-ethylimidazo[1,5-a]pyrazin-8(7H)-one (400 mg, 1.63 mmol) and Pd/C (dry, 10% Pd, 20 mg) in THF (15 mL) was stirred at 15° C. for 4 hours under H$_2$ (15 psi). The mixture was filtered and the filtrate was concentrated under vacuum to afford 6-ethyl-3-(tetrahydro-2H-pyran-4-yl)imidazo[1,5-a]pyrazin-8(7H)-one (300 mg, 74% yield). LC-MS: $t_R$=1.324 min (method 9), m/z=248.0 [M+H]$^+$.

Step 6: A mixture of 6-ethyl-3-(tetrahydro-2H-pyran-4-yl)imidazo[1,5-a]pyrazin-8(7H)-one (300 mg, 1.21 mmol), 1-(bromomethyl)-3-fluorobenzene (297 mg, 1.57 mmol) and K$_2$CO$_3$ (334 mg, 2.42 mmol) in DMF (20 mL) was stirred at 60° C. for 12 hours. The mixture was filtered and the filtrate was concentrated under vacuum. The residue was purified by silica gel chromatography (Petroleum ether/Ethyl acetate=3/1, 0/1) to afford 6-ethyl-7-(3-fluorobenzyl)-3-(tetrahydro-2H-pyran-4-yl)imidazo[1,5-a]pyrazin-8(7H)-one (150 mg, 34% yield).

$^1$H NMR (CDCl$_3$ 400 MHz): δ 7.94 (s, 1H), 7.32-7.27 (m, 1H), 6.98-6.94 (m, 2H), 6.86 (d, J=9.6 Hz, 1H), 6.72 (s, 1H), 5.25 (s, 2H), 4.14 (d, J=11.2 Hz, 2H), 3.64-3.58 (m, 2H), 3.15-3.09 (m, 1H), 2.53-2.48 (m, 2H), 2.18-2.13 (m, 2H), 1.91 (d, J=13.2 Hz, 2H), 1.25 (t, J=7.2 Hz, 2H).

LC-MS: $t_R$=2.475 min (method 3), m/z=356.1 [M+H]$^+$.

Example 55

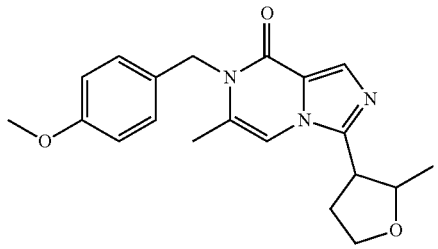

7-(4-methoxybenzyl)-6-methyl-3-(2-methyltetrahydrofuran-3-yl)imidazo[1,5-a]pyrazin-8(7H)-one, stereoisomers 1, 2, 3 and 4

Step 1: To a cooled (0° C.) solution of 2-methyltetrahydrofuran-3-carboxylic acid (110 mg, 845 µmol) in dry DCM (2 mL) was added oxalyl dichloride (107 mg, 845 µmol) dropwise. Then one drop of DMF was added and the mixture was stirred at 26° C. for 1 hour. The solution of 2-methyltetrahydrofuran-3-carbonyl chloride (126 mg) in DCM (2 mL) was directly used for the next step.

Step 2: To a cooled (0° C.) solution of 2-methyltetrahydrofuran-3-carbonyl chloride (160 mg, 844 µmol, HCl) in dry DCM (5 mL) was added triethylamine (256 mg, 2.53 mmol) and (3-methoxy-5-methylpyrazin-2-yl)methanamine (125 mg, 843.70 µmol) in DCM (2 mL) dropwise. The mixture was stirred at 26° C. for 1 hour. LCMS showed the reaction was completed. Water (5 mL) was added to the mixture. The mixture was extracted with DCM (30 mL×2). The combined organic layer was washed with H$_2$O (20 mL), brine (20 mL), dried over Na$_2$SO$_4$, filtered and concentrated. The crude product was purified by flash chromatography on silica gel (10-50% ethyl acetate in petroleum ether) to give N-((3-methoxy-5-methylpyrazin-2-yl)methyl)-2-methyltetrahydrofuran-3-carboxamide (100 mg, 45% yield) as a light yellow oil.

Step 3: To a solution of N-((3-methoxy-5-methylpyrazin-2-yl)methyl)-2-methyltetrahydrofuran-3-carboxamide (150 mg, 565 µmol) in dry dioxane (5 mL) was added POCl$_3$ (173 mg, 1.13 mmol). The mixture was heated at 80° C. for 2 hours. The mixture was cooled to 26° C. and the brown solution of 8-methoxy-6-methyl-3-(2-methyltetrahydrofuran-3-yl)imidazo[1,5-a]pyrazine (140 mg) in dioxane (5 mL) was directly used for the next step.

Step 4: To a solution of 8-methoxy-6-methyl-3-(2-methyltetrahydrofuran-3-yl)imidazo[1,5-a]pyrazine (140 mg, 566 µmol) in dioxane (5 mL) was added 2 N HCl (2 M, 2 mL). The mixture was heated at 80° C. for 1 hour. The mixture was cooled to 25° C., adjusted to pH=7 by saturated aqueous NaHCO$_3$ and extracted with DCM (20 mL×2). The combined organic phases were washed with H$_2$O (20 mL), brine (20 mL), dried over Na$_2$SO$_4$, filter and concentrated to give 6-methyl-3-(2-methyltetrahydrofuran-3-yl)imidazo[1,5-a]pyrazin-8(7H)-one (131 mg).

Step 5: To a solution of 6-methyl-3-(2-methyltetrahydrofuran-3-yl)imidazo[1,5-a]pyrazin-8(7H)-one (131 mg, 562 µmol) in dry DMF (5 mL) was added 1-(bromomethyl)-4-methoxybenzene (169 mg, 842 µmol) and Cs$_2$CO$_3$ (366 mg, 1.12 mmol). The mixture was heated at 60° C. for 16 hours.

The mixture was concentrated and water (10 mL) was added. The mixture was extracted with DCM (30 mL×2). The combined organic layer was washed with H$_2$O (30 mL×2), brine (30 mL), dried over Na$_2$SO$_4$, filtered and concentrated. The residue was purified by flash chromatography on silica gel (10%~100% ethyl acetate in petroleum ether) to give 7-(4-methoxybenzyl)-6-methyl-3-(2-methyltetrahydrofuran-3-yl)imidazo[1,5-a]pyrazin-8(7H)-one (90 mg, 45% yield).

7-(4-methoxybenzyl)-6-methyl-3-(2-methyltetrahydrofuran-3-yl)imidazo[1,5-a]pyrazin-8(7H)-one (100 mg, 283 µmol) was purified by SFC.

Stereoisomer 1:
(9.4 mg, 9% yield).
$^1$H NMR (CDCl$_3$ 400 MHz): δ 7.92 (s, 1H), 7.15 (d, J=8.8 Hz, 2H), 6.84 (d, J=8.4 Hz, 2H), 6.74 (s, 1H), 5.16 (s, 2H), 4.30-4.26 (m, 1H), 4.12-4.04 (m, 2H), 3.78 (s, 3H), 3.09-3.03 (m, 1H), 2.46-2.34 (m, 2H), 2.20 (s, 3H), 1.32 (d, J=6.0 Hz, 3H).
LC-MS: $t_R$=2.074 min (method 13), m/z=354.1 [M+H]$^+$. SFC: $t_R$=5.177 min, ee %>99%. $[α]_D^{20}$ −26 (C=0.10, DCM).

Stereoisomer 2:
(7.3 mg, 7% yield).
$^1$H NMR (CDCl$_3$ 400 MHz): δ 7.92 (s, 1H), 7.15 (d, J=8.8 Hz, 2H), 6.84 (d, J=8.4 Hz, 2H), 6.73 (s, 1H), 5.16 (s, 2H), 4.30-4.26 (m, 1H), 4.10-4.02 (m, 2H), 3.78 (s, 3H), 3.09-3.03 (m, 1H), 2.44-2.35 (m, 2H), 2.20 (s, 3H), 1.32 (d, J=6.0 Hz, 3H).
LC-MS: $t_R$=2.072 min (method 13), m/z=354.1 [M+H]$^+$. SFC: $t_R$=5.458 min, ee %=99.7%. $[α]_D^{20}$ +24 (c=0.10, DCM).

Stereoisomer 3:
(39.7 mg, 40% yield).
$^1$H NMR (CDCl$_3$ 400 MHz): δ 7.92 (s, 1H), 7.15 (d, J=8.4 Hz, 2H), 6.84 (d, J=8.4 Hz, 2H), 6.78 (s, 1H), 5.22-5.10 (m, 2H), 4.31-4.26 (m, 2H), 3.88-3.82 (m, 1H), 3.77 (s, 3H), 3.70-3.60 (m, 1H), 2.71-2.67 (m, 1H), 2.43-2.40 (m, 1H), 2.19 (s, 3H), 0.87 (d, J=4.4 Hz, 3H).
LC-MS: $t_R$=1.983 min (method 13), m/z=354.1 [M+H]$^+$. SFC: $t_R$=5.932 min, ee %=98.8%. $[α]_D^{20}$ +48 (c=0.10, DCM).

Stereoisomer 4:
(26.4 mg, 26% yield).
$^1$H NMR (CDCl$_3$ 400 MHz): δ 7.92 (s, 1H), 7.15 (d, J=8.8 Hz, 2H), 6.84 (d, J=8.4 Hz, 2H), 6.78 (s, 1H), 5.22-5.09 (m, 2H), 4.32-4.26 (m, 2H), 3.87-3.85 (m, 1H), 3.77 (s, 3H), 3.68-3.64 (m, 1H), 2.70-2.65 (m, 1H), 2.42-2.37 (m, 1H), 2.19 (s, 3H), 0.87 (d, J=6.4 Hz, 3H).
LC-MS: $t_R$=1.983 min (method 13), m/z=354.1 [M+H]$^+$. SFC: $t_R$=6.570 min, ee %=99.6%. $[α]_D^{20}$ −64 (c=0.10, DCM).

Example 56

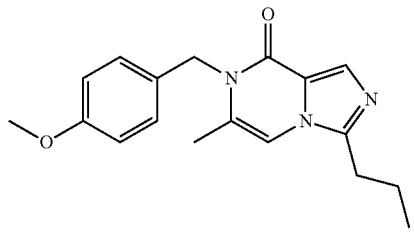 [SMILES: CCCc1ncc2c(=O)n(Cc3ccc(OC)cc3)c(C)cn12]

7-(4-methoxybenzyl)-6-methyl-3-propylimidazo[1,5-a]pyrazin-8(7H)-one

To a solution of 3-bromo-7-(4-methoxybenzyl)-6-methylimidazo[1,5-a]pyrazin-8(7H)-one (500 mg, 1.44 mmol, 1 eq) in THF (10 mL) was added Ni(dppp)Cl$_2$(327.83 mg, 604.80 µmol, 0.42 eq) at 0° C. over 10 min, then at −78° C. for 10 min. propylmagnesium bromide (1 M, 3 mL, 2.1 eq) was added dropwise at 0° C. The resulting mixture was stirred at 0° C. for 1.5 hour. The reaction was quenched by saturated NH$_4$Cl aqueous solution (5 mL). The residue was purified by silica column chromatography (Gradient: 0-50, EtOAc in PE with 1% triethylamine) to give 220 mg of crude product. The crude product was purified by preparative TLC (PE:EtOAc=1:1 with 1% triethylamine). The residue was washed with hexane (3 mL) and filtered and the filter cake was dried under vacuum to give 7-(4-methoxybenzyl)-6-methyl-3-propylimidazo[1,5-a]pyrazin-8(7H)-one (82 mg, 18% yield).

$^1$HNMR (CDCl$_3$, 400 MHz): δ 7.90 (s, 1H), 7.16 (d, J=8.8, 2H), 6.85 (d, J=8.8, 2H), 6.68 (s, 1H), 5.17 (s, 2H), 3.78 (s, 3H), 2.82 (t, J=7.2, 2H), 2.19 (s, 3H), 1.90-1.81 (m, 2H), 1.03 (t, J=7.2, 3H).
LC-MS: tR=1.927 min (method 13), m/z=312.1 [M+H]$^+$.

Example 57

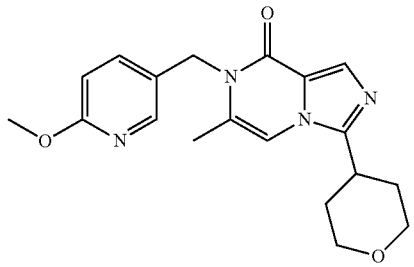 [SMILES: COc1ccc(Cn2c(C)cn3c(C4CCOCC4)ncc3c2=O)cn1]

7-((6-methoxypyridin-3-yl)methyl)-6-methyl-3-(tetrahydro-2H-pyran-4-yl)imidazo[1,5-a]pyrazin-8(7H)-one Into a vial was added 6-methyl-3-(tetrahydro-2H-pyran-4-yl)imidazo[1,5-a]pyrazin-8(7H)-one (200 mg, 0.86 mmol), 5-(chloromethyl)-2-methoxypyridine (162 mg, 1.03 mmol), cesium carbonate (559 mg, 1.72 mmol) and sodium iodide (154 mg, 1.03 mmol) in DMF (9.44 g, 10 ml, 129 mmol). The reaction was stirred overnight at 70° C. To the reaction was added ethylacetate, and it was filtered and concentrated. The reaction was purified by chromatography on silicagel to obtain 7-((6-methoxypyridin-3-yl)methyl)-6-methyl-3-(tetrahydro-2H-pyran-4-yl)imidazo[1,5-a]pyrazin-8(7H)-one (127 mg, 0.358 mmol) in 42% yield.

$^1$H NMR (600 MHz, CDCl$_3$) δ 8.06 (dd, J=2.5, 0.8 Hz, 1H), 7.91 (d, J=0.6 Hz, 1H), 7.55 (dd, J=8.6, 2.5 Hz, 1H), 6.74 (t, J=1.1 Hz, 1H), 6.71 (dd, J=8.6, 0.7 Hz, 1H), 5.15 (s, 2H), 4.12 (m, 2H), 3.91 (s, 3H), 3.58 (td, J=11.7, 2.2 Hz, 2H), 3.07 (tt, J=11.4, 3.9 Hz, 1H), 2.25 (d, J=1.2 Hz, 3H), 2.12 (dtd, J=13.7, 11.6, 4.3 Hz, 2H), 1.87 (ddd, J=13.5, 4.2, 2.1 Hz, 2H).
LC-MS: $t_R$=0.38 min (method 6), m/z=355.2 [M+H]$^+$.

Example 58

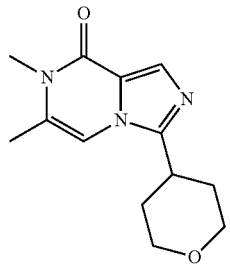 [SMILES: Cc1cn2c(C3CCOCC3)ncc2c(=O)n1C]

6,7-dimethyl-3-(tetrahydro-2H-pyran-4-yl)imidazo[1,5-a]pyrazin-8(7H)-one

To a solution of 6-methyl-3-(tetrahydro-2H-pyran-4-yl)imidazo[1,5-a]pyrazin-8(7H)-one (100 mg, 428.69 μmol, 1 eq) in DMSO (2 mL) was added Cs$_2$CO$_3$ (139.68 mg, 428.69 μmol, 1 eq) and methyliodide (121.70 mg, 858 μmol, 53.38 μL, 2 eq). The mixture was stirred at 50° C. for 12 hour. The reaction mixture was diluted with H$_2$O (25 mL) and extracted with DCM (50 mL×2). The combined organic layers were washed with brine (15 mL), dried over Na$_2$SO$_4$, filtered and concentrated under reduced pressure. The residue was purified by preparative TLC (ethyl acetate). 6,7-dimethyl-3-(tetrahydro-2H-pyran-4-yl)imidazo[1,5-a]pyrazin-8(7H)-one (73 mg, 68% yield, 98% purity) was obtained.

$^1$H NMR (CDCl$_3$ 400 MHz): δ 7.87 (s, 1H), 6.76 (s, 1H), 4.13 (d, J=11.2 Hz, 2H), 3.59 (t, J=11.2 Hz, 2H), 3.46 (s, 3H), 3.11-3.05 (m, 1H), 2.28 (s, 3H), 2.16-2.08 (m, 2H), 1.88 (d, J=14.0 Hz, 2H).

LC-MS: $t_R$=1.300 min (method 13), m/z=248.1 [M+H]$^+$.

Example 59

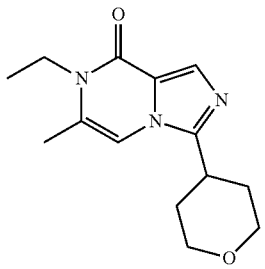 [SMILES: CCn1c(C)cn2c(C3CCOCC3)ncc2c1=O]

7-ethyl-6-methyl-3-(tetrahydro-2H-pyran-4-yl)imidazo[1,5-a]pyrazin-8(7H)-one

To a solution of 6-methyl-3-(tetrahydro-2H-pyran-4-yl)imidazo[1,5-a]pyrazin-8(7H)-one (100 mg, 429 μmol, 1 eq) in anhydrous DMF (2 mL) was added K$_2$CO$_3$ (119 mg, 858 μmol, 2 eq) and iodoethane (134 mg, 858 μmol, 69 μL, 2 eq). The mixture was stirred at 50° C. for 12 hour. The reaction mixture was concentrated under reduced pressure. The residue was diluted with H$_2$O (20 mL) and extracted with EA (40 mL×2). The combined organic layers were washed with brine (15 mL), dried over Na$_2$SO$_4$, filtered and concentrated under reduced pressure to afford a residue. 7-ethyl-6-methyl-3-(tetrahydro-2H-pyran-4-yl)imidazo[1,5-a]pyrazin-8(7H)-one (40 mg, 34% yield, 96% purity) was obtained.

$^1$H NMR (CDCl$_3$ 400 MHz): δ 7.85 (s, 1H), 6.73 (s, 1H), 4.12 (d, J=10.8 Hz, 2H), 4.03-3.99 (m, 2H), 3.58 (t, J=10.8 Hz, 2H), 3.10-3.04 (m, 1H), 2.30 (s, 3H), 2.16-2.07 (m, 2H), 1.87 (d, J=13.2 Hz, 2H), 1.29 (t, J=6.8 Hz, 3H).

LC-MS: $t_R$=1.490 min (method 11), m/z=262.1 [M+H]$^+$.

Example 60

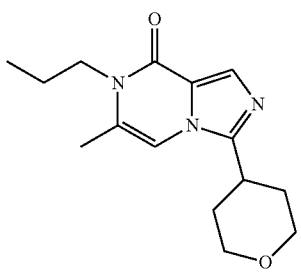 [SMILES: CCCn1c(C)cn2c(C3CCOCC3)ncc2c1=O]

6-methyl-7-propyl-3-(tetrahydro-2H-pyran-4-yl)imidazo[1,5-a]pyrazin-8(7H)-one

To a solution of 6-methyl-3-(tetrahydro-2H-pyran-4-yl)imidazo[1,5-a]pyrazin-8(7H)-one (100 mg, 429 μmol, 1 eq) in anhydrous DMF (2 mL) was added K$_2$CO$_3$ (119 mg, 858 μmol, 2 eq) and 1-bromopropane (105 mg, 858 μmol, 78.11 μL, 2 eq). The mixture was stirred at 50° C. for 12 hours. The reaction mixture was concentrated under reduced pressure to remove DMF. The residue was diluted with H$_2$O (20 mL) and extracted with EA (40 mL×2). The combined organic layers were washed with brine (15 mL), dried over Na$_2$SO$_4$, filtered and concentrated under reduced pressure. The residue was purified by preparative TLC (ethyl acetate). 6-methyl-7-propyl-3-(tetrahydro-2H-pyran-4-yl)imidazo[1,5-a]pyrazin-8(7H)-one (45 mg, 37% yield, 98% purity) was obtained.

$^1$H NMR (CDCl$_3$ 400 MHz): δ 7.85 (s, 1H), 6.72 (s, 1H), 4.12 (d, J=10.4 Hz, 2H), 3.88 (t, J=8.0 Hz, 2H), 3.62-3.56 (m, 2H), 3.10-3.07 (m, 1H), 2.28 (s, 3H), 2.14-2.09 (m, 2H), 1.87 (d, J=13.2 Hz, 2H), 1.73-1.67 (m, 2H), 1.00 (t, J=7.2 Hz, 3H).

LC-MS: $t_R$=1.666 min (method 11), m/z=276.1 [M+H]$^+$.

Example 61

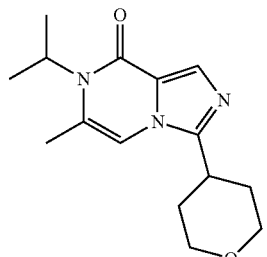

7-isopropyl-6-methyl-3-(tetrahydro-2H-pyran-4-yl)imidazo[1,5-a]pyrazin-8(7H)-one To a solution of 6-methyl-3-(tetrahydro-2H-pyran-4-yl)imidazo[1,5-a]pyrazin-8(7H)-one (350 mg, 1.50 mmol, 1 eq) in anhydrous DMF (4 mL) was added $Cs_2CO_3$ (978 mg, 3 mmol, 2 eq) and 2-iodopropane (510 mg, 3 mmol, 300 μL, 2 eq). The mixture was stirred at 50° C. for 12 hours. The reaction mixture was concentrated under reduced pressure to remove DMF. The residue was diluted with $H_2O$ (15 mL) and extracted with EtOAc (40 mL×2). The combined organic layers were washed with brine (10 mL), dried over $Na_2SO_4$, filtered and concentrated under reduced pressure. The residue was purified by preparative TLC (ethyl acetate). 7-isopropyl-6-methyl-3-(tetrahydro-2H-pyran-4-yl)imidazo[1,5-a]pyrazin-8(7H)-one (68 mg, 16% yield, 96% purity) was obtained.

$^1$H NMR (CDCl$_3$ 400 MHz): δ 7.81 (s, 1H), 6.67 (s, 1H), 4.40 (m, 1H), 4.12 (d, J=11.6 Hz, 2H), 3.58 (t, J=11.3 Hz, 2H), 3.09-3.03 (m, 1H), 2.27 (s, 3H), 2.14-2.06 (m, 2H), 1.86 (d, J=13.2 Hz, 2H), 1.62-1.61 (m, 6H).

LC-MS: $t_R$=1.576 min (method 13), m/z=276.1 [M+H]$^+$.

Example 62

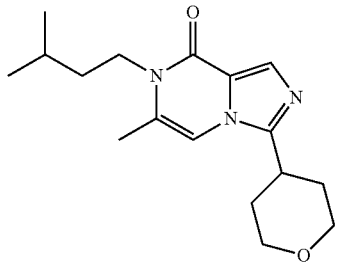 [SMILES: Cc1cn2c(C3CCOCC3)ncc2c(=O)n1CCC(C)C]

7-isopentyl-6-methyl-3-(tetrahydro-2H-pyran-4-yl)imidazo[1,5-a]pyrazin-8(7H)-one To a solution of 6-methyl-3-(tetrahydro-2H-pyran-4-yl)imidazo[1,5-a]pyrazin-8(7H)-one (100 mg, 428.69 μmol, 1 eq) in anhydrous DMF (2 mL) was added $K_2CO_3$ (118.50 mg, 858 μmol, 2 eq) and 1-bromo-3-methylbutane (129.50 mg, 858 μmol, 108 μL, 2 eq). The mixture was stirred at 50° C. for 12 hours. The reaction mixture was concentrated under reduced pressure to remove DMF. The residue was diluted with $H_2O$ (20 mL) and extracted with EtOAc (40 mL×2). The combined organic layers were washed with brine (15 mL), dried over $Na_2SO_4$, filtered and concentrated under reduced pressure. The residue was purified by preparative TLC (ethyl acetate). 7-isopentyl-6-methyl-3-(tetrahydro-2H-pyran-4-yl)imidazo[1,5-a]pyrazin-8(7H)-one (65 mg, 50% yield) was obtained.

$^1$H NMR (CDCl$_3$ 400 MHz): δ 7.84 (s, 1H), 6.73 (s, 1H), 4.12 (d, J=10.4 Hz, 2H), 3.93 (t, J=8.0 Hz, 2H), 3.61-3.55 (m, 2H), 3.08-3.04 (m, 1H), 2.28 (s, 3H), 2.10-2.09 (m, 2H), 1.87 (d, J=14.0 Hz, 2H), 1.74-1.69 (m, 1H), 1.56-1.52 (m, 2H), 1.00-0.98 (m, 6H).

LC-MS: $t_R$=1.968 min (method 13), m/z=304.2 [M+H]$^+$.

Example 63

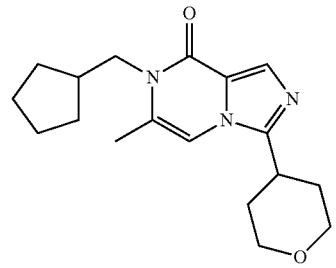 [SMILES: Cc1cn2c(C3CCOCC3)ncc2c(=O)n1CC1CCCC1]

7-(cyclopentylmethyl)-6-methyl-3-(tetrahydro-2H-pyran-4-yl)imidazo[1,5-a]pyrazin-8(7H)-one To a mixture of 6-methyl-3-(tetrahydro-2H-pyran-4-yl)imidazo[1,5-a]pyrazin-8(7H)-one (150 mg, 0.64 mmol) and (bromomethyl)cyclopentane (157 mg, 0.96 mmol) in DMSO (2 mL) was added $Cs_2CO_3$ (419 mg, 1.29 mmol). The mixture was stirred at 60° C. for 12 hours. The mixture was diluted with water (10 mL) and extracted with DCM (5 mL×3). The combine organic layer was washed with water (5 mL×2) and dried over $Na_2SO_4$. The organic layers was evaporated under vacuum. The residue was purified by preparative TLC (ethyl acetate) to give 7-(cyclopentylmethyl)-6-methyl-3-(tetrahydro-2H-pyran-4-yl)imidazo[1,5-a]pyrazin-8(7H)-one (95 mg, 46% yield). $^1$HNMR (CDCl$_3$, 400 MHz): δ 7.85 (s, 1H), 6.72 (s, 1H), 4.14-4.11 (m, 2H), 3.91 (d, J=7.6 Hz, 2H), 3.61-3.56 (m, 2H), 3.12-3.05 (m, 1H), 2.29 (s, 3H), 2.27-2.25 (m, 1H), 2.14-2.10 (m, 2H), 1.90-1.86 (m, 2H), 1.71-1.54 (m, 6H), 1.34-1.32 (m, 2H).

LC-MS: tR=1.98 min (method 13), m/z=316.2 [M+H]+.

Example 64

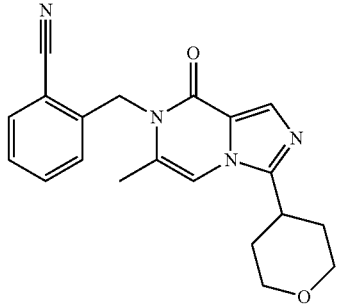 [SMILES: Cc1cn2c(C3CCOCC3)ncc2c(=O)n1Cc1ccccc1C#N]

2-((6-methyl-8-oxo-3-(tetrahydro-2H-pyran-4-yl)imidazo[1,5-a]pyrazin-7(8H)-yl)methyl)benzonitrile A mixture of 6-methyl-3-(tetrahydro-2H-pyran-4-yl)imidazo[1,5-a]pyrazin-8(7H)-one (100 mg, 429 μmol), 2-(bromomethyl)benzonitrile (126 mg, 643 μmol) and $Cs_2CO_3$ (279 mg, 857 μmol) in DMF (3.0 mL) was stirred at 70° C. for 6 hours. The mixture was filtered and the filtrate was concentrated under vacuum. The residue was purified by silica gel chromatography (Petroleum ether/Ethyl acetate=10/1, 0/1) to afford 2-((6-methyl-8-oxo-3-(tetrahydro-2H-pyran-4-yl)imidazo[1,5-a]pyrazin-7(8H)-yl) methyl)benzonitrile (92 mg, 59% yield).

¹H NMR (CDCl₃ 400 MHz): δ 7.96 (s, 1H), 7.72 (d, J=7.6 Hz, 1H), 7.55 (t, J=7.2 Hz, 1H), 7.40 (t, J=7.2 Hz, 1H), 7.19 (d, J=8.0 Hz, 1H), 6.80 (s, 1H), 5.45 (s, 2H), 4.14 (d, J=12.0 Hz, 2H), 3.63-3.57 (m, 2H), 3.14-3.08 (m, 1H), 2.20-2.09 (m, 5H), 1.90 (d, J=13.2 Hz, 2H).

LC-MS: $t_R$=2.202 min (method 3), m/z=349.1 [M+H]⁺.

Example 65

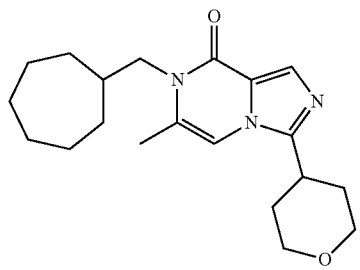 [SMILES: Cc1cn2c(C3CCOCC3)ncc2c(=O)n1CC1CCCCCC1]

7-(cycloheptyl methyl)-6-methyl-3-(tetrahydro-2H-pyran-4-yl)imidazo[1,5-a]pyrazin-8(7H)-one Step 1: To a solution of cycloheptanecarboxylic acid (500 mg, 3.52 mmol) in THF (40 mL) was added LiAlH₄ (401 mg, 10.6 mmol) in portions at 0° C. The mixture was stirred at 65° C. for 3 hours. The reaction was quenched with H₂O (0.4 mL) and 10% NaOH (0.4 mL, aq). To the mixture was added Na₂SO₄. The mixture was filtered. The filtrate was concentrated. The residue was purified by flash silica gel chromatography to give cycloheptylmethanol (383 mg, 85% yield).

¹H NMR (CDCl₃ 400 MHz): δ 3.43 (d, J=6.4 Hz, 2H), 1.80-1.62 (m, 5H), 1.56-1.40 (m, 4H), 1.31 (br, s, 1H), 1.84 (s, 3H), 1.10-1.22 (m, 2H).

Step 2: To a solution of cycloheptylmethanol (313 mg, 2.44 mmol) and triethylamine (494 mg, 4.88 mmol) in DCM (5 mL) was added MsCl (490 mg, 4.28 mmol) at 0° C. and it was stirred at 20° C. for 40 min. The solution was washed with NaHCO₃ (saturated aqueous 5 mL×4), water (5 mL×2), brine (3 mL) and then was dried over Na₂SO₄, filtered and concentrated to give cycloheptylmethyl methanesulfonate (381 mg) which was used in the next step directly without further purification.

Step 3: To a solution of 6-methyl-3-(tetrahydro-2H-pyran-4-yl)imidazo[1,5-a]pyrazin-8(7H)-one (150 mg, 643 μmol) and cycloheptylmethyl methanesulfonate (159 mg, 772 μmol) in DMF (3 mL) was added Cs₂CO₃ (419 mg, 1.29 mmol). The mixture was stirred at 60° C. for 6 hours. The mixture was diluted with DCM (20 mL) and washed with water (5 mL×2), brine (10 mL), dried over Na₂SO₄, filtered and concentrated. The residue was purified by flash silica gel chromatography and then was purified by preparative LC-MS to give 7-(cycloheptylmethyl)-6-methyl-3-(tetrahydro-2H-pyran-4-yl)imidazo[1,5-a]pyrazin-8(7H)-one (25.15 mg, 11% yield).

¹H NMR (CDCl₃ 400 MHz): δ 7.84 (s, 1H), 6.71 (s, 1H), 4.12 (d, J=5.2 Hz, 2H), 3.77 (d, J=3.6 Hz, 2H), 3.65-3.52 (m, 2H), 3.15-3.02 (m, 1H), 2.26 (s, 3H), 2.17-2.07 (m, 2H), 2.07-2.98 (m, 1H), 1.87 (d, J=6.6 Hz, 2H), 1.63-1.75 (m, 4H), 1.55-1.62 (m, 2H), 1.54-1.45 (m, 2H), 1.44-1.33 (m, 2H), 1.30-1.18 (m, 2H).

LC-MS: $t_R$=2.227 min (method 13), m/z=344.2 [M+H]⁺.

Example 66

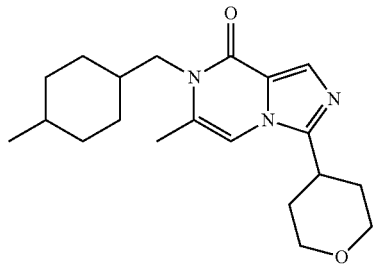 [SMILES: Cc1cn2c(C3CCOCC3)ncc2c(=O)n1CC1CCC(C)CC1]

6-methyl-7-((4-methylcyclohexyl)methyl)-3-(tetrahydro-2H-pyran-4-yl)imidazo[1,5-a]pyrazin-8(7H)-one, cis and trans Step 1: To a solution of (4-methylcyclohexyl)methanol (400 mg, 3.12 mmol, 1 eq) in anhydrous DCM (20 mL) was added triethylamine (631 mg, 6.24 mmol, 865 μL, 2 eq). The mixture was dropwise added methanesulfonyl chloride (465 mg, 4.06 mmol, 314 μL, 1.30 eq) at 0° C. and it was stirred at 0° C. for 1 hour. The reaction mixture was washed with water (5 mL×3), brine (3 mL), dried and concentrated. (4-methylcyclohexyl)methyl methanesulfonate (700 mg) was obtained.

Step 2: To a solution of 6-methyl-3-(tetrahydro-2H-pyran-4-yl)imidazo[1,5-a]pyrazin-8(7H)-one (260 mg, 1.11 mmol, 1 eq) and (4-methylcyclohexyl)methyl methanesulfonate (572 mg, 2.78 mmol, 2.50 eq) in anhydrous DMF (6 mL) was added Cs₂CO₃ (723 mg, 2.22 mmol, 2 eq). The mixture was stirred at 60° C. for 12 hours. The reaction mixture was concentrated under reduced pressure to remove DMF. The residue was diluted with H₂O (3 mL) and extracted with DCM (10 mL×2). The combined organic layers were dried over Na₂SO₄, filtered and concentrated. The residue was purified by preparative TLC (SiO₂, EA). 6-methyl-7-((4-methylcyclohexyl)methyl)-3-(tetrahydro-2H-pyran-4-yl)imidazo[1,5-a]pyrazin-8(7H)-one (175 mg, 45% yield) was obtained.

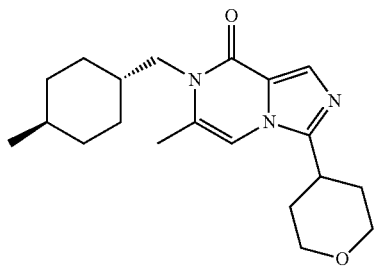 [SMILES: Cc1cn2c(C3CCOCC3)ncc2c(=O)n1C[C@H]1CC[C@H](C)CC1]

trans-6-methyl-7-((−4-methylcyclohexyl)methyl)-3-(tetrahydro-2H-pyran-4-yl)imidazo[1,5-a]pyrazin-8(7H)-one 6-methyl-7-((4-methylcyclohexyl)methyl)-3-(tetrahydro-2H-pyran-4-yl)imidazo[1,5-a]pyrazin-8(7H)-one (160 mg, 466 μmol, 1 eq) was purified by SFC to give 6-methyl-7-

(((trans)-4-methylcyclohexyl)methyl)-3-(tetrahydro-2H-pyran-4-yl)imidazo[1,5-a]pyrazin-8(7H)-one (60 mg, 37% yield, 98% purity).

¹H NMR (CDCl₃ 400 MHz): δ 7.84 (s, 1H), 6.71 (s, 1H), 4.12 (d, J=10.8 Hz, 2H), 3.79-3.77 (m, 2H), 3.61-3.55 (m, 2H), 3.09-3.05 (m, 1H), 2.26 (s, 3H), 2.14-2.07 (m, 2H), 1.88 (d, J=10.8 Hz, 2H), 1.69-1.67 (m, 5H), 1.34-1.32 (m, 2H), 1.11-1.09 (m, 2H), 0.91-0.86 (m, 4H).

LC-MS: t$_R$=2.256 min (method 13), m/z=344.2 [M+H]⁺.

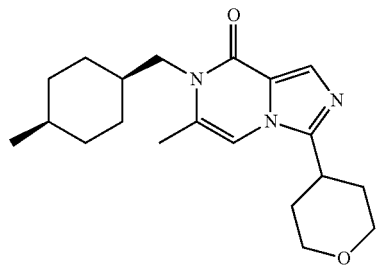 [SMILES: Cc1cn2c(C3CCOCC3)ncc2c(=O)n1C[C@H]1CC[C@@H](C)CC1]

cis-6-methyl-7-((-4-methylcyclohexyl)methyl)-3-(tetrahydro-2H-pyran-4-yl)imidazo[1,5-a]pyrazin-8(7H)-one 6-methyl-7-(((cis)-4-methylcyclohexyl)methyl)-3-(tetrahydro-2H-pyran-4-yl)imidazo[1,5-a]pyrazin-8(7H)-one (90 mg, 54% yield).

¹H NMR (CDCl₃ 400 MHz): δ 7.85 (s, 1H), 6.72 (s, 1H), 4.12 (d, J=10.8 Hz, 2H), 3.89-3.87 (m, 2H), 3.61-3.55 (m, 2H), 3.09-3.05 (m, 1H), 2.28 (s, 3H), 2.14-2.11 (m, 2H), 1.87 (d, J=14.4 Hz, 2H), 1.50-1.40 (m, 8H), 0.97-0.95 (m, 3H).

LC-MS: t$_R$=2.240 min (method 13), m/z=344.2 [M+H]⁺.

Example 67

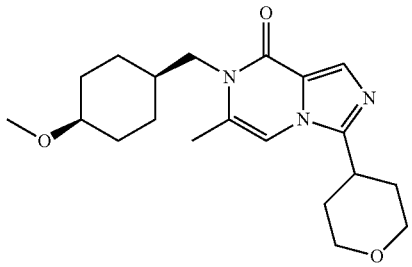 [SMILES: CO[C@H]1CC[C@@H](Cn2c(C)cn3c(C4CCOCC4)ncc3c2=O)CC1]

7-(((cis)-4-methoxycyclohexyl)methyl)-6-methyl-3-(tetrahydro-2H-pyran-4-yl)imidazo[1,5-a]pyrazin-8(7H)-one To a solution of 6-methyl-3-(tetrahydro-2H-pyran-4-yl)imidazo[1,5-a]pyrazin-8(7H)-one (60 mg, 257 μmol, 1 eq) in dry DMF (5 mL) was added ((cis)-4-methoxycyclohexyl)methyl methanesulfonate (74 mg, 334 μmol, 1.30 eq) and Cs₂CO₃ (168 mg, 514 μmol, 2 eq). The mixture was heated at 60° C. for 16 hours. The mixture was concentrated. DCM (20 mL) and H₂O (10 mL) was added. The mixture was extracted with DCM (20 mL). The organic layer was washed with H₂O (20 mL), dried over Na₂SO₄, filtered and concentrated. The residue was purified by preparative TLC (DCM/MeOH=20/1) to give 7-(((cis)-4-methoxycyclohexyl)methyl)-6-methyl-3-(tetrahydro-2H-pyran-4-yl)imidazo[1,5-a]pyrazin-8(7H)-one (15 mg, 16% yield).

¹H NMR (CDCl₃ 400 MHz): δ 7.83 (s, 1H), 6.69 (s, 1H), 4.10 (d, J=11.2 Hz, 2H), 3.75 (d, J=7.2 Hz, 2H), 3.56 (t, J=11.2 Hz, 2H), 3.42 (m, 1H), 3.29 (s, 3H), 3.11-3.03 (m, 1H), 2.24 (s, 3H), 2.15-2.06 (m, 2H), 1.94-1.84 (m, 5H), 1.44-1.37 (m, 6H).

LC-MS: t$_R$=1.887 min (method 13), m/z=360.2 [M+H]⁺.

Example 68

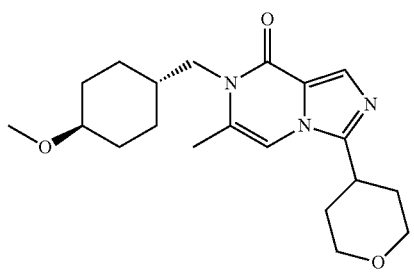 [SMILES: CO[C@H]1CC[C@H](Cn2c(C)cn3c(C4CCOCC4)ncc3c2=O)CC1]

7-(((trans)-4-methoxycyclohexyl)methyl)-6-methyl-3-(tetrahydro-2H-pyran-4-yl)imidazo[1,5-a]pyrazin-8(7H)-one To a solution of 6-methyl-3-(tetrahydro-2H-pyran-4-yl)imidazo[1,5-a]pyrazin-8(7H)-one (60 mg, 257 μmol, 1 eq) in dry DMF (5 mL) was added ((trans)-4-methoxycyclohexyl)methyl methanesulfonate (74 mg, 334 μmol, 1.30 eq) and Cs₂CO₃ (168 mg, 514 μmol, 2 eq). The mixture was heated at 60° C. for 16 hours. The mixture was concentrated. DCM (20 mL) and H₂O (10 mL) were added. The mixture was extracted with DCM (20 mL). The organic layer was washed with H₂O (20 mL), dried over Na₂SO₄, filtered and concentrated. The residue was purified by preparative TLC (DCM/MeOH=20/1) to give 7-(((trans)-4-methoxycyclohexyl)methyl)-6-methyl-3-(tetrahydro-2H-pyran-4-yl)imidazo[1,5-a]pyrazin-8(7H)-one (35 mg, 38% yield).

¹H NMR (CDCl₃ 400 MHz): δ 7.84 (s, 1H), 6.71 (s, 1H), 4.11 (d, J=10.4 Hz, 2H), 3.79 (d, J=5.6 Hz, 2H), 3.57 (t, J=10.0 Hz, 2H), 3.33 (s, 3H), 3.10-3.05 (m, 2H), 2.26 (s, 3H), 2.15-2.07 (m, 4H), 1.88-1.84 (m, 2H), 1.75-1.71 (m, 3H), 1.15-1.11 (m, 4H).

LC-MS: t$_R$=1.831 min (method 13), m/z=360.2 [M+H]⁺.

Example 69

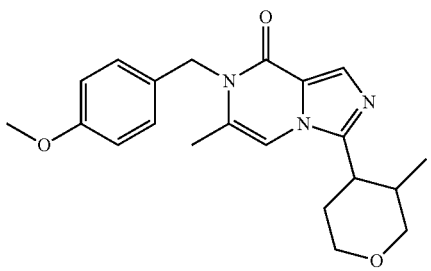

7-(4-methoxybenzyl)-6-methyl-3-(3-methyltetrahydro-2H-pyran-4-yl)imidazo[1,5-a]pyrazin-8(7H)-one Step 1: To a solution of (3-methoxy-5-methylpyrazin-2-yl)methanamine hydrochloride (150 mg, 0.79 mmol, 1 eq) and 3-methyltetrahydro-2H-pyran-4-carboxylic acid (125 mg, 870 μmol, 1.1 eq) in DCM (5 mL) was added HATU (451 mg, 1.19 mmol, 1.5 eq) and DIPEA (204 mg, 1.58 mmol, 276 μL, 2 eq). The mixture was stirred at 25° C. for 18 hours. The mixture was concentrated. The crude product was purified by flash chromatography with petroleum ether: ethyl acetate=3:1 2:1. N-((3-methoxy-5-methylpyrazin-2-yl)methyl)-3-methyltetrahydro-2H-pyran-4-carboxamide (220 mg, 780 μmol, 99% yield) was obtained.

Step 2: To a solution of N-((3-methoxy-5-methylpyrazin-2-yl)methyl)-3-methyltetrahydro-2H-pyran-4-carboxamide (220 mg, 788 μmol, 1 eq) in dioxane (8 mL) was added POCl$_3$ (242 mg, 1.58 mmol, 146 μL, 2 eq). The mixture was stirred at 80° C. for 2 hours. The mixture was concentrated. 6-methyl-3-(3-methyltetrahydro-2H-pyran-4-yl)imidazo[1,5-a]pyrazin-8-ol (223 mg, hydrochloride salt) was used in the next step without further purification.

Step 3: To a solution of 6-methyl-3-(3-methyltetrahydro-2H-pyran-4-yl)imidazo[1,5-a]pyrazin-8-01 (170 mg, 0.6 mmol) in DMF (5 mL) was added Cs$_2$CO$_3$ (586 mg, 1.80 mmol, 3 eq) and 1-(chloromethyl)-4-methoxybenzene (113 mg, 719 μmol, 98 μL, 1.20 eq). The mixture was stirred at 60° C. for 18 hours. The reaction mixture was filtered, and the filtrate was concentrated. The crude mixture was purified by preparative LC-MS, and then by preparative TLC with ethyl acetate as eluent. 7-(4-methoxybenzyl)-6-methyl-3-(3-methyltetrahydro-2H-pyran-4-yl)imidazo[1,5-a]pyrazin-8(7H)-one (76 mg, 207 μmol, 35% yield) was obtained.

$^1$H NMR, a mixture of diastereoisomers (CDCl$_3$ 400 MHz): δ 7.96-7.94 (m, 1H), 7.18 (d, J=8.0 Hz, 2H), 6.86 (d, J=8.0 Hz, 2H), 6.76 (s, 0.73H), 6.71 (s, 0.28H), 5.22-5.12 (m, 2H), 4.17-4.01 (m, 2H), 3.79 (s, 3H), 3.55-3.49 (m, 1H), 3.19-3.14 (m, 1H), 2.66-2.64 (m, 1H), 2.36-2.33 (m, 1H), 2.21 (s, 3H), 2.13-2.10 (m, 1H), 1.78-1.61 (m, 1H), 0.87 (d, J=7.2 Hz, 1H), 0.71 (d, J=6.8 Hz, 2H).

LC-MS: $t_R$=2.370 min (method 11), m/z=368.1 [M+H]$^+$.

Example 70

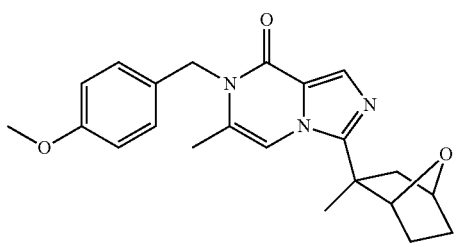 [SMILES: COc1ccc(Cn2c(C)cn3c(C4(C)CC5CCC4O5)ncc3c2=O)cc1]

racemic 7-(4-methoxybenzyl)-6-methyl-3-((1R, 2R, 4S)-2-methyl-7-oxabicyclo[2.2.1]heptan-2-yl)imidazo[1,5-a]pyrazin-8(7H)-one Step 1: To a solution of (3-methoxy-5-methylpyrazin-2-yl)methanamine hydrochloride (150 mg, 791 μmol, 1 eq) in dry DCM (5 mL) was added triethylamine (240 mg, 2.37 mmol, 329 μL, 3 eq), racemic (1R,2S,4S)-2-methyl-7-oxabicyclo[2.2.1]heptane-2-carboxylic acid (124 mg, 791 μmol, 1 eq) and HATU (361 mg, 949 μmol, 1.20 eq). The mixture was stirred at 15° C. for 16 hours. H$_2$O (5 mL) was added and the mixture was extracted with DCM (20 mL×2). The combined organic layer was washed with H$_2$O (20 mL), brine (20 mL), dried over Na$_2$SO$_4$, filtered and concentrated. The residue was purified by flash chromatography on silica gel (0%~50% ethyl acetate in petroleum ether) to give racemic (1R,2S,4S)—N-((3-methoxy-5-methylpyrazin-2-yl)methyl)-2-methyl-7-oxabicyclo[2.2.1]heptane-2-carboxamide (200 mg, 87% yield).

Step 2: To a solution of racemic (1R,2S,4S)—N-((3-methoxy-5-methylpyrazin-2-yl)methyl)-2-methyl-7-oxabicyclo[2.2.1]heptane-2-carboxamide (150 mg, 515 μmol, 1 eq) in dry dioxane (5 mL) was added POCl$_3$ (158 mg, 1.03 mmol, 96 μL, 2 eq). The mixture was heated at 80° C. for 2 hours. The mixture was cooled to 15° C. and poured into water (5 mL). The mixture was adjusted to pH 8 by saturated aqueous NaHCO$_3$ and extracted with DCM (20 mL×2). The combined organics were washed with H$_2$O (20 mL), brine (20 mL), dried over Na$_2$SO$_4$, filtered and concentrated to give racemic 6-methyl-3-((1R, 2R, 4S)-2-methyl-7-oxabicyclo[2.2.1]heptan-2-yl)imidazo[1,5-a]pyrazin-8-ol (120 mg).

Step 3: To a solution of racemic 6-methyl-3-((1R,2R,4S)-2-methyl-7-oxabicyclo[2.2.1]heptan-2-yl)imidazo[1,5-a]pyrazin-8-ol (100 mg, 386 μmol, 1 eq) in dry DMF (5 mL) was added 1-(chloromethyl)-4-methoxy-benzene (72 mg, 463 μmol, 63 μL, 1.20 eq) and Cs$_2$CO$_3$ (251 mg, 771 μmol, 2 eq). The mixture was heated at 60° C. for 2 hours. The mixture was concentrated. DCM (20 mL) and H$_2$O (10 mL) was added. The mixture was extracted with DCM (20 mL). The organic layer was washed with H$_2$O (20 mL), dried over Na$_2$SO$_4$, filtered and concentrated. The residue was purified by preparative LC-MS to give racemic 7-(4-methoxybenzyl)-6-methyl-3-((1R, 2R, 4S)-2-methyl-7-oxabicyclo[2.2.1]heptan-2-yl)imidazo[1,5-a]pyrazin-8(7H)-one (40 mg, 27% yield).

$^1$H NMR (CDCl$_3$ 400 MHz): δ 7.87 (s, 1H), 7.17 (d, J=8.4 Hz, 2H), 6.84 (d, J=8.8 Hz, 2H), 6.69 (s, 1H), 5.23-5.07 (m, 2H), 4.67 (d, J=4.8 Hz, 2H), 3.78 (s, 3H), 2.71 (d, J=12.0 Hz, 1H), 2.20 (s, 3H), 1.90-1.86 (m, 1H), 1.70-1.66 (m, 2H), 1.57 (s, 3H), 1.39-1.37 (m, 1H), 1.25-1.22 (m, 1H).

LC-MS: $t_R$=2.228 min (method 13), m/z=380.2 [M+H]$^+$.

Example 71

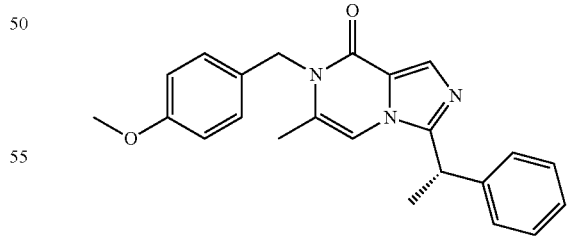

(S)-7-(4-methoxybenzyl)-6-methyl-3-(1-phenylethyl)imidazo[1,5-a]pyrazin-8(7H)-one Step 1: To a solution of (3-methoxy-5-methylpyrazin-2-yl)methanamine hydrochloride (300 mg, 1.58 mmol) and (S)-2-phenylpropanoic acid (261 mg, 1.74 mmol, 237 μL, 1.10 eq) in DCM (10 mL) was added triethylamine (400 mg, 3.95 mmol, 548 μL, 2.50 eq) and HATU (901 mg, 2.37 mmol, 1.50 eq). The mixture was stirred at 15° C. for 12 hours. Water (50 mL) was added to the solution. The mixture was extracted with DCM (50 mL×2). The combined organic layers were washed with brine (50 mL), dried over $Na_2SO_4$, filtered and concentrated under reduced pressure. The residue was purified by flash silica gel chromatography (Eluent of 0-20% Ethyl acetate/petroleum ether). (S)—N-((3-methoxy-5-methylpyrazin-2-yl)methyl)-2-phenylpropanamide (450 mg, 1.56 mmol, 99% yield) was obtained.

$^1$H NMR ($CDCl_3$ 400 MHz): δ 7.81 (s, 1H), 7.24-7.37 (m, 5H), 6.74 (s, 1H), 4.37-4.52 (m, 2H), 3.92 (s, 3H), 3.67 (q, J=7.1 Hz, 1H), 2.40 (s, 3H), 1.56 (d, J=7.2 Hz, 3H).

Step 2: To a solution of (S)-N-((3-methoxy-5-methyl pyrazin-2-yl)methyl)-2-phenylpropanamide (450 mg, 1.58 mmol, 1 eq) in dioxane (10 mL) was added $POCl_3$ (485 mg, 3.16 mmol, 294 μL, 2 eq). The mixture was stirred at 90° C. for 12 hours. The reaction mixture was concentrated under reduced pressure to remove dioxane. The residue was quenched by addition $H_2O$ (50 mL) at 0° C., basified by addition saturated aqueous $NaHCO_3$ (10 mL) and then extracted with EtOAc (50 mL×2). The combined organic layers were washed with brine (50 mL), dried over $Na_2SO_4$, filtered and concentrated under reduced pressure. The residue was purified by flash silica gel chromatography (Eluent of 0~100% Ethyl acetate/petroleum ether). (S)-6-methyl-3-(1-phenylethyl)imidazo[1,5-a]pyrazin-8-ol (128 mg, 505 μmol, 32% yield).

Step 3: To a solution of (S)-6-methyl-3-(1-phenylethyl) imidazo[1,5-a]pyrazin-8-ol (128 mg, 505 μmol, 1 eq) and 1-(chloromethyl)-4-methoxybenzene (95 mg, 0.61 mmol, 83 μL, 1.20 eq) in DMF (10 mL) was added $Cs_2CO_3$ (329.29 mg, 1.01 mmol, 2 eq). The mixture was stirred at 60° C. for 3 hours. The reaction mixture was concentrated under reduced pressure.

The residue was purified by preparative LC-MS was further purified by SFC. (S)-7-(4-methoxybenzyl)-6-methyl-3-(1-phenylethyl)imidazo[1,5-a]pyrazin-8(7H)-one (76.40 mg, 203 μmol, 40% yield) was obtained.

$^1$H NMR ($CDCl_3$ 400 MHz): δ 7.98 (s, 1H), 7.17-7.31 (m, 5H), 7.12 (d, J=8.4 Hz, 2H), 6.82 (d, J=8.4 Hz, 2H), 6.46 (s, 1H), 5.10 (dd, J=15.6 Hz, 2H), 4.26 (q, J=7.2 Hz, 1H), 3.76 (s, 3H), 2.05 (s, 3H), 1.81 (d, J=7.6 Hz, 3H).

LC-MS: $t_R$=2.218 min (method 17), m/z=374.2 [M+H]$^+$. SFC: $t_R$=1.641 min, ee %>99%, $[α]_D^{20}$=-51.4 (c=0.11, MeOH).

and (R)-2-phenylpropanoic acid (190 mg, 1.27 mmol, 173 μL, 1.20 eq) in DCM (10 mL) was added triethylamine (267 mg, 2.64 mmol, 365 μL, 2.50 eq) and HATU (602 mg, 1.58 mmol, 1.50 eq). The mixture was stirred at 15° C. for 12 hours. Water (50 mL) was added to the solution. The mixture was extracted with DCM (50 mL×2). The combined organic layers were washed with brine (50 mL), dried over $Na_2SO_4$, filtered and concentrated under reduced pressure. The residue was purified by flash silica gel chromatography (Eluent of 0~20% Ethyl acetate/petroleum ether). (R)—N-((3-methoxy-5-methylpyrazin-2-yl)methyl)-2-phenylpropanamide (300 mg, 1.02 mmol, 97% yield) was obtained.

$^1$H NMR ($CDCl_3$ 400 MHz): δ 7.81 (s, 1H), 7.24-7.37 (m, 5H), 6.75 (s, 1H), 4.37-4.52 (m, 2H), 3.91 (s, 3H), 3.67 (q, J=7.2 Hz, 1H), 2.40 (s, 3H), 1.56 (d, J=7.2 Hz, 3H).

Step 2: To a solution of (R)—N-((3-methoxy-5-methyl-pyrazin-2-yl)methyl)-2-phenylpropanamide (450 mg, 1.58 mmol, 1 eq) in dioxane (10 mL) was added $POCl_3$ (727 mg, 4.74 mmol, 440 μL, 3 eq). The mixture was stirred at 90° C. for 12 hours. The reaction mixture was concentrated under reduced pressure to remove dioxane. The residue was quenched by addition of $H_2O$ (50 mL) at 0° C., basified by addition saturated aqueous $NaHCO_3$ (10 mL) and then extracted with EtOAc (50 mL×2). The combined organic layers were washed with brine (50 mL), dried over $Na_2SO_4$, filtered and concentrated under reduced pressure. The residue was purified by flash silica gel chromatography (Eluent of 0~100% Ethyl acetate/petroleum ether). (R)-6-methyl-3-(1-phenylethyl)imidazo[1,5-a]pyrazin-8-ol (150 mg, 592 μmol, 37% yield) was obtained.

Step 3: To a solution of (R)-6-methyl-3-(1-phenylethyl) imidazo[1,5-a]pyrazin-8-ol (100 mg, 395 μmol, 1 eq) and 1-(chloromethyl)-4-methoxybenzene (74 mg, 474 μmol, 65 μL, 1.20 eq) in DMF (5 mL) was added $Cs_2CO_3$ (257 mg, 790 μmol, 2 eq). The mixture was stirred at 60° C. for 3 hours. The reaction mixture was concentrated under reduced pressure. The residue was purified by preparative LC-MS. (R)-7-(4-methoxybenzyl)-6-methyl-3-(1-phenylethyl)imidazo[1,5-a]pyrazin-8(7H)-one (140 mg, 95% yield) was obtained.

$^1$H NMR ($CDCl_3$ 400 MHz): δ 7.98 (s, 1H), 7.17-7.32 (m, 5H), 7.12 (d, J=8.4 Hz, 2H), 6.82 (d, J=8.4 Hz, 2H), 6.46 (s, 1H), 5.10 (dd, J=16.0 Hz, 2H), 4.26 (q, J=7.2 Hz, 1H), 3.76 (s, 3H), 2.05 (s, 3H), 1.81 (d, J=6.8 Hz, 3H).

LC-MS: $t_R$=2.184 min (method 18), m/z=374.1 [M+H]$^+$. SFC: $t_R$=1.324 min, ee %=97.8%, $[α]_D^{20}$=+50.7 (c=0.11, MeOH).

Example 72

Example 73

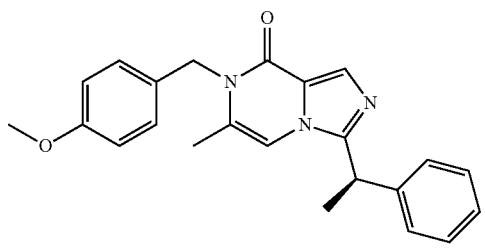 [SMILES: COc1ccc(Cn2c(C)cn3c([C@H](C)c4ccccc4)ncc3c2=O)cc1]

(R)-7-(4-methoxybenzyl)-6-methyl-3-(1-phenyl-ethyl)imidazo[1,5-a]pyrazin-8(7H)-one

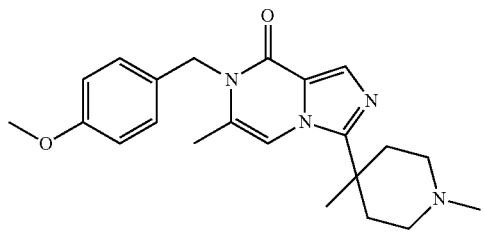

3-(1,4-dimethylpiperidin-4-yl)-7-(4-methoxyben-zyl)-6-methylimidazo[1,5-a]pyrazin-8(7H)-one Step 1: To a solution of (3-methoxy-5-methylpyrazin-2-yl)methanamine hydrochloride (200 mg, 1.05 mmol, 1 eq)

Step 1: To a solution of (3-methoxy-5-methylpyrazin-2-yl)methanamine hydrochloride (150 mg, 791 μmol) in DCM (5 mL) was added 1,4-dimethylpiperidine-4-carboxylic acid hydrochloride (169 mg, 870 µmol, 1.10 eq, HCl), triethylamine (240 mg, 2.37 mmol, 329 µL, 3 eq) and HATU (361 mg, 949 µmol, 1.20 eq). The mixture was stirred at 15° C. for 16 hours. The mixture was concentrated. The residue was purified by preparative TLC (DCM/MeOH=10/1) to give N-((3-methoxy-5-methylpyrazin-2-yl)methyl)-1,4-dimethylpiperidine-4-carboxamide (150 mg, 65% yield).

Step 2: To a solution of N-((3-methoxy-5-methylpyrazin-2-yl)methyl)-1,4-dimethylpiperidine-4-carboxamide (100 mg, 342 µmol, 1 eq) in dry dioxane (5 mL) was added POCl$_3$ (105 mg, 684 µmol, 64 µL, 2 eq). The mixture was heated at 80° C. for 4 hours. The mixture was cooled to 15° C. and poured into water (5 mL). The mixture was adjusted to pH 8 by saturated aqueous NaHCO$_3$ and concentrated. 10% MeOH in DCM (20 mL) was added to the residue and filtered, the filtrate was concentrated to give 3-(1,4-dimethylpiperidin-4-yl)-6-methylimidazo[1,5-a]pyrazin-8-ol (90 mg).

Step 3: To a solution of 3-(1,4-dimethylpiperidin-4-yl)-6-methylimidazo[1,5-a]pyrazin-8-ol (60 mg, 230 µmol, 1 eq) in DMF (2 mL) was added 1-(chloromethyl)-4-methoxybenzene (54 mg, 346 µmol, 47 µL, 1.50 eq) and Cs$_2$CO$_3$ (150 mg, 461 µmol, 2 eq). The mixture was heated at 60° C. for 2 hours. The mixture was concentrated. DCM (20 mL) and H$_2$O (10 mL) were added. The mixture was extracted with DCM (20 mL). The organic layer was washed with H$_2$O (20 mL), dried over Na$_2$SO$_4$, filtered and concentrated. The residue was purified by preparative LC-MS to give 3-(1,4-dimethyl piperidin-4-yl)-7-(4-methoxybenzyl)-6-methyl-imidazo[1,5-a]pyrazin-8(7H)-one (20 mg, 23% yield).

$^1$H NMR (CDCl$_3$ 400 MHz): δ 7.92 (s, 1H), 7.17 (d, J=8.8 Hz, 2H), 6.94 (s, 1H), 6.84 (d, J=8.8 Hz, 2H), 5.15 (s, 2H), 3.78 (s, 3H), 2.58-2.56 (m, 2H), 2.49-2.45 (m, 2H), 2.38-2.35 (m, 2H), 2.25 (s, 3H), 2.19 (s, 3H), 1.86-1.80 (m, 2H), 1.42 (s, 3H).

LC-MS: $t_R$=1.747 min (method 13), m/z=381.2 [M+H]$^+$.

Example 74

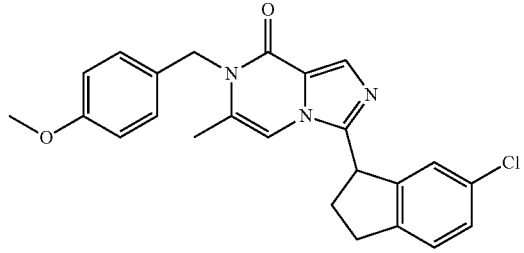 [SMILES: COc1ccc(Cn2c(C)cn3c(C4CCc5ccc(Cl)cc54)ncc3c2=O)cc1]

3-(6-chloro-2,3-dihydro-1H-inden-1-yl)-7-(4-methoxybenzyl)-6-methylimidazo[1,5-a]pyrazin-8(7H)-one Step 1: To a solution of (3-methoxy-5-methylpyrazin-2-yl)methanamine hydrochloride (200 mg, 1.05 mmol) and 6-chloro-2,3-dihydro-1H-indene-1-carboxylic acid (206 mg, 1.05 mmol, 1 eq) in DCM (5 mL) was added HATU (479 mg, 1.26 mmol, 1.20 eq) and DIPEA (407 mg, 3.15 mmol, 550 µL, 3 eq). The mixture was stirred at 18° C. for 16 hours. The mixture washed with H$_2$O (20 mL) and extracted with DCM (20 mL×3). The combined organic was dried over Na$_2$SO$_4$ and concentrated under vacuum. 6-chloro-N-((3-methoxy-5-methylpyrazin-2-yl)methyl)-2,3-dihydro-1H-indene-1-carboxamide (312 mg, 864 µmol, 82% yield) was obtained.

Step 2: To a solution of 6-chloro-N-((3-methoxy-5-methylpyrazin-2-yl)methyl)-2,3-dihydro-1H-indene-1-carboxamide (0.262 g, 1 eq) in dioxane (10 mL) was added POCl$_3$ (363 mg, 2.37 mmol, 220 µL, 3 eq). The mixture was stirred at 80° C. for 3 hours. The mixture was quenched by H$_2$O (20 mL) and adjusted pH>7 by saturated aqueous NaHCO$_3$. The mixture was extracted with DCM (25 mL×3). The combined organic was dried over Na$_2$SO$_4$ and concentrated under vacuum. 3-(6-chloro-2,3-dihydro-1H-inden-1-yl)-6-methylimidazo[1,5-a]pyrazin-8(7H)-one (236 mg) was obtained and directly used to next step.

Step 3: To a solution of 3-(6-chloro-2,3-dihydro-1H-inden-1-yl)-6-methylimidazo[1,5-a]pyrazin-8(7H)-one (236 mg, 787 µmol, 1 eq) and 1-(chloromethyl)-4-methoxybenzene (148 mg, 945 µmol, 1.20 eq) in DMF (12 mL) was added Cs$_2$CO$_3$ (513 mg, 1.57 mmol, 2 eq). The mixture was stirred at 60° C. for 2.5 hours. The mixture was concentrated under vacuum. The residue was quenched with H$_2$O (15 mL) and extracted with DCM (20 mL×3). The combined organic phases were dried over Na$_2$SO$_4$ and concentrated under vacuum. The residue was purified by preparative HPLC. 3-(6-chloro-2,3-dihydro-1H-inden-1-yl)-7-(4-methoxybenzyl)-6-methylimidazo[1,5-a]pyrazin-8(7H)-one (99 mg, 237 µmol, 30% yield) was obtained.

$^1$H NMR (CDCl$_3$ 400 MHz): δ 7.93 (s, 1H), 7.30-7.18 (m, 4H), 6.98 (s, 1H), 6.88 (d, J=8.8 HZ, 2H), 6.64 (s, 1H), 5.18 (s, 2H), 4.71 (t, J=8.4 HZ 1H), 3.79 (s, 3H), 3.16-3.13 (m, 1H), 3.05-2.96 (m, 1H), 2.64-2.61 (m, 1H), 2.52-2.49 (m, 1H), 2.17 (s, 3H).

LC-MS: $t_R$=2.358 min (method 17), m/z=420.1 [M+H]$^+$.

Example 75

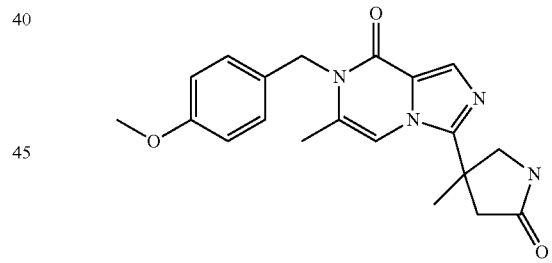

7-(4-methoxybenzyl)-6-methyl-3-(3-methyl-5-oxopyrrolidin-3-yl)imidazo[1,5-a]pyrazin-8(7H)-one Step 1: To a solution of ethyl 3-methyl-5-oxopyrrolidine-3-carboxylate (200 mg, 1.17 mmol, 1 eq) in THF (4 mL) and H$_2$O (2 mL) was added LiOH.H$_2$O (147.06 mg, 3.50 mmol, 3 eq). The mixture was stirred at 20° C. for 16 hours. The mixture was acidified to pH=2 by 1 M HCl and extracted with ethyl acetate (20 mL×3). The combined organic layers were washed with H$_2$O (20 mL), brine (20 mL), dried over Na$_2$SO$_4$, filtered and concentrated to give 3-methyl-5-oxopyrrolidine-3-carboxylic acid (100 mg, 60% yield).

Step 2: To a cooled (0° C.) solution of 3-methyl-5-oxopyrrolidine-3-carboxylic acid (100 mg, 0.7 mmol, 1 eq) in DCM (2 mL) was added oxalyl dichloride (98 mg, 768 µmol, 67 µL, 1.10 eq) and one drop of dry DMF was added.

The mixture was stirred at 20° C. for 1 hour. The colorless solution of 3-methyl-5-oxopyrrolidine-3-carbonyl chloride (112.89 mg) in DCM (2 mL) was directly used for the next step.

Step 3: To a cooled (0° C.) solution of (3-methoxy-5-methylpyrazin-2-yl)methanamine (120 mg, 633 μmol, 1 eq, HCl) in dry DCM (3 mL) was added triethylamine (192 mg, 1.90 mmol, 263 μL, 3 eq) and a solution of 3-methyl-5-oxopyrrolidine-3-carbonyl chloride (112 mg, 696 μmol, 1.10 eq) in dry DCM (2 mL) dropwise. The mixture was stirred at 20° C. for 1 hour. $H_2O$ (5 mL) was added and the mixture was extracted with DCM (20 mL×2). The combined organic layer was washed with $H_2O$ (20 mL), brine (20 mL), dried over $Na_2SO_4$, filtered and concentrated. The residue was purified by preparative TLC (DCM/MeOH=10/1) to give N-((3-methoxy-5-methylpyrazin-2-yl)methyl)-3-methyl-5-oxopyrrolidine-3-carboxamide (75 mg, 42% yield).

Step 4: A solution of N-((3-methoxy-5-methyl pyrazin-2-yl)methyl)-3-methyl-5-oxopyrrolidine-3-carboxamide (100 mg, 359 μmol, 1 eq) in Eaton's reagent (7.7 wt % phosphorus pentoxide solution in methanesulfonic acid) (2 mL) was heated at 60° C. for 16 hours. The mixture was cooled to 15° C. and poured into ice (5 g). The mixture was adjusted to pH=8 by 7 M $NH_3$/MeOH and concentrated. 10% MeOH in DCM (20 mL) was added to the residue and filtered, the filtrate was concentrated to give 4-(8-hydroxy-6-methylimidazo[1,5-a]pyrazin-3-yl)-4-methylpyrrolidin-2-one (100 mg).

Step 5: To a solution of 4-(8-hydroxy-6-methylimidazo[1,5-a]pyrazin-3-yl)-4-methylpyrrolidin-2-one (100 mg, 406 μmol, 1 eq) in DMF (5 mL) was added 1-(chloromethyl)-4-methoxybenzene (76 mg, 487 μmol, 66 μL, 1.20 eq) and $Cs_2CO_3$ (265 mg, 812 μmol, 2 eq). The mixture was heated at 60° C. for 2 h. The mixture was concentrated. DCM (20 mL) and $H_2O$ (10 mL) was added. The mixture was extracted with DCM (20 mL). The organic layers were washed with $H_2O$ (20 mL), dried over $Na_2SO_4$, filtered and concentrated. The mixture was purified by preparative HPLC to give 7-(4-methoxybenzyl)-6-methyl-3-(3-methyl-5-oxopyrrolidin-3-yl)imidazo[1,5-a]pyrazin-8(7H)-one (40 mg, 27% yield).

$^1$H NMR (CDCl$_3$ 400 MHz): δ 7.87 (s, 1H), 7.15 (d, J=8.4 Hz, 2H), 6.84 (d, J=8.4 Hz, 2H), 6.65 (s, 1H), 5.93 (brs, 1H), 5.16 (s, 2H), 4.25 (d, J=9.6 Hz, 1H), 3.77 (s, 3H), 3.53 (d, J=10.4 Hz, 1H), 3.00 (d, J=16.8 Hz, 1H), 2.57 (d, J=16.4 Hz, 1H), 2.20 (s, 3H), 1.63 (s, 3H).

LC-MS: $t_R$=1.764 min (method 11), m/z=367.1 [M+H]$^+$.

Example 76

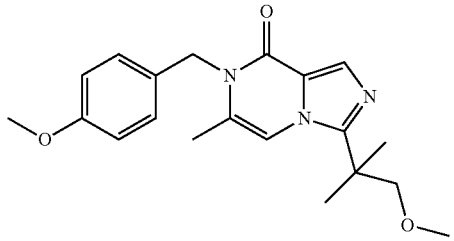

3-(1-methoxy-2-methylpropan-2-yl)-7-(4-methoxybenzyl)-6-methylimidazo[1,5-a]pyrazin-8(7H)-one Step 1: To a solution of 3-methoxy-2,2-dimethylpropanoic acid (115 mg, 870 μmol, 1 eq) in DCM (5 mL) was added oxalyl dichloride (121 mg, 957 μmol, 84 μL, 1.10 eq) at 0° C., followed by one drop of DMF. The mixture was stirred at 20° C. for 1 hour. The mixture was directly used to next step.

Step 2: To a solution of 3-methoxy-2,2-dimethylpropanoyl chloride (150 mg, 791 μmol, 1 eq, HCl) and triethylamine (120 mg, 1.19 mmol, 164 μL, 1.50 eq) in DCM (10 mL) was added (3-methoxy-5-methylpyrazin-2-yl)methanamine (131 mg, 870 μmol, 1.10 eq) in DCM (5 mL). The mixture was stirred at 20° C. for 1 hour. The mixture was quenched with $H_2O$ (20 mL) and extracted with DCM (15 mL×3). The combined organic layers were dried over $Na_2SO_4$ and concentrated under vacuum. 3-methoxy-N-((3-methoxy-5-methylpyrazin-2-yl)methyl)-2,2-dimethylpropanamide (142 mg, 522 μmol, 66% yield) was obtained.

Step 3: To a solution of 3-methoxy-N-((3-methoxy-5-methylpyrazin-2-yl)methyl)-2,2-dimethylpropanamide (102 mg, 382 μmol, 1 eq) in dioxane (5 mL) was added POCl$_3$ (117 mg, 763 μmol, 71 μL, 2 eq). The mixture was stirred at 80° C. for 2 hours. The mixture was quenched with water (20 mL) and extracted with DCM (20 mL×3). The combined organic layers were dried with $Na_2SO_4$ and concentrated under vacuum. 3-(1-methoxy-2-methylpropan-2-yl)-6-methylimidazo[1,5-a]pyrazin-8(7H)-one (45 mg, 191 μmol, 50% yield) was obtained.

Step 4: To a solution of 3-(1-methoxy-2-methylpropan-2-yl)-6-methylimidazo[1,5-a]pyrazin-8(7H)-one (62 mg, 264 μmol, 1 eq) and 1-(chloromethyl)-4-methoxybenzene (49.52 mg, 316 μmol, 43.06 μL, 1.20 eq) in DMF (5 mL) was added $Cs_2CO_3$ (171.72 mg, 527 μmol, 2 eq). The mixture was stirred at 60° C. for 3 hours. The mixture washed with $H_2O$ (20 mL) and extracted with DCM (20 mL×3). The combined organic layers were dried over $Na_2SO_4$ and concentrated under vacuum. The residue was purified by preparative HPLC. 3-(1-methoxy-2-methylpropan-2-yl)-7-(4-methoxybenzyl)-6-methylimidazo[1,5-a]pyrazin-8(7H)-one (25.15 mg, 71 μmol, 27% yield) was obtained.

$^1$H NMR (CDCl$_3$ 400 MHz): δ 7.91 (s, 1H), 7.20-7.17 (m, 3H), 6.86 (d, J=8.4 Hz, 2H), 5.15 (s, 2H), 3.79 (s, 3H), 3.59 (s, 2H), 3.35 (s, 3H), 2.18 (s, 3H), 1.52 (s, 6H).

LC-MS: $t_R$=2.050 min (method 13), m/z=356.1 [M+H]$^+$.

Example 77

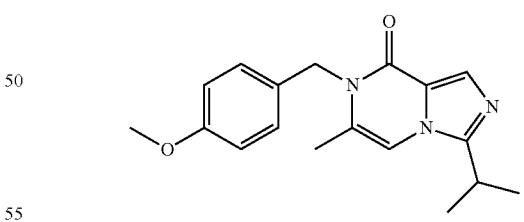

3-isopropyl-7-(4-methoxybenzyl)-6-methylimidazo[1,5-a]pyrazin-8(7H)-one

Step 1: To a cold (0° C.) solution of (3-methoxy-5-methylpyrazin-2-yl)methanamine hydrochloride (150 mg, 791 μmol), Et$_3$N (176 mg, 1.74 mmol, 241 μL, 2.20 eq) in anhydrous DCM (5 mL) was added isobutyryl chloride (93 mg, 870 μmol, 91 μL, 1.10 eq). The solution was stirred at 0° C. for 0.5 h. The mixture was diluted with water (20 mL), extracted with DCM (20 mL×2). The organic layer was washed with brine (20 ml), dried over Na₂SO₄ and concentrated in vacuo. N-((3-methoxy-5-methylpyrazin-2-yl)methyl)isobutyramide (160 mg, 717 μmol, 91% yield) was obtained.

Step 2: To a solution of N-((3-methoxy-5-methylpyrazin-2-yl)methyl)isobutyramide (160 mg, 717 μmol, 1 eq) in dioxanedioxane (5 mL) was added POCl₃ (220 mg, 1.43 mmol, 133 μL, 2 eq). The mixture was stirred at 90° C. 2 hours. The mixture was concentrated in vacuo. 3-isopropyl-8-methoxy-6-methylimidazo[1,5-a]pyrazine (130 mg, 633 μmol, 88% yield) was obtained.

Step 3: A solution of 3-isopropyl-8-methoxy-6-methylimidazo[1,5-a]pyrazine (130 mg, 633 μmol, 1 eq) in 2M HCl(aq) (4 mL) and dioxane (8 mL) was stirred at 90° C. for 2 hours. The mixture was concentrated in vacuo. The residue was purified by silica gel chromatography (DCM:MeOH=10:1). 3-isopropyl-6-methylimidazo[1,5-a]pyrazin-8(7H)-one (120 mg, 628 μmol, 99% yield) was obtained.

Step 4: To a solution of 3-isopropyl-6-methylimidazo[1,5-a]pyrazin-8(7H)-one (120 mg, 628 μmol, 1 eq) in DMF (8 mL) was added 1-(chloromethyl)-4-methoxy-benzene (118 mg, 753 μmol, 103 μL, 1.20 eq) and Cs₂CO₃ (307 mg, 941 μmol, 1.50 eq). The mixture was stirred at 60° C. for 16 hours. The mixture was filtered. The filtrate was purified by pre-HPLC (base). 3-isopropyl-7-(4-methoxybenzyl)-6-methylimidazo[1,5-a]pyrazin-8(7H)-one (90 mg, 287 μmol, 46% yield) was obtained.

¹H NMR (CDCl₃ 400 MHz): δ 7.90 (s, 1H), 7.16 (d, J=8.4 Hz, 1H), 6.85 (d, J=8.4 Hz, 1H), 6.71 (s, 1H), 5.16 (s, 2H), 3.78 (s, 2H), 3.18-3.11 (m, 1H), 2.19 (s, 3H), 1.41-1.79 (d, J=7.2 Hz, 6H).

LC-MS: $t_R$=1.92 min (method 13), m/z=312.1 [M+H]⁺.

Example 78

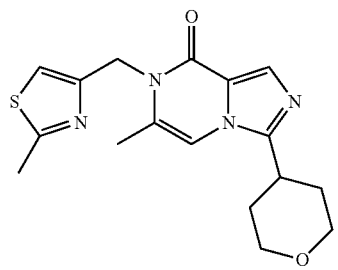 [SMILES: Cc1nc(Cn2c(C)cn3c(C4CCOCC4)ncc3c2=O)cs1]

6-methyl-7-((2-methylthiazol-4-yl)methyl)-3-(tetrahydro-2H-pyran-4-yl)imidazo[1,5-a]pyrazin-8(7H)-one Into a vial was added 6-methyl-3-(tetrahydro-2H-pyran-4-yl)imidazo[1,5-a]pyrazin-8(7H)-one (30 mg, 0.13 mmol), cesium carbonate (84 mg, 0.26 mmol), 4-(chloromethyl)-2-methylthiazole (23 mg, 0.15 mmol) and sodium iodide (23 mg, 0.15 mmol) in DMF (2 mL). The reaction was heated to 70° C., and stirred over night. The mixture was filtered and evaporated and subsequently chromatographed on silicagel to obtain the crude product. Final purification on preparative LC-MS afforded 6-methyl-7-((2-methylthiazol-4-yl)methyl)-3-(tetrahydro-2H-pyran-4-yl)imidazo[1,5-a]pyrazin-8(7H)-one (3.9 mg, 0.013 mmol) in 10% yield.

¹H NMR (600 MHz, DMSO-d₆) δ 8.17 (s, 1H), 7.63 (m, 1H), 7.30 (m, 1H), 5.17 (s, 2H), 3.99 (t, J=3.3 Hz, 1H), 3.97 (t, J=3.1 Hz, 1H), 3.49 (m, 3H), 2.61 (s, 3H), 2.36 (d, J=1.2 Hz, 3H), 1.83 (m, 4H).

LC-MS: $t_R$=0.39 min (method 5), m/z=344.9 [M+H]⁺.

Example 79

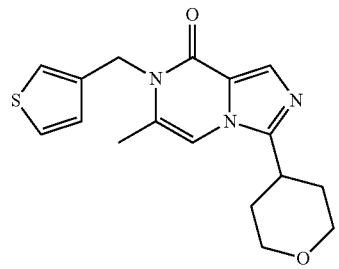 [SMILES: Cc1cn2c(C3CCOCC3)ncc2c(=O)n1Cc1ccsc1]

6-methyl-3-(tetrahydro-2H-pyran-4-yl)-7-(thiophen-3-ylmethyl)imidazo[1,5-a]pyrazin-8(7H)-one Into a vial was added 6-methyl-3-(tetrahydro-2H-pyran-4-yl)imidazo[1,5-a]pyrazin-8(7H)-one (30 mg, 0.129 mmol), cesium carbonate (84 mg, 0.26 mmol), 3-(chloromethyl)thiophene (20 mg, 0.15 mmol) and sodium iodide (23 mg, 0.15 mmol) in DMF (2 mL). The reaction was heated to 70° C., and stirred over night. The mixture was filtered and evaporated and subsequently chromatographed on silicagel to obtain the crude product. Final purification on preparative LC-MS afforded 6-methyl-3-(tetrahydro-2H-pyran-4-yl)-7-(thiophen-3-ylmethyl)imidazo[1,5-a]pyrazin-8(7H)-one (10 mg, 0.0324 mmol) in 25% yield.

¹H NMR (600 MHz, DMSO-d₆) δ 8.21 (s, 1H), 7.66 (m, 1H), 7.53 (dd, J=5.0, 2.9 Hz, 1H), 7.35 (dq, J=2.2, 1.0 Hz, 1H), 7.05 (dd, J=5.0, 1.3 Hz, 1H), 5.17 (s, 2H), 3.98 (dt, J=11.4, 3.4 Hz, 2H), 3.49 (m, 3H), 2.26 (d, J=1.2 Hz, 3H), 1.84 (m, 4H).

LC-MS: $t_R$=0.45 min (method 5), m/z=329.9 [M+H]⁺.

Example 80

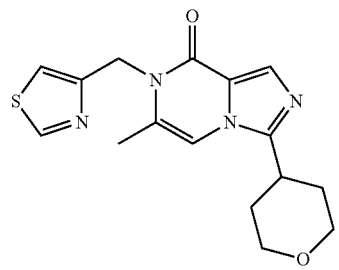 [SMILES: Cc1cn2c(C3CCOCC3)ncc2c(=O)n1Cc1cscn1]

6-methyl-3-(tetrahydro-2H-pyran-4-yl)-7-(thiazol-4-ylmethyl)imidazo[1,5-a]pyrazin-8(7H)-one Into a vial was added 6-methyl-3-(tetrahydro-2H-pyran-4-yl)imidazo[1,5-a]pyrazin-8(7H)-one (30 mg, 0.129 mmol), cesium carbonate (147 mg, 0.450 mmol), 4-(chloromethyl)thiazole hydrochloride (26 mg, 0.15 mmol) and sodium iodide (23 mg, 0.15 mmol) in DMF (2 mL). The reaction was heated to 70° C., and stirred over night. The mixture was filtered and evaporated and subsequently chromatographed on silicagel to obtain the crude product. Final purification on preparative LC-MS afforded 6-methyl-3-(tetrahydro-2H-pyran-4-yl)-7-(thiazol-4-ylmethyl)imidazo[1,5-a]pyrazin-8(7H)-one (7 mg, 0.0153 mmol) in 12% yield.

$^1$H NMR (600 MHz, DMSO-d$_6$) δ 9.07 (d, J=1.9 Hz, 1H), 8.12 (s, 1H), 7.63 (m, 1H), 7.57 (dd, J=1.9, 0.9 Hz, 1H), 5.27 (s, 2H), 3.97 (dt, J=11.3, 3.3 Hz, 2H), 3.48 (m, 3H), 2.36 (d, J=1.2 Hz, 3H), 1.84 (m, 4H).

LC-MS: $t_R$=0.34 min (method 5), m/z=331.0 [M+H]$^+$.

Example 81

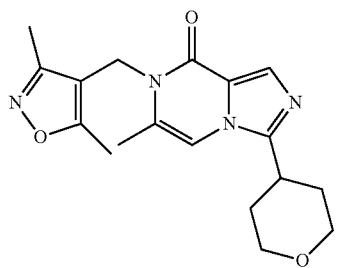 [SMILES: Cc1noc(C)c1Cn1c(C)cn2c(C3CCOCC3)ncc2c1=O]

7-((3,5-dimethylisoxazol-4-yl)methyl)-6-methyl-3-(tetrahydro-2H-pyran-4-yl)imidazo[1,5-a]pyrazin-8(7H)-one Into a vial was added 6-methyl-3-(tetrahydro-2H-pyran-4-yl)imidazo[1,5-a]pyrazin-8(7H)-one (25 mg, 0.107 mmol), cesium carbonate (70 mg, 0.21 mmol), 4-(chloromethyl)-3,5-dimethylisoxazole (19 mg, 0.129 mmol) and sodium iodide (19 mg, 0.129 mmol) in DMF (1.6 mL). The reaction was heated to 70° C., and stirred over night. The mixture was filtered and evaporated and subsequently chromatographed on silicagel to obtain the crude product. Final purification on preparative LC-MS afforded 7-((3,5-dimethylisoxazol-4-yl)methyl)-6-methyl-3-(tetrahydro-2H-pyran-4-yl)imidazo[1,5-a]pyrazin-8(7H)-one (11 mg, 0.024 mmol) in 23% yield.

$^1$H NMR (600 MHz, DMSO-d$_6$) δ 8.11 (s, 1H), 7.63 (m, 1H), 5.00 (s, 2H), 3.97 (dt, J=11.3, 3.3 Hz, 2H), 3.46 (m, 3H), 2.27 (s, 3H), 2.24 (d, J=1.2 Hz, 3H), 2.08 (s, 3H), 1.82 (dd, J=7.8, 3.5 Hz, 4H).

LC-MS: $t_R$=0.38 min (method 5), m/z=343.0 [M+H]$^+$.

Example 82

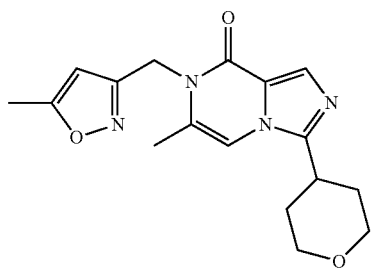 [SMILES: Cc1cc(Cn2c(C)cn3c(C4CCOCC4)ncc3c2=O)no1]

6-methyl-7-((5-methylisoxazol-3-yl)methyl)-3-(tetrahydro-2H-pyran-4-yl)imidazo[1,5-a]pyrazin-8(7H)-one Into a vial was added 6-methyl-3-(tetrahydro-2H-pyran-4-yl)imidazo[1,5-a]pyrazin-8(7H)-one (25 mg, 0.107 mmol), cesium carbonate (70 mg, 0.21 mmol), 3-(chloromethyl)-5-methylisoxazole (34 mg, 0.13 mmol, 50%) and sodium iodide (19 mg, 0.13 mmol) in DMF (1.6 mL). The reaction was heated to 70° C., and stirred over night. The mixture was filtered and evaporated and subsequently chromatographed on silicagel to obtain the crude product. Final purification on preparative LC-MS afforded 6-methyl-7-((5-methylisoxazol-3-yl)methyl)-3-(tetrahydro-2H-pyran-4-yl)imidazo[1,5-a]pyrazin-8(7H)-one (9 mg, 0.0194 mmol) in 18% yield.

$^1$H NMR (600 MHz, DMSO-d$_6$) δ 8.05 (s, 1H), 7.60 (m, 1H), 6.19 (q, J=0.8 Hz, 1H), 5.18 (s, 2H), 3.97 (dt, J=11.3, 3.4 Hz, 2H), 3.45 (m, 3H), 2.37 (d, J=0.9 Hz, 3H), 2.27 (d, J=1.2 Hz, 3H), 1.86-1.79 (m, 4H).

LC-MS: $t_R$=0.38 min (method 5), m/z=328.9 [M+H]$^+$.

Example 83

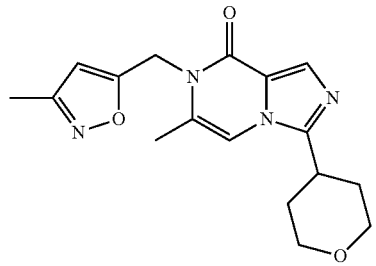 [SMILES: Cc1cc(Cn2c(C)cn3c(C4CCOCC4)ncc3c2=O)on1]

6-methyl-7-((3-methylisoxazol-5-yl)methyl)-3-(tetrahydro-2H-pyran-4-yl)imidazo[1,5-a]pyrazin-8(7H)-one Into a vial was added 6-methyl-3-(tetrahydro-2H-pyran-4-yl)imidazo[1,5-a]pyrazin-8(7H)-one (25 mg, 0.107 mmol), cesium carbonate (70 mg, 0.21 mmol), 5-(chloromethyl)-3-methylisoxazole (17 mg, 0.13 mmol) and sodium iodide (19 mg, 0.13 mmol) in DMF (1.6 mL). The reaction was heated to 70° C., and stirred over night. The mixture was filtered and evaporated and subsequently chromatographed on silicagel to obtain the crude product. Final purification on preparative LC-MS afforded 6-methyl-7-((3-methylisoxazol-5-yl)methyl)-3-(tetrahydro-2H-pyran-4-yl)imidazo[1,5-a]pyrazin-8(7H)-one (14 mg, 0.0313 mmol) in 29% yield.

$^1$H NMR (600 MHz, DMSO-d$_6$) δ 8.20 (s, 1H), 7.70 (m, 1H), 6.31 (s, 1H), 5.29 (m, 2H), 3.98 (dt, J=11.4, 3.5 Hz, 2H), 3.49 (m, 3H), 2.32 (d, J=1.2 Hz, 3H), 2.19 (s, 3H), 1.85 (m, 4H).

LC-MS: $t_R$=0.37 min (method 5), m/z=328.9 [M+H]$^+$.

Example 84

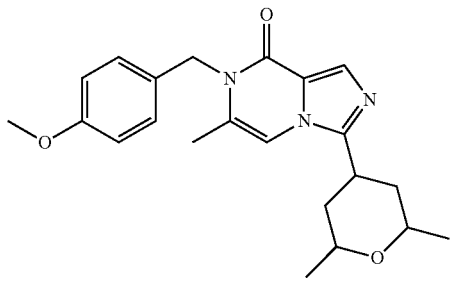

3-(2,6-dimethyltetrahydro-2H-pyran-4-yl)-7-(4-methoxybenzyl)-6-methylimidazo[1,5-a]pyrazin-8(7H)-one Step 1: To a solution of (3-methoxy-5-methylpyrazin-2-yl)methanamine hydrochloride (200 mg, 1.05 mmol, 1 eq) and 2,6-dimethyltetrahydro-2H-pyran-4-carboxylic acid (167 mg, 1.05 mmol, 1 eq) in DCM (10 mL) was added HATU (481 mg, 1.27 mmol, 1.20 eq) and DIPEA (409 mg, 3.16 mmol, 552 µL, 3 eq). The mixture was stirred at 18° C. for 16 hours. The mixture washed with H$_2$O (20 mL) and extracted with DCM (20 mL×3). The combined organic layers were dried over Na$_2$SO$_4$ and concentrated under vacuum. N-((3-methoxy-5-methylpyrazin-2-yl)methyl)-2,6-dimethyltetrahydro-2H-pyran-4-carboxamide (300 mg, 0.95 mmol, 90% yield) was obtained.

Step 2: To a solution of N-((3-methoxy-5-methylpyrazin-2-yl)methyl)-2,6-dimethyltetrahydro-2H-pyran-4-carboxamide (280 mg, 954 µmol, 1 eq) in dioxane (10 mL) was added POCl$_3$ (293 mg, 1.91 mmol, 177 µL, 2 eq). The mixture was stirred at 80° C. for 2 hours. The mixture washed with H$_2$O (20 mL) and extracted with DCM (20 mL×3). The combined organic layers were dried over Na$_2$SO$_4$ and concentrated under vacuum. 3-(2,6-dimethyltetrahydro-2H-pyran-4-yl)-6-methylimidazo[1,5-a]pyrazin-8(7H)-one (249 mg) was obtained. Step 3: To a solution of 3-(2,6-dimethyltetrahydro-2H-pyran-4-yl)-6-methylimidazo[1,5-a]pyrazin-8(7H)-one (200 mg, 765 µmol, 1 eq) and 1-(chloromethyl)-4-methoxybenzene (156 mg, 995 µmol, 135 µL, 1.30 eq) in DMF (10 mL) was added Cs$_2$CO$_3$ (500 mg, 1.53 mmol, 2 eq). The mixture was stirred at 60° C. for 4 hours. The mixture was concentrated under vacuum. The mixture was washed with H$_2$O (20 mL) and extracted with DCM (15 mL×3). The combined organic layers were washed with H$_2$O (40 mL×3, brine, dried over Na$_2$SO$_4$ and concentrated under vacuum. The residue was purified by preparative LC-MS to give 3-(2,6-dimethyltetrahydro-2H-pyran-4-yl)-7-(4-methoxybenzyl)-6-methylimidazo[1,5-a]pyrazin-8(7H)-one (48 mg, 126 µmol, 16% yield).

$^1$H NMR (CDCl$_3$ 400 MHz): δ 7.91 (s, 1H), 7.16 (d, J=8.4 HZ, 2H), 6.85 (d, J=8.4 HZ, 2H), 6.73 (s, 2H), 5.17 (s, 2H), 3.79 (s, 3H), 3.67-3.63 (m, 2H), 3.14-3.08 (m, 1H), 2.21 (s, 3H), 1.90-1.87 (m, 3H), 1.75-1.62 (m, 2H), 1.28 (d, J=6.0 HZ, 6H).

LC-MS: $t_R$=2.133 min (method 17), m/z=382.1 [M+H]$^+$.

Example 85

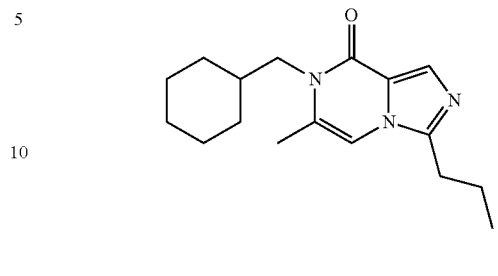

7-(cyclohexylmethyl)-6-methyl-3-propylimidazo[1,5-a]pyrazin-8(7H)-one

Step 1: To a solution of 3-bromo-6-methylimidazo[1,5-a]pyrazin-8(7H)-one (1 g, 4.39 mmol, 1 eq) and Cs$_2$CO$_3$ (2.86 g, 8.78 mmol, 2 eq) in DMF (20 mL) was added (bromomethyl)cyclohexane (1.55 g, 8.78 mmol, 1.22 mL, 2 eq). The mixture was stirred at 60° C. for 18 hour. The reaction mixture was filtered and the filtrate was concentrated. The crude mixture was purified by flash chromatography with petroleum ether:ethyl acetate=5:1~3:1. 3-bromo-7-(cyclohexylmethyl)-6-methylimidazo[1,5-a]pyrazin-8(7H)-one (1 g, 3.02 mmol, 69% yield) was obtained.

$^1$H NMR (CDCl$_3$, 400 MHz): δ 7.86 (s, 1H), 6.80 (s, 1H), 3.79 (d, J=7.2 Hz, 2H), 2.29 (s, 3H), 1.75-1.66 (m, 6H), 1.22-1.04 (m, 5H).

LC-MS: $t_R$=0.791 min (method 15), m/z=325.9 [M+H]$^+$.

Step 2: To a solution of 3-bromo-7-(cyclohexylmethyl)-6-methylimidazo[1,5-a]pyrazin-8(7H)-one (200 mg, 617 µmol, 1 eq) and (E)-4,4,5,5-tetramethyl-2-(prop-1-en-1-yl)-1,3,2-dioxaborolane (155 mg, 925 µmol, 1.50 eq) in dioxane (4 mL) and H$_2$O (1 mL) was added Pd(dppf)Cl2 (90 mg, 123 µmol, 0.20 eq) and Cs$_2$CO$_3$ (402 mg, 1.23 mmol, 2 eq) under a N$_2$ atmosphere. The mixture was stirred at 90° C. for 2 hours under microwave conditions. Water (50 mL) was added and the mixture was extracted with EtOAc (50 mL×3), the combined organic layers were washed with brine (20 mL), dried over Na$_2$SO$_4$ and concentrated. The crude mixture was purified by flash chromatography with petroleum ether:ethyl acetate=1:1. (E)-7-(cyclohexylmethyl)-6-methyl-3-(prop-1-en-1-yl)imidazo[1,5-a]pyrazin-8(7H)-one (150 mg, 504.59 µmol, 82% yield) was obtained.

Step 3: To a solution of (E)-7-(cyclohexylmethyl)-6-methyl-3-(prop-1-en-1-yl)imidazo[1,5-a]pyrazin-8(7H)-one (150 mg, 526 µmol, 1 eq) in EtOAc (30 mL) was added Pd—C(10%, 40 mg, wet) under N$_2$. The suspension was degassed under vacuum and purged with H$_2$ several times. The mixture was stirred under H$_2$ (15 psi) at 25° C. for 18 hours. The mixture was filtered and the residue was washed with EtOAc (20 mL×2). The combined organic layers were concentrated. The residue was purified by preparative LC-MS to give 7-(cyclohexylmethyl)-6-methyl-3-propylimidazo[1,5-a]pyrazin-8(7H)-one (95.5 mg, 321 µmol, 61% yield).

$^1$H NMR (400 MHz): δ 7.83 (s, 1H), 6.66 (s, 1H), 3.78 (d, J=7.2 Hz, 2H), 2.81 (t, J=7.6 Hz, 2H), 2.26 (s, 3H), 1.86-1.84 (m, 2H), 1.76-1.67 (m, 6H), 1.19-1.17 (m, 3H), 1.05-1.01 (m, 5H).

LC-MS: $t_R$=1.68 min (method 17), m/z=288.3 [M+H]$^+$.

Example 86

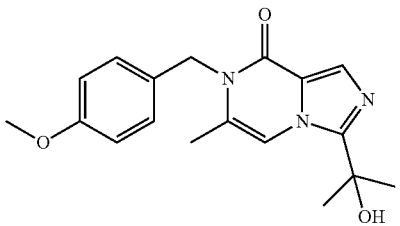 [SMILES: COc1ccc(Cn2c(C)cn3c(C(C)(C)O)ncc3c2=O)cc1]

3-(2-hydroxypropan-2-yl)-7-(4-methoxybenzyl)-6-methylimidazo[1,5-a]pyrazin-8(7H)-one Step 1: NaH (2.64 g, 66 mmol, 60% in mineral oil, 2.20 eq) was added to 2-hydroxy-2-methylpropanoic acid (3.12 g, 30 mmol, 1 eq) in DMF (30 mL) at 0° C. The mixture was stirred at 20° C. for 30 mins. (bromomethyl)benzene (10.26 g, 60 mmol, 7.13 mL, 2 eq) was added to the reaction mixture at 20° C. and stirred at 20° C. for 16 hours. The mixture was quenched by H₂O (30 mL) and adjusted pH=7 by HCl (1 M, aq). The mixture was extracted with ethyl acetate (30 mL×3). The combined organic layers were washed by H₂O (20 mL) and brine. The residue was dried over Na₂SO₄ and concentrated under vacuum. ¹H NMR showed the compound was desired product. benzyl 2-(benzyloxy)-2-methylpropanoate (3.98 g, 14 mmol, 47% yield) was obtained.

¹H NMR (CDCl₃ 400 MHz): δ 7.40-7.32 (m, 10H), 5.24 (s, 2H), 4.48 (s, 2H), 1.58 (s, 6H).

Step 2: To a solution of benzyl 2-(benzyloxy)-2-methylpropanoate (2 g, 7.03 mmol, 1 eq) in H₂O (20 mL), THF (20 mL) and MeOH (20 mL) was added NaOH (1.12 g, 27.98 mmol, 3.98 eq). The mixture was stirred at 80° C. for 1 hour. The mixture was adjusted pH=2 by aq. HCl (1 M) and extracted with DCM (10 mL×3). The combined organic layers were concentrated under vacuum. The residue was washed with aq. NaOH (1 M, 5 mL) and extracted with DCM (15 mL×3). The aqueous solution was adjusted pH=2 by aq. HCl (1 M, aq) and extracted with DCM (10 mL×3). The combined organic layers were washed with H₂O (15 mL×2) and brine. The mixture was dried over Na₂SO₄ and concentrated under vacuum. 2-(benzyloxy)-2-methylpropanoic acid (1.36 g, 7 mmol, 100% yield) was obtained.

Step 3: To a solution of 2-(benzyloxy)-2-methylpropanoic acid (500 mg, 2.64 mmol, 1 eq, HCl) in DCM (10 mL) was added DIPEA (1.02 g, 7.92 mmol, 1.38 mL, 3 eq). The mixture was added (3-methoxy-5-methylpyrazin-2-yl)methanamine hydrochloride (513 mg, 2.64 mmol, 1 eq) and HATU (1.20 g, 3.17 mmol, 1.20 eq). The mixture was stirred at 18° C. for 16 hours. The mixture washed with H₂O (20 mL) and extracted with DCM (20 mL×3). The combined organic layers were dried over Na₂SO₄ and concentrated under vacuum. 2-(benzyloxy)-N-((3-methoxy-5-methylpyrazin-2-yl)methyl)-2-methylpropanamide (617 mg, 1.75 mmol, 66% yield) was obtained.

Step 4: To a solution of 2-(benzyloxy)-N-((3-methoxy-5-methyl pyrazin-2-yl)methyl)-2-methylpropanamide (1.40 g, 4.25 mmol, 1 eq) in dioxane (20 mL) was added POCl₃ (1.30 g, 8.50 mmol, 790 μL, 2 eq). The mixture was stirred at 80° C. for 2 hours. The mixture was quenched with H₂O (15 mL) and adjusted pH>7 by saturated aqueous NaHCO₃. The mixture was extracted with DCM (20 mL×3). The combined organic layers were washed with brine, dried over Na₂SO₄ and concentrated under vacuum. 3-(2-(benzyloxy)propan-2-yl)-6-methylimidazo[1,5-a]pyrazin-8(7H)-one (375 mg, 1.26 mmol, 30% yield) was obtained.

Step 5: To a solution of 3-(2-(benzyloxy)propan-2-yl)-6-methylimidazo[1,5-a]pyrazin-8(7H)-one (264 mg, 888 μmol, 1 eq) in DMF (10 mL) was added Cs₂CO₃ (579 mg, 1.78 mmol, 2 eq) and 1-(chloromethyl)-4-methoxybenzene (180.76 mg, 1.15 mmol, 1578 μL, 1.30 eq). The mixture was stirred at 60° C. for 4 hours. The mixture was concentrated under vacuum. The mixture was washed with H₂O (25 mL) and extracted with DCM (20 mL). The combined organic layers were dried over Na₂SO₄ and concentrated under vacuum. 3-(2-(benzyloxy)propan-2-yl)-7-(4-methoxybenzyl)-6-methylimidazo[1,5-a]pyrazin-8(7H)-one (445 mg, 998 μmol, 64% yield) was obtained.

Step 6: To a solution of 3-(2-(benzyloxy)propan-2-yl)-7-(4-methoxybenzyl)-6-methylimidazo[1,5-a]pyrazin-8(7H)-one (345 mg, 826 μmol, 1 eq) in MeOH (60 mL) was added Pd/C (10%, wet) (40 mg). The mixture was stirred at pressure of H₂ (30 psi). The mixture was stirred at 18° C. for 8 hours. The mixture was filtered. The filtered solution was concentrated under vacuum. The residue was purified by TLC (petroleum ether:ethyl acetate=1.1). 3-(2-hydroxypropan-2-yl)-7-(4-methoxybenzyl)-6-methylimidazo[1,5-a]pyrazin-8(7H)-one (98 mg, 292 μmol, 35% yield) was obtained.

¹H NMR (CDCl₃ 400 MHz): δ 7.86 (s, 1H), 7.47 (s, 1H), 7.17 (d, J=12 Hz, 2H), 6.85 (d, J=8.4 Hz, 2H), 5.17 (s, 2H), 3.79 (s, 3H), 2.216-2.192 (m, 4H), 1.76 (s, 3H).

LC-MS: $t_R$=1.906 min (method 13), m/z=328.2 [M+H]⁺.

Example 87

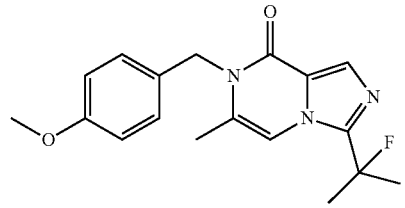 [SMILES: COc1ccc(Cn2c(C)cn3c(C(C)(C)F)ncc3c2=O)cc1]

3-(2-fluoropropan-2-yl)-7-(4-methoxybenzyl)-6-methylimidazo[1,5-a]pyrazin-8(7H)-one To a solution of 3-(2-hydroxypropan-2-yl)-7-(4-methoxybenzyl)-6-methylimidazo[1,5-a]pyrazin-8(7H)-one (75 mg, 229.09 μmol, 1 eq) in DCM (10 ml) was added DAST (40.6 mg, 252 μmol, 33 μL, 1.10 eq) at −78° C. The mixture was stirred at 18° C. for 2 hours. The mixture was quenched with H₂O (10 mL) and extracted with DCM (15 mL×3). The combined organic layers were dried over Na₂SO₄ and concentrated under vacuum. The residue was purified with TLC (petroleum ether:ethyl acetate=1:1). 3-(2-fluoropropan-2-yl)-7-(4-methoxybenzyl)-6-methylimidazo[1,5-a]pyrazin-8 (7H)-one (68 mg, 206 μmol, 64% yield) was obtained.

¹H NMR (CDCl₃ 400 MHz): δ 7.89 (s, 1H), 7.19-7.16 (m, 3H), 6.86 (d, J=8.4 Hz, 2H), 5.18 (s, 2H), 3.79 (s, 3H), 2.20 (s, 3H), 1.91 (s, 3H), 1.86 (s, 3H).

LC-MS: $t_R$=1.906 min (method 13), m/z=328.2 [M+H]⁺.

Example 88

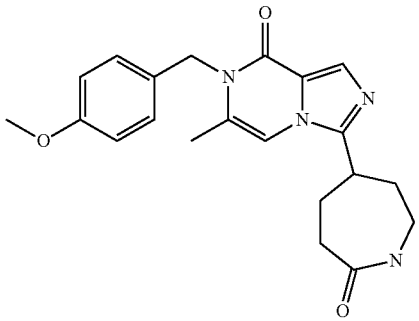 [SMILES: COc1ccc(Cn2c(C)cn3c(C4CCNC(=O)CC4)ncc3c2=O)cc1]

7-(4-methoxybenzyl)-6-methyl-3-(7-oxoazepan-4-yl) imidazo[1,5-a]pyrazin-8(7H)-one Step 1: To a solution of (3-methoxy-5-methylpyrazin-2-yl)methanamine hydrochloride (500 mg, 2.64 mmol, 1 eq) and 7-oxoazepane-4-carboxylic acid (456 mg, 2.90 mmol, 1.10 eq) in DCM (45 mL) was added HATU (1.20 g, 3.17 mmol, 1.20 eq) and DIPEA (1.02 g, 7.92 mmol, 1.38 mL, 3 eq). The mixture was stirred at 18° C. for 16 hours. The mixture was quenched with $H_2O$ (30 mL) and extracted with DCM (25 mL×3). The combined organic layers were dried over $Na_2SO_4$ and concentrated under vacuum. N-((3-methoxy-5-methylpyrazin-2-yl)methyl)-7-oxoazepane-4-carboxamide (493 mg, 1.58 mmol, 60% yield) was obtained.

Step 2: N-((3-methoxy-5-methylpyrazin-2-yl)methyl)-7-oxoazepane-4-carboxamide (463 mg, 1.58 mmol, 1 eq) was added to Eaton's reagent (7.7 wt % phosphorus pentoxide solution in methanesulfonic acid) (3.04 g, 12.77 mmol, 2 mL, 8.08 eq). The mixture was stirred at 60° C. for 7 hours. The mixture was added to ice (30 g). The mixture was adjusted pH>7 by $NH_3$ (MeOH). The mixture was concentrated under vacuum. The residue was washed with DCM: MeOH=10:1. The mixture was filtered. The filtered solution was concentrated under vacuum. 6-methyl-3-(7-oxoazepan-4-yl)imidazo[1,5-a]pyrazin-8(7H)-one (45 mg, 165.83 μmol, 11% yield) was obtained.

$^1$H NMR (MeOD 400 MHz): δ 7.77 (s, 1H), 7.23 (s, 2H), 3.49-3.39 (m, 3H), 2.83-2.79 (m, 2H), 2.55-2.51 (m, 1H), 2.19 (s, 3H), 2.11-2.09 (m, 2H), 1.93-1.86 (m, 2H).

Step 3: To a solution of 6-methyl-3-(7-oxoazepan-4-yl)imidazo[1,5-a]pyrazin-8(7H)-one (45 mg, 173 μmol, 1 eq) and 1-(chloromethyl)-4-methoxybenzene (32 mg, 207 μmol, 28 μL, 1.20 eq) in DMF (3 mL) was added $Cs_2CO_3$ (113 mg, 346 μmol, 2 eq). The mixture was stirred at 60° C. for 2 hours. The mixture was washed with $H_2O$ (10 mL) and extracted with DCM (15 mL×3). The combined organic layers were washed with water (30 mL×3), dried over $Na_2SO_4$ and concentrated under vacuum. The residue was purified by TLC (DCM: MeOH=10:1). 7-(4-methoxybenzyl)-6-methyl-3-(7-oxoazepan-4-yl)imidazo[1,5-a]pyrazin-8(7H)-one (12 mg, 32 μmol, 18% yield) was obtained.

$^1$H NMR (CDCl$_3$ 400 MHz): δ 7.89 (s, 1H), 7.15 (d, J=8.8 HZ, 2H), 6.84 (d, J=8.4 HZ, 2H), 6.70 (s, 1H), 6.36 (brs, 1H), 5.16 (s, 2H), 5.16 (s, 2H), 3.77 (s, 3H), 3.62-3.49 (m, 1H), 3.42-3.30 (m, 1H), 3.20-3.10 (m, 1H), 2.77-2.72 (m, 1H), 2.61-2.55 (m, 1H), 2.21 (s, 3H), 2.10-2.01 (m, 4H).

LC-MS: $t_R$=1.748 min (method 13), m/z=381.2 [M+H]$^+$.

Example 89

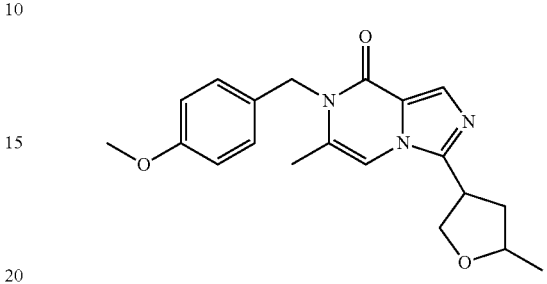

7-(4-methoxybenzyl)-6-methyl-3-(5-methyltetrahydrofuran-3-yl)imidazo[1,5-a]pyrazin-8(7H)-one Step 1: To a solution of (3-methoxy-5-methylpyrazin-2-yl)methanamine (200 mg, 1.05 mmol, 1 eq, HCl) and 5-methyltetrahydrofuran-3-carboxylic acid (137 mg, 1.05 mmol, 1 eq) in DCM (10 mL) was added HATU (481 mg, 1.27 mmol, 1.20 eq) and DIPEA (409 mg, 3.16 mmol, 553 μL, 3 eq). The mixture was stirred at 18° C. for 16 hours. The mixture washed with $H_2O$ (20 mL) and extracted with DCM (20 mL×3). The combined organic layers were dried over $Na_2SO_4$ and concentrated under vacuum. N-((3-methoxy-5-methylpyrazin-2-yl)methyl)-5-methyltetrahydrofuran-3-carboxamide (211 mg, 795 μmol, 76% yield) was obtained.

Step 2: To a solution of N-((3-methoxy-5-methylpyrazin-2-yl)methyl)-5-methyltetrahydrofuran-3-carboxamide (191 mg, 720 μmol, 1 eq) in dioxane (5 mL) was added POCl$_3$ (221 mg, 1.44 mmol, 134 μL, 2 eq). The mixture was stirred at 80° C. for 3 hours. The mixture washed with $H_2O$ (20 mL) and extracted with DCM (20 mL×3). The combined organic layers were dried over $Na_2SO_4$ and concentrated under vacuum. 6-methyl-3-(5-methyltetrahydrofuran-3-yl)imidazo[1,5-a]pyrazin-8(7H)-one (167 mg) was obtained.

Step 3: To a solution of 6-methyl-3-(5-methyltetrahydrofuran-3-yl)imidazo[1,5-a]pyrazin-8(7H)-one (138 mg, 592 μmol, 1 eq) and 1-(chloromethyl)-4-methoxybenzene (120 mg, 769 μmol, 1.30 eq) in DMF (10 mL) was added Cs$_2$CO$_3$ (386 mg, 1.18 mmol, 2 eq). The mixture was stirred at 60° C. for 4 hours. The mixture was concentrated under vacuum. The mixture was washed with $H_2O$ (20 mL) and extracted with DCM (15 mL×3). The combined organic layers were washed with $H_2O$ (40 mL×3, brine, dried over Na$_2$SO$_4$ and concentrated under vacuum. The residue was purified by pre-HPLC(base). 7-(4-methoxybenzyl)-6-methyl-3-(5-methyltetrahydrofuran-3-yl)imidazo[1,5-a]pyrazin-8(7H)-one (10 mg, 28 μmol, 5% yield) was obtained.

$^1$H NMR (CDCl$_3$ 400 MHz): δ 7.90 (s, 1H), 7.16 (d, J=8.4 HZ, 2H), 6.87-6.82 (m, 3H), 5.17 (s, 2H), 4.19-4.14 (m, 3H), 3.79-3.71 (m, 4H), 2.54-2.47 (m, 1H), 2.20 (s, 3H), 2.04-1.96 (m, 1H), 1.40 (s, J=6.0 HZ, 3H).

LC-MS: $t_R$=2.036 min (method 13), m/z=354.2 [M+H]$^+$.

Example 90

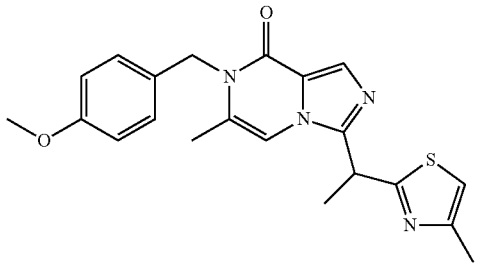

7-(4-methoxybenzyl)-6-methyl-3-(1-(4-methylthi-azol-2-yl)ethyl)imidazo[1,5-a]pyrazin-8(7H)-one Step 1: To a solution of (3-methoxy-5-methylpyrazin-2-yl)methanamine hydrochloride (150 mg, 791 µmol, 1 eq) in dry DMF (5 mL) was added triethylamine (240 mg, 2.37 mmol, 329 µL, 3 eq), sodium 2-(4-methylthiazol-2-yl)propanoate (153 mg, 791 µmol, 1 eq) and HATU (361 mg, 949 µmol, 1.20 eq). The mixture was stirred at 15° C. for 16 hours. The mixture was concentrated. H$_2$O (5 mL) was added and the mixture was extracted with DCM (20 mL×2). The combined organic layer was washed with H$_2$O (20 mL), brine (20 mL), dried over Na$_2$SO$_4$, filtered and concentrated. The residue was purified by flash chromatography on silica gel (0%~50% ethyl acetate in petroleum ether) to give N-((3-methoxy-5-methylpyrazin-2-yl)methyl)-2-(4-methylthiazol-2-yl)propanamide (210 mg, 87% yield).

Step 2: To a solution of N-((3-methoxy-5-methylpyrazin-2-yl)methyl)-2-(4-methylthiazol-2-yl)propanamide (200 mg, 653 µmol, 1 eq) in dry dioxane (5 mL) was added POCl$_3$ (200 mg, 1.31 mmol, 121 µL, 2 eq). The mixture was heated at 80° C. for 4 hours. The mixture was cooled to 15° C. and poured into water (5 mL). The mixture was adjusted to pH 8 by saturated aqueous NaHCO$_3$ and extracted with DCM (20 mL×2). The combined organics were washed with H$_2$O (20 mL), brine (20 mL), dried over Na$_2$SO$_4$, filtered and concentrated to give 6-methyl-3-(1-(4-methylthiazol-2-yl)ethyl)imidazo[1,5-a]pyrazin-8-ol (160 mg).

Step 3: To a solution of 6-methyl-3-(1-(4-methylthiazol-2-yl)ethyl)imidazo[1,5-a]pyrazin-8-ol (180 mg, 656 µmol, 1 eq) in DMF (5 mL) was added 1-(chloromethyl)-4-methoxybenzene (123 mg, 787 µmol, 107 µL, 1.20 eq) and Cs$_2$CO$_3$ (428 mg, 1.31 mmol, 2 eq). The mixture was heated at 60° C. for 2 h. The mixture was concentrated. DCM (20 mL) and H$_2$O (10 mL) was added. The mixture was extracted with DCM (20 mL). The organic layer was washed with H$_2$O (20 mL), dried over Na$_2$SO$_4$, filtered and concentrated. The residue was purified by preparative LC-MS to give 7-(4-methoxybenzyl)-6-methyl-3-(1-(4-methylthiazol-2-yl)ethyl)imidazo[1,5-a]pyrazin-8(7H)-one (30 mg, 12% yield).

$^1$H NMR (CDCl$_3$ 400 MHz): δ 7.95 (s, 1H), 7.13 (d, J=8.4 Hz, 2H), 6.91 (s, 1H), 6.82 (d, J=8.4 Hz, 2H), 6.79 (s, 1H), 5.19-5.06 (m, 2H), 4.76 (q, J=7.2 Hz, 1H), 3.76 (s, 3H), 2.41 (s, 3H), 2.14 (s, 3H), 1.92 (d, J=7.2 Hz, 1H).

LC-MS: t$_R$=2.532 min (method 11), m/z=395.1 [M+H]$^+$.

Example 91

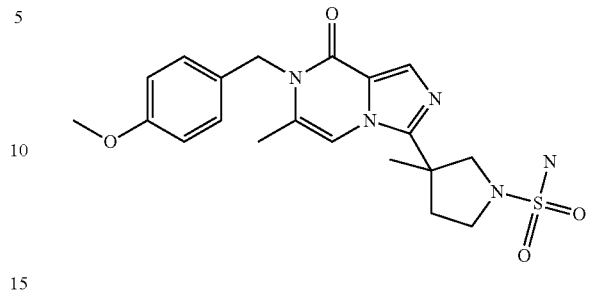

3-(7-(4-methoxybenzyl)-6-methyl-8-oxo-7,8-dihydroimidazo[1,5-a]pyrazin-3-yl)-3-methylpyrrolidine-1-sulfonamide Step 1: To a solution of (3-methoxy-5-methylpyrazin-2-yl)methanamine (200 mg, 1.05 mmol, 1 eq, HCl) and 1-((benzyloxy)carbonyl)-3-methylpyrrolidine-3-carboxylic acid (304 mg, 1.16 mmol, 1.10 eq) in DCM (10 mL) was added HATU (479 mg, 1.26 mmol, 1.20 eq) and DIPEA (407 mg, 3.15 mmol, 550 µL, 3 eq). The mixture was stirred at 18° C. for 16 hours. The mixture was quenched with H$_2$O (30 mL) and extracted with DCM (25 mL×3). The combined organic layers were dried over Na$_2$SO$_4$ and concentrated under vacuum. Benzyl 3-(((3-methoxy-5-methylpyrazin-2-yl)methyl)carbamoyl)-3-methylpyrrolidine-1-carboxylate (420 mg, 1.01 mmol, 96% yield) was obtained.

Step 2: To a solution of benzyl 3-(((3-methoxy-5-methylpyrazin-2-yl)methyl)carbamoyl)-3-methylpyrrolidine-1-carboxylate (390 mg, 979 µmol, 1 eq) in dioxane (15 mL) was added POCl$_3$ (300 mg, 1.96 mmol, 182 µL, 2 eq). The mixture was stirred at 80° C. for 3 hours. The solution was quenched with H$_2$O (20 mL) and extracted with DCM (20 mL×3). The combined organic layers were dried over Na$_2$SO$_4$ and concentrated under vacuum. Benzyl 3-methyl-3-(6-methyl-8-oxo-7,8-dihydroimidazo[1,5-a]pyrazin-3-yl)pyrrolidine-1-carboxylate (170 mg, 423 µmol, 43% yield) was obtained.

Step 3: To a solution of benzyl 3-methyl-3-(6-methyl-8-oxo-7,8-dihydroimidazo[1,5-a]pyrazin-3-yl)pyrrolidine-1-carboxylate (290 mg, 791 µmol, 1 eq) and di-tert-butyl dicarbonate (207 mg, 950 µmol, 218 µL, 1.20 eq) in MeOH (200 mL) was added Pd/C (10%, wet) (140 mg). The suspension was degassed under vacuum and purged with H$_2$ several times. The mixture was stirred under H$_2$ (30 psi) at 25° C. for 5 hours. The mixture was filtered. The filtered solution was concentrated under vacuum. tert-butyl 3-methyl-3-(6-methyl-8-oxo-7,8-dihydroimidazo[1,5-a]pyrazin-3-yl)pyrrolidine-1-carboxylate (204 mg, 614 µmol, 78% yield) was obtained.

Step 4: To a solution of tert-butyl 3-methyl-3-(6-methyl-8-oxo-7,8-dihydroimidazo[1,5-a]pyrazin-3-yl)pyrrolidine-1-carboxylate (274 mg, 824 µmol, 1 eq) and 1-(chloromethyl)-4-methoxybenzene (155 mg, 989 µmol, 135 µL, 1.20 eq) in DMF (15 mL) was added Cs$_2$CO$_3$ (537 mg, 1.65 mmol, 2 eq). The mixture was stirred at 80° C. for 14 hours. The mixture was concentrated under vacuum. The mixture was washed with H$_2$O (15 mL) and extracted with DCM (15 mL×3). The combined organic layers were washed with H$_2$O (30 mL×2), dried over Na$_2$SO$_4$ and concentrated under vacuum. tert-butyl 3-(7-(4-methoxybenzyl)-6-methyl-8- oxo-7,8-dihydroimidazo[1,5-a]pyrazin-3-yl)-3-methylpyrrolidine-1-carboxylate (291 mg, 537 µmol, 65% yield) was obtained.

Step 5: To a solution of tert-butyl 3-(7-(4-methoxybenzyl)-6-methyl-8-oxo-7,8-dihydroimidazo[1,5-a]pyrazin-3-yl)-3-methylpyrrolidine-1-carboxylate (288 mg, 636 µmol, 1 eq) in ethyl acetate (4 mL) was added HCl/EtOAc (4 M, 4 mL, 25 eq). The mixture was stirred at 18° C. for 4 hours. The mixture was concentrated under vacuum. 7-(4-methoxybenzyl)-6-methyl-3-(3-methylpyrrolidin-3-yl)imidazo[1,5-a]pyrazin-8(7H)-one (247 mg, crude, HCl) was obtained. The product was directly used next step.

Step 6: To a solution of 7-(4-methoxybenzyl)-6-methyl-3-(3-methylpyrrolidin-3-yl)imidazo[1,5-a]pyrazin-8(7H)-one (250 mg, 709 µmol, 1 eq) and sulfuric diamide (82 mg, 851 µmol, 51 µL, 1.20 eq) in dioxane (20 mL) was added DIPEA (183 mg, 1.42 mmol, 248 µL, 2 eq). The mixture was stirred at 100° C. for 24 hours. The mixture was quenched with H$_2$O (20 mL) and extracted with DCM (20 mL×3). The combined organic layers were dried over Na$_2$SO$_4$ and concentrated under vacuum. The residue was purified pre-HPLC (base). 3-(7-(4-methoxybenzyl)-6-methyl-8-oxo-7,8-dihydroimidazo[1,5-a]pyrazin-3-yl)-3-methylpyrrolidine-1-sulfonamide (14 mg, 32 µmol, 5% yield) was obtained.

$^1$H NMR (CDCl$_3$ 400 MHz): δ 7.91 (s, 1H), 7.16 (d, J=8.4 HZ, 2H), 7.85 (s, 1H), 7.18 (d, J=8.0 HZ, 2H), 6.88-6.82 (m, 3H), 5.17 (s, 2H), 4.79 (m, 1H), 4.30 (d, J=10.4 HZ, 1H), 3.79 (s, 3H), 3.52-3.47 (m, 2H), 3.26-3.20 (m, 1H), 2.73-2.64 (m, 1H), 2.23-2.17 (m, 5H), 1.65-1.59 (m, 4H).

LC-MS: t$_R$=2.055 min (method 13), m/z=432.2 [M+H]$^+$.

Example 92

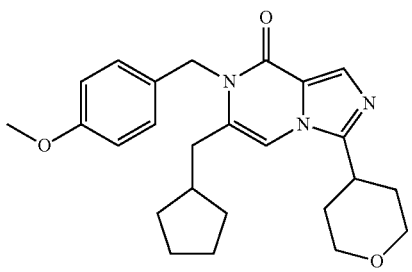 [SMILES: COc1ccc(Cn2c(CC3CCCC3)cn3c(C4CCOCC4)ncc3c2=O)cc1]

6-(cyclopentylmethyl)-7-(4-methoxybenzyl)-3-(tetrahydro-2H-pyran-4-yl)imidazo[1,5-a]pyrazin-8(7H)-one 6-(bromomethyl)-7-(4-methoxybenzyl)-3-(tetrahydro-2H-pyran-4-yl) imidazo[1,5-a]pyrazin-8(7H)-one (250 mg, 0.439 mmol) was dissolved in THF (20 ml), at −78° C. cyclopentylmagnesium bromide (0.9 ml, 1.8 mmol, 2 molar in ether) was added and the reaction was allowed to warm to room temperature overnight. Cyclopentylmagnesium bromide (0.9 ml, 1.8 mmol, 2 molar in ether) was added. After 1 hour the reaction was warmed to room temperature. After two hours, the reaction mixture was quenched with sat. NH$_4$Cl, extracted with AcOEt and organics were washed with brine. The combined organics layers were dried with Na$_2$SO$_4$, filtered and concentrated. The mixture was purified via preparative LC-MS and 6-(cyclopentylmethyl)-7-(4-methoxybenzyl)-3-(tetrahydro-2H-pyran-4-yl)imidazo[1,5-a]pyrazin-8(7H)-one (26 mg, 0.049 mmol) was isolated in 11% yield, as the TFA salt.

$^1$H NMR (500 MHz, Chloroform-d) δ 13.26 (bs, 1H), 8.14 (s, 1H), 7.12 (d, J=8.2 Hz, 2H), 6.88 (m, 3H), 5.21 (s, 2H), 4.16 (d, J=11.7 Hz, 2H), 3.80 (s, 3H), 3.60 (t, J=11.8 Hz, 2H), 3.46 (t, J=12.4 Hz, 1H), 2.74 (s, 1H), 2.57 (d, J=7.0 Hz, 2H), 2.25-2.07 (m, 2H), 1.90 (m, 4H), 1.65 (m, 4H), 1.23 (dt, J=13.2, 7.1 Hz, 2H).

LC-MS: t$_R$=0.69 min (method 5), m/z=422.0 [M+H]$^+$.

Example 93

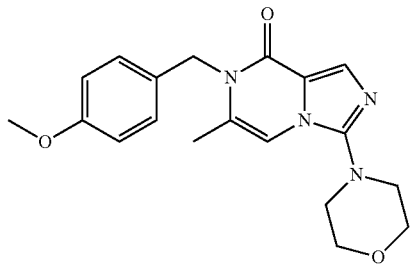 [SMILES: COc1ccc(Cn2c(C)cn3c(N4CCOCC4)ncc3c2=O)cc1]

7-(4-methoxybenzyl)-6-methyl-3-morpholinoimidazo[1,5-a]pyrazin-8(7H)-one

To a mixture of 3-bromo-7-(4-methoxybenzyl)-6-methylimidazo[1,5-a]pyrazin-8(7H)-one (300 mg, 0.86 mmol) and morpholine (150 mg, 1.72 mmol) in DMSO (5 mL) were added CsF (261 mg, 1.72 mmol) and K$_2$CO$_3$ (238 mg, 1.72 mmol). The mixture was stirred at 100° C. for 24 hours. The mixture was diluted with water (20 mL) and extracted with DCM (10 mL×3). The combine organic layers were washed with water (10 mL×2); dried over Na$_2$SO$_4$ and evaporated under vacuum. The residue was purified by preparative TLC (ethyl acetate) to give 7-(4-methoxybenzyl)-6-methyl-3-morpholinoimidazo[1,5-a]pyrazin-8(7H)-one (18 mg, 6% yield).

$^1$H NMR (CDCl$_3$, 400 MHz): δ 7.76 (s, 1H), 7.16 (d, J=8.8 Hz, 2H), 6.85 (d, J=8.8 Hz, 2H), 6.63 (s, 1H), 5.15 (s, 2H), 3.89 (t, J=4.8 Hz, 4H), 3.79 (s, 3H), 3.21 (t, J=4.8 Hz, 4H), 2.18 (s, 3H).

LC-MS: t$_R$=2.03 min (method 13), m/z=355.1 [M+H]$^+$.

Example 94

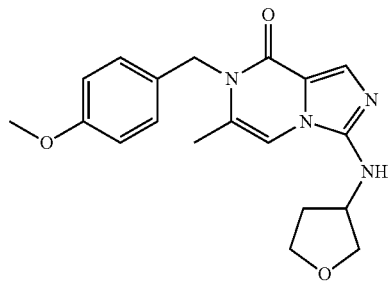 [SMILES: COc1ccc(Cn2c(C)cn3c(NC4CCOC4)ncc3c2=O)cc1]

7-(4-methoxybenzyl)-6-methyl-3-((tetrahydrofuran-3-yl)amino)imidazo[1,5-a]pyrazin-8(7H)-one 3-bromo-7-(4-methoxybenzyl)-6-methylimidazo[1,5-a]pyrazin-8(7H)-one (60 mg, 0.172 mmol) and tetrahydrofuran-3-amine (0.04 ml, 0.465 mmol) were mixed in NMP (2 mL) and DIPEA (0.23 ml, 1.317 mmol).

The reaction was heated for 4 hours at 250° C. in the microwave oven.

The reaction was purified on silica gel, via preparative LC-MS, and preparative TLC (10% EtOH in ethyl acetate) to give 7-(4-methoxybenzyl)-6-methyl-3-((tetrahydrofuran-3-yl)amino)imidazo[1,5-a]pyrazin-8(7H)-one (2 mg, 0.005 mmol) in 3% yield.

$^1$H NMR (600 MHz, Dimehtylsulfoxide-$d_6$) δ 8.50 (m, NH), 7.68 (s, 1H), 7.31 (s, 1H) 7.22 (d, J=7.1 Hz, 2H), 6.88 (d, J=7.1 Hz, 2H), 4.87 (m, 1H), 4.35 (d, J=14 Hz, 2H), 4.11 (m, 1H), 4.02 (m, 1H), 3.92 (m, 1H), 3.86 (m, 1H), 3.71 (s, 3H), 2.60 (m, 1H), 2.5 (m, 1H) 2.31 (s, 3H).

LC-MS: $t_R$=0.54 min (method 19), m/z=355.2 [M+H]$^+$.

Example 95

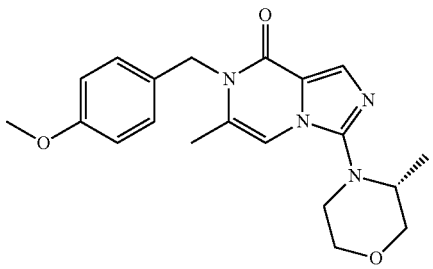

(R)-7-(4-methoxybenzyl)-6-methyl-3-(3-methylmorpholino)imidazo[1,5-a]pyrazin-8(7H)-one 3-bromo-7-(4-methoxybenzyl)-6-methylimidazo[1,5-a]pyrazin-8(7H)-one (80 mg, 0.23 mmol) and (R)-3-methylmorpholine (34.7 mg, 0.039 ml, 0.343 mmol) were mixed in NMP (2.0 mL) and DIPEA (0.2 ml, 1.1 mmol) was added.

The reaction was heated for 6.5 hours at 250° C. in the microwave oven.

The reaction was purified directly by preparative LC-MS to give (R)-7-(4-methoxybenzyl)-6-methyl-3-(3-methylmorpholino)imidazo[1,5-a]pyrazin-8(7H)-one (10 mg, 0.024 mmol) in 10% yield.

$^1$H NMR (500 MHz, Chloroform-d) δ 8.00 (s, 1H), 7.18 (d, J=7.1 Hz, 2H), 6.90 (d, J=7.1 Hz, 2H), 6.79 (s, 1H), 5.23 (d, J=14.0 Hz, 1H), 5.13 (d, J=15.7 Hz, 1H), 3.94 (m, 1H), 3.85 (m, 1H), 3.81 (s, 3H), 3.60 (m, 1H), 3.48 (dd, J=11.7, 7.9 Hz, 1H), 3.32 (t, J=10.3 Hz, 1H), 3.22 (d, J=12.2 Hz, 1H), 2.28 (d, J=1.6 Hz, 3H), 1.29 (td, J=7.1, 1.6 Hz, 1H), 1.00 (dd, J=6.4, 1.5 Hz, 3H).

LC-MS: $t_R$=0.65 min (method 7), m/z=369.1 [M+H]$^+$.

Example 96

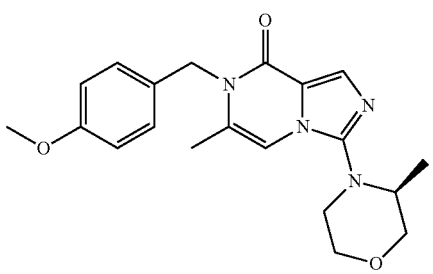

(S)-7-(4-methoxybenzyl)-6-methyl-3-(3-methylmorpholino)imidazo[1,5-a]pyrazin-8(7H)-one 3-bromo-7-(4-methoxybenzyl)-6-methylimidazo[1,5-a]pyrazin-8(7H)-one (80 mg, 0.230 mmol) and (S)-3-methylmorpholine (0.039 ml, 0.343 mmol) were mixed in NMP (2 mL) and DIPEA (148 mg, 0.2 ml, 1.1 mmol).

The reaction was heated for 6.5 hours at 250° C., in the microwave oven. The reaction was purified directly by preparative LC-MS to give (S)-7-(4-methoxybenzyl)-6-methyl-3-(3-methylmorpholino)imidazo[1,5-a]pyrazin-8(7H)-one (10 mg, 0.028 mmol) in 12% yield.

$^1$H NMR (500 MHz, Chloroform-d) δ 8.00 (s, 1H), 7.18 (d, J=7.1 Hz, 2H), 6.90 (d, J=7.1 Hz, 2H), 6.79 (s, 1H), 5.23 (d, J=14.0 Hz, 1H), 5.13 (d, J=15.7 Hz, 1H), 3.94 (m, 1H), 3.85 (m, 1H), 3.81 (s, 3H), 3.60 (m, 1H), 3.48 (dd, J=11.7, 7.9 Hz, 1H), 3.32 (t, J=10.3 Hz, 1H), 3.22 (d, J=12.2 Hz, 1H), 2.28 (d, J=1.6 Hz, 3H), 1.29 (td, J=7.1, 1.6 Hz, 1H), 1.00 (dd, J=6.4, 1.5 Hz, 3H).

LC-MS: $t_R$=0.65 min (method 7), m/z=369.1 [M+H]$^+$.

Example 97

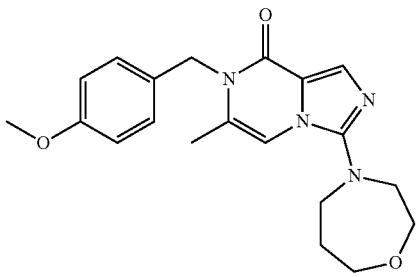 [SMILES: COc1ccc(Cn2c(C)cn3c(N4CCCOCC4)ncc3c2=O)cc1]

7-(4-methoxybenzyl)-6-methyl-3-(1,4-oxazepan-4-yl)imidazo[1,5-a]pyrazin-8(7H)-one 3-bromo-7-(4-methoxybenzyl)-6-methylimidazo[1,5-a]pyrazin-8(7H)-one (149 mg, 0.428 mmol) and 1,4-oxazepane hydrochloride (100 mg, 0.727 mmol) were mixed in NMP (2.2 mL) and DIPEA (296 mg, 0.4 mL, 2.29 mmol). The reaction was heated for 3 hours at 250° C.

The reaction was purified directly via preparative LC-MS to afford 7-(4-methoxybenzyl)-6-methyl-3-(1,4-oxazepan-4-yl)imidazo[1,5-a]pyrazin-8(7H)-one (27 mg, 0.073 mmol) in 17% yield.

$^1$H NMR (500 MHz, Chloroform-d) δ 7.84 (s, 1H), 7.14 (m, 2H), 6.87 (m, 2H), 6.64 (s, 1H), 5.13 (s, 2H), 3.93 (m, 2H), 3.88 (m, 2H), 3.80 (d, J=1.7 Hz, 3H), 3.73 (m, 4H), 2.22 (s, 3H), 2.09 (m, 2H).

LC-MS: $t_R$=0.56 min (method 7), m/z=369.1 [M+H]$^+$.

Example 98

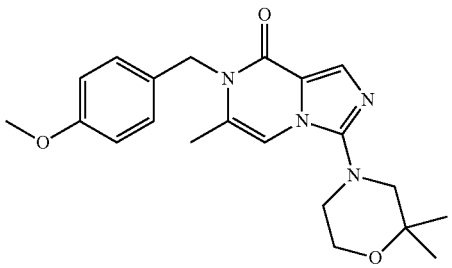

3-(2,2-dimethylmorpholino)-7-(4-methoxybenzyl)-6-methylimidazo[1,5-a]pyrazin-8(7H)-one To a mixture of 3-bromo-7-(4-methoxybenzyl)-6-methyl-imidazo[1,5-a]pyrazin-8(7H)-one (500 mg, 1.44 mmol) and 2,2-dimethylmorpholine (331 mg, 2.88 mmol) in DMSO (5 mL) were added CsF (328 mg, 2.88 mmol) and $K_2CO_3$ (299 mg, 2.88 mmol). The mixture was stirred at 100° C. for 24 hours. The mixture was diluted with water (20 mL) and extracted with DCM (10 mL×3). The combined organic layer was washed with water (10 mL×2); dried over $Na_2SO_4$ and evaporated under vacuum. The residue was purified by preparative TLC (ethyl acetate) to give 3-(2,2-dimethylmorpholino)-7-(4-methoxybenzyl)-6-methylimidazo[1,5-a]pyrazin-8(7H)-one (15 mg, 3% yield).

$^1$H NMR (CDCl$_3$, 400 MHz): δ 7.75 (s, 1H), 7.15 (d, J=8.8 Hz, 2H), 6.85 (d, J=8.8 Hz, 2H), 6.60 (s, 1H), 5.15 (s, 2H), 3.93 (t, J=4.8 Hz, 2H), 3.79 (s, 3H), 3.16 (t, J=4.8 Hz, 2H), 2.98 (s, 2H), 2.18 (s, 3H), 1.37 (s, 6H).

LC-MS: $t_R$=2.26 min (method 13), m/z=383.1 [M+H]$^+$.

Example 99

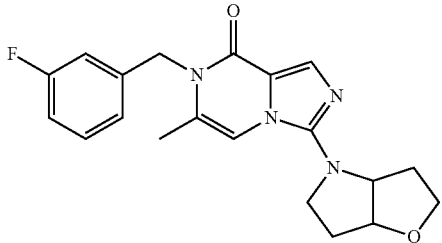 [SMILES: Cc1cn2c(N3CCC4OCCC43)ncc2c(=O)n1Cc1cccc(F)c1]

7-(3-fluorobenzyl)-3-(hexahydro-4H-furo[3,2-b]pyrrol-4-yl)-6-methylimidazo[1,5-a]pyrazin-8(7H)-one, stereoisomer 1 and 2

Step 1: To a solution of 3-bromo-6-methylimidazo[1,5-a]pyrazin-8(7H)-one (3 g, 13.16 mmol) and 1-(bromomethyl)-3-fluorobenzene (2.99 g, 15.79 mmol) in DMF (50 mL) was added $K_2CO_3$ (3.64 g, 26.3 mmol). The mixture was stirred at 60° C. for 12 hours. The mixture was diluted with water (100 mL) and extracted with EtOAc (50 mL×3). The combined organic layer was washed with water (50 mL×2); dried over $Na_2SO_4$ and evaporated under vacuum. The residue was washed with EtOAc (10 mL) and filtrated. The filter cake was dried under vacuum to give 3-bromo-7-(3-fluorobenzyl)-6-methylimidazo[1,5-a]pyrazin-8(7H)-one (2 g, 45% yield).

Step 2: To a mixture of 3-bromo-7-(3-fluorobenzyl)-6-methylimidazo[1,5-a]pyrazin-8(7H)-one (1.2 g, 3.57 mmol) and hexahydro-2H-furo[3,2-b]pyrrole (0.5 oxalc acid salt) (678 mg, 4.28 mmol) in DMSO (20 mL) were added CsF (542 mg, 3.57 mmol) and $K_2CO_3$ (1.23 g, 8.92 mmol). The mixture was stirred at 120° C. for 72 hours. The mixture was diluted with water (100 mL) and extracted with DCM (50 mL×3). The combined organic layer was washed with water (50 mL×2); dried over $Na_2SO_4$ and evaporated under vacuum. The residue was purified by prep-HPLC to give compound 3 (200 mg, 15% yield).

Step 3: 7-(3-fluorobenzyl)-3-(hexahydro-4H-furo[3,2-b]pyrrol-4-yl)-6-methylimidazo[1,5-a]pyrazin-8(7H)-one (200 mg, 0.54 mmol) was purified by SFC to give stereoisomer 1 (48 mg).

$^1$H NMR (CDCl$_3$, 400 MHz): δ 7.74 (s, 1H), 7.33-7.29 (m, 1H), 7.01-6.89 (m, 3H), 6.73 (s, 1H), 5.19 (s, 2H), 4.72-4.66 (m, 2H), 3.92-3.86 (m, 2H), 3.75-3.73 (m, 1H), 3.50-3.47 (m, 1H), 2.16-2.09 (m, 6H), 1.91-1.86 (m, 1H).

LC-MS: $t_R$=1.90 min (method 12), m/z=369.1 [M+H]$^+$.
SFC-MS: $t_R$=4.44 min, ee %>99%. [α]$_D^{20}$ +133.00 (c=0.10, DCM).

stereoisomer 2 (32 mg).

$^1$H NMR (CDCl$_3$, 400 MHz): δ 7.74 (s, 1H), 7.32-7.28 (m, 1H), 7.01-6.89 (m, 3H), 6.73 (s, 1H), 5.19 (s, 2H), 4.74-4.67 (m, 2H), 3.92-3.87 (m, 2H), 3.75-3.72 (m, 1H), 3.50-3.47 (m, 1H), 2.16-2.09 (m, 6H), 1.91-1.86 (m, 1H).

LC-MS: $t_R$=1.89 min (method 12), m/z=369.1 [M+H]$^+$.
SFC-MS: $t_R$=5.71 min, ee %>99%. [α]$_D^{20}$ −82.00 (c=0.10, DCM).

Example 100

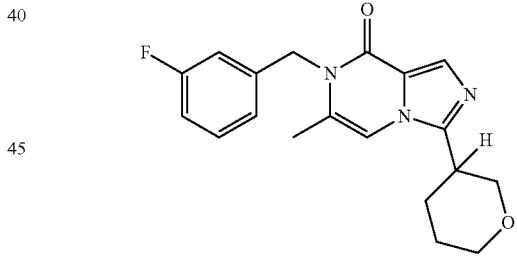

7-(3-fluorobenzyl)-6-methyl-3-(tetrahydro-2H-pyran-3-yl)imidazo[1,5-a]pyrazin-8(7H)-one, stereoisomer 1 and 2

Step 1: To a solution of (3-methoxy-5-methylpyrazin-2-yl)methanamine (150 mg, 979.2 μmol), tetrahydro-2H-pyran-3-carboxylic acid (127.4 mg, 979.2 μmol) in DCM (10 mL) was added HATU (670.2 mg, 1.8 mmol) and triethylamine (198.2 mg, 1.9 mmol). The mixture was stirred at 25° C. for 16 hours. The mixture was diluted with water (15 mL), extracted with DCM (3×30 mL). The combined organic layer was washed with brine (30 mL), dried over $Na_2SO_4$, filtered and concentrated. The residue was purified by preparative TLC (EA/MeOH=20/1) to give N-((3-methoxy-5-methylpyrazin-2-yl)methyl)tetrahydro-2H-pyran-3-carboxamide (130 mg, 50% yield).

Step 2: To a solution of N-((3-methoxy-5-methylpyrazin-2-yl)methyl)tetrahydro-2H-pyran-3-carboxamide (130 mg, 490 μmol) in dioxane (3 mL) was added POCl$_3$ (1.28 g, 490 μmol). The mixture was stirred at 80° C. for 3 h. The mixture was cooled down to 25° C. and concentrated. The residue was neutralized by saturated aq.NaHCO$_3$, extracted with ethyl acetate (2×20 mL). The combined organic layer was washed with brine (20 mL), dried over Na$_2$SO$_4$, filtered and concentrated to give crude 8-methoxy-6-methyl-3-(tetrahydro-2H-pyran-3-yl)imidazo[1,5-a]pyrazine (120 mg, 99% yield). The crude was used directly for the next step.

Step 3: To a solution of 8-methoxy-6-methyl-3-(tetrahydro-2H-pyran-3-yl)imidazo[1,5-a]pyrazine (120 mg, 485.3 μmol) in dioxane (3 mL) was added HCl (2 M, 3 mL). The mixture was stirred at 80° C. for 3 h. The mixture was cooled down to 25° C. and concentrated, neutralized with saturated aq.NaHCO$_3$, extracted with DCM (3×30 mL). The combined organic layer was washed with brine (20 mL), dried over Na$_2$SO$_4$, filtered and concentrated to give crude 6-methyl-3-(tetrahydro-2H-pyran-3-yl)imidazo[1,5-a]pyrazin-8(7H)-one (110 mg, 97% yield). The crude product was used directly for the next step.

Step 4: To a solution of 6-methyl-3-(tetrahydro-2H-pyran-3-yl)imidazo[1,5-a]pyrazin-8(7H)-one (100.0 mg, 428.7 μmol) and 1-(bromomethyl)-3-fluorobenzene (121.6 mg, 643.0 μmol) in DMF (5 mL) was added K$_2$CO$_3$ (118.5 mg, 857.4 μmol). The mixture was stirred at 80° C. for 2 h. The mixture was cooled down to 25° C. and diluted with water (20 mL), extracted with ethyl acetate (3×30 mL). The combined organic layer was washed with brine (30 mL), dried over Na$_2$SO$_4$, filtered and concentrated. The residue was purified by preparative TLC (PE/EA=1/1) to give 7-(3-fluorobenzyl)-6-methyl-3-(tetrahydro-2H-pyran-3-yl)imidazo[1,5-a]pyrazin-8(7H)-one (80 mg, 54% yield).

7-(3-fluorobenzyl)-6-methyl-3-(tetrahydro-2H-pyran-3-yl)imidazo[1,5-a]pyrazin-8(7H)-one (80 mg, 234.3 μmol) was purified by SFC.

7-(3-fluorobenzyl)-6-methyl-3-(tetrahydro-2H-pyran-3-yl)imidazo[1,5-a]pyrazin-8(7H)-one, stereisomer 1 (26 mg, 33% yield) was obtained.

$^1$H NMR (CDCl$_3$ 400 MHz): δ 7.92 (s, 1H), 7.33-7.27 (m, 1H), 7.00-6.89 (m, 3H), 6.81 (s, 1H), 5.23 (s, 2H), 4.11-4.03 (m, 2H), 3.69 (t, J=11.2 Hz, 1H), 3.57-3.53 (m, 1H), 3.17-3.14 (m, 1H), 2.18-2.11 (m, 5H), 1.85-1.79 (m, 2H).

LC-MS: $t_R$=2.06 min (method 3), m/z=342.1 [M+H]$^+$. SFC: $t_R$=5.286 min, ee %>99%. $α_D^{20}$=−3.0 (c=0.10, CHCl$_3$).

7-(3-fluorobenzyl)-6-methyl-3-(tetrahydro-2H-pyran-3-yl)imidazo[1,5-a]pyrazin-8(7H)-one, stereoisomer 2 (28 mg, yield: 35%) was obtained.

$^1$H NMR (CDCl$_3$ 400 MHz): δ 7.92 (s, 1H), 7.31-7.27 (m, 1H), 7.00-6.89 (m, 3H), 6.81 (s, 1H), 5.22 (s, 2H), 4.11-4.03 (m, 2H), 3.68 (t, J=11.2 Hz, 1H), 3.57-3.53 (m, 1H), 3.17-3.14 (m, 1H), 2.18-2.11 (m, 5H), 1.84-1.78 (m, 2H).

LC-MS: $t_R$=2.06 min (method 3), m/z=342.2 [M+H]$^+$. SFC: $t_R$=6.404 min, ee %>99%. $α_D^{20}$=+3.0 (c=0.10, CHCl$_3$).

In Vitro Testing

PDE1 Inhibition Assay

PDE1A, PDE1B and PDE1C assays were performed as follows: the assays was performed in 60 μL samples containing a fixed amount of the PDE1 enzym1 (sufficient to convert 20-25% of the cyclic nucleotide substrate), a buffer (50 mM HEPES pH 7.6; 10 mM MgCl$_2$; 0.02% Tween20), 0.1 mg/ml BSA, 15 nM tritium labelled cAMP and varying amounts of inhibitors. Reactions were initiated by addition of the cyclic nucleotide substrate, and reactions are allowed to proceed for 1 h at room temperature before being terminated through mixing with 20 μL (0.2 mg) yttrium silicate SPA beads (PerkinElmer). The beads were allowed to settle for 1 h in the dark before the plates were counted in a Wallac 1450 Microbeta counter. The measured signals were converted to activity relative to an uninhibited control (100%) and IC$_{50}$ values were calculated using XlFit (model 205, IDBS).

PDE9 Inhibition Assay

A PDE9 assay may for example, be performed as follows: The assay is performed in 60 μL samples containing a fixed amount of the relevant PDE enzyme (sufficient to convert 20-25% of the cyclic nucleotide substrate), a buffer (50 mM HEPES7.6; 10 mM MgCl$_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 μL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and IC$_{50}$ values can be calculated using the Xlfit extension to EXCEL.

In the context of the present invention the assay was performed in 60 μL assay buffer (50 mM HEPES pH 7.6; 10 mM MgCl$_2$; 0.02% Tween20) containing enough PDE9 to convert 20-25% of 10 nM $^3$H-cAMP and varying amounts of inhibitors. Following a 1 hr incubation the reactions were terminated by addition of 15 μL 8 mg/mL yttrium silicate SPA beads (Amersham). The beads were allowed to settle for one hr in the dark before the plates were counted in a Wallac 1450 Microbeta counter.

What is claimed is:

1. A compound selected from the group consisting of:
   (A) (4) 7-(Cyclohexylmethyl)-6-methyl-3-(tetrahydro-2H-pyran-4-yl)imidazo[1,5-a]pyrazin-8(7H)-one;
   (5) 7-(3-Fluorobenzyl)-6-methyl-3-(tetrahydro-2H-pyran-4-yl)imidazo[1,5-a]pyrazin-8(7H)-one;
   (6) 3-Cyclopropyl-7-(3-fluorobenzyl)imidazo[1,5-a]pyrazin-8(7H)-one;
   (7) 7-(Cyclopentylmethyl)-3-cyclopropylimidazo[1,5-a]pyrazin-8(7H)-one;
   (8) 7-(Cyclohexylmethyl)-3-cyclopropylimidazo[1,5-a]pyrazin-8(7H)-one;
   (9) 7-(3-Fluorobenzyl)-3-(tetrahydro-2H-pyran-4-yl)imidazo[1,5-a]pyrazin-8(7H)-one;
   (10) 7-(Cyclopentylmethyl)-3-(tetrahydro-2H-pyran-4-yl)imidazo[1,5-a]pyrazin-8(7H)-one;
   (11) 7-(Cyclohexylmethyl)-3-(tetrahydro-2H-pyran-4-yl)imidazo[1,5-a]pyrazin-8(7H)-one;
   (12) 7-(Cycloheptylmethyl)-3-(tetrahydro-2H-pyran-4-yl)imidazo[1,5-a]pyrazin-8(7H)-one;
   (13) 7-(Cycloheptylmethyl)-3-cyclopropylimidazo[1,5-a]pyrazin-8(7H)-one;
   (14) 7-(4-Chlorobenzyl)-6-methyl-3-(tetrahydro-2H-pyran-4-yl)imidazo[1,5-a]pyrazin-8(7H)-one;
   (15) 6-Bromo-7-(3-fluorobenzyl)-3-(tetrahydro-2H-pyran-4-yl)imidazo[1,5-a]pyrazin-8(7H)-one;
   (16) 7-Benzyl-6-methyl-3-(tetrahydro-2H-pyran-4-yl)imidazo[1,5-a]pyrazin-8(7H)-one;
   (17) 7-(2-Fluorobenzyl)-6-methyl-3-(tetrahydro-2H-pyran-4-yl)imidazo[1,5-a]pyrazin-8(7H)-one;
   (18) 7-(3-Chlorobenzyl)-6-methyl-3-(tetrahydro-2H-pyran-4-yl)imidazo[1,5-a]pyrazin-8(7H)-one;

(19) 7-(2-Chlorobenzyl)-6-methyl-3-(tetrahydro-2H-pyran-4-yl)imidazo[1,5-a]pyrazin-8(7H)-one;
(20) 7-(3-Methoxybenzyl)-6-methyl-3-(tetrahydro-2H-pyran-4-yl)imidazo[1,5-a]pyrazin-8(7H)-one;
(21) 6-Methyl-7-(2-methylbenzyl)-3-(tetrahydro-2H-pyran-4-yl)imidazo[1,5-a]pyrazin-8(7H)-one;
(22) 6-Methyl-7-(4-methylbenzyl)-3-(tetrahydro-2H-pyran-4-yl)imidazo[1,5-a]pyrazin-8(7H)-one;
(23) 7-(4-Methoxybenzyl)-6-methyl-3-(tetrahydro-2H-pyran-4-yl)imidazo[1,5-a]pyrazin-8(7H)-one;
(24) 7-(4-Fluorobenzyl)-6-methyl-3-(tetrahydro-2H-pyran-4-yl)imidazo[1,5-a]pyrazin-8(7H)-one; and
(25) 6-Methyl-7-(3-methylbenzyl)-3-(tetrahydro-2H-pyran-4-yl)imidazo[1,5-a]pyrazin-8(7H)-one;
or
(B) a pharmaceutically acceptable salt thereof.

2. The compound of claim 1, wherein the compound is:
(4) 7-(Cyclohexylmethyl)-6-methyl-3-(tetrahydro-2H-pyran-4-yl)imidazo[1,5-a]pyrazin-8(7H)-one;
or a pharmaceutically acceptable salt thereof.

3. The compound of claim 1, wherein the compound is:
(5) 7-(3-Fluorobenzyl)-6-methyl-3-(tetrahydro-2H-pyran-4-yl)imidazo[1,5-a]pyrazin-8(7H)-one;
or a pharmaceutically acceptable salt thereof.

4. The compound of claim 1, wherein the compound is:
(6) 3-Cyclopropyl-7-(3-fluorobenzyl)imidazo[1,5-a]pyrazin-8(7H)-one;
or a pharmaceutically acceptable salt thereof.

5. The compound of claim 1, wherein the compound is:
(7) 7-(Cyclopentylmethyl)-3-cyclopropylimidazo[1,5-a]pyrazin-8(7H)-one;
or a pharmaceutically acceptable salt thereof.

6. The compound of claim 1, wherein the compound is:
(8) 7-(Cyclohexylmethyl)-3-cyclopropylimidazo[1,5-a]pyrazin-8(7H)-one;
or a pharmaceutically acceptable salt thereof.

7. The compound of claim 1, wherein the compound is:
(9) 7-(3-Fluorobenzyl)-3-(tetrahydro-2H-pyran-4-yl)imidazo[1,5-a]pyrazin-8(7H)-one;
or a pharmaceutically acceptable salt thereof.

8. The compound of claim 1, wherein the compound is:
(10) 7-(Cyclopentylmethyl)-3-(tetrahydro-2H-pyran-4-yl)imidazo[1,5-a]pyrazin-8(7H)-one;
or a pharmaceutically acceptable salt thereof.

9. The compound of claim 1, wherein the compound is:
(11) 7-(Cyclohexylmethyl)-3-(tetrahydro-2H-pyran-4-yl)imidazo[1,5-a]pyrazin-8(7H)-one;
or a pharmaceutically acceptable salt thereof.

10. The compound of claim 1, wherein the compound is:
(12) 7-(Cycloheptylmethyl)-3-(tetrahydro-2H-pyran-4-yl)imidazo[1,5-a]pyrazin-8(7H)-one;
or a pharmaceutically acceptable salt thereof.

11. The compound of claim 1, wherein the compound is:
(13) 7-(Cycloheptylmethyl)-3-cyclopropylimidazo[1,5-a]pyrazin-8(7H)-one;
or a pharmaceutically acceptable salt thereof.

12. The compound of claim 1, wherein the compound is:
(14) 7-(4-Chlorobenzyl)-6-methyl-3-(tetrahydro-2H-pyran-4-yl)imidazo[1,5-a]pyrazin-8(7H)-one;
or a pharmaceutically acceptable salt thereof.

13. The compound of claim 1, wherein the compound is:
(15) 6-Bromo-7-(3-fluorobenzyl)-3-(tetrahydro-2H-pyran-4-yl)imidazo[1,5-a]pyrazin-8(7H)-one;
or a pharmaceutically acceptable salt thereof.

14. The compound of claim 1, wherein the compound is:
(16) 7-Benzyl-6-methyl-3-(tetrahydro-2H-pyran-4-yl)imidazo[1,5-a]pyrazin-8(7H)-one;
or a pharmaceutically acceptable salt thereof.

15. The compound of claim 1, wherein the compound is:
(17) 7-(2-Fluorobenzyl)-6-methyl-3-(tetrahydro-2H-pyran-4-yl)imidazo[1,5-a]pyrazin-8(7H)-one;
or a pharmaceutically acceptable salt thereof.

16. The compound of claim 1, wherein the compound is:
(18) 7-(3-Chlorobenzyl)-6-methyl-3-(tetrahydro-2H-pyran-4-yl)imidazo[1,5-a]pyrazin-8(7H)-one;
or a pharmaceutically acceptable salt thereof.

17. The compound of claim 1, wherein the compound is:
(19) 7-(2-Chlorobenzyl)-6-methyl-3-(tetrahydro-2H-pyran-4-yl)imidazo[1,5-a]pyrazin-8(7H)-one;
or a pharmaceutically acceptable salt thereof.

18. The compound of claim 1, wherein the compound is:
(20) 7-(3-Methoxybenzyl)-6-methyl-3-(tetrahydro-2H-pyran-4-yl)imidazo[1,5-a]pyrazin-8(7H)-one;
or a pharmaceutically acceptable salt thereof.

19. The compound of claim 1, wherein the compound is:
(21) 6-Methyl-7-(2-methylbenzyl)-3-(tetrahydro-2H-pyran-4-yl)imidazo[1,5-a]pyrazin-8(7H)-one;
or a pharmaceutically acceptable salt thereof.

20. The compound of claim 1, wherein the compound is:
(22) 6-Methyl-7-(4-methylbenzyl)-3-(tetrahydro-2H-pyran-4-yl)imidazo[1,5-a]pyrazin-8(7H)-one;
or a pharmaceutically acceptable salt thereof.

21. The compound of claim 1, wherein the compound is:
(23) 7-(4-Methoxybenzyl)-6-methyl-3-(tetrahydro-2H-pyran-4-yl)imidazo[1,5-a]pyrazin-8(7H)-one;
or a pharmaceutically acceptable salt thereof.

22. The compound of claim 1, wherein the compound is:
(24) 7-(4-Fluorobenzyl)-6-methyl-3-(tetrahydro-2H-pyran-4-yl)imidazo[1,5-a]pyrazin-8(7H)-one;
or a pharmaceutically acceptable salt thereof.

23. The compound of claim 1, wherein the compound is:
(25) 6-Methyl-7-(3-methylbenzyl)-3-(tetrahydro-2H-pyran-4-yl)imidazo[1,5-a]pyrazin-8(7H)-one;
or a pharmaceutically acceptable salt thereof.

24. A pharmaceutical composition comprising a therapeutically effective amount of the compound of claim 1 and one or more pharmaceutically acceptable carriers.

\* \* \* \* \*